(12) United States Patent
Azam et al.

(10) Patent No.: US 10,342,767 B2
(45) Date of Patent: *Jul. 9, 2019

(54) THERAPY FOR KINASE-DEPENDENT MALIGNANCIES

(71) Applicant: CHILDREN'S HOSPITAL MEDICAL CENTER, Cincinnati, OH (US)

(72) Inventors: Mohammad Azam, Mason, OH (US); Meenu Kesarwani, Mason, OH (US)

(73) Assignee: CHILDREN'S HOSPITAL MEDICAL CENTER, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/900,201

(22) Filed: Feb. 20, 2018

(65) Prior Publication Data

US 2018/0360777 A1    Dec. 20, 2018

Related U.S. Application Data

(63) Continuation-in-part of application No. 15/866,544, filed on Jan. 10, 2018, which is a continuation of application No. 14/048,806, filed on Oct. 8, 2013, now Pat. No. 9,877,934, which is a continuation-in-part of application No. PCT/US2012/034359, filed on Apr. 20, 2012.

(60) Provisional application No. 61/477,853, filed on Apr. 21, 2011.

(51) Int. Cl.
| | |
|---|---|
| *A61K 31/12* | (2006.01) |
| *A61K 45/06* | (2006.01) |
| *A61K 31/045* | (2006.01) |
| *A61K 31/135* | (2006.01) |
| *A61K 31/506* | (2006.01) |
| *A61K 31/517* | (2006.01) |

(52) U.S. Cl.
CPC .......... *A61K 31/135* (2013.01); *A61K 31/045* (2013.01); *A61K 31/12* (2013.01); *A61K 31/506* (2013.01); *A61K 31/517* (2013.01); *A61K 45/06* (2013.01); *A61K 2300/00* (2013.01)

(58) Field of Classification Search
CPC ........ A61K 31/12; A61K 45/06; A61K 31/45; A61K 31/135; A61K 31/506; A61K 31/517

See application file for complete search history.

(56) References Cited

U.S. PATENT DOCUMENTS

| | | | |
|---|---|---|---|
| 7,045,523 B2 | 5/2006 | Tauchi | |
| 8,318,815 B2 | 11/2012 | Huang | |
| 2004/0127470 A1 | 7/2004 | Masferrer | |
| 2006/0189543 A1 | 8/2006 | Rosenbloom | |
| 2008/0207532 A1 | 8/2008 | Huang | |
| 2009/0311702 A1 | 12/2009 | Shak et al. | |
| 2010/0184779 A1 | 7/2010 | Hughes | |
| 2011/0118298 A1 | 5/2011 | Fritz et al. | |
| 2014/0031356 A1 | 1/2014 | Azam et al. | |

FOREIGN PATENT DOCUMENTS

| | | |
|---|---|---|
| WO | WO 2010/108058 A2 | 9/2010 |
| WO | WO 2010/108058 A3 | 9/2010 |
| WO | WO 2010/124283 A2 | 10/2010 |
| WO | WO 2011/014825 A2 | 2/2011 |

OTHER PUBLICATIONS

Jabbour et al. Clin Lymphoma Myeloma Leuk. 2013; 13(5): 515-529.*
Aikawa et al. "Treatment of arthritis with a selective inhibitor of c-Fos/activator protein-1," Nature Biotechnology, vol. 26, No. 7 (2008), pp. 817-823.
Azam et al. Anticipating Clinical Resistance to Target-Directed Agents The BCR-ABL Paradigm. Mol Diag Ther 10 (2006) 67-76.
Azam et al. Mechanisms of Autoinhibition and STI-571/Imatinib Resistance Revealed by Mutagenesis of BCR-ABL. Cell 112 (2003) 831-843.
Bakan, Ahmet, et al.; "Toward a Molecular Understanding of the Interaction of Dual Specificity Phosphatases with Substrates: Insights from Structure-Based Modeling and High Throughput Screening"; Current Medicinal Chemistry, 15;.pp. 2536-2544 (2008).
Communication pursuant to Article 94(3) EPC for EP 12774776.4, dated Feb. 6, 2017 (4 pages).
Doddareddy, M. R., et al.; "Targeting Mitogen-Activated Protein Kinase Phosphatase-1 (MKP-1): Structure-Based Design of MKP-1 Inhibitors and Upregulators"; Current Medicinal Chemistry, 19; pp. 163-173 (2012).
Drug Ther Perspect. 2000; 16(10).
Extended European Search Report comprised of Supplementary European Search Report and the European Search Opinion PCT/US2012/034359, dated Oct. 10, 2014 (9 pages).
He, Rong-jun, et al.; "Protein tyrosine phosphatases as potential therapeutic targets"; Acta Pharmacological Sinica, 35; pp. 1227-1246.
Henkes et al., (ther Clin Risk Manag (2008)4(1): 163-187.
Huang et al. Suppression of c-Jun / AP-1 activation by an inhibitor of tumor promotion in mouse fibroblast cells. Proc. Natl. Acad. Sci. USA 88 (1991) 5292-5296.
International Preliminary Report on Patentability for PCT/US2015/033269, dated Dec. 6, 2016 (6 pages).

(Continued)

Primary Examiner — Shirley V Gembeh
(74) Attorney, Agent, or Firm — Thompson Hine L.L.P.

(57) ABSTRACT

A pharmaceutically acceptable composition and method of therapy for a kinase-dependent malignancy in a patient in need of such therapy is provided. The composition contains, as the only active agents, the combination of (a) an inhibitor of c-Fos, (b) an inhibitor of Dusp-1, and (c) an inhibitor of a tyrosine kinase. The composition is administered to the patient in a dosing regimen for a period sufficient to provide therapy for kinase-dependent malignancy. Also provided is a method to eradicate leukemia initiating cells (LIC) or cancer stem cells (CSC) in a patient being treated with a tyrosine kinase inhibitor.

7 Claims, 97 Drawing Sheets

(58 of 97 Drawing Sheet(s) Filed in Color)

(56) References Cited

OTHER PUBLICATIONS

International Preliminary Report on Patentability PCT/US2012/034359, dated Oct. 22, 2013 (7 pages).
International Search Report and Written Opinion PCT/US2012/034359, dated Nov. 29, 2012 (10 pages).
International Search Report and Written Opinion PCT/US2015/33269, dated Aug. 19, 2015, 8 pages.
Knight et al. Features of Selective Kinase Inhibitors. Chemistry & Biology 12 (2005) 621-637.
Korhonen, Riku, et al.; "Mitogen-Activated Protein Kinase Phosphatase 1 as an Inflammatory Factor and Drug Target"; Basic & Clinical Pharmacology & Toxicology, 114; DOI: 10.1111/bcpt12141; pp. 24-36 (2014).
Kundu, Suman, et al.; "Tyrosine Phosphatase Inhibitor-3 Sensitizes Melanoma and Colon Cancer to Biotherapeutics and Chemotherapeutics"; Preclinical Development; Molecular Cancer Therapeutics 9 (8); DOI: 10.1158/1535-7163.MCT-10-0159; pp. 2287-2296 (2010).
Mahon, Hematology 2012; 122-128.
Molina et al., Zebrafish chemical screening reveals an inhibitor of Dusp6 that expands cardiac cell lineages. Nature Chemical Biology 5 (2009) 680-687.
Nabavi et al. Curcumin and Liver Disease: from Chemistry to Medicine. Comprehensive Reviews in Food Science and Food Safety 13 (2014) 62-77.
Nardi et al. Mechanisms and implications of imatinib resistance mutations in BCR-ABL. Curr Opin Hematology 11 (2004) 35-43 and 1 page Figure 1.
Nunes-Xavier, Caroline, et al.; "Dual-Specificity MAP Kinase Phosphatases as Targets of Cancer Treatment"; Anti-Cancer Agents in Medicinal Chemistry, 11; pp. 109-132 (2011).
Padhye et al. Fluorocurcumins as Cyclooxygenase-2 Inhibitor: Molecular Docking, Pharmacokinetics and Tissue Distribution in Mice. Pharmaceutical Research, vol. 26, No. 11 (2009), pp. 2438-2445.
Padhye et al. New Difluoro Knoevenagel Condensates of Curcumin, Their Schiff Bases and Copper Complexes as Proteasome Inhibitors and Apoptosis Inducers in Cancer Cells. Pharmaceutical Research, vol. 26, No. 8 (2009), pp. 1874-1880.
Park et al., "Inhibition of fos-jun-DNA complex formation by dihydroguaiaretic acid and in vitro cytotoxic effects on cancer cells," Cancer Letters, vol. 127 (1998), pp. 23-28.
Purwana et al. Induction of Dual Specificity Phosphatase 1 (DUSP1) by Gonadotropin-Releasing Hormone (GnRH) and the Role for Conadotropin Subunit Gene Expression in Mouse Pituitary Gonadotroph LbetaT2 Cells. Biology of Reproduction 82 (2010) 352-362.
Rios, Pablo et al.,; "Dual-Specificity Phosphatases as Molecular Targets for Inhibition in Human Disease"; Antioxidants & Redox Signaling; vol. 20, No. 14; DOI: 10.1089/ars2013.5709; pp. 2251-2274 (2014).
Shi et al. Triptolide Inhibits Bcr-Abl Transcription and Induces Apoptosis in STI571-resistant Chronic Myelogenous Leukemia Cells Harboring T315I Mutation. Clin Cancer Res 15 (2009) 1686-1697.
Angel, P. & Karin, M. The role of Jun, Fos and the AP-1 complex in cell-proliferation and transformation. Biochim. Biophys. Acta 1072, 129-157 (1991).
Azam, M., Seeliger, M.A., Gray, N.S., Kuriyan, J. & Daley, G.Q. Activation of tyrosine kinases by mutation of the gatekeeper threonine. Nat. Struct. Mol. Biol. 15, 1109-1118 (2008).
Bagger, F.O. et al. BloodSpot: a database of gene expression profiles and transcriptional programs for healthy and malignant haematopoiesis. Nucleic Acids Res. 44D1, D917-D924 (2016).
Bennett, B.L. et al. SP600125, an anthrapyrazolone inhibitor of Jun N-terminal kinase. Proc. Natl. Acad. Sci. USA 98, 13681-13686 (2001).
Boutros, T., Chevet, E. & Metrakos, P. Mitogen-activated protein (MAP) kinase/MAP kinase phosphatase regulation: roles in cell growth, death, and cancer. Pharmacol. Rev. 60, 261-310 (2008).

Brooks, S.A. & Blackshear, P.J. Tristetraprolin (TTP): interactions with mRNA and proteins, and current thoughts on mechanisms of action. Biochim. Biophys. Acta 1829, 666-679 (2013).
Bruennert, D. et al. Early in vivo changes of the transcriptome in Philadelphia chromosome-positive CD34+ cells from patients with chronic myelogenous leukaemia following imatinib therapy. Leukemia 23, 983-985 (2009).
Chang, K.H. et al. Vav3 collaborates with p190-BCR-ABL in lymphoid progenitor leukemogenesis, proliferation, and survival. Blood 120, 800-811 (2012).
Chu, S. et al. Detection of BCR-ABL kinase mutations in CD34+ cells from chronic myelogenous leukemia patients in complete cytogenetic remission on imatinib mesylate treatment. Blood 105, 2093-2098 (2005).
Copland, M. et al. BMS-214662 potently induces apoptosis of chronic myeloid leukemia stem and progenitor cells and synergizes with tyrosine kinase inhibitors. Blood 111, 2843-2853 (2008).
Corbin, A.S. et al. Human chronic myeloid leukemia stem cells are insensitive to imatinib despite inhibition of BCR-ABL activity. J. Clin. Invest. 121, 396-409 (2011).
Daley, G.Q., Van Etten, R.A. & Baltimore, D. Induction of chronic myelogenous leukemia in mice by the P210bcr/abl gene of the Philadelphia chromosome. Science 247, 824-830 (1990).
Dorfman, K. et al. Disruption of the erp/mkp-1 gene does not affect mouse development: normal MAP kinase activity in ERP/MKP-1-deficient fibroblasts. Oncogene 13, 925-931 (1996).
Druker, B.J. et al. Activity of a specific inhibitor of the BCR-ABL tyrosine kinase in the blast crisis of chronic myeloid leukemia and acute lymphoblastic leukemia with the Philadelphia chromosome. N. Engl. J. Med. 344, 1038-1042 (2001).
Druker, B.J. et al. Effects of a selective inhibitor of the Abl tyrosine kinase on the growth of Bcr-Abl positive cells. Nat. Med. 2, 561-566 (1996).
Eferl, R. & Wagner, E.F. Ap-1: a double-edged sword in tumorigenesis. Nat. Rev. Cancer 3, 859-868 (2003).
Fjeld, C.C., Rice, A.E., Kim, Y., Gee, K.R. & Denu, J.M. Mechanistic basis for catalytic activation of mitogen-activated protein kinase phosphatase 3 by extracellular signal-regulated kinase. J. Biol. Chem. 275, 6749-6757 (2000).
Groom, L.A., Sneddon, A.A., Alessi, D.R., Dowd, S. & Keyse, S.M. Differential regulation of the MAP, SAP and RK/p38 kinases by Pystl, a novel cytosolic dual-specificity phosphatase. EMBO J. 15, 3621-3632 (1996).
Hirsch, D.D. & Stork, P.J. Mitogen-activated protein kinase phosphatases inactivate stress-activated protein kinase pathways in vivo. J. Biol. Chem. 272, 4568-4575 (1997).
Holyoake, T.L. & Vetrie, D. The chronic myeloid leukemia stem cell: stemming the tide of persistence. Blood https://doi.org/10.1182/blood-2016-09-696013 (2017).
Hrustanovic, G. et al. RAS-MAPK dependence underlies a rational polytherapy strategy in EML4-ALK-positive lung cancer. Nat. Med. 21, 1038-1047 (2015).
Jeffrey, K.L., Camps, M., Rommel, C. & Mackay, C.R. Targeting dual-specificity phosphatases: manipulating MAP kinase signalling and immune responses. Nat. Rev. Drug Discov. 6, 391-403 (2007).
Jorgensen, H.G., Allan, E.K., Jordanides, N.E., Mountford, J.C. & Holyoake, T.L. Nilotinib exerts equipotent antiproliferative effects to imatinib and does not induce apoptosis in CD34+ CML cells. Blood 109, 4016-4019 (2007).
Kaelin, W.G., Jr. The concept of synthetic lethality in the context of anticancer therapy. Nat. Rev. Cancer 5, 689-698 (2005).
Kamb, A. Consequences of nonadaptive alterations in cancer. Mol. Biol. Cell 14, 2201-2205 (2003).
Kesarwani, M. et al. Targeting substrate-site in Jak2 kinase prevents emergence of genetic resistance. Sci. Rep. 5, 14538 (2015).
Kesarwani, Meenu et al., "Targeting c-FOS and DUSP1 abrogates intrinsic resistance to tyrosine-kinase inhibitor therapy in BCR-ABL-induced leukemia," Nature Medicine, published online Mar. 20, 2017, 47 pages.
Komurov, K., Dursun, S., Erdin, S. & Ram, P.T. NetWalker: A contextual network analysis tool for functional genomics. BMC Genomics 13, 282 (2012).

(56) References Cited

OTHER PUBLICATIONS

Koschmieder, S. et al. Inducible chronic phase of myeloid leukemia with expansion of hematopoietic stem cells in a transgenic model of BCR-ABL leukemogenesis. Blood 105, 324-334 (2005).

Krause, D.S. & Van Etten, R.A. Tyrosine kinases as targets for cancer therapy. N. Engl. J. Med. 353, 172-187 (2005).

Lawan, A., Shi, H., Gatzke, F. & Bennett, A.M. Diversity and specificity of the mitogen-activated protein kinase phosphatase-1 functions. Cell. MoL Life Sci. 70, 223-237 (2013).

Li, L. et al. Activation of p53 by SIRT1 inhibition enhances elimination of CML leukemia stem cells in combination with imatinib. Cancer Cell 21, 266-281 (2012).

Mahon, F.X. et al. Discontinuation of imatinib in patients with chronic myeloid leukaemia who have maintained complete molecular remission for at least 2 years: the prospective, multicentre Stop Imatinib (STIM) trial. Lancet Oncol. 11, 1029-1035 (2010).

Mills, G.B., Lu, Y. & Kohn, E.C. Linking molecular therapeutics to molecular diagnostics: inhibition of the FRAP/RAFT/TOR component of the PI3K pathway preferentially blocks PTEN mutant cells in vitro and in vivo. Proc. Natl. Acad. Sci. USA 98, 10031-10033 (2001).

O'Hare, T., Zabriskie, M.S., Eiring, A.M. & Deininger, M.W. Pushing the limits of targeted therapy in chronic myeloid leukaemia. Nat. Rev. Cancer 12, 513-526 (2012).

Owens, D.M. & Keyse, S.M. Differential regulation of MAP kinase signalling by dual-specificity protein phosphatases. Oncogene 26, 3203-3213 (2007).

Pagliarini, R., Shao, W. & Sellers, W.R. Oncogene addiction: pathways of therapeutic response, resistance, and road maps toward a cure. EMBO Rep. 16, 280-296 (2015).

Ransone, L.J., Visvader, J., Wamsley, P. & Verma, I.M. Transdominant negative mutants of Fos and Jun. Proc. Natl. Acad. Sci. USA 87, 3806-3810 (1990).

Reddy, A. & Kaelin, W.G., Jr. Using cancer genetics to guide the selection of anticancer drug targets. Curr. Opin. PharmacoL 2, 366-373 (2002).

Reynaud, D. et al. IL-6 controls leukemic multipotent progenitor cell fate and contributes to chronic myelogenous leukemia development. Cancer Cell 20, 661-673 (2011).

Roberts, K.G. et al. Genetic alterations activating kinase and cytokine receptor signaling in high-risk acute lymphoblastic leukemia. Cancer Cell 22, 153-166 (2012).

Ross, D.M. et al. Safety and efficacy of imatinib cessation for CML patients with stable undetectable minimal residual disease: results from the TWISTER study. Blood 122, 515-522 (2013).

Rousselot, P. et al. Imatinib mesylate discontinuation in patients with chronic myelogenous leukemia in complete molecular remission for more than 2 years. Blood 109, 58-60 (2007).

Savona, M. & Talpaz, M. Getting to the stem of chronic myeloid leukaemia. Nat. Rev. Cancer 8, 341-350 (2008).

Sawyers, C.L. Shifting paradigms: the seeds of oncogene addiction. Nat. Med. 15, 1158-1161 (2009).

Sharma, S.V. & Settleman, J. Exploiting the balance between life and death: targeted cancer therapy and "oncogenic shock". Biochem. Pharmacol. 80, 666-673 (2010).

Sharma, S.V. & Settleman, J. Oncogene addiction: setting the stage for molecularly targeted cancer therapy. Genes Dev. 21, 3214-3231 (2007).

Shojaee, S. et al. Erk negative feedback control enables pre-B cell transformation and represents a therapeutic target in acute lymphoblastic leukemia. Cancer Cell 28, 114-128 (2015).

Straussman, R. et al. Tumour micro-environment elicits innate resistance to RAF inhibitors through HGF secretion. Nature 487, 500-504 (2012).

Weiner, R.S. et al. Treatment of chronic myelogenous leukemia by blocking cytokine alterations found in normal stem and progenitor cells. Cancer Cell 27, 671-681 (2015).

Weinstein, I. B. Cancer. Addiction to oncogenes—the Achilles heal of cancer. Science 297, 63-64 (2002).

Wilson, T.R. et al. Widespread potential for growth-factor-driven resistance to anticancer kinase inhibitors. Nature 487, 505-509 (2012).

Young, P.R. et al. Pyridinyl imidazole inhibitors of p38 mitogen-activated protein kinase bind in the ATP site. J. Biol. Chem. 272, 12116-12121 (1997).

Zhang, B. et al. Altered microenvironmental regulation of leukemic and normal stem cells in chronic myelogenous leukemia. Cancer Cell 21, 577-592 (2012).

Zhang, J. et al. c-fos regulates neuronal excitability and survival. Nat. Genet. 30, 416-420 (2002).

Zhao, C. et al. Hedgehog signalling is essential for maintenance of cancer stem cells in myeloid leukaemia. Nature 458, 776-779 (2009).

Zhao, Q. et al. MAP kinase phosphatase 1 controls innate immune responses and suppresses endotoxic shock J. Exp. Med. 203, 131-140 (2006).

Dorfman, K. et al. Disruption of the erp/mkp-1 gene does not affect mouse development: normal MAP kinase activity in ERP/MKP-1-deficient fibroblasts. Oncogene 13, 925-931 (1996), 7 pages.

* cited by examiner

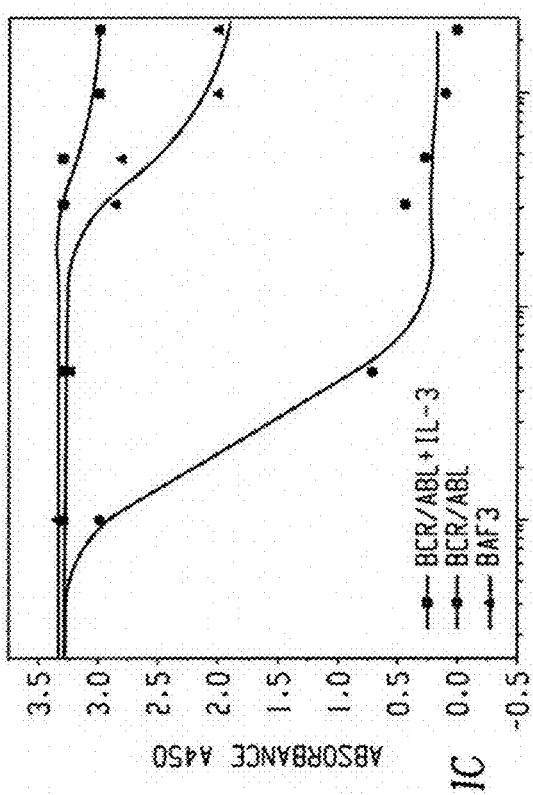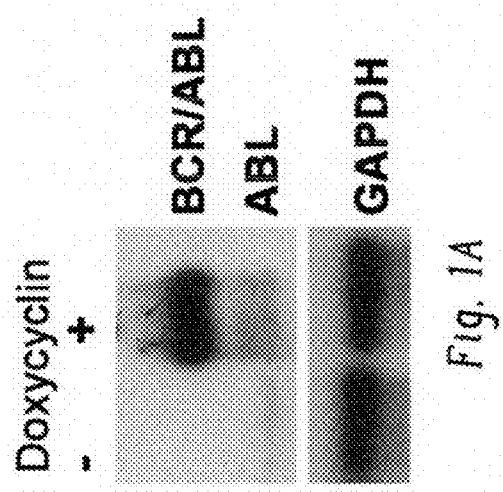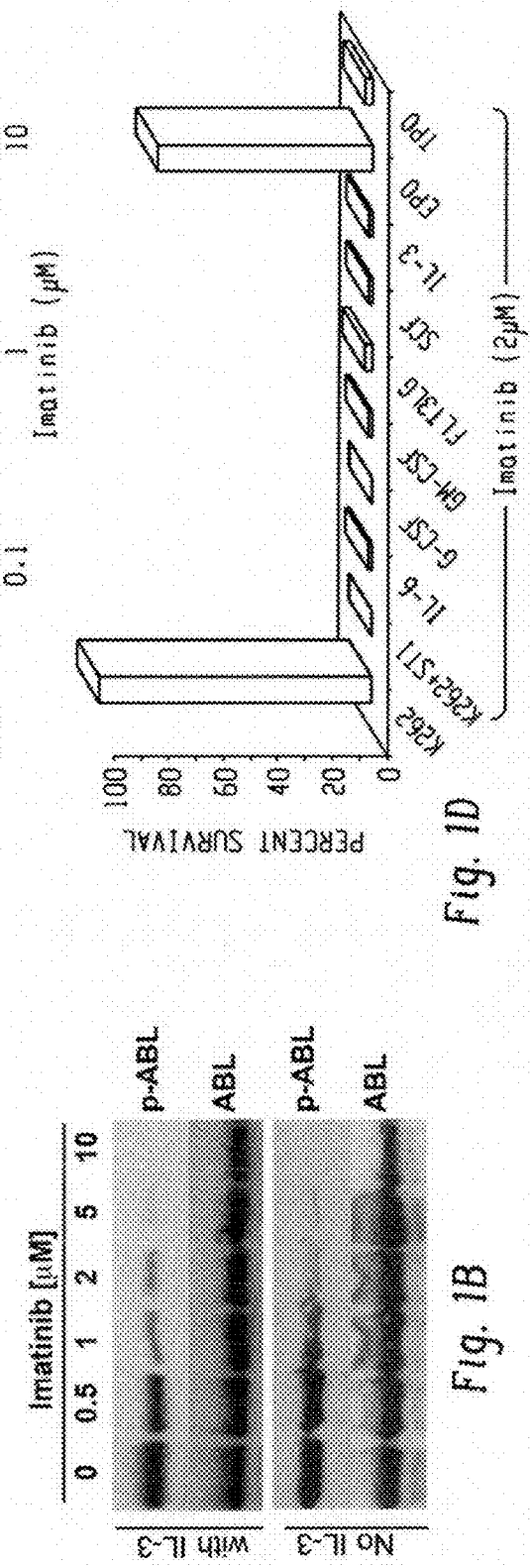

Fig. 2A1

MATCH TO FIG.2A1 slingshot homolog 2 (Drosophilia)
DEP domain containing 1a
DEP domain containing 1a
N/A
olfactory receptor 1252
N/A
N/A
RIKEN cDNA 2810021G02 gene
N/A
splicing factor, arginine/serine-rich 3(...
Gen homolog 1, endonuclease (Drosop...
similar to PBZ binding kinase (predicted)
RIKEN cDNA 5730449L18 gene
RIKEN cDNA 1810054D07 gene
polymerase (DNA directed), epsilon 2 (...
zinc finger protein 294
RIKEN cDNA D030056L22 gene
transmembrane protein 69
ATPase type 13A3
polymerase (DNA directed), alpha 1
centromere protein H
similar to multi sex combs CG12058-PA
N/A
centromere protein H
proteoglycan 3
similar to protein phosphatase 1, catal...
N/A
Shc-SH2-domain binding protein 1
fatty acid synthase
U3A small nuclear RNA
gastric inhibitory polypeptide receptor
MAX dimerization protein 1
zinc finger CCCH type containing 12C
syntaxin 11
N/A
interleukin-1 receptor-associated kina...
N/A

MATCH TO FIG.2A3

Fig. 2A2

MATCH TO FIG.2A2 benzodiazepine receptor associated pr...
neutrophil cytosolic factor 4
killer cell lectin-like receptor subfamily
N/A
N/A
aquaporin 8
dual specificity phosphatase 1
DNA-damage-inducible transcript 4
N/A
cyclin G2
N-myc downstream regulated gene 1
N/A
growth arrest and DNA-damage-induci...
cyclin Y-like 1
RIKEN cDNA 2610301F02 gene
neuropilin (NRP) and tolloid (TLL)-like 2
cyclin B1 interacting protein 1
phosphoribosylglycinamide formyltran...
gene model 807, (NCBI)
RIKEN cDNA E430024C06 gene
RIKEN cDNA E430024C06 gene
ribonuclease P 40 subunit (human)
RIKEN cDNA 2610301F02 gene
olfactomedin 3
ornithine decarboxylase, structural 1
UDP-GlcNAc:betaGal beta-1,3-N-acetyl...
similar to transcription elongation fact...
N/A
RAD51 homolog (S. cerevisiae)
gem (nuclear organelle) associated pr...
N/A
N/A
N/A
growth arrest specific 5
N/A
small nucleolar RNA host gene (non-pr...
N/A

MATCH TO FIG.2A4

Fig. 2A3

MATCH TO FIG.2A3

RAD1 homolog (S. pombe)
Fanconi anemia, complementation gro...
adenosine deaminase
N/A
Sjogren's syndrome/scleroderma auto...
N/A
growth arrest specific 5
N/A
N/A
small nucleolar RNA host gene (non-pr...
KDEL (Lys-Asp-Glu-Leu) containing 1
N/A
GINS complex subunit 1 (Psf1 homolog)
zinc finger protein 204
C-type lectin domain family 4, member...
similar to mitochondrial ribosomal pro...
inosine 5'-phosphate dehydrogenase 2
thymidine kinase 1
RIKEN cDNA 2610318N02 gene
N-6 adenine-specific DNA methyltransf...
cysteine conjugate-beta lyase 2
DNA segment, Chr 10, ERATO Doi 322....
transmembrane protein 176B
membrane-spanning 4-domains, subfa...
defective in sister chromatid cohesion...
N/A
N/A
Josephin domain containing 3
N/A
N/A
N/A
similar to ubiquitin specific protease 1
N/A
N/A
N/A
N/A
N/A

MATCH TO FIG.2A5

Fig. 2A4

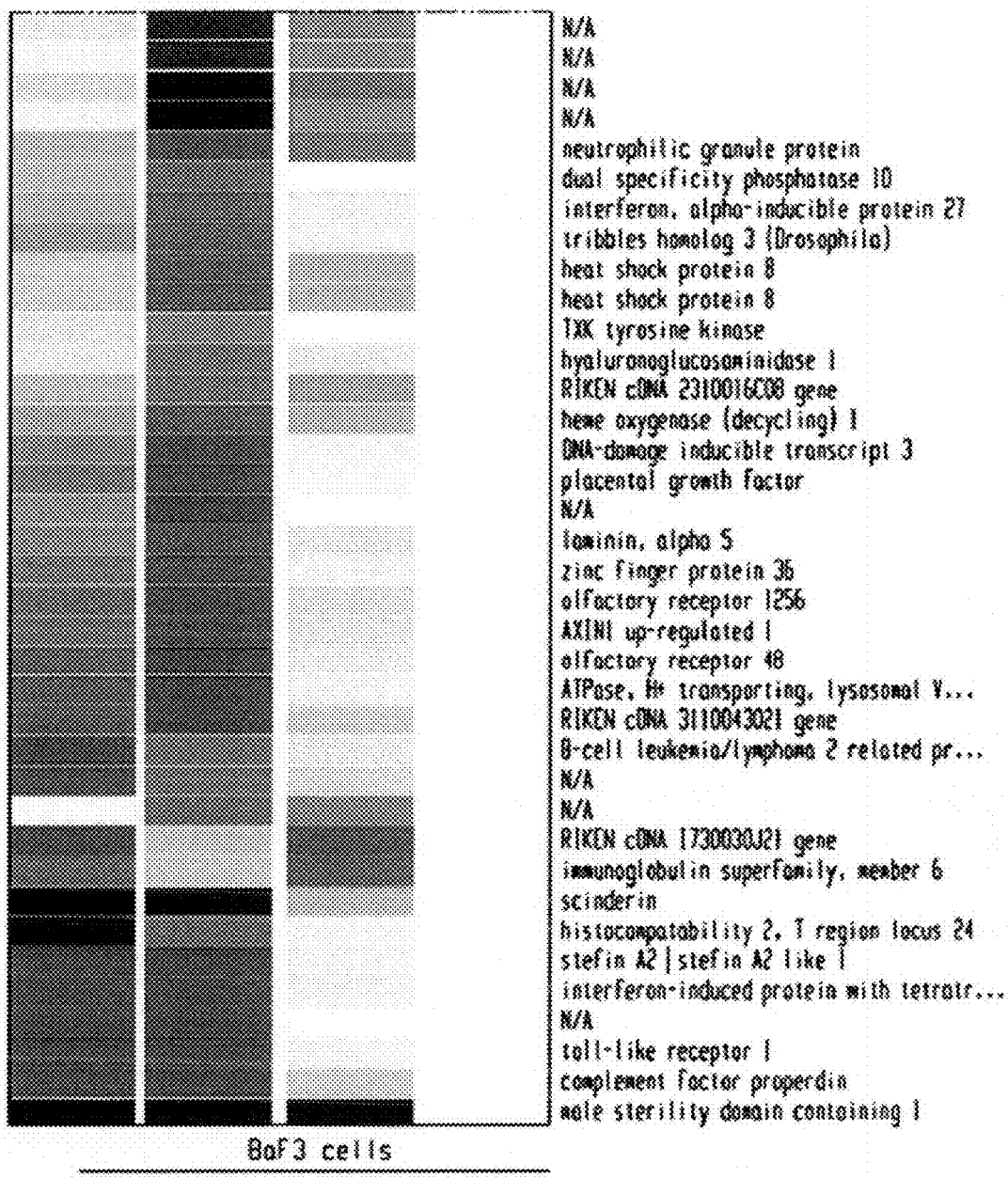
Fig. 2A5

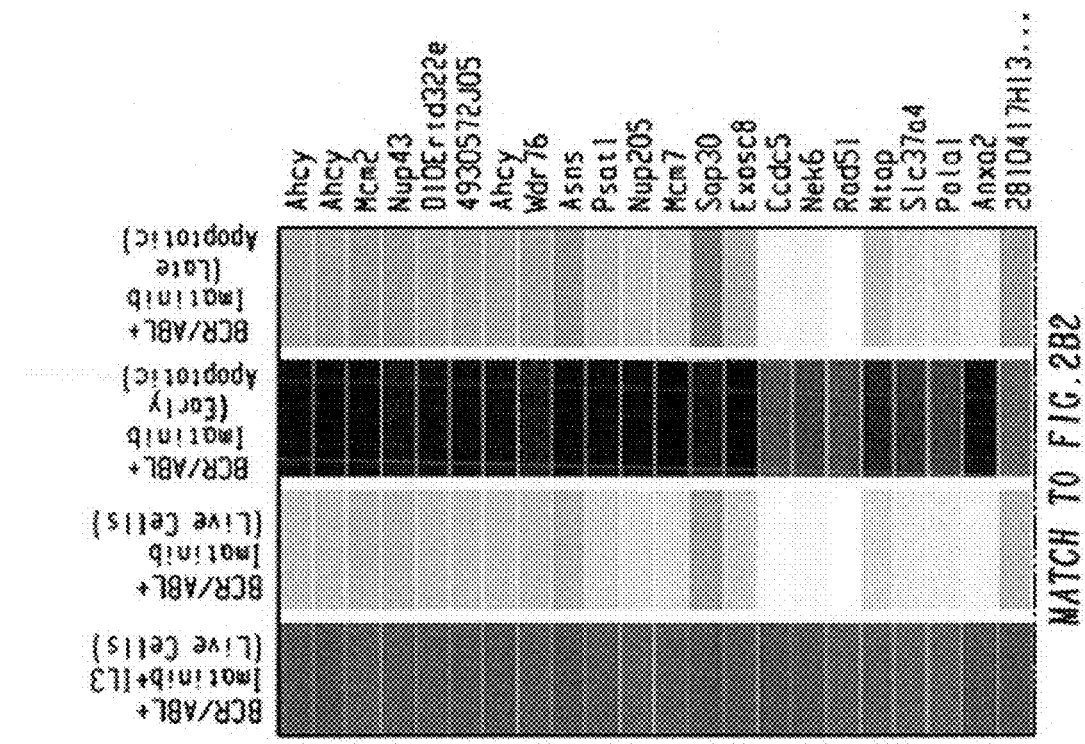

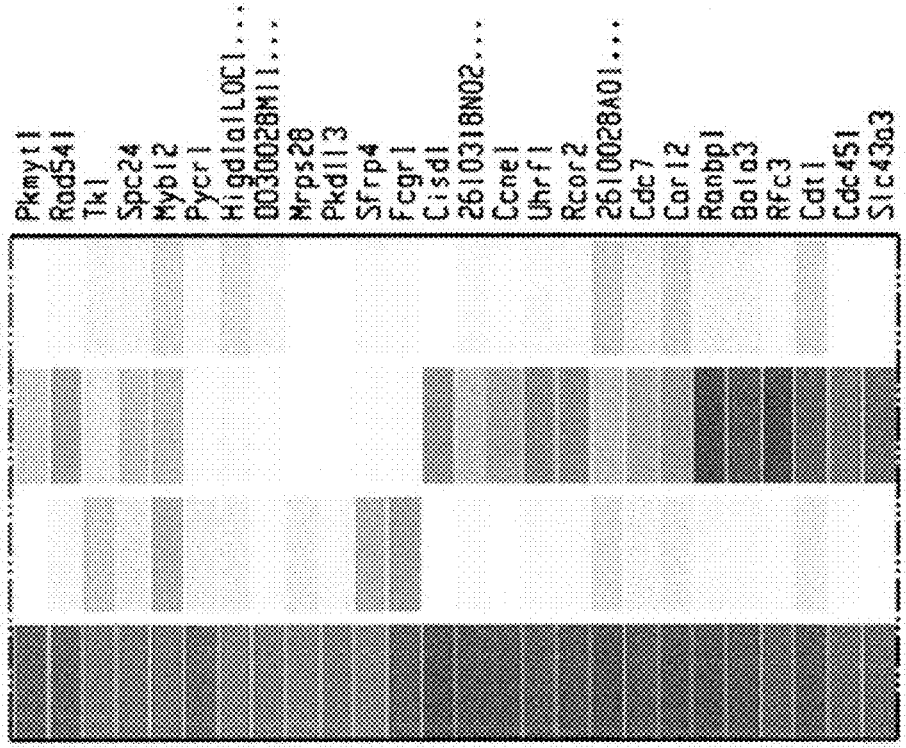
Fig. 2B4
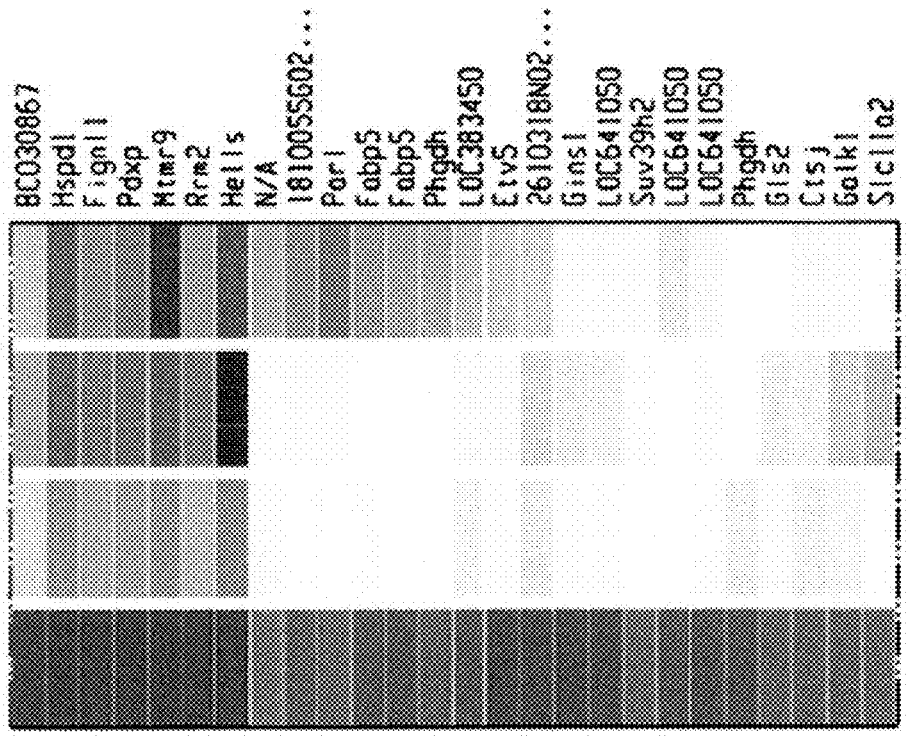
Fig. 2B3

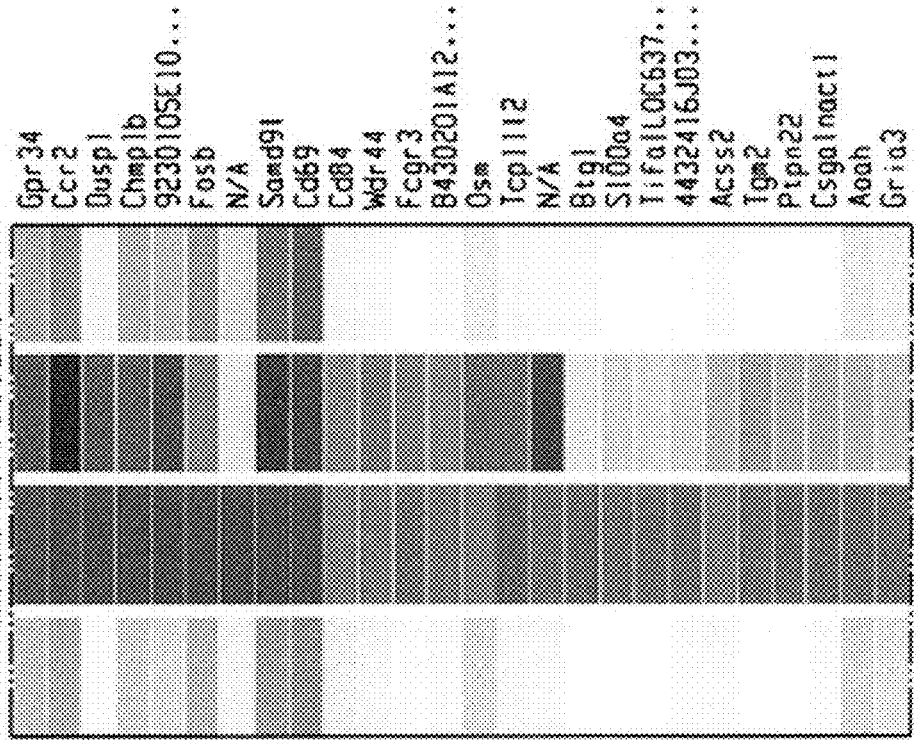
Fig. 2B5
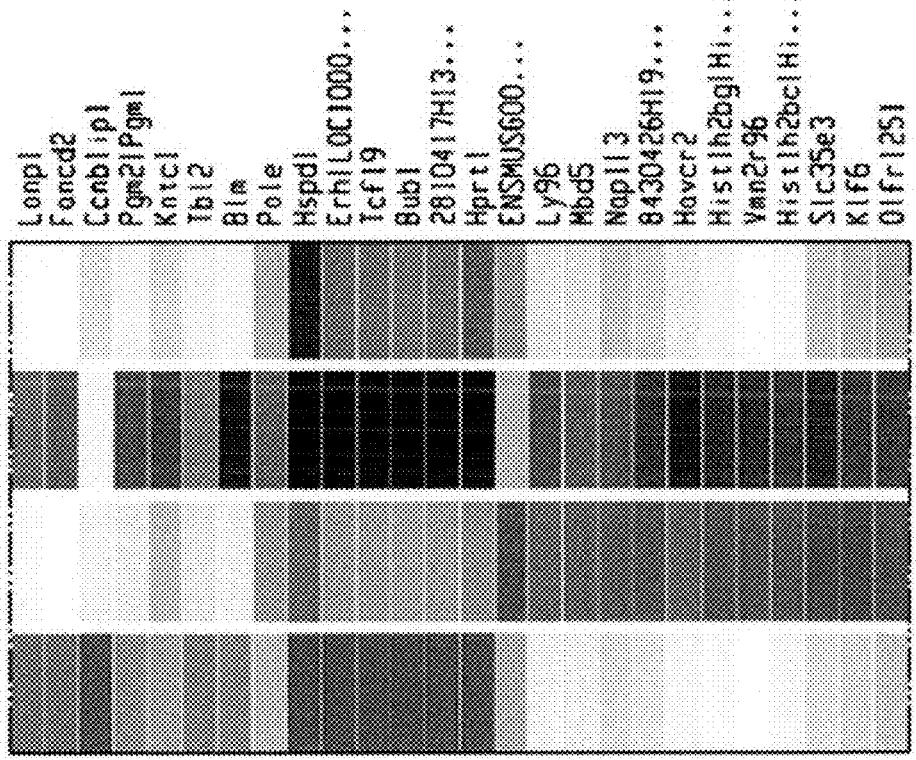
Fig. 2B6

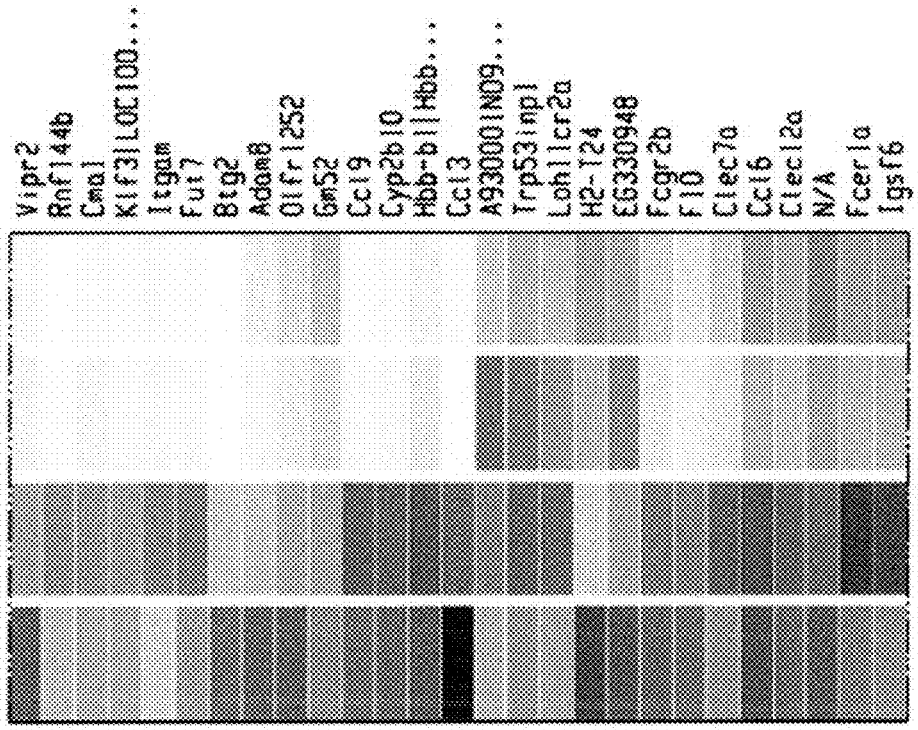
Fig. 2B10
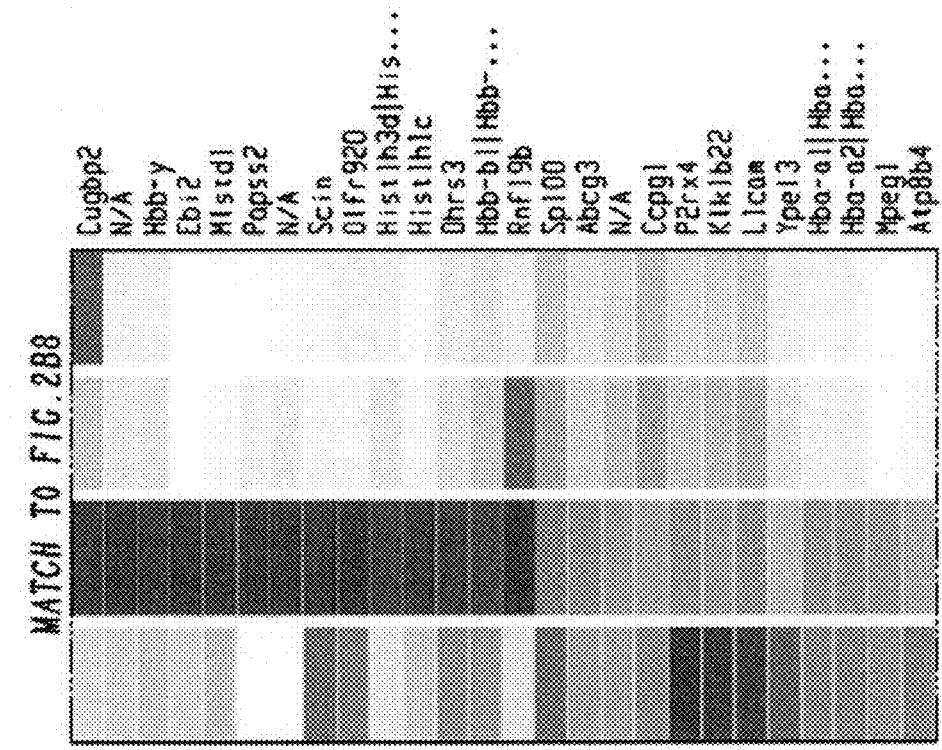
Fig. 2B9

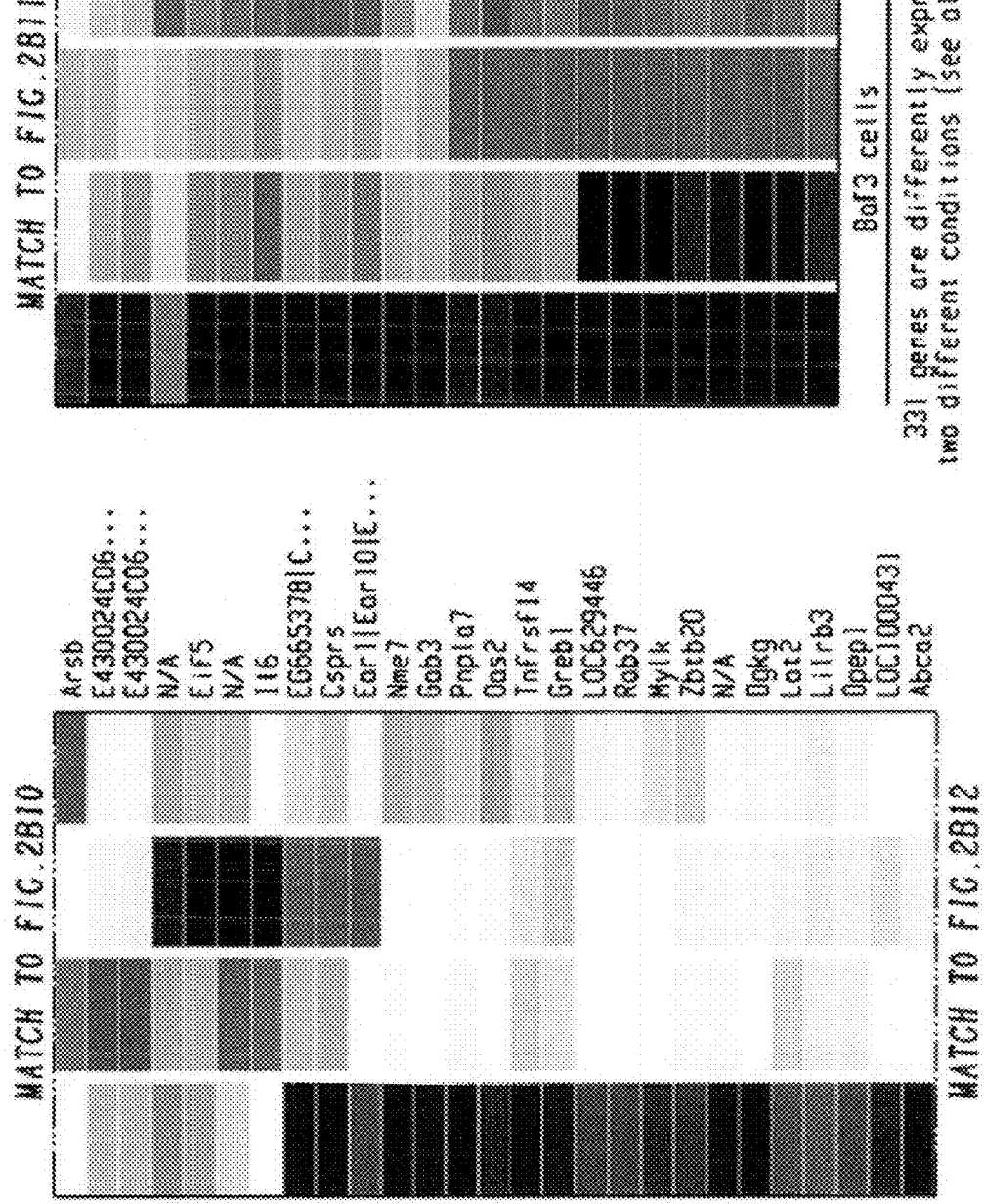

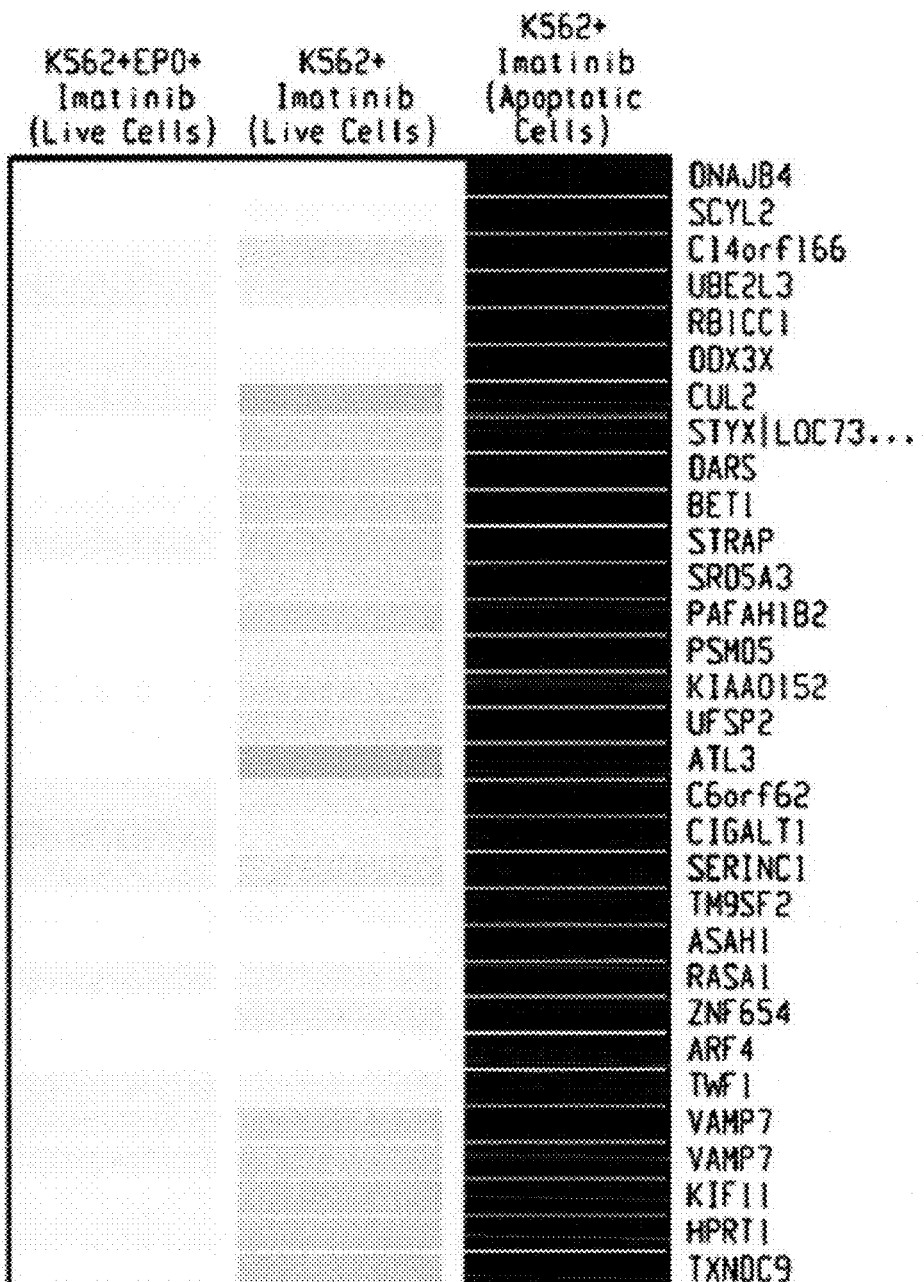
Fig. 2C1

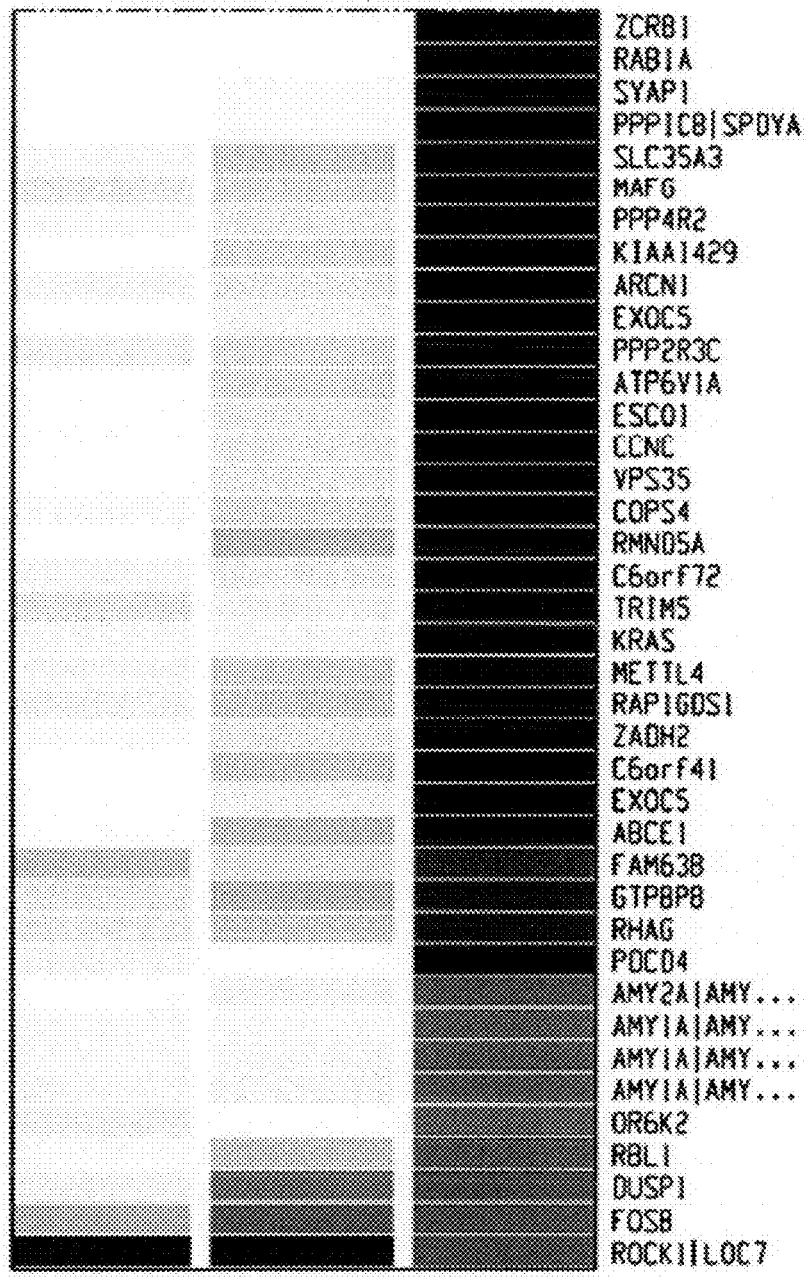
Fig. 2C2

|  | Before Treatment | One week of Imatinib Treatment |
|---|---|---|

Gene labels (top to bottom):
HLA-E, YPEL5, BAALC, IL10RA, PTPRO, CLK1, IRF7, NLRP1, IRF1, BCL2A1, TNFAIP2, TYROBP, GBP2, EVI2B, SORL1, SELL, PROM1, GLIPR1, SORL1, ZNF185, GLIPR1, STAG3L1, CRHBP, ZNF91, ANPEP, CSF3R, TSC22D3, BTG2, RHOB, BCL6, ORM1 /// OR..., TCN1, KLF2, GPR109B, IGHM, IGHM, JUNB, NFKBIA, TNFAIP3, GADD45B, ZFP36, TNFAIP3

MATCH TO FIG.2D2

Fig. 2D1

MATCH TO FIG. 2D1

PTGS2
ID2
ID2
CXCR4
HIST2H2BE
HIST2H2AA3...
HIST2H2AA3...
DUSP1
MS4A3
MMP9
S100P
LCN2
ARG1
CD24
GOS2
BHLHE40
DDIT4
STK17B
IER3
HES1
IL8
DDIT3
RGS1
CXCL2
JUN
KLF10
EGR1
FOS
FCGR3B
MNDA
IL8RB
SERPINA1
FPR1
CSTA
CFD
ELA2
AZU1
LTF
S100A8
S100A9
S100A12
IL8
MAFF

CD34+cells from CML pts.

Fig. 2D2

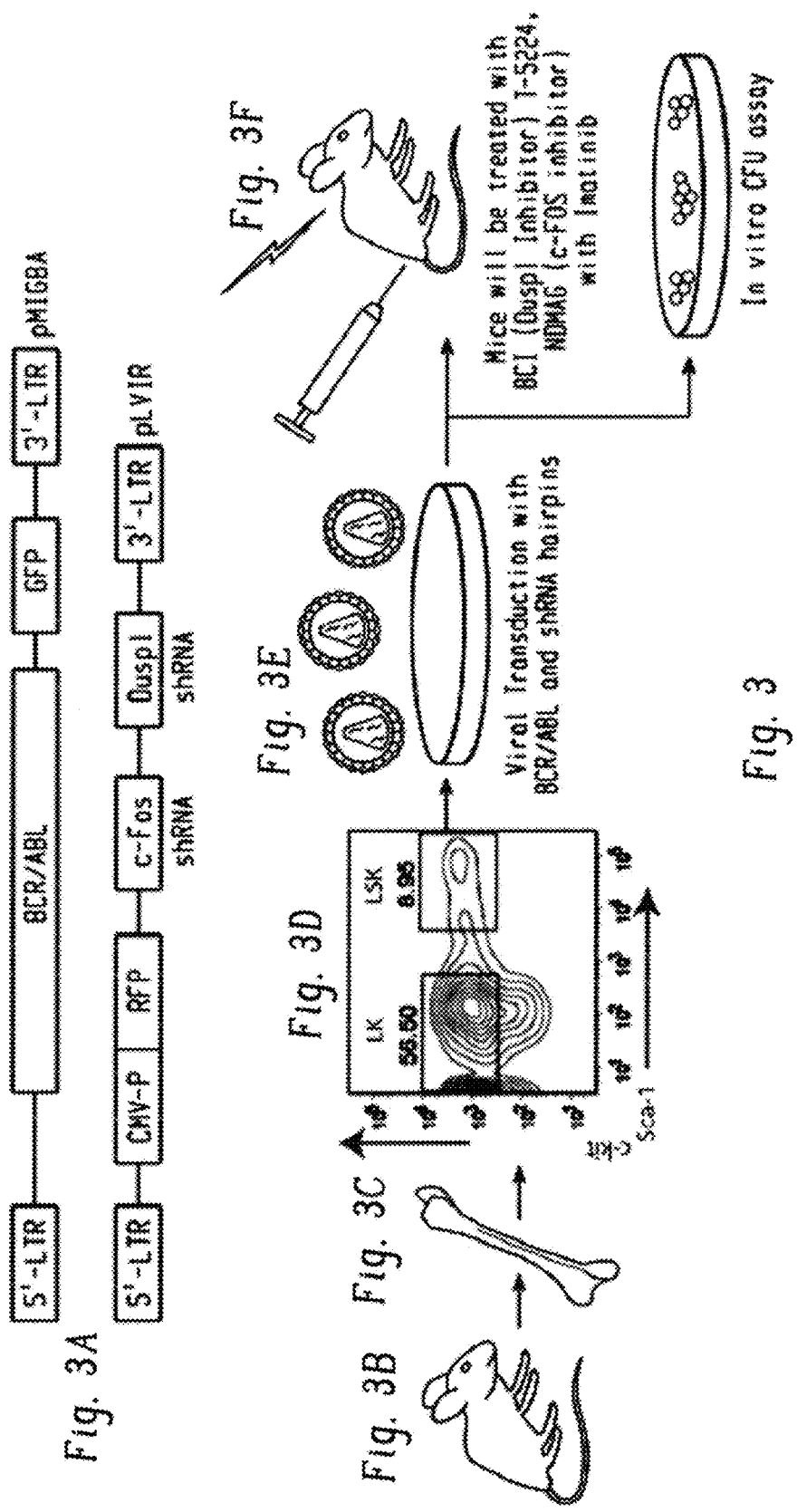

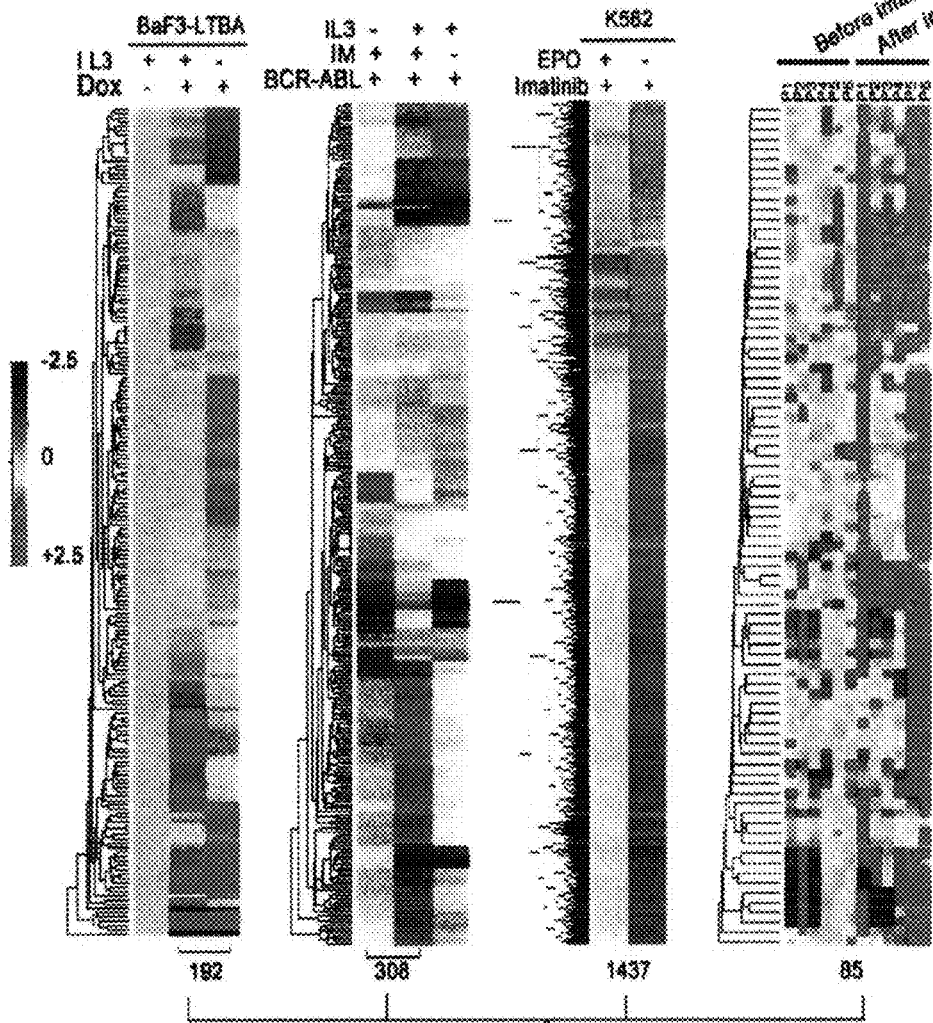

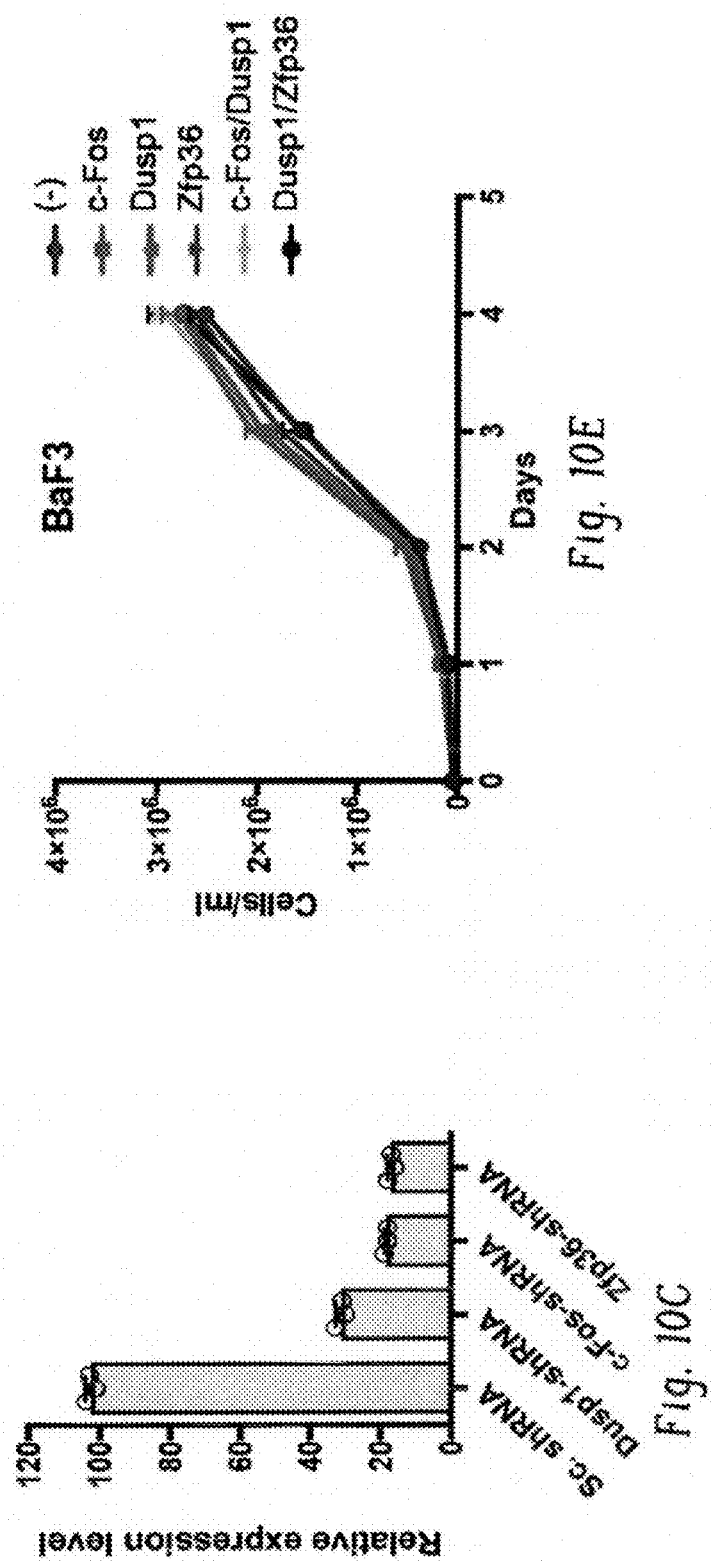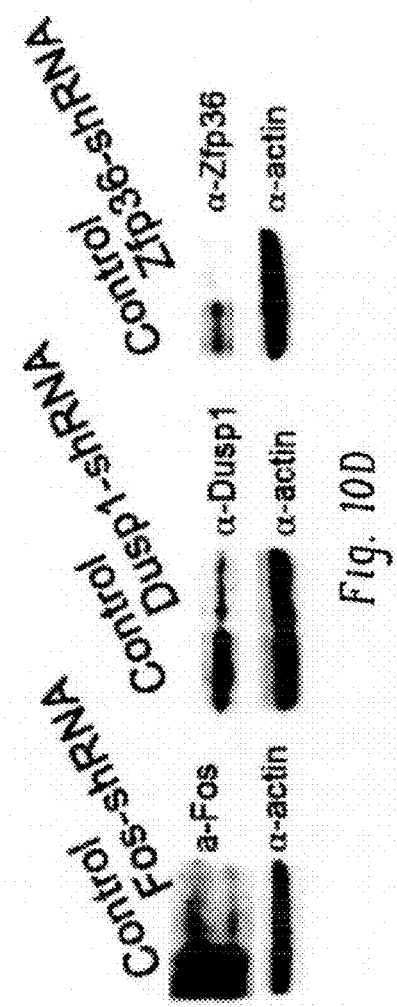

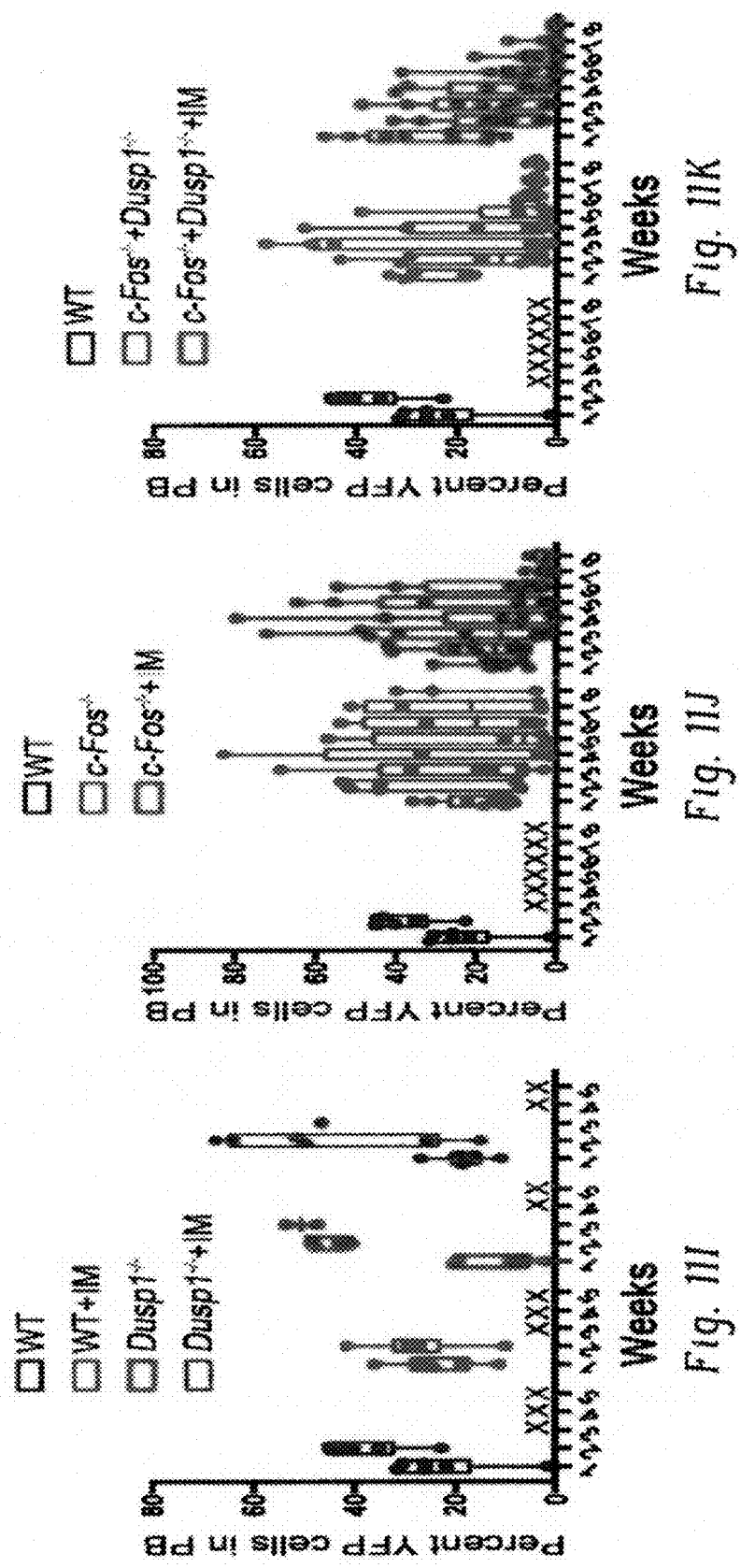

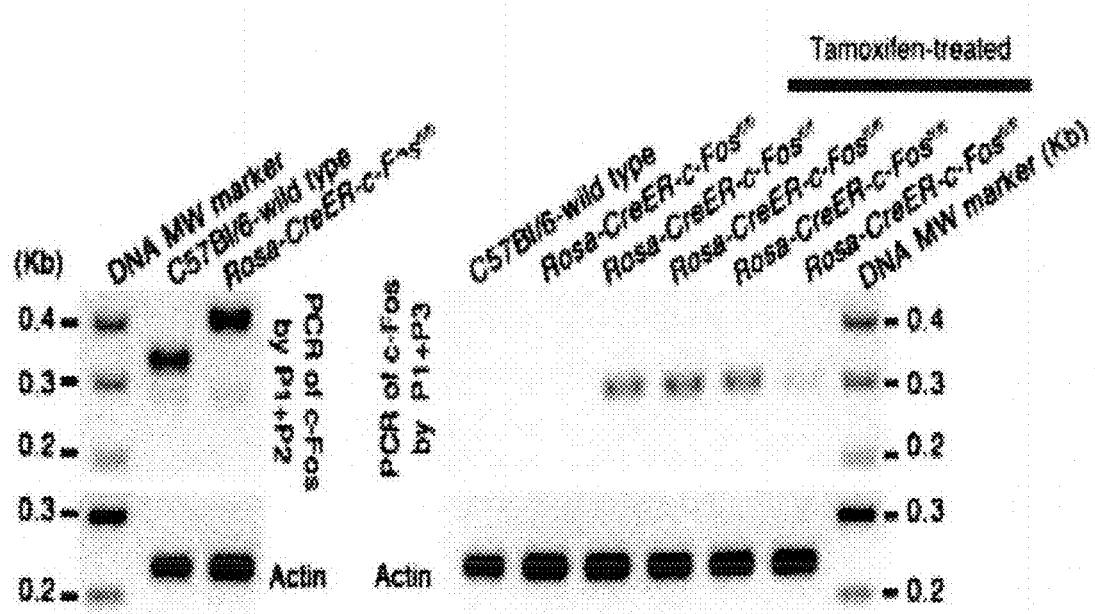
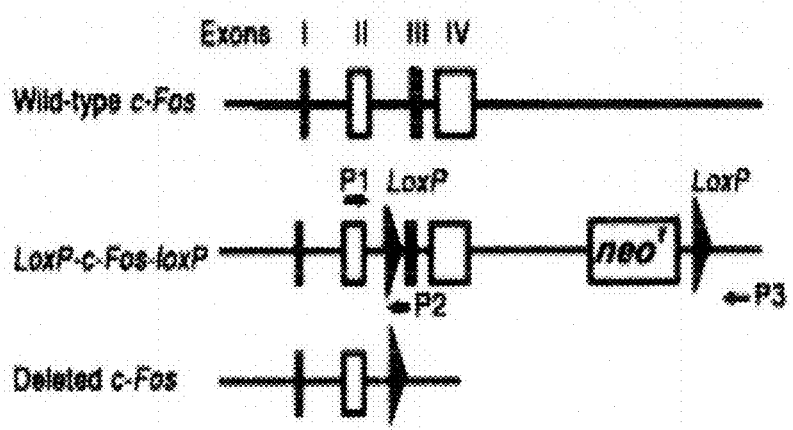
Fig. 12F

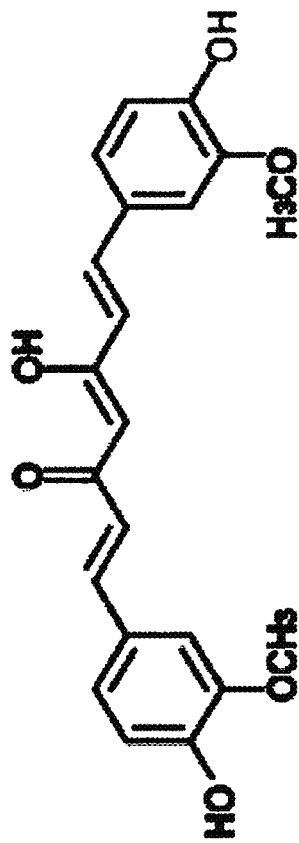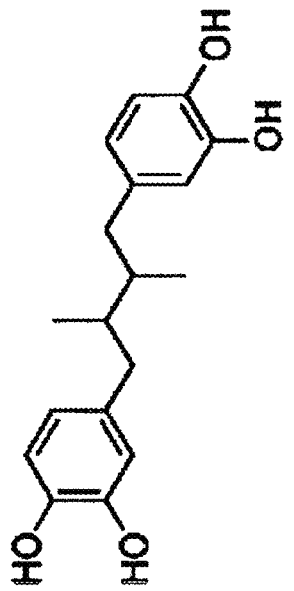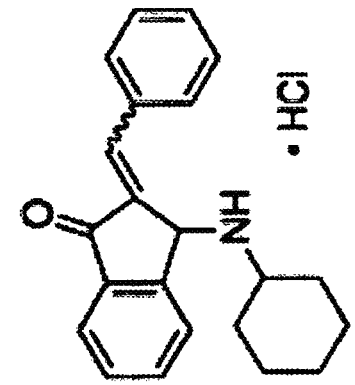
Fig. 14A

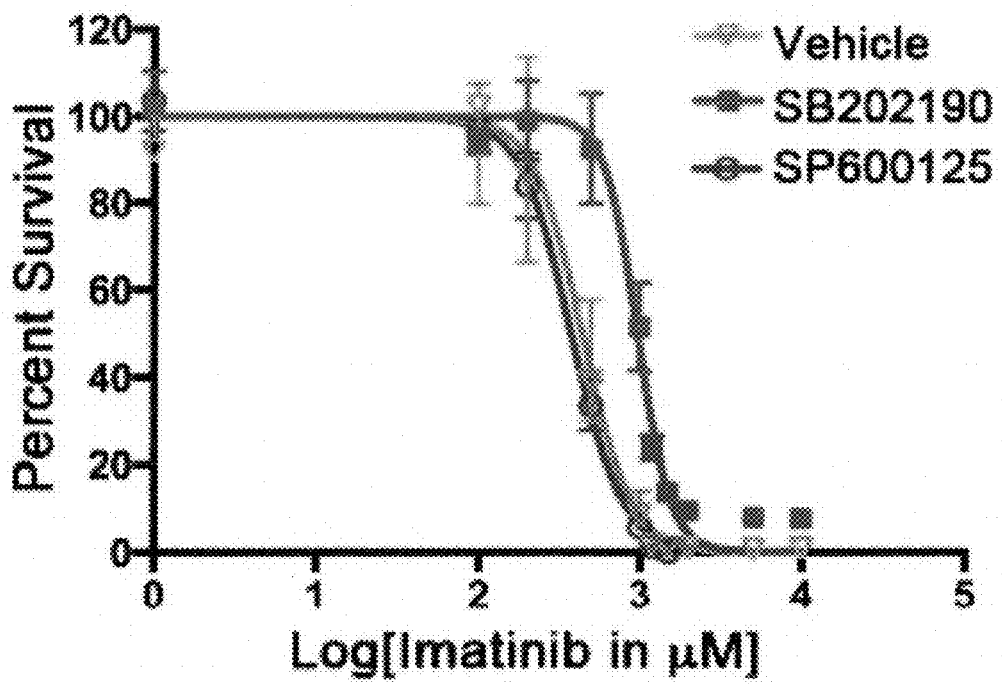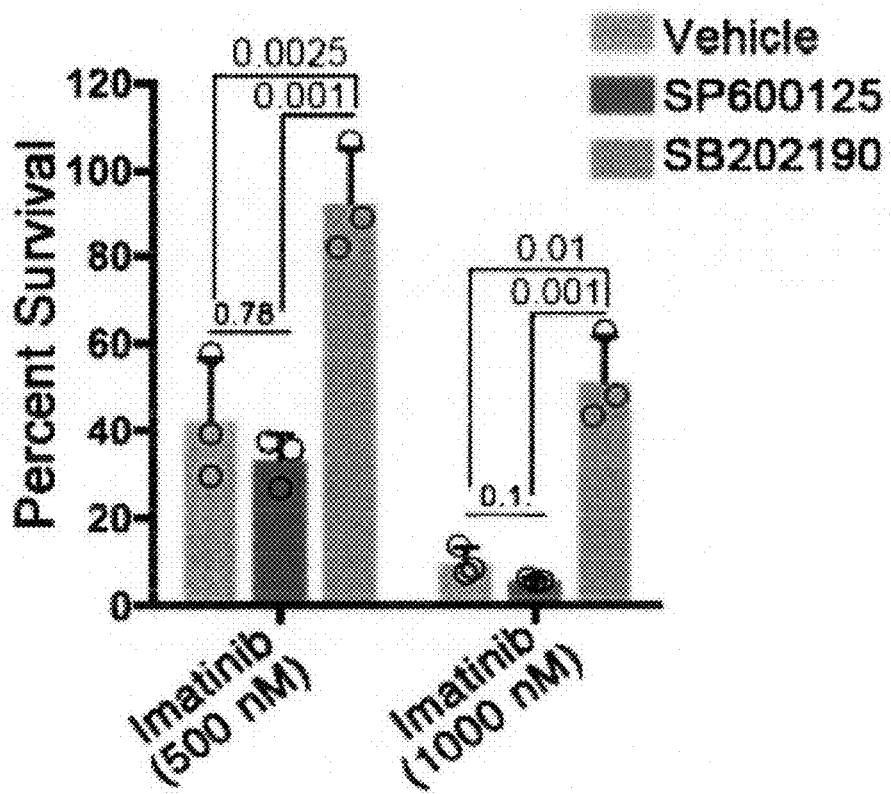
Fig. 18C

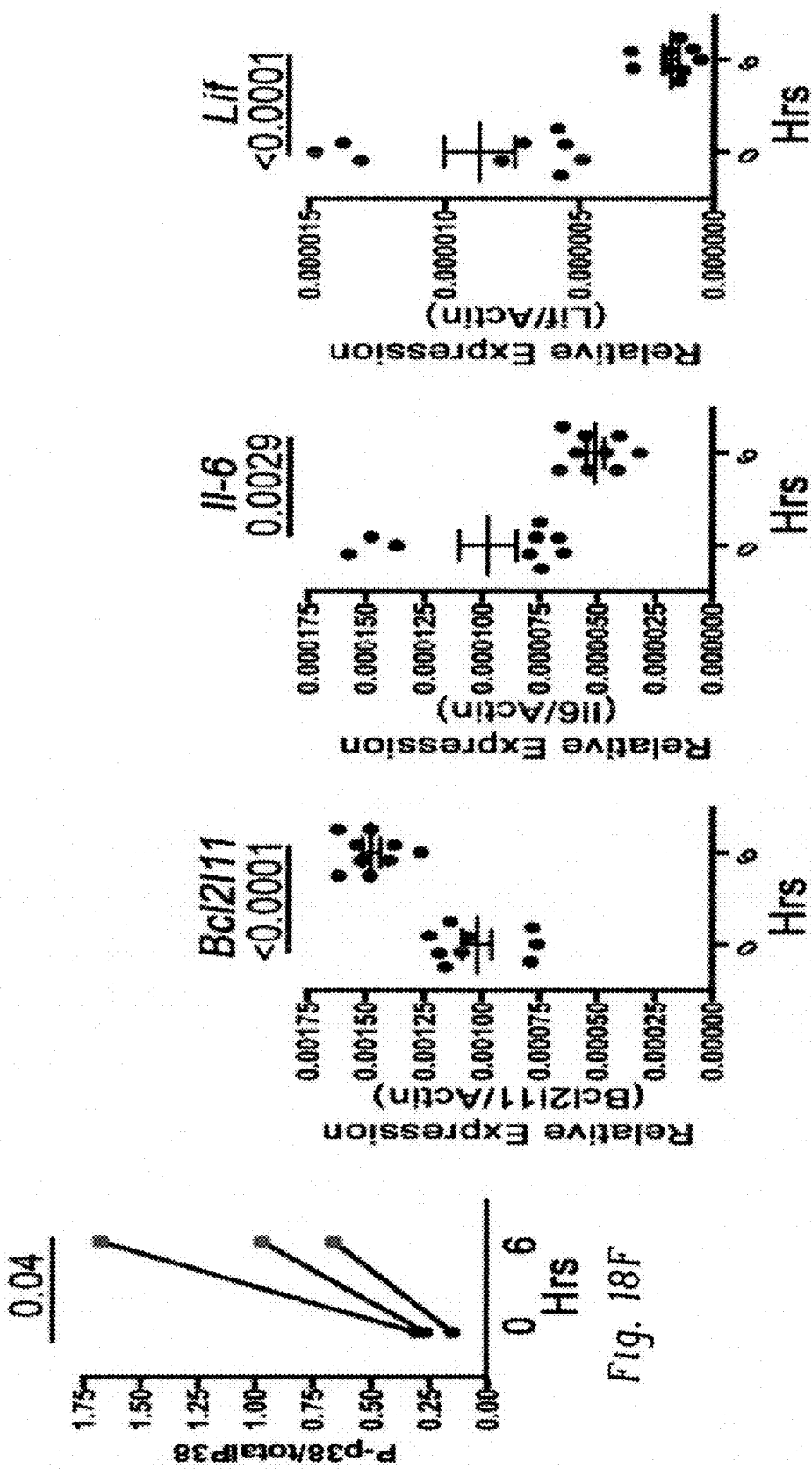

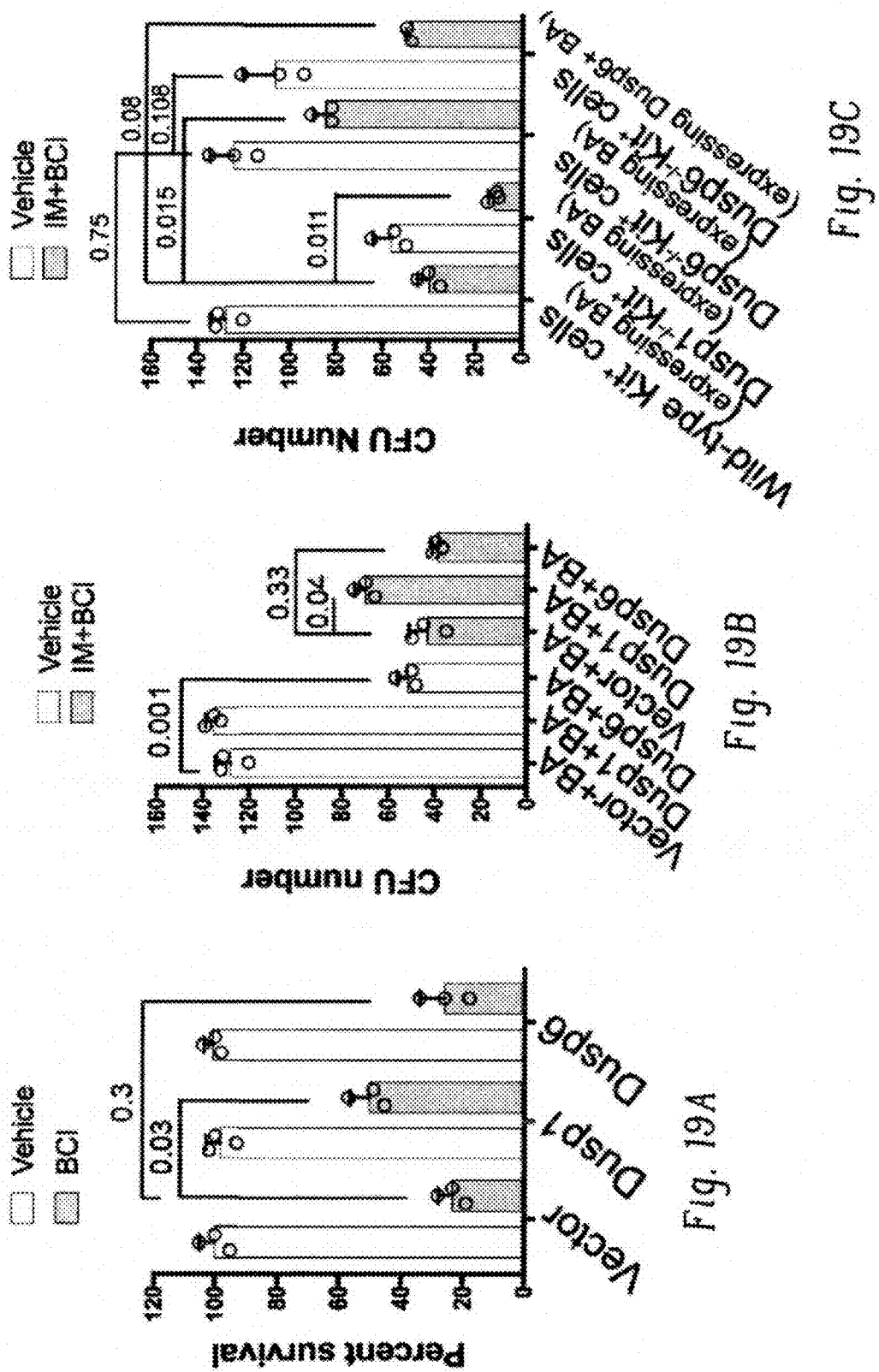

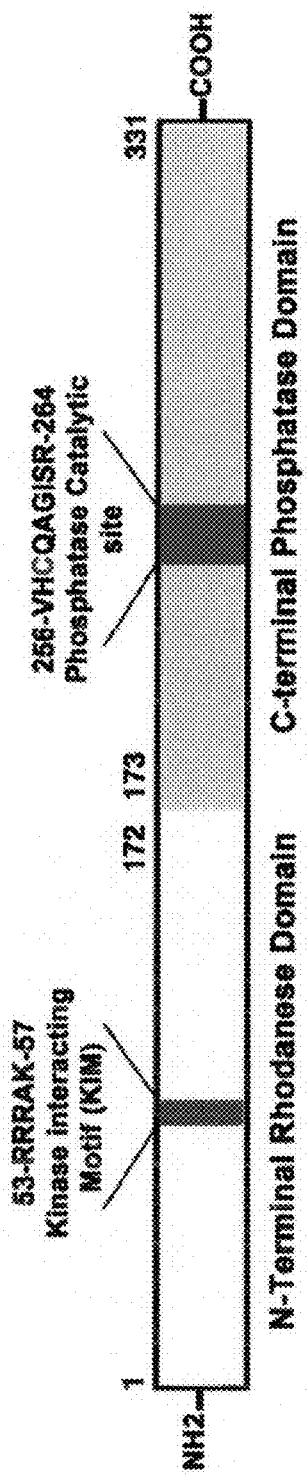
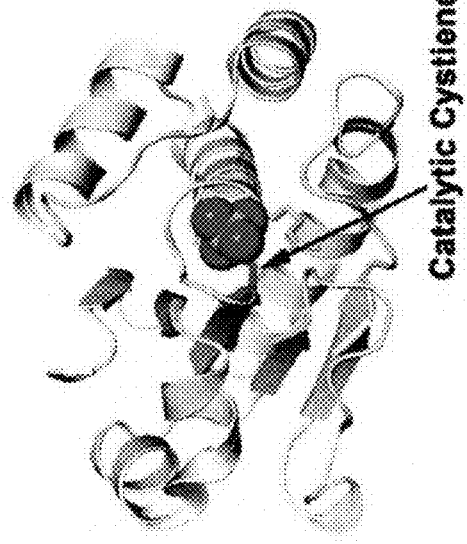
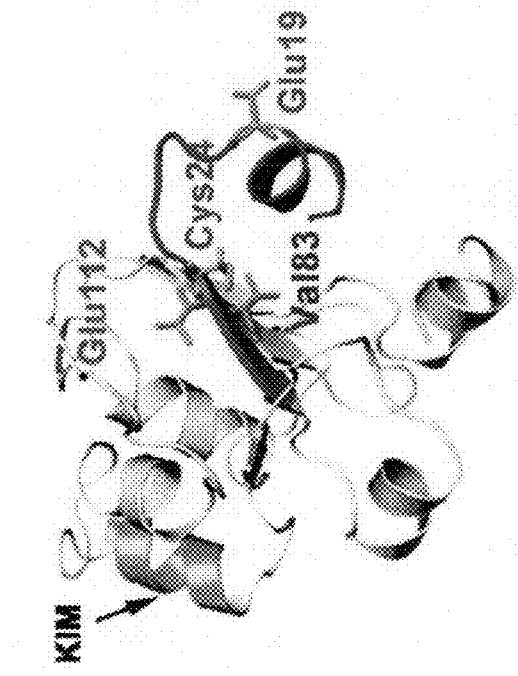
Fig. 20A
Fig. 20B A homology model of Dusp1 rhodanese domain using Dusp16 structure.
Fig. 20C A homology model of Dusp1 catalytic domain using Dusp6 structure.

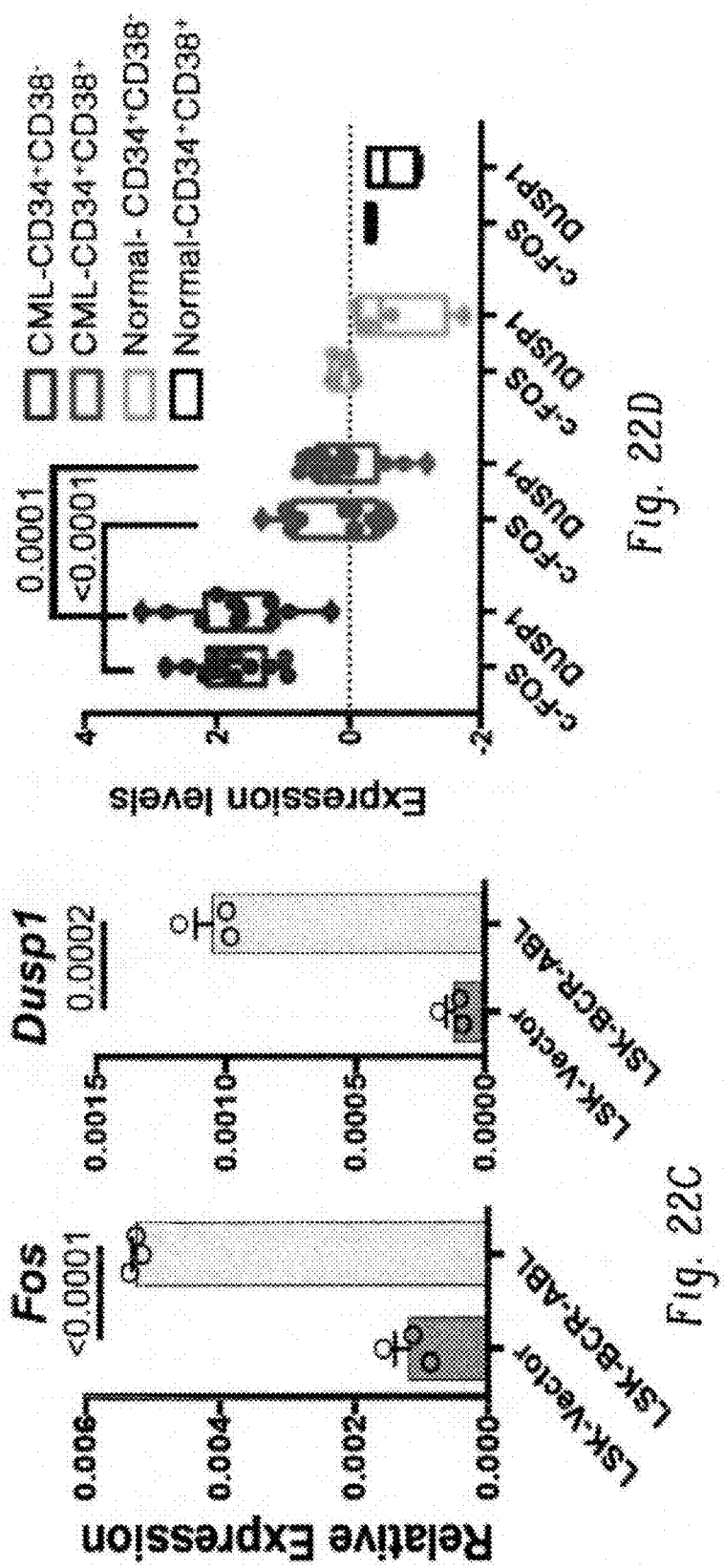

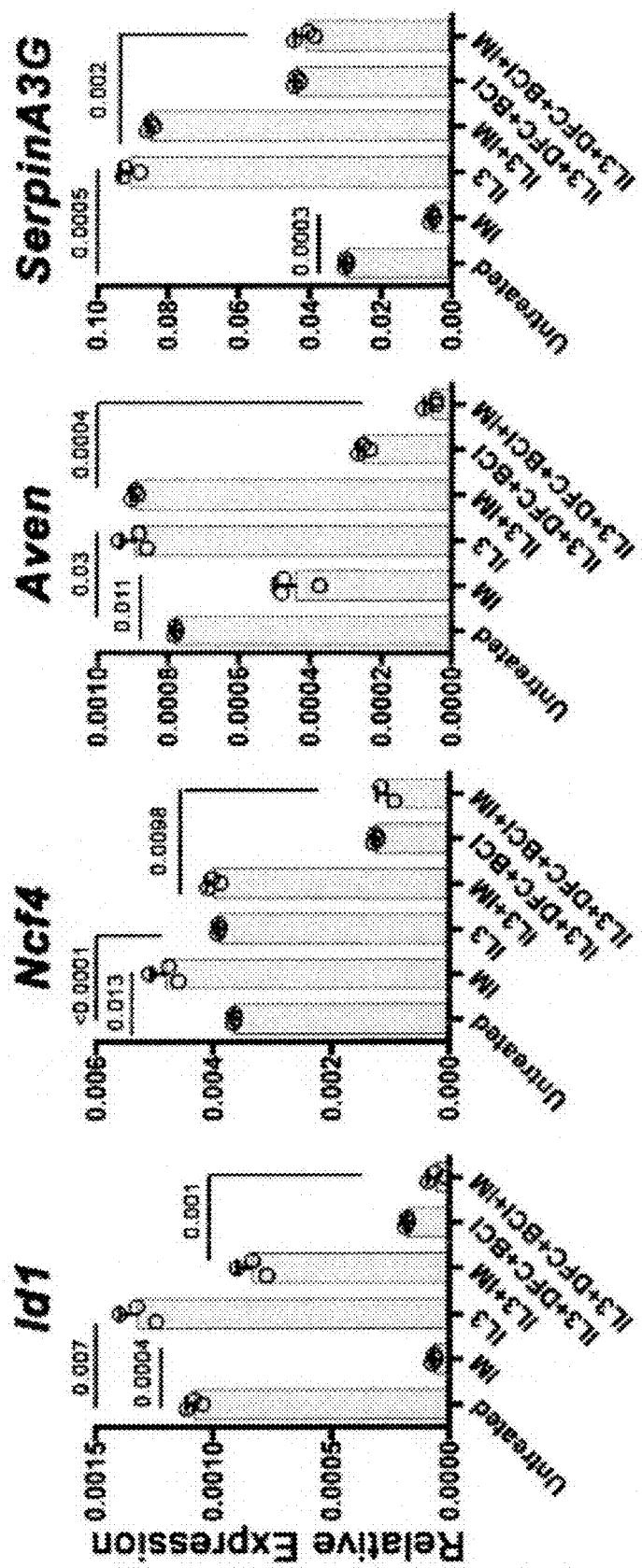
Fig. 22F1

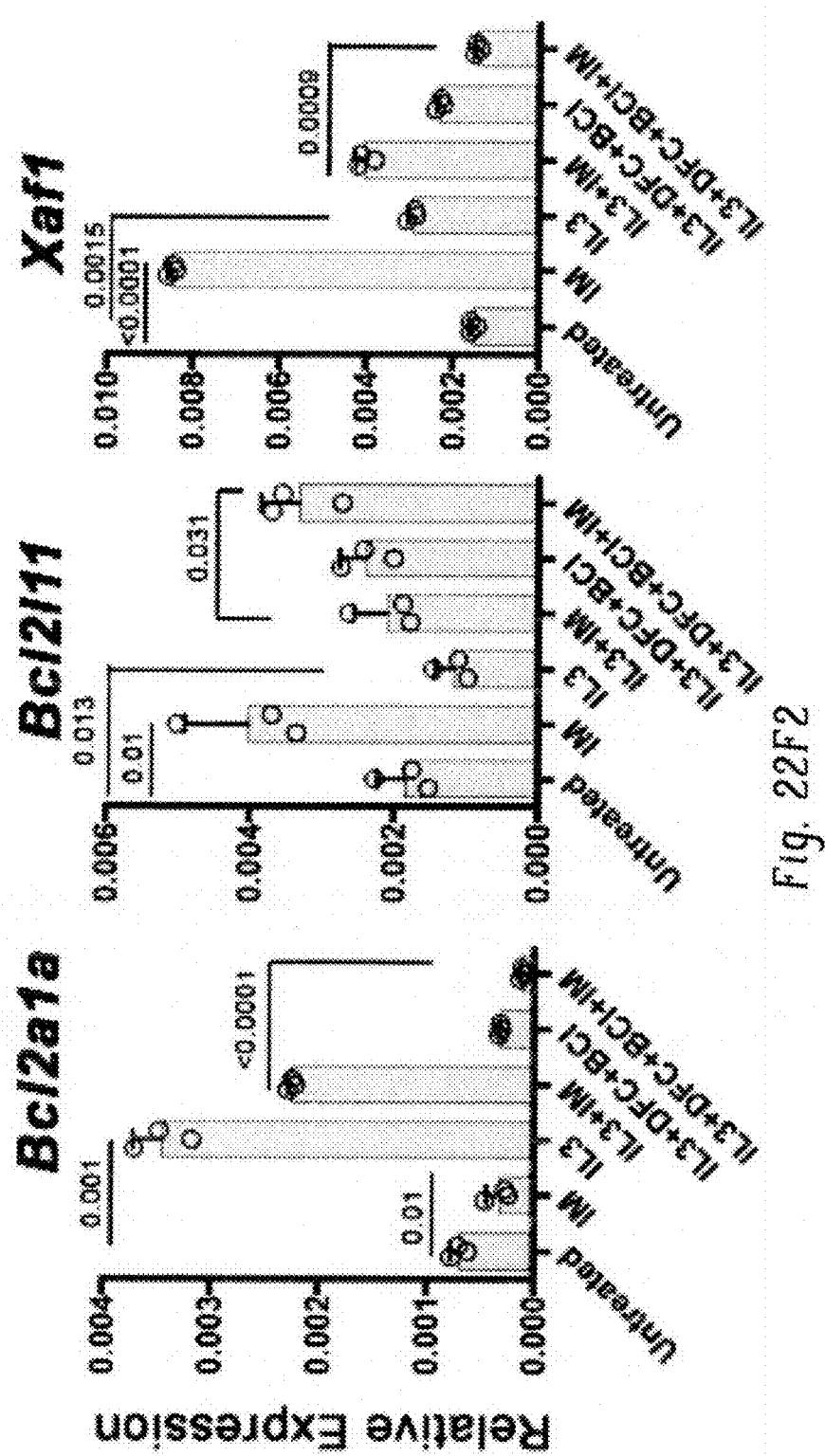
Fig. 22F2

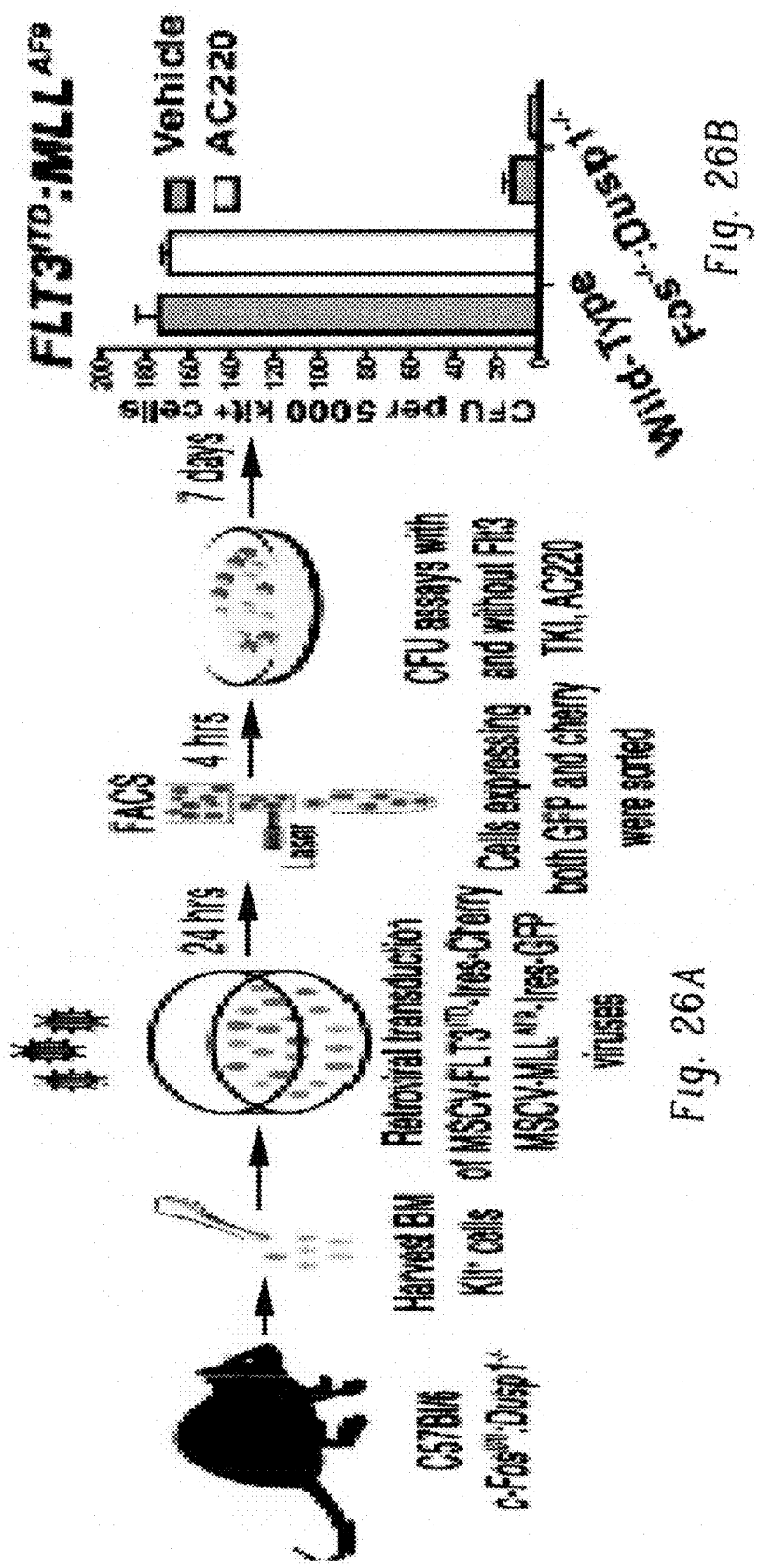

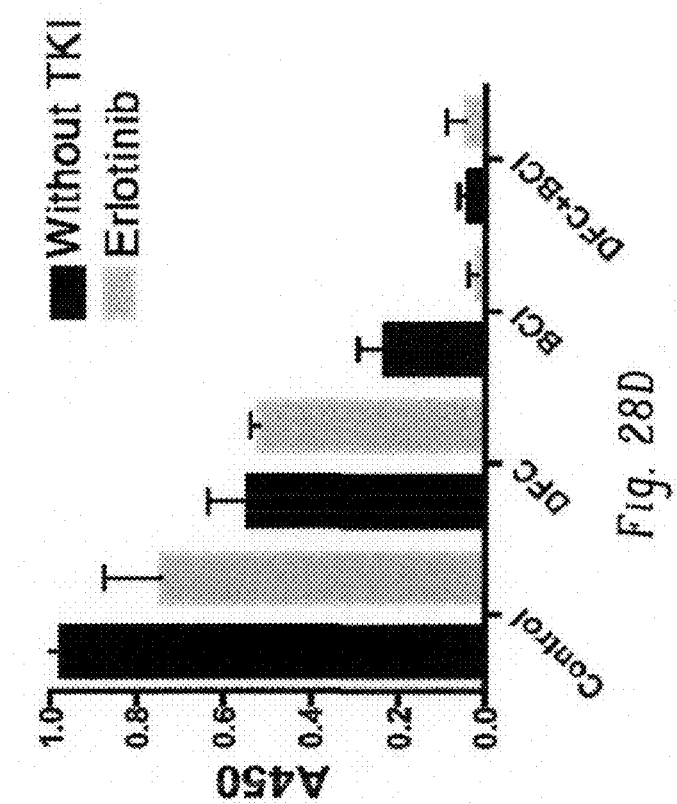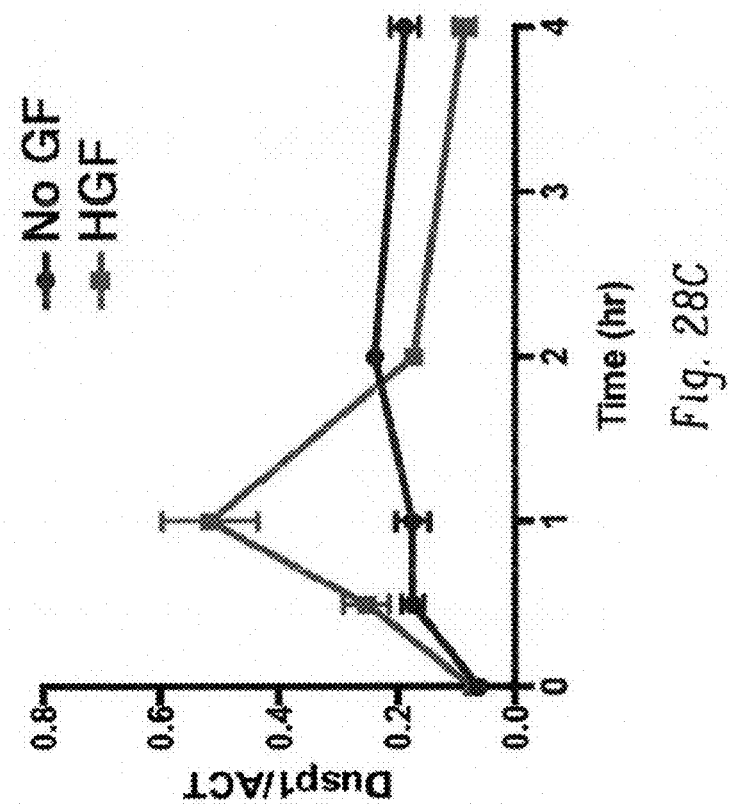
Fig. 28D
Fig. 28C

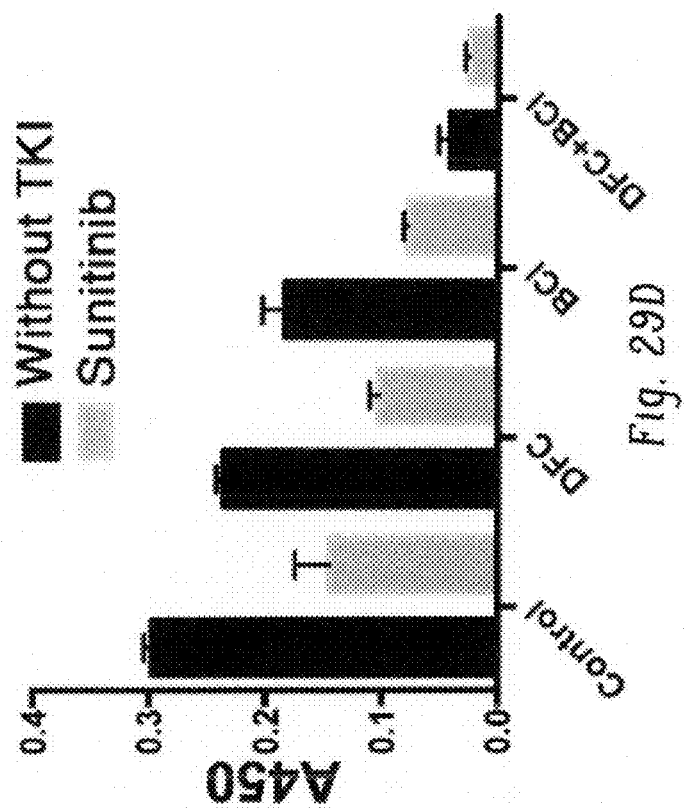
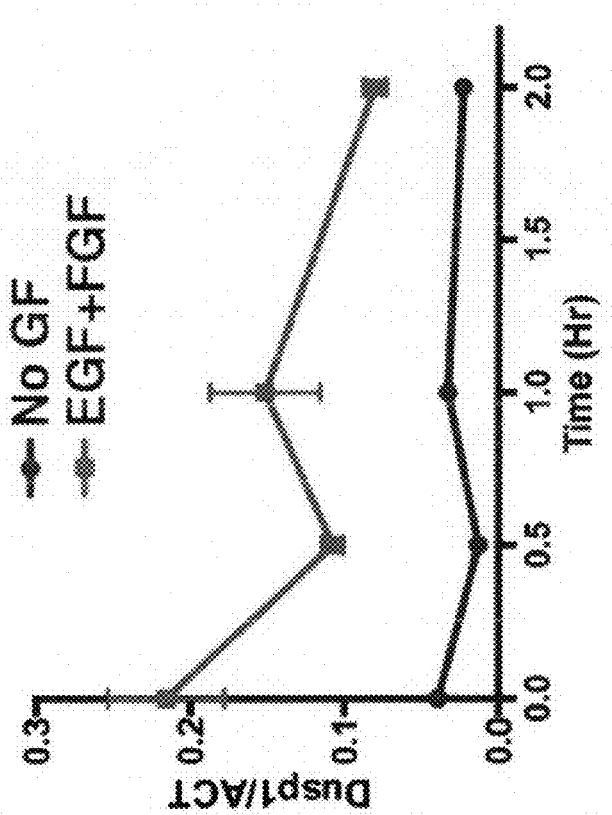
Fig. 29D
Fig. 29C

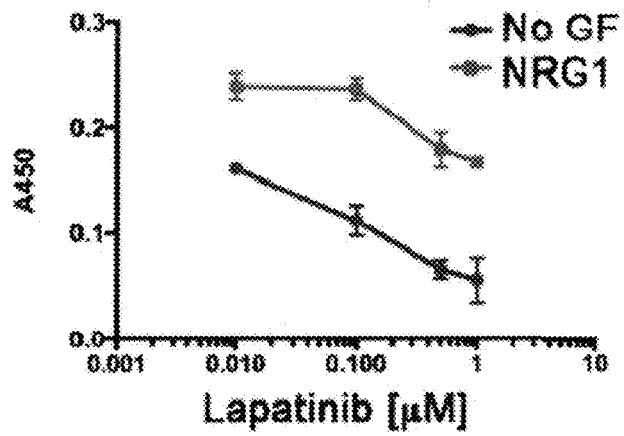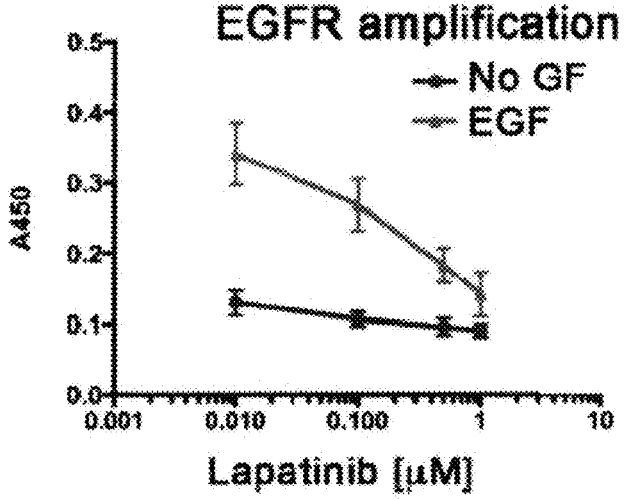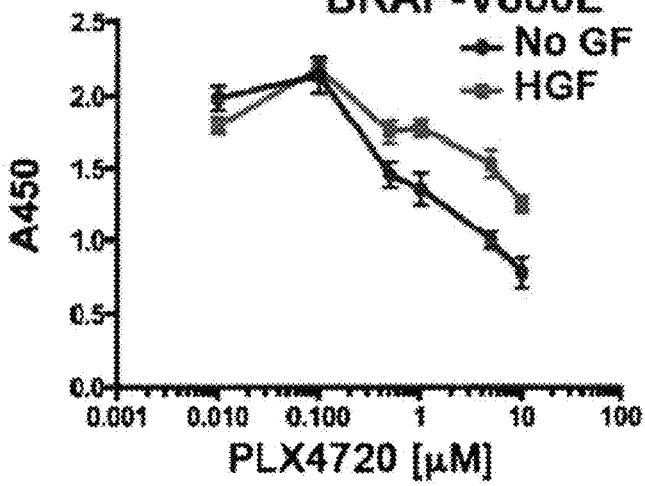
Fig. 30A

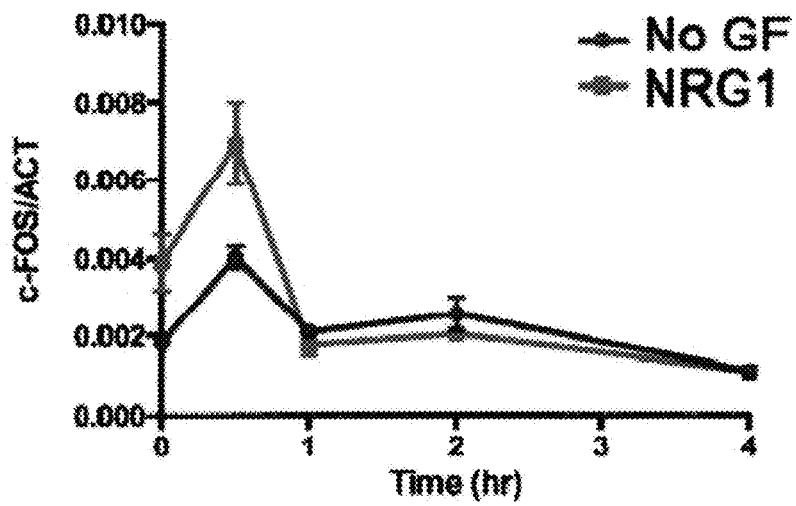
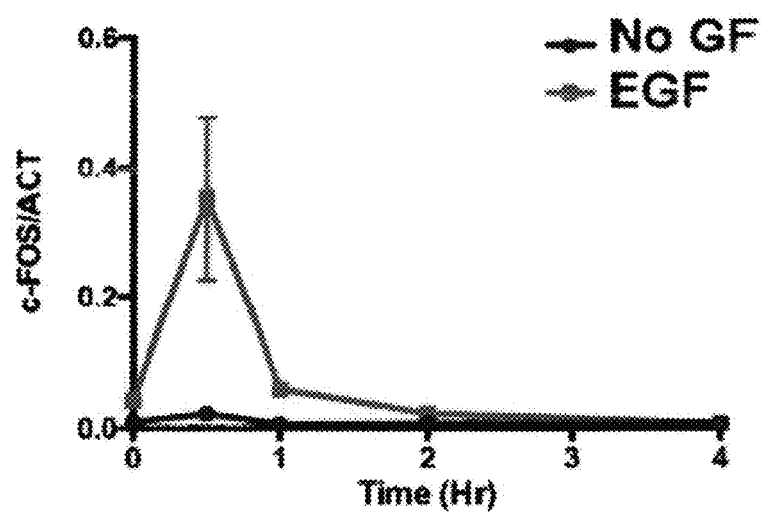
Fig. 30B
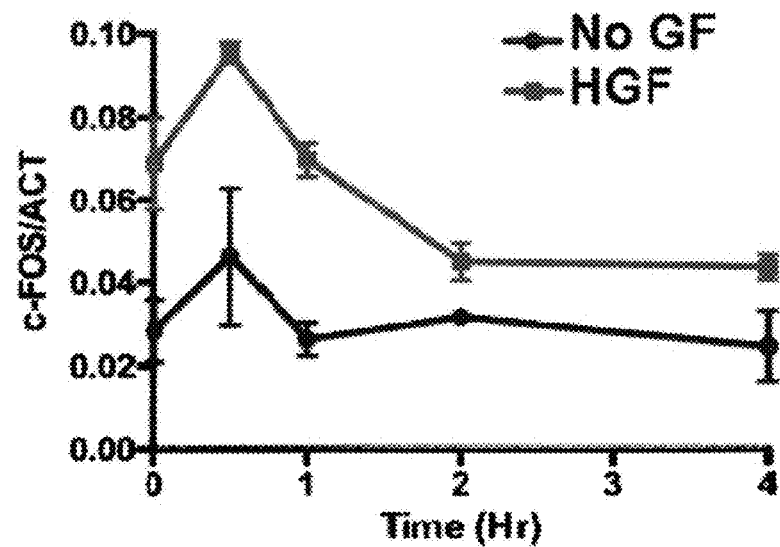

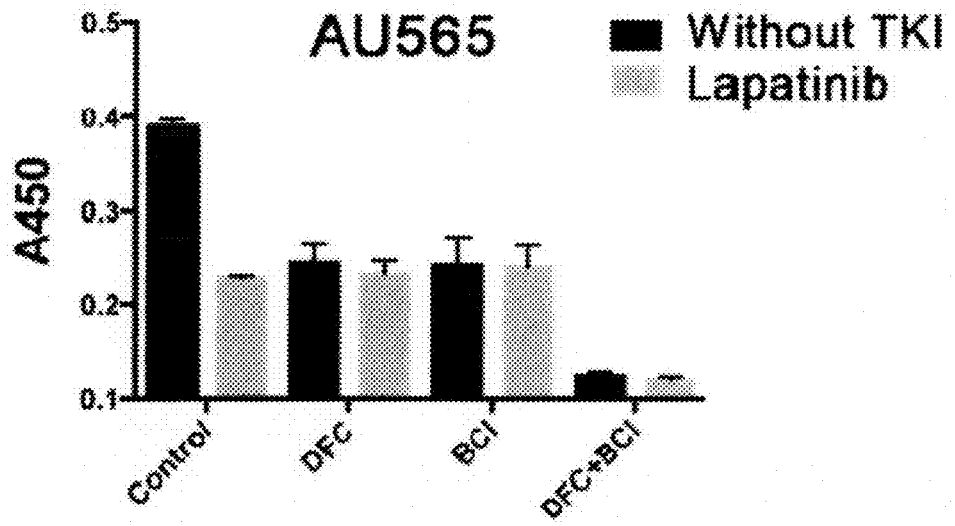
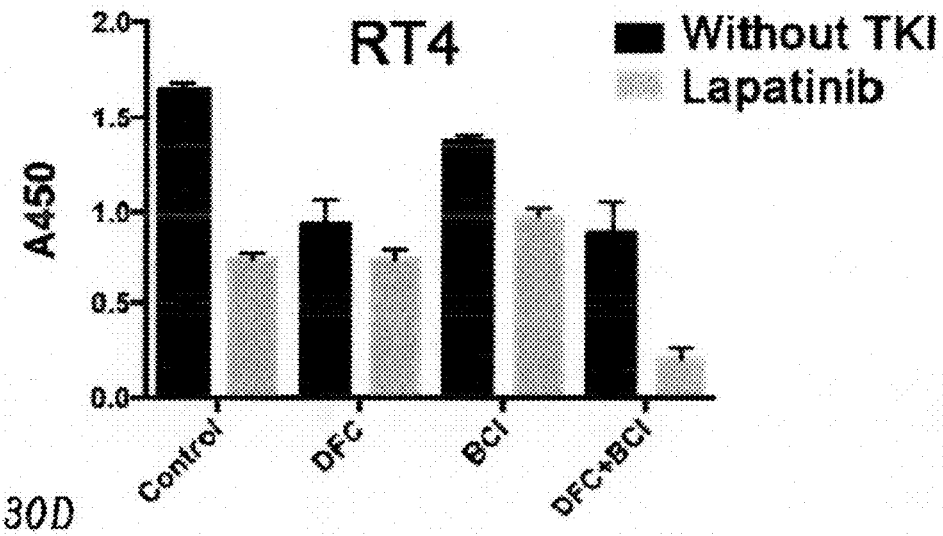
Fig. 30D
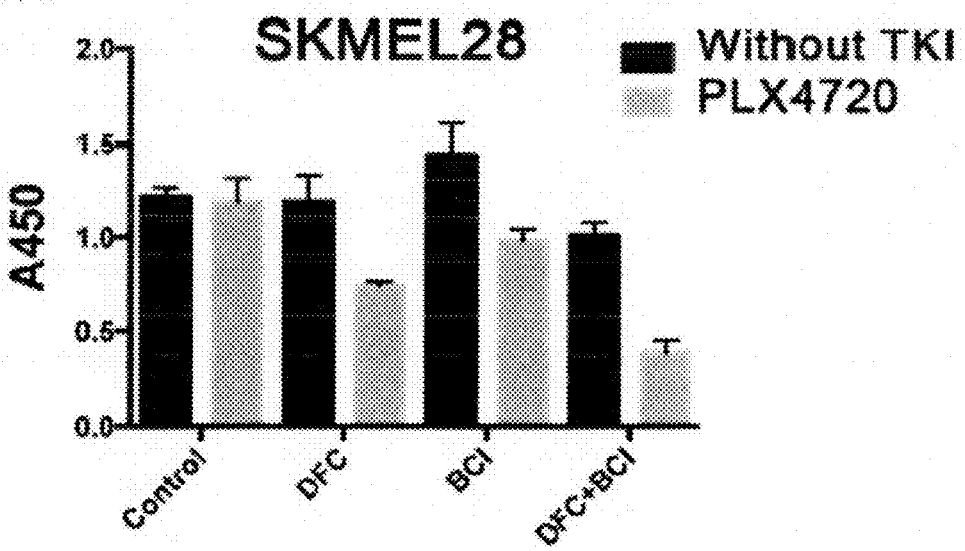

THERAPY FOR KINASE-DEPENDENT MALIGNANCIES

This application is a continuation-in-part of co-pending U.S. application Ser. No. 15/866,544 filed Jan. 10, 2018, which is a continuation of U.S. application Ser. No. 14/048,806 filed Oct. 8, 2013, which is a continuation-in-part of International Application Serial No. PCT/US2012/034359 filed Apr. 20, 2012, which claims priority to U.S. Provisional Application Ser. No. 61/477,853 filed Apr. 21, 2011, each of which is expressly incorporated by reference herein in its entirety.

In one embodiment, a composition and method of using the composition to effect therapy for a kinase-dependent malignancy is provided. In one embodiment, a composition and method of using the composition to effect therapy for leukemia is provided. In one embodiment, therapy is for chronic myelogenous leukemia. In one embodiment, therapy is for acute myelogenous leukemia. Therapy for targeting cancer stem cells and other leukemias are included. In one embodiment, the kinase-dependent malignancy is a solid tumor. As used herein, therapy and treatment are broadly defined to encompass disease cure, or any lessening of disease presence, prevalence, severity, symptoms, etc. In one embodiment, therapy means curative therapy.

In one embodiment, the composition contains at least one biocompatible excipient and, as its only active agents, the combination of at least one inhibitor of c-Fos, at least one inhibitor of Dusp-1, and at least one inhibitor of an oncogenic kinase. In one embodiment, the patient is already receiving at least one inhibitor of an oncogenic kinase for a kinase-dependent malignancy, and the composition contains at least one biocompatible excipient and, as its only active agents, the combination of at least one inhibitor of c-Fos and at least one inhibitor of Dusp-1. In one embodiment, the oncogenic kinase is at least one of the tyrosine kinases listed in Table 1, and the at least one inhibitor of a tyrosine kinase is selected from Imatinib, Dasatinib, Ponatinib, Nilotinib, Ibrutinib, Ruxolitinib, Crizotinib, Quizartinib, Trametinib, Gefitinib, Axitinib, Dasatinib, Vemurafenib, Sorafenib, Ceritinib, Alectinib, Vemurafenib, and Idelalisib.

TABLE 1

| | |
|---|---|
| BCR-ABL | A gene formed when pieces of chromosomes 9 and 22 break off and trade places. The ABL gene from chromosome 9 joins to the BCR gene on chromosome 22, to form the BCR-ABL fusion gene. The changed chromosome 22 with the fusion gene on it is called the Philadelphia chromosome. The BCR-ABL fusion gene is found in most patients with chronic myelogenous leukemia (CML), and in some patients with acute lymphoblastic leukemia (ALL) or acute myelogenous leukemia (AML).<br>Inhibitors - Imatinib, Dasatinib, Ponatinib and Nilotinib |
| BTK | Bruton's tyrosine kinase (BTK) also known as tyrosine-protein kinase BTK is an enzyme that in humans is encoded by the BTK gene. BTK is a kinase that plays a crucial role in B-cell development. |
| FLT3 | FMS-like tyrosine kinase 3 (FLT3), which is involved in the formation and growth of new blood cells. Mutated (changed) forms of the FLT3 gene may cause an over-active FLT3 protein to be made. This may cause the body to make too many immature white blood cells. These changes have been found in some types of leukemia, including acute myeloid leukemia (AML) and acute lymphoblastic leukemia (ALL). |
| MET | a member of the receptor tyrosine kinase family of proteins and the product of the proto-oncogene MET |
| KIT | Mast/stem cell growth factor receptor (SCFR), also known as proto-oncogene c-Kit or tyrosine-protein kinase Kit or CD117, is a receptor tyrosine kinase protein that in humans is encoded by the KIT gene. |
| JAK2 | Janus kinase 2 (commonly called JAK2) is a non-receptor tyrosine kinase. It is a member of the Janus kinase family and has been implicated in signaling by members of the type II cytokine receptor family (e.g. interferon receptors), the GM-CSF receptor family (IL-3R, IL-5R and GM-CSF-R), the gp130 receptor family (e.g., IL-6R), and the single chain receptors (e.g. Epo-R, Tpo-R, GH-R, PRL-R). JAK2 signaling is activated downstream from the prolactin receptor. |
| MEK | Mitogen-activated protein kinase kinase (also known as MAP2K, MEK, MAPKK) is a kinase enzyme which phosphorylates mitogen-activated protein kinase (MAPK). |
| EGFR | The epidermal growth factor receptor (EGFR; ErbB-1; HER1 in humans) is a transmembrane protein that is a receptor for members of the epidermal growth factor family (EGF family) of extracellular protein ligands. The epidermal growth factor receptor is a member of the ErbB family of receptors, a subfamily of four closely related receptor tyrosine kinases: EGFR (ErbB-1), HER2/neu (ErbB-2), Her3 (ErbB-3) and Her4 (ErbB-4). |
| PDGFR | Platelet-derived growth factor receptors (PDGF-R) are cell surface tyrosine kinase receptors for members of the platelet-derived growth factor (PDGF) family. PDGF subunits-A and -B are important factors regulating cell proliferation, cellular differentiation, cell growth, development and many diseases including cancer. |
| ALK | Anaplastic lymphoma kinase (ALK) also known as ALK tyrosine kinase receptor or CD246 (cluster of differentiation 246) is an enzyme that in humans is encoded by the ALK gene. |
| HER2 | Receptor tyrosine-protein kinase erbB-2, also known as CD340 (cluster of differentiation 340), proto-oncogene Neu, Erbb2 (rodent), or ERBB2 (human), is a protein that in humans is encoded by the ERBB2 gene. It is also frequently called HER2 (from human epidermal growth factor receptor 2) or HER2/neu. HER2 is a member of the human epidermal growth factor receptor (HER/EGFR/ERBB) family. |
| B-Raf | BRAF is a human gene that encodes a protein called B-Raf. The gene is also referred to as proto-oncogene B-Raf and v-Raf murine sarcoma viral oncogene homolog B, while the protein is more formally known as serine/threonine-protein kinase B-Raf. The B-Raf protein is involved in sending signals inside cells which are involved in directing cell growth. |
| FGFR2 | Fibroblast growth factor receptor 2 (FGFR2) also known as CD332 (cluster of differentiation 332) is a protein that in humans is encoded by the FGFR2 gene residing on chromosome 10. FGFR2 is a receptor for fibroblast growth factor. |

TABLE 1-continued

| | |
|---|---|
| RAF | RAF kinases are a family of three serine/threonine-specific protein kinases that are related to retroviral oncogenes. RAF is an acronym for Rapidly Accelerated Fibrosarcoma. RAF kinases participate in the RAS-RAF-MEK-ERK signal transduction cascade, also referred to as the mitogen-activated protein kinase (MAPK) cascade. Activation of RAF kinases requires interaction with RAS-GTPases. The three RAF kinase family members are A-RAF, B-RAF, and c-Raf. |
| PI3K | Phosphatidylinositol-4,5-bisphosphate 3-kinase (also called phosphatidylinositide 3-kinases, phosphatidylinositol-3-kinases, PI 3-kinases, PI(3)Ks, or PI-3Ks) are a family of enzymes involved in cellular functions such as cell growth, proliferation, differentiation, motility, survival and intracellular trafficking, which in turn are involved in cancer. PI3Ks are a family of related intracellular signal transducer enzymes capable of phosphorylating the 3 position hydroxyl group of the inositol ring of phosphatidylinositol (PtdIns). |

In one embodiment, the composition contains at least one biocompatible excipient and, as its only active agents, the combination of at least one inhibitor of c-Fos, at least one inhibitor of Dusp-1, and at least one inhibitor of BCR-ABL tyrosine kinase. In one embodiment, the composition contains at least one biocompatible excipient and, as its only active agents, the combination of one inhibitor of c-Fos, one inhibitor of Dusp-1, and one inhibitor of BCR-ABL tyrosine kinase. In the aforementioned embodiments, the inhibitor may inhibit the gene and/or the protein, i.e., the c-Fos inhibitor may inhibit the c-Fos gene and/or protein, the Dusp-1 inhibitor may inhibit the Dusp-1 gene and/or protein, and the BCR-ABL tyrosine kinase inhibitor may inhibit the BCR-ABL tyrosine kinase gene and/or protein. Such inhibitors include commercially available inhibitors and inhibitors under development. Small molecule inhibitors, such as curcumin, difluorinated curcumin (DFC), [3-{5-[4-(cyclopentyloxy)-2-hydroxybenzoyl]-2-[(3-hydroxy-1,2-benzisoxazol-6-yl) methoxy]phenyl}propionic acid] (T5224, Roche), nordihydroguaiaretic acid (NDGA), dihydroguaiaretic acid (DHGA), [(E,E,Z,E)-3-methyl-7-(4-methylphenyl)-9-(2,6,6-trimethyl-1-cyclohexen-1-yl)-2,4,6,8-nonatetraenoic acid (SR11302, Tocris Biosciences), (E)-2-benzylidene-3-(cyclohexylamino)-2,3-dihydro-1H-inden-1-one (BCI), TPI-2, TPI-3, triptolide, Imatinib mesylate (Gleevec™), Nilotinib, Dasatinib and Ponatinib, are encompassed. In one embodiment, inhibitors of c-Fos used in the composition are curcumin, difluorinated curcumin (DFC), [3-{5-[4-(cyclopentyloxy)-2-hydroxybenzoyl]-2-[(3-hydroxy-1,2-benzisoxazol-6-yl) methoxy]phenyl}propionic acid] (T5224, Roche), nordihydroguaiaretic acid (NDGA), dihydroguaiaretic acid (DHGA), and [(E,E,Z,E)-3-methyl-7-(4-methylphenyl)-9-(2,6,6-trimethyl-1-cyclohexen-1-yl)-2,4,6,8-nonatetraenoic acid (SR11302, Tocris Biosciences). In one embodiment, inhibitors of Dusp-1 are (E)-2-benzylidene-3-(cyclohexylamino)-2,3-dihydro-1H-inden-1-one (BCI), also known as NSC 150117, TPI-2, TPI-3, and triptolide. In one embodiment, inhibitors of BCR-ABL tyrosine kinase are Imatinib mesylate (Gleevec™), Nilotinib, Dasatinib and Ponatinib. In one embodiment, the composition administered is curcumin, BCI, and Imatinib. In one embodiment, the composition administered is difluorinated curcumin (DFC), BCI, and Imatinib. In one embodiment, the composition administered is NDGA, BCI, and Imatinib. In one embodiment, the composition is T5224, BCI, and Imatinib. In one embodiment, the composition is administered to the patient at a concentration of 2 grams per day to 8 grams per day, inclusive, of the c-Fos inhibitor, 100 mg per day to 600 mg per day, inclusive, of BCI, and 400 mg to 800 mg per day, inclusive, of the BCR-ABL tyrosine kinase inhibitor Imatinib mesylate (Gleevec™). The composition is alkaline, about pH 8.5. In one embodiment, the composition is administered to the patient for 30 days. The composition may be administered by any route including but not limited to intravenous administration. The composition is preferably administered intravenously, orally, intramuscularly, transdermally, and/or intraperitoneally. Any biocompatible excipient may be used in the inventive composition, as known to one skilled the art. Biocompatible excipients include, but are not limited to, buffers, tonicity agents, pH modifying agents, preservatives, stabilizers, penetrant enhances, osmolality adjusting agents, etc. In one embodiment, the composition components are administered as individual components by the same route of administration or by different routes of administration, with administration of each component or components at substantially the same time. In one embodiment, the composition components are formulated into a cocktail, using methods known by one skilled in the art.

Cancer can be treated by identifying a molecular defect. This was demonstrated with chronic myelogenous leukemia (CML), the first cancer to be associated with a defined genetic abnormality, BCR-ABL, and the success of the small molecule tyrosine kinase inhibitor (TKI) Imatinib.

Despite Imatinib's efficacy in treating CML patients, it failed to provide a curative response because it preferentially targets the differentiated and dividing cells, therefore causing relapse upon Imatinib withdrawal. The major limitation to develop curative therapy is lack of understanding of the molecular and patho-physiological mechanisms driving cancer maintenance, progression, mechanisms of therapeutic response and relapse. As in the case of CML, differentiated and dividing cells undergo apoptosis following the acute inhibition of BCR-ABL, termed "oncogene addiction". In contrast, leukemic stem cells (LSCs) do not show similar response. Given the intrinsic resistance of LSCs to TKI therapy in CML, understanding the molecular mechanisms of oncogene addiction in therapeutically responsive cells would allow strategies to target the LSCs.

More specifically, the BCR-ABL tyrosine kinase inhibitor Imatinib improved the survival of patients with leukemia, but did not eliminate leukemia initiating cells (LIC). This suggested that LICs were not addicted to BCR-ABL.

In one aspect, the inventive method demonstrates that the down-regulation of c-Fos and Dusp-1 mediate BCR-ABL addiction, and that inhibition of c-Fos and Dusp-1 together induces apoptosis in BCR-ABL positive cells following Imatinib treatment. Furthermore, it has also been found that inhibition of c-Fos and Dusp-1 induces apoptosis in various oncogenic kinase positive cells following treatment with an oncogenic kinase inhibitor in various kinase-dependent malignancies. The combination of c-Fos and Dusp-1 inhibition has no effect on survival and apoptosis of parental BaF3 cells, a hematopoietic cell line; Dusp-1 and c-Fos knockout mice are viable and survive without any serious phenotype, suggesting that these targets are suitable for therapeutic development. In one aspect, the inventive method assessed effectiveness of targeted c-Fos and Dusp-1 inhibition in LICs for Imatinib response. Assessment included both genetic (shRNA) and pharmacological inhibitors. This provided a basis for clinical application of a composition containing Imatinib, a c-Fos inhibitor, and a Dusp-1 inhibitor to target leukemic cells, such as CML initiating cells and AML initiating cells. This finding also provided the basis for extending the utility of inhibition of c-Fos and Dusp-1 into other kinase-dependent malignancies, including solid tumors, as described in detail below.

Chronic myelogenous leukemia (CML) is a slow-growing bone marrow cancer resulting in overproduction of white blood cells. CML is caused by the abnormal phosphorylation of cellular proteins by a deregulated enzyme, BCR-ABL tyrosine kinase. A small molecule inhibitor Imatinib mesylate (Gleevec™) was developed to block aberrant BCR-ABL tyrosine kinase activity. Gleevec™ was a major breakthrough in fighting cancer; Imatinib treatment not only revolutionized CML management but also paved the way for development of tyrosine kinase inhibitor therapy for other diseases.

However, imatinib treatment is not curative. Many patients develop resistance despite continued treatment and some patients simply do not respond to treatment. Evidence suggests that a subset of cancer cells, termed "cancer stem cells", drive tumor development and are refractory to most treatments. In other words, cancer cells that respond to the drug treatment are critically dependent upon uninterrupted oncogene function, are "addicted to oncogene", whereas cancer stem cells are not dependent or addicted to oncogene. Thus, eradication of these cancer stem cells is a critical part of any successful anti-cancer therapy.

CML has long served as a paradigm for generating new insights into the cellular origin, pathogenesis and improved approaches to treating many types of human cancer. Cancer stem cells in CML serve as safe reservoir to develop therapeutic resistance. This emphasizes the need for new agents that effectively and specifically target CML stem cells.

In one aspect, the inventive method targeted the CML stem cells to produce curative therapies that do not require lifelong treatments. The inventive method served as a paradigm to investigate other disease models and provided the described improved strategies for curative therapeutics for kinase-dependent malignancies.

Oncogene addiction is the "Achilles' heel" of many cancers. The major limitation to develop curative cancer therapy has been a lack of understanding of the molecular and patho-physiological mechanisms driving cancer maintenance, progression, and mechanisms of therapeutic response and relapse. In 2002, Bernard Weinstein proposed the concept that cancer cells acquire abnormalities in multiple oncogenes and tumor suppressor genes. Inactivation of a single critical gene can induce cancer cells to differentiate into cells with normal phenotype, or to undergo apoptosis, which is popularly known as "oncogene addiction". This dependence or addiction for maintaining the cancer phenotype provides an Achilles heel for tumors that can be exploited in cancer therapy. In CML, differentiated and dividing cells undergo apoptosis following acute inhibition of BCR-ABL, and are thus "BCR-ABL addicted". However, CML LICs, as well as kinase-dependent cancers' stem cells, do not show a similar response and are thus not "addicted" to BCR-ABL function or oncogenic kinase activity.

The clinical activity of Imatinib in multiple disease settings, together with numerous cancer cell line studies demonstrating an apoptotic response to drug treatment, suggests that clinical responses are likely to reflect oncogene dependency on activated kinases for their survival. Likewise, EGFR inhibitors in the treatment of lung cancer represents another example of oncogene addiction that has yielded clinical success in a subset of patients with advanced disease that are otherwise refractory to conventional chemotherapy treatment. Mutations in the kinase domain of EGFR are found in a small subset of non-small cell lung cancers (NSCLC), and clinical responses to EGFR inhibitors, Gefitinib and Erlotinib, have been well correlated with such mutations. Further, cancer genome sequencing data have also highlighted the likely role of "kinase addiction" in a variety of human cancers, e.g., activation of MET, BRAF, FGFR2, FGFR3, ALK, AURK and RET kinase in various different malignancies. Underscoring the importance of oncogene addiction is the fact that in all of these kinase-dependent malignancies, acute inactivation of the mutated kinase by either genetic or pharmacological means results in growth inhibition or tumor cell death. In sum, the potential and importance of oncogene addiction in molecularly targeted cancer therapy highlights the fact that activated oncogenes, especially kinases, represent cancer culprits that frequently contribute to a state of oncogene dependency.

Cell culture models, genetically engineered mice, and clinical testing of targeted drugs support a widespread role for oncogene addiction in tumor cell maintenance and response to acute oncoprotein inactivation. The precise mechanism by which cells acquire dependency on a single pathway or activated protein is not clear in most cases, but multiple theories have nonetheless been put forth; signaling network dysregulation, synthetic lethality genetic streamlining, and oncogenic shock. However, experimental evidence to prove these models is generally lacking, and it is unlikely that a single mechanism accounts for the numerous reported experimental findings that appear to represent examples of oncogene dependency, and therefore it represents an important area of investigation. Additionally, mechanisms governing oncogene addiction may vary according to the cellular and extracellular context.

Given the intrinsic resistance of LICs to TKI therapy in CML, a detailed understanding of oncogene dependency in therapeutically responsive cells permits engineering the therapeutically resistant cells LICs to achieve drug sensitivity. mRNA and miRNA expression studies were thus performed in BCR-ABL addicted and non-addicted cells to identify the candidate gene(s) mediating the drug response.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-D demonstrate that growth factor signaling in leukemic cells abrogates BCR-ABL dependence.

Figure 2A1:
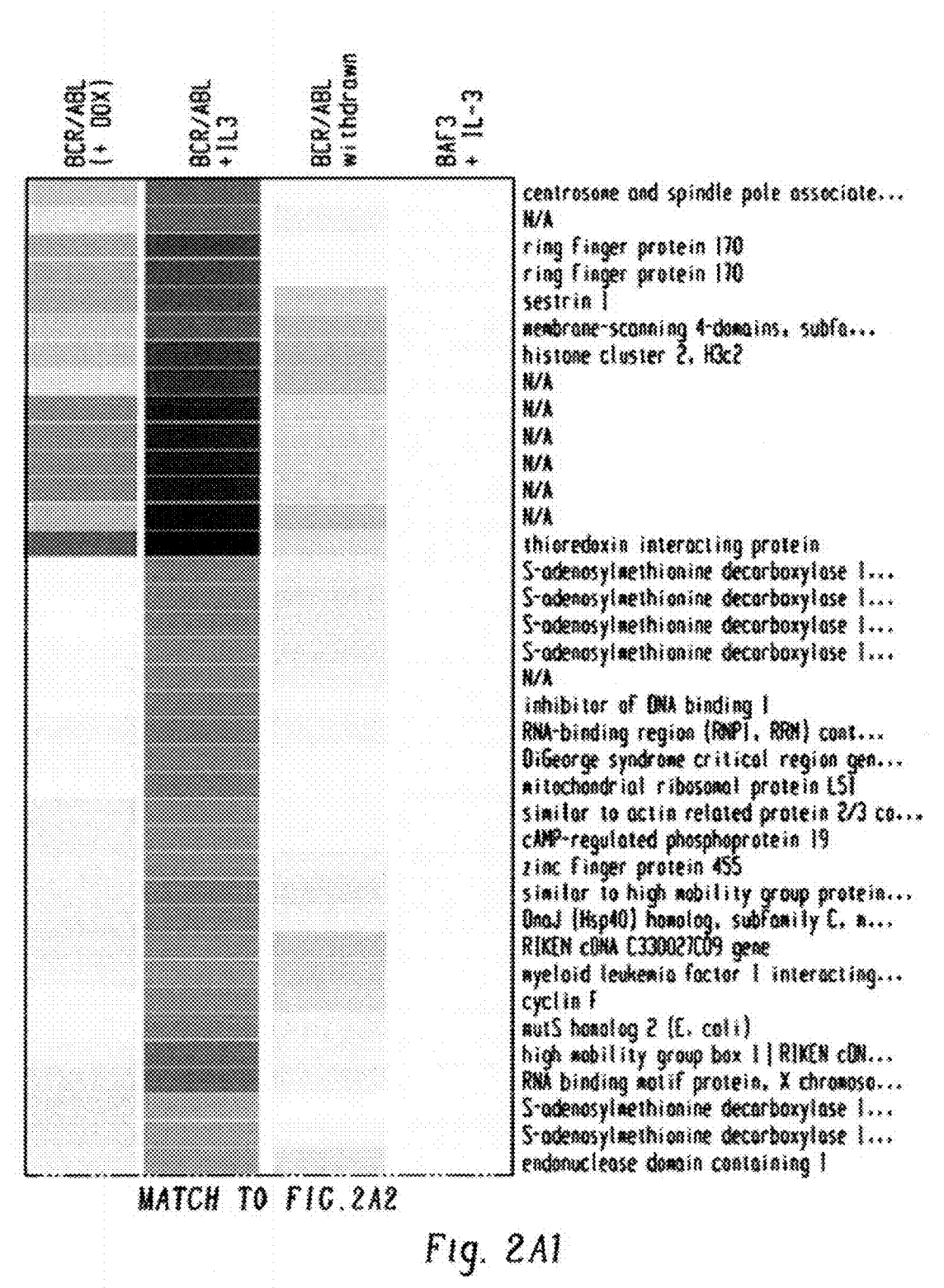
Figures 2B7, 2B8:
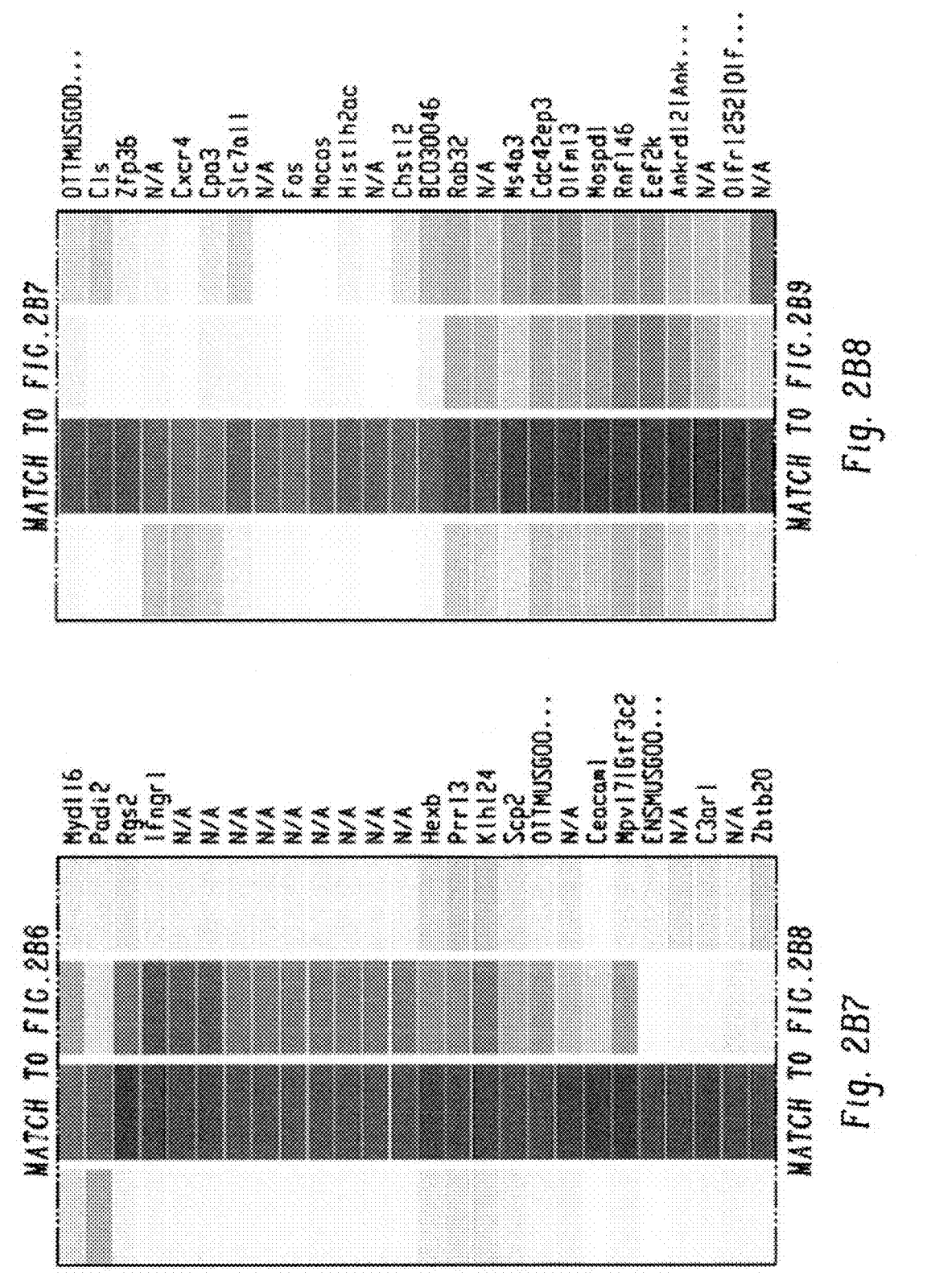

FIGS. 2A1-F demonstrate that AP-1 transcription factor c-Fos and dual specificity phosphatase-1 mediate BCR-ABL addiction.

FIGS. 3A-F schematically demonstrate in vitro and in vivo evaluation of c-Fos and Dusp-1 to induce BCR-ABL addiction in leukemic stem cells (LSCs).

FIGS. 8A-J show expression of c-Fos, Dusp1, and Zfp36 constitutes a common signature of imatinib-resistant cells. FIG. 8A shows immunoblot analysis of BCR-ABL expression in the indicated cell lines. Doxycycline (Dox) was used to induce BCR-ABL expression in BaF3-LTBA cells. Actin was used as a loading control. The band labeled c-Abl represents endogenous c-Abl kinase. FIG. 8B shows percentage survival of BaF3 or BaF3-LBTA (LTBA) cells treated with imatinib (3 µM) without or with IL-3. FIG. 8C shows percentage survival of BaF3 or BaF3-BA cells treated with imatinib (3 µM) without or with IL-3. FIG. 8D shows immunoblot analysis of BCR-ABL expression in BaF3-BA cells treated with increasing concentrations of imatinib with or without IL-3, pBCR-ABL is phosphorylated-BCR-ABL. FIG. 8E shows percentage survival of K562 cells treated with (3 µM) imatinib alone or with the indicated cytokines. FIG. 8F shows Venn diagram showing three commonly expressed genes among four different experiments, described in FIG. 9G. FIG. 8G shows real-time qPCR analysis of Fos, Dusp1, and Zfp36 expression in BaF3 cells, either untreated or 1 h after IL-3 was withdrawn from IL-3 treated cells (−IL-3), and in BaF3-BA cells with or without IL-3 treatment or 1 h imatinib (IM) treatment. The data shown are mean±s.d. from three technical replicates of qPCR (P values are shown above the compared bars; Student's t-test). FIG. 8H shows immunoblot analysis and FIG. 8I shows densitometric quantification from one representative blot of c-Fos, Dusp1, and Zfp36 expression in BaF3 cells and BaF3-BA cells+/−IL-3. FIG. 8J shows real-time qPCR analysis of c-FOS, DUSP1, and ZFP36 expression in primary CML patient-derived peripheral blood mononuclear cells (except for sample CP4, for which CD34+ cells were analyzed) normalized to expression in normal donor CD34+ cells (black bar). Four chronic phase (CP) and three blast-crisis (BC) patients were analyzed. Data are shown from two independent qPCR analysis±s.d.

FIGS. 9A-G show expression of c-Fos, Dusp1, and Zfp36 constitutes a common signature of imatinib-resistant cells. FIG. 9A shows representative scatter plots of BaF3-BCR-ABL cells stained with Annexin V and propidium iodide to quantify and sort the live (pink), early-apoptotic (blue) and dead cells (green), treated with Imatinib with IL3 (left panel) and without IL3 (right panel). Live cells from both groups (labeled as A and B), early apoptotic (labeled as C) and apoptotic or dead cells (labeled as D) from imatinib treated cells without IL3 were sorted by FACS to determine differential expression of genes. FIG. 9B shows scatter plots showing the live and dead K562 cells treated with imatinib+/−Epo. Live and early apoptotic cells were sorted for gene expression studies. FIG. 9C shows heat map showing differential expression of 192 genes by BCR-ABL in the presence of IL3. To identify the genes that are directly modulated by BCR-ABL and IL3, we used doxycycline inducible BaF3-LTBA cells. As constitutive expression of BCR-ABL destabilizes the genome by modulating several checkpoint and DNA repair enzymes causing irreversible genetic and epigenetic changes. Therefore, it makes difficult to identify genes that are modulated directly by BCR-ABL. To address this we made BaF3-LTBA using a third generation Tet-on promoter that lacks basal expression (shown in FIG. 8A). Total RNA was isolated from the LTBA cells after 12 hrs of doxycycline induction+/−IL3. Likewise, total RNA from the parental BaF3 cells grown with IL3 and doxycycline was used to filter out the background noise. FIG. 9D shows heat map showing differential expression of 308 genes between live cells treated with imatinib+/−IL3. FIG. 9E shows heat map showing modulation of 1437 genes in K562 cells treated with imatinib+/−erythropoietin. FIG. 9F shows heat map of expression profiles from CML CD34+ cells showing differential expression of 85 genes in untreated and after two weeks of imatinib treatment. FIG. 9G shows a Venn diagram showing induced expression of three genes (c-Fos, Dusp1 and Zfp36) by BCR-ABL, IL3 and imatinib.

FIGS. 10A-G show c-Fos, Dusp1 and Zfp36 is required for BCR-ABL dependent survival. FIG. 10A shows a cartoon depiction of retroviral vectors expressing BCR-ABL, c-Fos, Dusp1, and Zfp36 cDNAs with different fluorescent proteins in the BaF3-BCR-ABL cells. FIG. 10B shows a dose response curve showing overexpression of all three genes, c-Fos, Dusp1 and Zfp36, confers resistance to imatinib in the absence of growth factor, IL3. FIG. 10C shows a Q-PCR analysis showing the relative expression of c-Fos, Dusp1 and Zfp36 in BaF3-BCRABL cells expressing shRNAs for c-Fos, Dusp1 and Zfp36, a scrambled SC-shRNA was used as a control. FIG. 10D shows immunoblots showing reduced protein expression of Fos, Dusp1 and Zfp36 in BaF3-BA cells expressing gene specific shRNAs in comparison to control (scrambled shRNA). FIG. 10E shows a cell proliferation curve of parental BaF3 cells expressing shRNAs for c-Fos, Dusp1 and Zfp36. Depletion of c-Fos, Dusp1 and Zfp36 did not show any adverse effect on survival and proliferation of BaF3 cells. FIG. 10F shows cell proliferation curve of BaF3-BA cells, showing significant reduction in proliferation and survival (>50%) by genetic depletion or c-Fos, Dusp1 and Zfp36 alone or a combination of c-Fos+Dusp1 or Dusp1+Zfp36. BaF3 or BaF3-BCRABL cells expressing shRNAs for c-Fos+Zfp36 or c-Fos+Dusp1+ Zfp36 did not survive, thus precluded further analysis. FIG. 10G shows bar graph showing c-Fos, and Dusp1 knockdown sensitized the BaF3-BA cells to imatinib compared to BaF3 cells in the presence of GF, while depletion of Zfp36 equally sensitized both BaF3 and BaF3-BA cells. Individual data points are shown as empty circles in all bar graphs.

FIG. 11A shows experimental design of in vitro and in vivo experiments to analyze BCR-ABL disease using Dusp1$^{-/-}$, ROSACre$^{ERT2}$Fos$^{fl/fl}$, and ROSACre$^{ERT2}$Fos$^{fl/fl}$; Dusp1$^{-/-}$ mice. Kit$^+$ cells from mouse bone marrow were transduced with BCR-ABL-IRES-YFP retrovirus. 5,000 GFP$^+$ cells were plated for in vitro CFU assays, and 40,000 YFP$^+$ cells were transplanted to monitor leukemia development in vivo in lethally irradiated C57BL/6 mice.

log-rank Mantel-Cox test: P<0.0001 between WT and Dusp1$^{-/-}$ with or without imatinib (FIG. 11F); n=12 log-ranked Mantel-Cox test P<0.0001 between WT and Fos$^{-/-}$ with or without imatinib (FIG. 11H); n=12 log-rank Mantel-Cox test P<0.0001 between WT and Fos$^{-/-}$Dusp1$^{-/-}$ with or without Imatinib (FIGS. 11H, J). FIG. 11O shows percentage of CFUs from Fos$^{-/-}$Dusp1$^{-/-}$ Kit+ cells with retroviral-vector-mediated rescue of c-Fos and Dusp1 expression. Data shown are from two independent experiments±s.d. (n=3, P values are indicated above the compared bars by Student's t-test).

FIGS. 12A-I show reduced expression of c-Fos in c-Fos$^{fl/fl}$/Dusp1$^{-/-}$ mice prolonged the survival of CML mice. FIG. 12A shows survival curve of mice transplanted with BCR-ABL-YFP transduced Kit+ cells from ROSACre$^{ERT2}$c-Fos$^{fl/fl}$ mice, showing no significant difference with imatinib treatment compared to wild type (WT) donor cells. Data shown are from two independent transplant experiments (n=12). FIG. 12B shows survival curve of mice transplanted with BCR-ABL-YFP transduced cells from ROSACre$^{ERT2}$c-Fos$^{fl/fl}$Dusp1$^{-/-}$ mice. Data shown are from two independent transplant experiments (n=12; p=0.017). Note the leukemia free survival of 30-40% of mice transplanted with ROSACre$^{ERT2}$c-Fos$^{fl/fl}$Dusp1$^{-/-}$ cells FIG. 12C, D shows bar graphs illustrating leukemic burden in mice transplanted with ROSACre$^{ERT2}$c-Fos$^{fl/fl}$ (FIG. 12C), and ROSACre$^{ERT2}$c-Fos$^{fl/fl}$Dusp1-/- (FIG. 12D). Leukemic burden was measured by the level of YFP in peripheral blood as a surrogate for BCR-ABL expression. Cohorts of mice that died are represented as X. FIG. 12E shows q-PCR analysis of c-Fos in wild type (WT) and ROSACre$^{ERT2}$c-Fos$^{fl/fl}$Dusp1$^{-/-}$ bonemarrow cells showing reduced expression of c-Fos (5 fold) in ROSACre$^{ERT2}$c-Fos$^{fl/fl}$Dusp1$^{-/-}$ mice, suggesting that the reduced expression of c-Fos in the absence Dusp1 is sufficient to reduce the MRD by imatinib treatment in the absence of full deletion of c-Fos (FIG. 12D). FIG. 12F shows agarose gel showing a representative PCR analysis of c-Fos gene from the peripheral blood of ROSACre$^{ERT2}$c-Fos$^{fl/fl}$ or ROSACre$^{ERT2}$c-Fos$^{fl/fl}$Dusp1$^{-/-}$ mice treated with or without tamoxifen. Note amplification of c-Fos deletion specific PCR product (280 bp) by primer P1 and P3 (shown below in a cartoon representation) after tamoxifen treatment, while non-deleted PCR product (0.4 kb) amplified by P1 and P2 are present before or non-tamoxifen treated mice. These mice were monitored for six months after tamoxifen injection and deletion specific PCR were performed periodically that showed persistent presence of Fos deleted cells. Mice were sacrificed after six months, and we did not observe any defect in blood and organs, suggesting that therapeutic targeting of these two genes will not have any adverse effect on normal tissues and organs. FIG. 12G shows bar graph showing the levels of granulocytes, monocytes, B, and T cells after two weeks of transplantation from the peripheral blood of mice transplanted with Kit+ from wild type and ROSACre$^{ERT2}$:c-Fos$^{fl/fl}$/Dusp1$^{-/-}$ mice expressing vector (pMSCV-Ires-YFP) and BCR-ABL. Expression of BCR-ABL induces granulocytosis at the expense of B cells in both wild-type and Fos$^{fl/fl}$/Dusp1$^{-/-}$ recipient mice. Representative data showing mean values of peripheral blood cells±S.D. (n=5; **=p<0.01). FIG. 12H shows survival curves of mice transplanted with vector (MIY) and BCR-ABL-YFP transduced Kit+ cells from wild type (WT), and ROSACre$^{ERT2}$c-Fos$^{fl/fl}$Dusp1$^{-/-}$. c-Fos was deleted by tamoxifen after establishing the CML (after three weeks of transplantation). FIG. 12I shows graph showing the leukemic burden in transplanted mice measured by YFP positive cells in peripheral blood. Note, deletion of both Fos and Dusp1 do not affect the chimerism of vector (MIY) expressing cells, while their deletions in leukemic cells show gradual decrease in chimerism and imatinib treatment completely eradicated the leukemic cells. Individual data points are shown as circles in all bar graphs.

FIG. 13A shows experimental design for testing the efficacy of small-molecule inhibitors of c-Fos (difluorocurumin, DFC) and Dusp1 ((E)-2-benzylidene-3-(cyclohexylamino)-2,3-dihydro-1H-inden-1-one, BCI) in vitro and in vivo in CML mice. FIG. 13B shows percentage of CFUs from WT and BCR-ABL LSK (Lin-Sca1+Kit+) cells treated with the indicated drugs. Data shown are the mean colony numbers from two independent experiments±s.d. (n=3, P values are indicated above the compared bars by Student's t-test). FIG. 13C shows survival curve of BCR-ABL-expressing Kit+ cell recipients treated with vehicle (blue), imatinib (red), or a combination of imatinib with DFC and BCI (green). The time period during which the drugs were administered is indicated by light-blue shading. Data shown are from one of the two independent transplantation experiments with similar results (n=5 mice per group; P=0.0285). FIG. 13D shows percentage of YFP+ cells in peripheral blood of mice treated with imatinib or imatinib+DFC+BCI. FIG. 13E shows schematic structures of the transgenes used in transgenic mice to drive BCR-ABL expression in stem cells. Top, Scl-3' enhancer drives expression of the tetracycline transactivator protein (tTA); bottom, a tetracycline-responsive promoter (Tet-P) drives BCR-ABL expression. Transgenic mice are fed doxycycline-containing chow; doxycycline withdrawal induces expression of BCR-ABL in hematopoietic stem cells. FIG. 13F shows experimental design for studying the effects of Dusp1 and c-Fos inhibition in leukemic stem cells. Mice received a competitive transplant of 3,000-5,000 LSK Scl-BCR-ABL cells in combination with 500,000 WT total bone marrow cells. Engraftment was evaluated 1 month after transplantation by flow cytometry (CD45.1 versus CD45.2); the mice were then treated with imatinib alone or imatinib+DFC+BCI for 3 months, and the presence of MRD was evaluated at indicated times. FIG. 13G shows percentage of leukemic cells (CD45.2) in bone marrow of BoyJ recipients (CD45.1) at the indicated time points after cell transplantation and treatment with imatinib or imatinib+DFC+BCI.

FIGS. 14A-D show chemical inhibition of c-Fos and Dusp1 sensitized leukemic cells to imatinib. FIG. 14A shows chemical structures of small molecule inhibitors targeting Dusp1 ((E)-2-Benzylidene-3-(cyclohexylamino)-2,3-dihydro-1H-inden-1-one; BCI) and Fos (Diflourinated curcumin, DFC; Curcumin and NDGA). FIG. 14B,C show bar graphs showing percent CFU from normal and BCR- ABL LSK cells (Lin-Sca1+Kit+), with single and combinations of inhibitors utilizing different c-Fos inhibitors, curcumin (FIG. 14B) and NDGA (FIG. 14C). Representative data shown are the mean colony number from two independent experiments±S.D. P values are indicated above the compared bars). FIG. 14D shows survival curve of mice of two independent experiments transplanted with Kit+ expressing BCR-ABL-YFP. Treatments with single drugs or combination of two inhibitors are ineffective in treating these mice, most mice showed a marginal 5-7 days prolongation of their survival except BCI+curcumin treated cohort (20% of CML mice survived). Groups of CML mice treated with triple combinations, imatinib+Curcumin+BCI and imatinib+NDGA+BCI, showed prolonged survival, 50 and 60%, respectively. Individual data points are shown as empty circles in all bar graphs.

FIG. 15A shows representative scatter plots showing minimal effect by imatinib treatment on BCR-ABL (CD45.2) and (BCR-ABL-Lin-Sca+Kit+) cells. FIG. 15B shows representative scatter plots showing eradication of BCR-ABL (CD45.2) and (BCR-ABL-Lin-Sca+Kit+) by imatinib+DFC+BCI treatment. FIG. 15C shows percentage of leukemic cells (CD45.2) in bone marrow of BoyJ recipients (CD45.1). Imatinib treatment (blue bars) reduces leukemic burden (month 3=<20%), which after treatment discontinuation rebounds (month 6=>60%). Treatment with imatinib+curcumin+BCI (red bar) and imatinib+NDGA+BCI (purple) reduces leukemic burden but they relapse after treatment discontinuation. Treatment with imatinib+DFC+BCI (green bar) reduces leukemic burden (month 3=<10%), without relapse (month 6=no detection). FIG. 15D shows graphs showing the level of human leukemic cells in NSG mice at week seven, chimerism at week 2 and 4 are shown in FIG. 16B.

FIG. 16A shows experimental design for the analysis of DUSP1 and c-FOS inhibitor treatment of patient-derived CML CD34+ cells. Primary CML cells from CP4 were transplanted into NOD scid-$\gamma C^{-/-}$ mice recipients, which transgenically express human IL-3, IL-6, and GM-CSF (NSGS); engraftment was assessed 2 weeks after transplanatation, engrafted mice were treated for 6 weeks with drug combinations, and leukemic burden was determined at 4 and 7 weeks after transplantation. FIG. 16B shows percentage of human leukemic cells in the bone marrow of NSGS mice at week 2 (left) and week 4 (right) of treatment. Data shown are from one of two experiments with similar results (n=6 mice per group. P values are indicated above the compared bars by Student's t-test). FIG. 16C shows percentage of CFU numbers determined by LTC-IC assay for samples from two patients with CML, and a normal donor treated with vehicle or the indicated drug combinations. Data shown are mean CFU numbers±s.d. (n=3; P values are indicated above the compared bars).

FIG. 17A shows heat map showing commonly modulated genes in BCR-ABL expressing Kit+ cells with c-Fos and Dusp1 deletion and WT cells treated with Fos (DFC) and Dusp1 (BCI) inhibitors alone or with imatinib. Genetic and chemical inhibition resulted in the modulation of 146 genes in common (58 overexpressed and 88 underexpressed). FIG. 17B,C show netwalker analysis shows that overexpressed genes are enriched for genes participating in a Jun-JunD regulated network (FIG. 17B), whereas downregulated genes are enriched for genes participating in a Fos-Jun regulated network (FIG. 17C).

FIGS. 18A-G show inhibition of Dusp1 activates p38. FIG. 18A shows immunoblot analysis of phospho-p38, total p38, and p-JNK expression in BaF3 and BaF3-BA cells with or without IL-3, showing increased p-p38 levels in BCI-treated cells. FIG. 18B shows immunoblot analysis of the indicated proteins in BaF3 and BaF3-BA cells, with or without IL-3, expressing Dusp1, Dusp6, and pMSCV (empty vector). FIG. 18C shows, left, dose-response curve for survival of BaF3-BA cells at increasing imatinib doses, treated with vehicle or the p38-specific inhibitor (SB202190, 500 nM) or a JNK-specific inhibitor (SP600125, 500 nM); right, percentage of cell survival at 500 nM and 1,000 nM imatinib. The data shown are mean values±s.d. (n=3; P values are indicated above the compared bars). FIG. 18D shows CFU numbers from Kit+ cells coexpressing BCR-ABL (BA) and WT or drug-resistant Dusp1 variants. The data shown are mean colony number±s.d. (n=3; P values are indicated above the compared bars). FIG. 18E shows surface depiction of a structural model of the Dusp1 rhodanese domain, highlighting amino acids affected by BCI-resistance mutations, as well as a deletion mutant causing resistance (red). A putative binding pocket for BCI and kinase-interacting motifs (KIMs) are indicated. Mutations are clustered together in the structure, and outline a pocket to which BCI seemingly binds ($\Delta G$=−7.6). FIG. 18F shows ratio of the levels of phospho-p38 to total p38 in peripheral blood cells before and 6 h after BCI injection into leukemic mice. Data are shown for three mice (n=3; P=0.04). FIG. 18G shows real-time qPCR analysis showing expression of Bcl2l11, Il6, and Lif in mice before and 6 h after DFC+BCI injection. Data shown are means±s.d. from three mice in triplicates. (P values are indicated above each comparison; Student's t-test.)

FIGS. 19A-H show BCI resistant screening identified drug resistant mutations in the Dusp1. FIG. 19A shows bar graph showing overexpression of Dusp1, not the Dusp6, confers resistance to BCI in BaF3-BA cells. Data shown are from two independent experiments±S.D (n=3; P values are indicated above the compared bars). FIG. 19B shows bar graphs showing CFU numbers derived from Kit+ cells from WT mouse coexpressing BCR-ABL with either Dusp1 or Dusp6. Expression of Dusp1 show normal CFU numbers but confers modest resistance to IM [3 μM]+BCI [0.5 μM] treatment. Surprisingly, expression of Dusp6 show significantly reduced CFU number and treatment with IM+BCI did not show any significant change. Data shown are from two independent experiments±S.D (n=3; P values are indicated above the compared bars). FIG. 19C shows bar graphs showing CFU numbers derived from Kit+ cells from wild-type, Dusp1$^{-/-}$ and Dusp6$^{-/-}$ mice expressing BCR-ABL and BCR-ABL+Dusp6. Unlike Dusp1$^{-/-}$ cells, Dusp6$^{-/-}$ cells expressing BCR-ABL show normal CFU numbers compared to WT, but conferred drug resistance to IM+BCI treatment. Expression of Dusp6 in Dusp$^{-/-}$ cells with BCR-ABL partially reduced the CFU numbers and abrogated the drug resistance. Data shown are from two independent experiments±S.D (n=3; coexpressing BCR-ABL with either Dusp1 or Dusp6). FIG. 19D shows a schematic of random mutagenesis of Dusp1 for in vitro screening of BCI resistant clones. FIG. 19E shows bar graph showing frequency of resistant clones per million of BaF3-BA cells expressing randomly mutagenized Dusp1. FIG. 19F shows bar graph showing BCI resistance conferred by 25 out of 27 clones (except #9 and #16), isolated from the resistant screen selected at 1.5 μM of BCI. FIG. 19G shows bar graph showing the frequency of mutations in 25 sequenced resistant clones. FIG. 19H shows expression of Dusp1 mutants in BaF3-BA cells conferred resistance to BCI and imatinib+BCI. Note, Dusp1-V83G as a single mutation conferred significant resistance to both BCI alone and in combination of imatinib. Individual data points are shown as empty circles in all bar graphs.

FIGS. 20A-E show BCI resistant mutations are clustered in allosteric domain. FIG. 20A shows primary structure of Dusp1 where catalytic domain lies at the C-terminus of protein. Catalytic cysteine in catalytic-site is shown in red. The N-terminal rhodanese domain harboring kinase interaction motif (KIM) required for binding with MAPKs shown in green. FIG. 20B shows a ribbon depiction of homology based model of Dusp1 rhodanese domain. Mapping of BCI resistant mutations identified a single cluster in the rhodanese domain. Deletion mutations are shown in red while point mutations are shown in golden. FIG. 20C shows a cartoon depiction homology based model of Dusp1 catalytic domain. Catalytic lysine and an inorganic phosphate are shown in red. FIG. 20D shows surface depiction of Dusp1 rhodanese domain showing the BCI resistant mutations clustered at the N-terminus of allosteric domain. Deletion mutations are shown in red while point mutations are shown in golden. FIG. 20E shows unbiased in silico docking of BCI revealed a binding pocket to which BCI seemingly binds (ΔG=−7.6).

FIG. 21A shows survival curves of mice transplanted with vector and BCR-ABL-YFP (p190) transduced Kit+ cells from wild type (WT), and ROSACre$^{ERT2}$c-Fos$^{fl/fl}$Dusp1$^{−/−}$ mice. c-Fos was deleted by tamoxifen injection (three doses of 2 mg/kg) after two weeks of transplantation. Mice transplanted with wild-type cells expressing p190 BCR-ABL developed lethal B-ALL and died within 4-5 weeks, while mice transplanted with Fos$^{fl/fl}$Dusp1$^{−/−}$ cells show gradual depletion of BCR-ABL expressing cells (FIG. 21B), and do not develop leukemia determined by WBC count (FIG. 21C). Deletion of Fos accelerates the depletion of BCR-ABL positive cells compared to Fos non-deleted cells. FIG. 21D shows dose response analysis of BaF3 cells expressing FLT3-ITD showing complete resistance to AC220 under growth factor signaling (IL3). FIG. 21E shows bar graph showing induced expression of c-Fos and Dusp1 by FLT3-ITD with additional induction by IL3. Data for qPCR analysis are shown±S.D. (P values are indicated between the compared bars). FIG. 21F shows dose response analysis of BaF3 cells expressing Jak2-V617F showing 7-8-fold résistance to ruxolitinib in the presence of IL3. FIG. 21G shows bar graph showing induced expression of c-Fos and Dusp1 by JAK2-V617F under growth factor signaling. Data for qPCR analysis are shown±S.D. (P values are indicated between the compared bars). Individual data points are shown as empty circles in all bar graphs.

FIGS. 22A-I show a model for therapeutic mechanism of TKI efficacy. FIG. 22A shows graph showing the expressions of c-Fos (cyan) and Dusp1 (pink) in hematopoietic cells in mouse (left) and human (right). Each dot in the plot corresponds the expression of FOS and DUSP1 in a microarray. FIG. 22B shows a cartoon depiction showing downregulation of c-Fos and Dusp1 with differentiation during normal hematopoiesis. FIG. 22C shows bar graph showing the overexpression of c-Fos and Dusp1 in leukemic stem cells of mice (BCRABL+LSK-Lin-Sca1+Kit+ cells). Representative data shown are from two independent experiments±S.D. (P values are indicated above the compared bars). FIG. 22D shows bar graph showing the overexpression of c-FOS and DUSP1 in human leukemic stem cells (CD34+CD38−) from CML patients. Each dot in the plot corresponds the expression of c-FOS and DUSP1 in a microarray (GSE40721). P values are indicated above the compared samples. FIG. 22E shows histograms showing the overexpression of cell proliferation genes (left panel) and anti-apoptotic genes (right panel) in BaF3-LTBA cells grown with IL-3. FIG. 22F shows bar graph showing q-PCR analysis of expression of proliferative or survival genes (Id1 and Ncf4) and anti-apoptotic genes (Aven, SerpinA3G, Bcl2a1a, Bcl2l11 and Xaf1) in BaF3-BCR-ABL cells+1L3 with and without drug treatments (imatinib, DFC+BCI and DFC+BCI+Imatinib). Note, treatment with Fos and Dusp1 inhibitor (DFC+BCI) and in combination with imatinib suppressed their expression suggesting their regulation by Fos and Dusp1. Representative data shown are the mean values of qPCR analysis±S.D. (P values are indicated above the compared bars). FIG. 22G-1 shows a model of TKI response in drug sensitive and leukemic stem cells. Our model suggests that during normal hematopoiesis c-Fos and Dusp1 are downregulated with differentiation. In differentiated bulk of leukemia cells which is sensitive to TKI, expression of an activated kinase induces the expression of c-Fos and Dusp1, which induces both proliferative and proapoptotic signal. Therefore, an acute inhibition of activated oncogene induces oncogenic shock resulting to apoptosis in cells expressing suboptimal level of c-Fos and Dusp1 (FIG. 22G). In leukemic stem cells, convergence of oncogenic and growth factor signaling induces high levels of c-Fos and Dusp1 expression, which seemingly reprograms transcriptional network to induce pro-survival and anti-apoptotic genes. Thus, levels of c-Fos and Dusp1 determines the net transcriptional output for proliferative/pro-apoptotic genes or pro-survival/anti-apoptotic genes in oncogenic condition. Thus, inhibition of oncogene by TKI is ineffective against leukemic stem/progenitor cells (FIG. 22H), failure to induce apoptosis under TKI treatment results into MRD (FIG. 22I). Individual data points in each bar graphs are shown as empty circles.

FIG. 23A shows overexpression of DUSP1 in MPN patients. CD34+ cells from six patients representing each subtype were analyzed. P values: **=>0.001 and *=>0.01. FIG. 23B shows induction of Dusp1 in MPN cells. Bar graph showing q-PCR analysis of Dusp1 in Kit+ cells expressing Jak2-V617F, CSF3R-WT, CSF3R-T618 and Mpl-W515L normalized to vector control.

FIG. 23A shows mice transplanted with wild type cells showing robust leukemia development by CSF3R and Mpl mutants, while mice received Jak2-V617F cells showed mild elevation in WBC, but showed significant increase in red cells and reticulocytes. FIG. 23B shows leukemic burden as GFP+ cells over a period of eight weeks. FIG. 23C shows mice that received cells lacking Dusp1 did not show any signs of leukemia. FIG. 23D shows that all the GFP positive cells were abolished over the period of seven weeks in oncogenic conditions, while vector transduced cells have maintained normal engraftments. These data clearly show that Lack of Dusp1 is synthetic lethal to MPD development.

FIG. 25A shows a dose response curve of BaF3 and BaF3-FLT3ITD cells showing resistance to Flt3 inhibitor (AC220 or quizartinib) in the presence of growth factor, IL3. IC50 for AC220 is shown in the parenthesis. FIG. 25B shows bar graphs showing the induction of c-Fos and Dusp1 by both FLT3ITD and GF signaling.

FIGS. 26A-B show deletion of FOS and DUSP1 is synthetic lethal to AML development. c-Fos and Dusp1 constitute non-oncogene addiction in FLT3ITD:MLLAF9 driven AML. FIG. 26 A shows a scheme to test the role of Fos and Dusp1 in AML. FIG. 26B shows a bar graph showing CFU assays using Kit+ cells from the wild type and Fos-/-/Dusp1-/- mice. CFU assays were performed with and without Flt3 TKI (5 nM of AC220). Note, cells expressing FLT3ITD and MLLAF9 are resistant to TKI while cells lacking Fos and Dusp1 show synthetic lethality to oncogene expression, suggesting these genes are essential for AML development, however, they are indispensable for normal hematopoiesis because vector transduced cells do not show any defect in CFU formation (data not presented).

FIG. 27A shows a humanized AML model. CD34 cells from human cord blood were transduced by retroviruses expressing FLT3ITD-Ires-Cherry and MLLAF9-Ires-GFP. Double positive (GFP+Cherry) cells were sorted by FACS followed with in vitro and in vivo analysis. FIG. 27B shows histograms showing resistance to AC220 in the presence of GF (IL3, IL6, SCF and TPO) in in-vitro assay. FIG. 27C shows transplanted NSGS mice die of leukemia within six weeks and show complete eradication of leukemic cells when treated with combination of DFC+BCI+AC220 while AC220 or DFC+BCI alone are ineffective.

FIGS. 28A-F show inhibition of FOS and DUSP1 with TKI treatment cured EGFR driven lung cancers. Growth-factor-induced TKI resistance in solid tumors is mediated by c-FOS and DUSP1. FIG. 28A shows a dose response curve of the HCC827 cell line (lung adenocarcinoma; EGFR-DelE746A750) to erlotinib+/-hepatocyte growth factor (HGF). FIGS. 28B-C show real-time qPCR analysis illustrating induction of c-FOS (FIG. 28B) and DUSP1 (FIG. 28C) expression by HGF (indicated times after addition of erlotinib). FIG. 28D shows cell survival of HCC827 cells (WST assay) when treated with DFC, BCI and erlotinib alone and in combination. Note inhibition of DUSP1 alone sensitized the cells for erlotinib, while concomitant inhibition of both DUSP1 and c-FOS is sufficient to inhibit proliferation and survival. FIG. 28E shows HCC827 xenograft growth in recipients treated with erlotinib (red), DFC+BCI (green) and DFC+BCI+erlotinib (purple). Treatment started after one week of transplant (n=8 per group, each mouse represented by single dot). FIG. 28F shows representative images of mouse tumors from cohorts in panel E.

FIGS. 29A-F show inhibition of FOS and DUSP1 is sufficient to cure PDGFR driven lung cancer. FIG. 20A shows a dose response curve of NCI-H1703 (lung squamous carcinoma; PDGFR amplification) showing resistance to sunitinib in the presence of epidermal growth factor and fibroblast growth factor (EGF+FGF). FIGS. 29B-C show real-time qPCR analysis illustrating induction of FOS (FIG. 29B) and DUSP1 (FIG. 29C) expression by EGF and FGF (indicated times after addition of sunitinib). FIG. 29D shows cell survival of NCI-H1703 cells (WST assay) when treated with DFC, BCI and sunitinib alone and in combination. Concomitant inhibition of both DUSP1 and c-FOS is sufficient to inhibit proliferation and survival. FIG. 29E shows mouse xenografts of NCI-H1703 treated with sunitinib, DFC+BCI and sunitinib+DFC+BCI (n=5). Treatments were started two weeks after xenotransplantation. Mice treated with either DFC+BCI or sunitinib+DFC+BCI showed complete response. Treatment with sunitinib alone showed initial response but three mice showed tumor regrowth after three weeks of treatment. FIG. 29F shows representative images of mouse tumors from cohorts in FIG. 29E.

FIGS. 30A-D show induction of FOS and DUSP1 in solid tumors confers TKI resistance. Growth factor induced TKI resistance in solid tumors is mediated by c-FOS and DUSP1. FIG. 30A shows dose response curves showing TKI resistance in solid tumor cell lines in the presence of growth factors. AU565 (breast cancer HER2 amplified AU565) conferred resistance to lapatinib by growth factor, neuregulin 1-NRG1. RT4 (bladder carcinoma, EGFR amplified) conferred resistance to lapatinib in the presence of EGF. SKMEL28 (melanoma, BRAF-V600E) conferred resistance to PLX4720 in the [presence of HGF. FIGS. 30B-C show real-time qPCR analysis illustrating induction of c-FOS (FIG. 30B) and DUSP1 (FIG. 30C) expression by growth factors (indicated times after addition of erlotinib). Time at 0 hours represents the level of expression without TKI+/- GF. Note that the growth factors induce higher expression of c-FOS in all cell lines and DUSP1 in RT4 at 0 hours, while the addition of both TKI and growth factors induced both c-FOS and DUSP1. FIG. 30D shows bar graphs showing cell survival by WST assay when treated with DFC, BCI and TKI alone and in combination. Note that inhibition of c-FOS and DUSP1 is sufficient to kill AU565 cells, while their inhibition in RT4 and SKMEL28 cells restored the TKI sensitivity in the presence of growth factors.

Figure 2E:
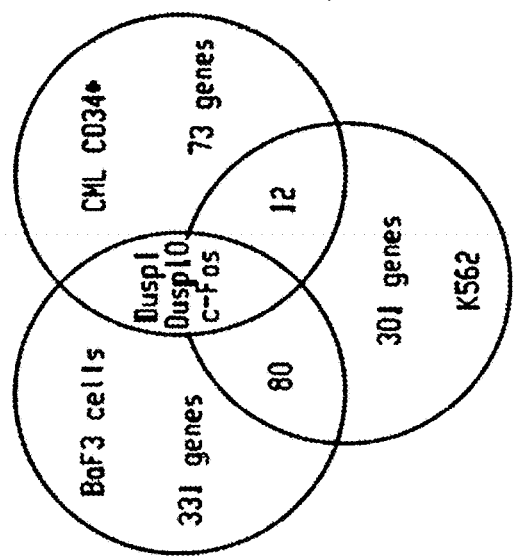

In one aspect, a pharmaceutically acceptable composition is provided comprising at least one biocompatible excipient and, as the only active agents, (a) a c-Fos inhibitor, (b) a Dusp-1 inhibitor, and (c) at least one oncogenic kinase inhibitor, where the oncogenic kinase is selected from the group consisting of BCR-ABL, BTK, FLT3, MET, KIT, JAK2, MEK, EGFR, PDGFR, ALK, HER2, B-Raf, FGFR2, RAF, PI3K, and combinations thereof. In one embodiment, the c-Fos inhibitor is selected from the group consisting of curcumin, difluorinated curcumin (DFC), [3-{5-[4-(cyclopentyloxy)-2-hydroxybenzoyl]-2-[(3-hydroxy-1,2-benzisoxazol-6-yl) methoxy]phenyl}propionic acid] (T5224), nordihydroguaiaretic acid (NDGA), dihydroguaiaretic acid (DHGA), and [(E,E,Z,E)-3-methyl-7-(4-methylphenyl)-9-(2,6,6-trimethyl-1-cyclohexen-1-yl)-2,4,6,8-nonatetraenoic acid (SR11302). In one embodiment, the Dusp-1 inhibitor is selected from the group consisting of (E)-2-benzylidene-3-(cyclohexylamino)-2,3-dihydro-1H-inden-1-one (BCI—also known as NSC 150117), TPI-2, TPI-3, and triptolide. In one embodiment, the tyrosine kinase inhibitor is selected from the group consisting of Imatinib, Dasatinib, Ponatinib or Nilotinib when the oncogenic kinase is BCR-ABL; Ibrutinib when the oncogenic kinase is BTK; Ruxolitinib, Crizotinib, or Quizartinib when the oncogenic kinase is one of FLT3, MET, KIT, or JAK2; Ruxolitinib or Trametinib when the oncogenic kinase is JAK2 or MEK; Gefitinib or Axitinib when the oncogenic kinase is one of EGFR, PDGFR, or ALK; Gefitinib, Axitinib, or dasatinib when the oncogenic kinase is one of EGFR or PDGFR; Gefitinib or Axitinib when the oncogenic kinase is one of HER2 or EGFR; Vemurafenib or Sorafenib when the oncogenic kinase is one of B-Raf or MEK; Crizotinib or Dasatinib when the oncogenic kinase is one of MET, FGFR2, or HER2; Ceritinib, Alectinib or Crizotinib when the oncogenic kinase is one of MET, FGFR2, or HER2; Ceritinib, Alectinib or Crizotinib when the oncogenic kinase is one of ALK, KIT, or FGFR; and Vemurafenib, Sorafenib or Idelalisib when the oncogenic kinase is one of RAF or PI3K. In one embodiment, a pharmaceutically acceptable composition is provided comprising at least one biocompatible excipient and, as the only active agents, (E)-2-benzylidene-3-(cyclohexylamino)-2,3-dihydro-1H-inden-1-one (BCI), difluorinated curcumin (DFC), and at least one oncogenic kinase inhibitor selected from the group consisting of Imatinib, Dasatinib, Ponatinib, Nilotinib, Ibrutinib, Ruxolitinib, Crizotinib, Quizartinib, Trametinib, Gefitinib, Axitinib, Dasatinib, Vemurafenib, Sorafenib, Ceritinib, Alectinib, Vemurafenib, and Idelalisib.

In one aspect, a method of treating a kinase-dependent malignancy in a patient is provided. In one embodiment, the method comprises administering to the patient in need thereof a composition containing at least one biocompatible excipient and, as the only active agents, a combination of (a) an inhibitor of c-Fos resulting in inhibition of c-Fos, (b) an inhibitor of Dusp-1 resulting in inhibition of Dusp-1, and (c) at least one inhibitor of an oncogenic kinase resulting in inhibition of the oncogenic kinase, where the composition is administered to the patient in a dosing regimen for a period sufficient to provide treatment for the kinase-dependent malignanancy in the patient in need thereof. In one embodiment, the c-Fos inhibitor is selected from the group consisting of curcumin, difluorinated curcumin (DFC), [3-{5-[4-(cyclopentyloxy)-2-hydroxybenzoyl]-2-[(3-hydroxy-1,2-benzisoxazol-6-yl) methoxy]phenyl}propionic acid] (T5224), nordihydroguaiaretic acid (NDGA), dihydroguaiaretic acid (DHGA), and [(E,E,Z,E)-3-methyl-7-(4-methylphenyl)-9-(2,6,6-trimethyl-1-cyclohexen-1-yl)-2,4,6,8-nonatetraenoic acid (SR11302). In one embodiment, the Dusp-1 inhibitor is selected from the group consisting of (E)-2-benzylidene-3-(cyclohexylamino)-2,3-dihydro-1H-inden-1-one (BCI—also known as NSC 150117), TPI-2, TPI-3, and triptolide. In one embodiment, the kinase-dependent malignancy is chronic myeloid leukemia (CML) and the at least one inhibitor is Imatinib, Dasatinib, Ponatinib and/or Nilotinib; chronic lymphocytic leukemia (CLL) and the at least one inhibitor is Ibrutinib; acute myeloid leukemia (AML) and the at least one inhibitor is Ruxolitinib, Crizotinib, and/or Quizartinib; myeloproliferative neoplasm (MPN) and the at least one inhibitor is Ruxolitinib and/or Trametinib; lung cancer and the at least one inhibitor is Gefitinib and/or Axitinib; brain tumor and the at least one inhibitor is Gefitinib, Axitinib, and/or Dasatinib; breast cancer and the at least one inhibitor is Gefitinib and/or Axitinib; bladder carcinoma and the at least one inhibitor is Gefitinib and/or Axitinib; melanoma and the at least one inhibitor is Vemurafenib and/or Sorafenib; pancreatic cancer and the at least one inhibitor is Crizotinib and/or Dasatinib; colon cancer and the at least one inhibitor is Ceritinib, Alectinib and/or Crizotinib; and prostate cancer and the at least one inhibitor is Vemurafenib, Sorafenib and/or Idelalisib. In one embodiment, the treatment is curative.

In another aspect, a method to eradicate leukemia initiating cells (LIC) or cancer stem cells (CSC) in a patient being treated with a tyrosine kinase inhibitor (TKI) is provided. In one embodiment, the method comprises administering to the patient in need thereof a composition containing at least one biocompatible excipient and a combination of (a) an inhibitor of c-Fos resulting in inhibition of c-Fos, and (b) an inhibitor of Dusp-1 resulting in inhibition of Dusp-1, where the composition is administered to the patient in a dosing regimen for a period sufficient to eradicate the LIC or CSC cells.

Chronic myelogenous leukemia (CML) initiating cells are intrinsically resistant to small-molecule kinase inhibitors. This discovery has prompted interest in developing strategies to more effectively target CML initiating cells. One line of activity involves global gene expression analyses. Another line of activity involves identification of downstream partners essential for maximum BCR-ABL oncoprotein activity. These have reinforced early evidence of activation of the JAK/STAT, PI3K/AKT, RAS/MAPK and NFKB pathways in the primitive CML LIC. These studies have also identified differentially expressed genes involved in regulation of DNA repair, cell cycle control, cell adhesion, homing, transcription factors, and drug metabolism. None of these studies identified potential therapeutic targets useful to eradicate the CML LIC. Failure to identify such a target may be due to the fact that, in many studies, expression profiling was done either on total bone-marrow samples or CD34+ fractionated cells. Apart from constitutional BCR-ABL expression that causes genetic instability in time dependent fashion, CD34+ fractionated cells carry a good degree of heterogeneity in itself. Thus, variations in patients sample and use of a heterogeneous cell population obscured identification of meaningful targets. Based on these observations, knowing the mechanisms of oncogene addiction in Imatinib sensitive cells will permit engineering of CML LIC to achieve sensitivity for kinase inhibitors.

In one embodiment, the BCR-ABL tyrosine kinase inhibitor is at least one of Imatinib (Novartis), Nilotinib (Novartis), Dasatinib (BMS), and Ponatinib (Ariad). In one embodiment, the BCR-ABL tyrosine kinase inhibitor is Imatinib.

In one embodiment, the Dusp-1 inhibitor is at least one of BCI, TPI-2, TPI-3, and triptolide. In one embodiment, the Dusp-1 inhibitor is BCI.

In one embodiment, the c-Fos inhibitor is at least one of curcumin, difluorinated curcumin (DFC), T5224, nordihydroguaiaretic acid (NDGA), dihydroguaiaretic acid (DHGA), and SR11302. In one embodiment, the c-Fos inhibitor is curcumin. In one embodiment, the c-Fos inhibitor is difluorinated curcumin (DFC). In one embodiment, the c-Fos inhibitor is NDGA. In one embodiment, the c-Fos inhibitor is T5224.

An unbiased mRNA expression profiling was performed using BAF3 cells, which requires IL-3 for survival, expressing the BCR-ABL tyrosine kinase under a Tet-R responsive promoter that renders them IL-3-independent. BaF3 cells were used because it is homogeneous in terms of gene expression, and because BCR-ABL dependence is reversible. Specifically, in the presence of exogenous IL-3, BAF3 cells no longer depend on BCR-ABL for survival, as shown in FIG. 1.

More specifically, FIG. 1 shows that growth factor signaling in leukemic cells abrogates the BCR-ABL dependence. FIG. 1A shows conditional expression of BCR-ABL in BaF3 cells; without doxycycline there is no expression of BCR-ABL in BaF3 cells. FIG. 1B is a Western blot showing the kinase activity of BCR-ABL at different concentrations of inhibitor. This demonstrated that IL-3 had no effect on mediated kinase inhibition. FIG. 1C shows a dose response curve for Imatinib on BAF3-BCR-ABL cells, where squares are BCR-ABL+IL-3, circles are BCR-ABL, and triangles are BAF3. This demonstrated that Imatinib was no longer effective when cells were grown with IL-3. FIG. 1D shows cell proliferation assays showing the abrogation of BCR- ABL addiction K562 cells when grown with erythropoietin (EPO), while other hematopoietic cytokines did not have a significant effect.

This biology is reminiscent of CD34+ CML stem cell behavior. The data were obtained on freshly made BaF3 cells expressing BCR-ABL conditionally, because long-term expression of BCR-ABL in any cell causes severe genomic instability and permanent irreversible changes in gene expression. This likely would exacerbate problems identifying the critical gene or genes involved in BCR-ABL addiction.

To define the differential expression of gene(s) in BCR-ABL addicted and non-addicted conditions, expression analysis was performed using total RNA from BaF3 cells, BaF3 cells expressing BCR-ABL conditionally in the presence and absence of exogenously added IL-3 (FIG. 2A1) and BaF3-BCR-ABL cells treated with Imatinib in the presence and absence of IL-3 (FIG. 2B1).

AP-1 transcription factor c-Fos and dual specificity phosphatase-1 mediated the BCR-ABL addiction. Comparative analysis of gene expression from these two data sets would allow identification of the sets of genes involved in BCR-ABL addiction, and identified 331 genes that were differently expressed in these conditions. Given BCR-ABL addiction in K562 cells and attenuation of addiction by erythropoietin, similar gene expression analysis in K562 cells would permit sorting out the false positives and may corroborate the data sets. Expression profiling of K562 cells identified 301 differently expressed genes; about one third of the genes are common to the gene list of BCR-ABL-BaF3 (FIG. 2B1). To narrow the list to identify clinically significant candidate genes, these data sets were compared with the expression profiling of CD34+ cells from CML patients before and after Imatinib treatment. Only three genes, Dusp-1, Dusp-10, and c-Fos, were down regulated in BCR-ABL addicted cells, while they were upregulated to 3-5 fold in non-addicted cells. This suggested their role in BCR-ABL dependence. The role of these three genes in mediating BCR-ABL addiction were evaluated; specifically, whether their down-regulation in non-addicted cells would sensitize them to Imatinib induced apoptosis. c-Fos, Dusp-1 and Dusp-10 were knocked down using shRNA hairpin, and cell survival analysis was performed in the presence of 5 µM Imatinib, which typically kills addicted cells in 24 hrs at this concentration, and IL-3. Dusp-1 and c-Fos knockdown alone induced 30% and 40% sensitivity to Imatinib, respectively. Dusp-10 knock down did not show any significant sensitivity to Imatinib. This suggested that double knock down of c-Fos and Dusp-1 may sensitize the BCR-ABL cells fully. To test this, instead of using shRNA mediated gene knock down of Dusp-1, a small molecule inhibitor that targets Dusp-I, BCI, was used. In cell proliferation assays, BaF3-BCR-ABL cells with c-Fos knockdown were fully sensitive to Imatinib when combined with BCI (FIG. 2F). The same combinations of drugs had no effect on BCR-ABL positive and parental BaF3 cells, highlighting the response specificity.

Figure 2F:
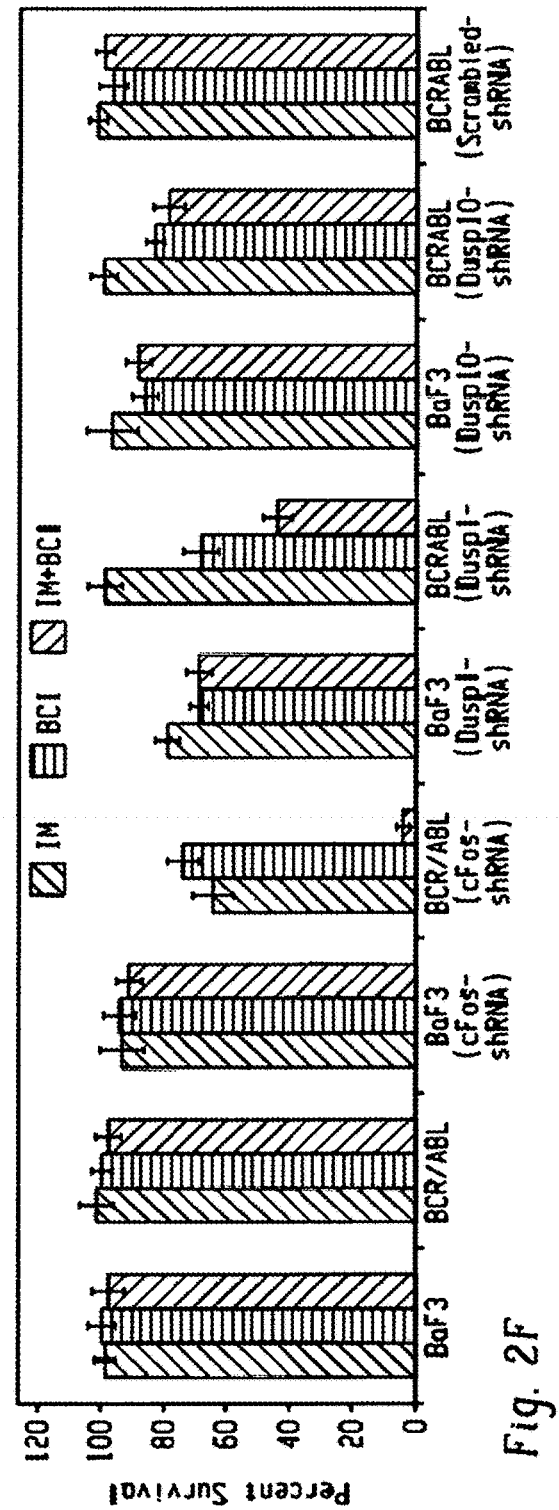
Figure 4:
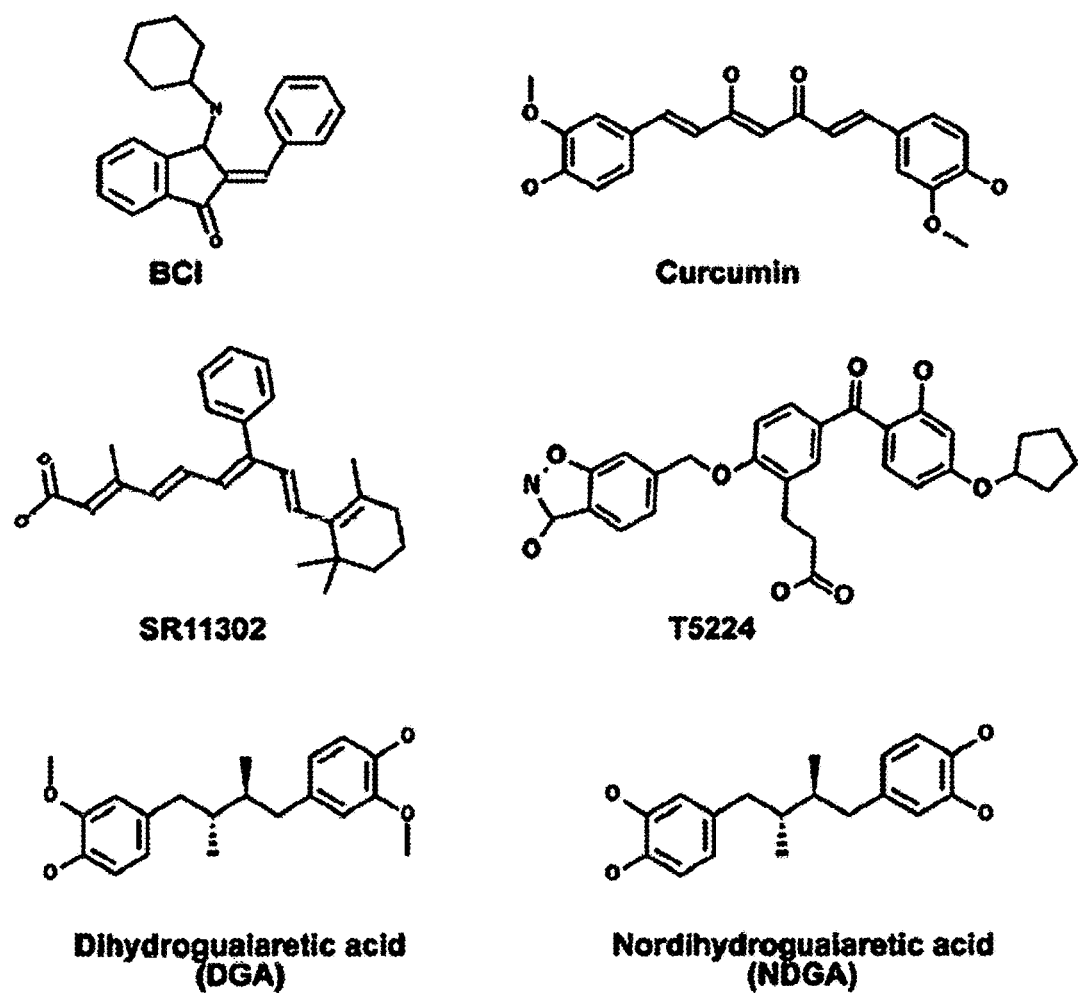
FIG. 4 shows the chemical structure of selected inhibitors.
Figure 5:
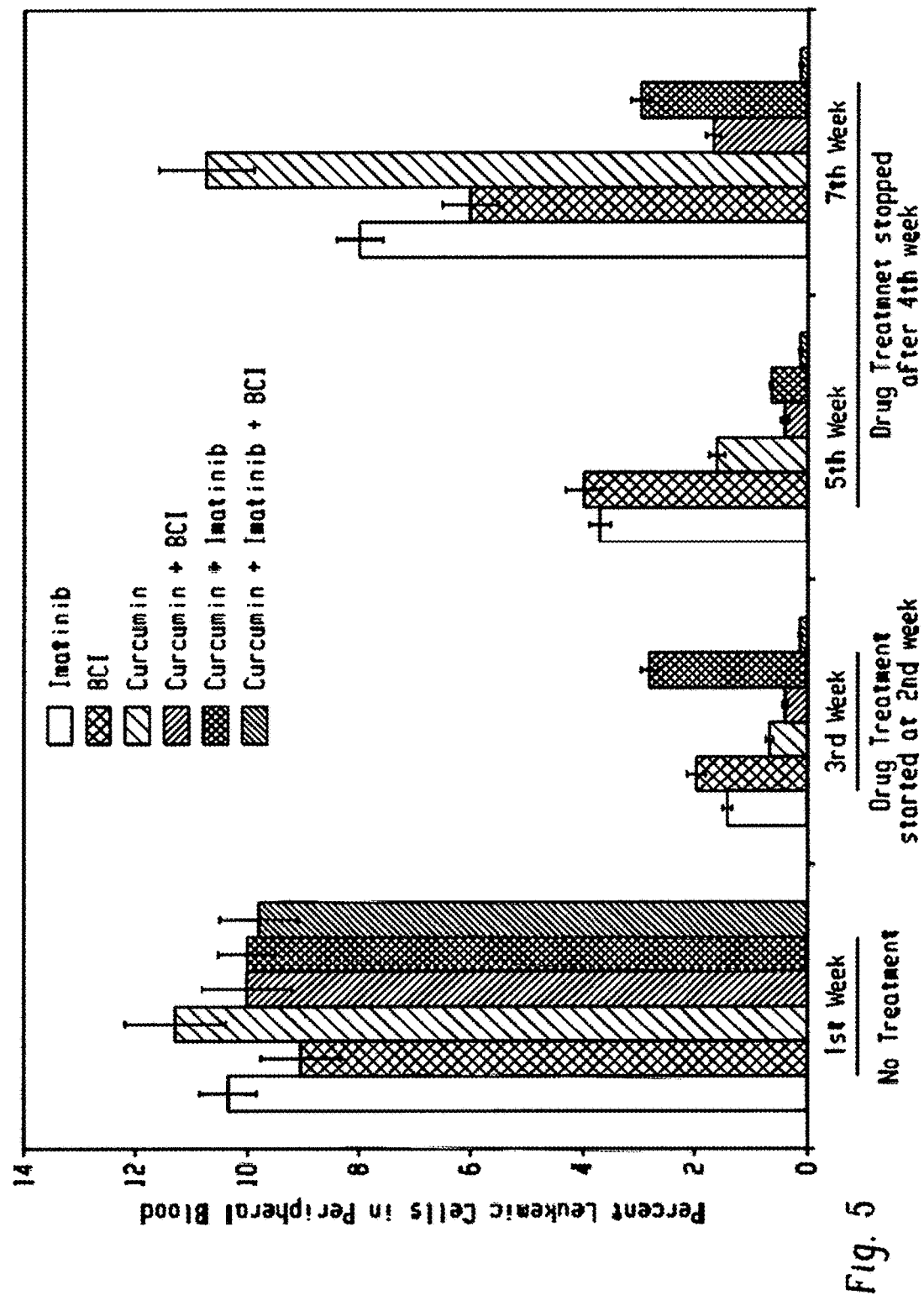
FIG. 5 demonstrates treatment effects for Imatinib, (E)-2-benzylidene-3-(cyclohexylamino)-2,3-dihydro-1H-inden-1-one (BCI), and curcumin separately and combined.

FIGS. 2A1-2A5 are a heat map of differential gene expression in BaF3 cells expressing the BCR-ABL grown with and without exogenously added IL-3. Expression of BCR-ABL was induced by adding doxycycline in the growth media. This expression profile was normalized with parental BaF3 cells grown with IL-3. This analysis identified 809 genes that were differently regulated by BCR-ABL in the presence of IL-3. FIGS. 2B1-2B12 are a heat map showing that 900 genes were differently expressed in the BCR-ABL-BaF3 cells treated with Imatinib in the presence and absence of IL-3. Cells treated with IL-3 and Imatinib are resistant to apoptosis and are represented as live cells; cells treated with Imatinib in the absence of IL-3 will apoptose. To identify the critical genes that mediates resistance or sensitivity to Imatinib in addicted cells, cells were separated into three distinct sub-populations: live, early-apoptotic, and late-apoptotic using Annexin V and propidium iodide staining. Comparing gene lists from A and B identified that 331 genes are common and are differently regulated. FIGS. 2C1-2C2 show expression profiling of K562 cells treated with Imatinib in the presence and absence of erythropoietin (EPO). This analysis identified 301 genes that were expressing differently in K562 cells. FIGS. 2D1-2D2 show expression profiling of CD34+ positive cells from CML patients before and after one week of Imatinib treatment (gene set enrichment (GSE) 12211) which identified 87 genes that were differently expressed. FIG. 2E is a Venn diagram showing overexpression of three genes Dusp-1, Dusp-10, and c-Fos in BaF3 cells, K562, and CML-CD34+ cells. FIG. 2F is a cell proliferation assay of BCR-ABL cells expressing shRNA hairpins for c-Fos, Dusp1 and Dusp-10 was performed in the presence of IL-3 with 5 µM Imatinib and 1 µM of the Dusp-1 inhibitor (E)-2-benzylidene-3-(cyclohexylamino)-2,3-dihydro-1H-inden-1-one (BCI), alone or in combination. In each group of three, the top bar indicates Imatinib, the middle bar indicates BCI, and the lower bar indicates Imitinib+BCI. The results revealed that down regulation of c-Fos and Dusp-1 together mediated the BCR-ABL addiction.

Efficacy of Dusp-1 and c-Fos inhibition in mouse model of CML and CD34+ cells from CML patients was shown. The BCR-ABL tyrosine kinase inhibitor Imatinib improves the survival of patients but does not eliminate LICs. This suggested that these cells are not addicted to BCR-ABL. The data demonstrated that downregulation of c-Fos and Dusp-1 mediated BCR-ABL addiction. Inhibition of c-Fos and Dusp-1 together induced apoptosis in BCR-ABL positive cells following Imatinib treatment. The same combination has no effect on survival and apoptosis of parental BaF3 cells. Dusp-1 and c-Fos knockout mice were viable and survived without any serious phenotype, suggesting that these targets were suitable for therapeutic development. The effectiveness of c-Fos and Dusp-1 inhibition in LICs for Imatinib response was determined before making any therapeutic utility.

c-Fos and Dusp-1 were targeted using both genetic (shRNA) and pharmacological inhibitors to provide a basis for clinical application to target CML initiating cells. The retroviral bone marrow transduction transplantation model of BCR-ABL-induced CML was established. FIG. 3 shows schema for in vitro and in vivo evaluation of c-Fos and Dusp-1 to induce BCR-ABL addiction in LSCs. FIG. 3A shows retrovirus and lentivirus constructs for hematopoietic stem/progenitor transduction. FIGS. 3B, C and D show bone marrow harvesting and sorting of Kit+ cells. FIG. 3E shows viral transduction of K+L-S+ cells with pMIGBA and pLVIR viruses followed by cell sorting for doubly positive cells GFPIRFP cells. FIG. 3F shows that these doubly positive cells will be injected to mice followed with treatment by Imatinib alone and in combination with Dusp-1 and Fos inhibitors. CFU assays in the presence and absence of Imatinib, and also in combination with Dusp-1 and Fos inhibitors are performed.

Therapeutic response of Imatinib in LICs following the c-Fos and Dusp-1 knock down using shRNA overexpression was evaluated. As shown in FIG. 3, flow-sorted Kit+Lin-Sca1+ cells from C51BU6 mice were transduced with retroviruses expressing BCR-ABL-Ires-GFP and lentiviruses overexpressing shRNAs for c-Fos and Dusp-1 with RFP. The transduced cells were sorted again for GFP and RFP positivity. These doubly positive cells were used for in vitro and in vivo analysis. As a control, vector containing scrambled shRNA transduced cells and cells expressing the shRNA for Dusp-1 and Fos alone in the presence and absence of BCR-ABL were used. For each condition, 10 mice were injected through tail vein with $10^4$ sorted cells mixed with $5\times10^5$ RBC depleted total bone marrow. After seven days, mice were subjected to drug, Imatinib, BCI, treatments. To evaluate the effect of drug administration on apoptosis of stem cells in vivo, a set of leukemic mice were sacrificed on day 5 of treatment and apoptosis in the KLS population was measured by labeling with Annexin V and DAPI. For in vitro CFU assays, methylcellulose colonogenic assays are performed by plating $10^3$ sorted cells in 0.9% MethoCult (Stem Cell Technologies) with hematopoietic growth factors in the presence of Imatinib alone, BCI alone, and in combination of both inhibitors. Colonies (>100 μm) from primary cells are scored after 7-15 days. If good transduction efficiency is not achieved due to use of two different viruses, inducible transgenic Scl-tTaBCRIABL are used. BM cells are obtained from Scl-tTa-BCRABL-GFP mice 4 weeks after induction of BCR-ABL expression by tetracycline withdrawal, and a pure population of KLS/GFP-expressing cells are sorted by flow cytometry followed with viral transduction expressing shRNA hairpins for Dusp-1 and c-Fos. These transduced cells are subjected to in vitro and in vivo analysis.

Inhibition of c-Fos and Dusp-1 in primary CML $CD34^+$ cells was shown to evaluate the inventive composition as a therapeutic agent on primary human samples. Quiescent $CD34^+$ CML cells from chronic phase patients are known to be less sensitive than the bulk of the $CD34^+$ leukemic cells to the cytotoxic effects of Imatinib inhibition in vitro. This quiescent population is enriched in CML stem cells ($CD34^+$ $CD38^-$ cells), but also typically still contains large numbers of more mature $CD34^+CD38^+$ cells.

To determine the effect of c-Fos and Dusp-1 inhibition with Imatinib, $Lin^-CD34^+CD38^+$ primitive CML stem cells were isolated followed with in vitro colony forming unit (CFU) assay. Additionally, 50,000 $Lin^-CD34^+CD38^-$ cells were grown in liquid culture with and without the presence of growth factors IL-3, IL-6, G-CSF, Flt3-LG, SCF and EPO in the presence of Imatinib (alone), BCI (alone), and with all compounds in combination. After 72 hrs cells were stained with Annexin V and PI to analyze apoptosis. Clinical samples from CML patients were tested.

mRNA expression studies were performed in BCR-ABL addicted and non-addicted cells to identify the candidate gene or genes mediating drug response. Of several candidate genes, inhibition of Dual-specificity phosphatase-1 (Dusp-1) and c-Fos by ShRNA and/or small molecule inhibitors greatly sensitized the LSCs for Imatinib. This suggested intrinsic resistance of cancer stem cells could be targeted and may provide curative benefit.

To validate the role of Dusp-1 and c-Fos in Imatinib response and therapeutic targeting of leukemic stem cells in vivo, a bone marrow transduction transplantation model was used. Bone marrow cells from normal C57Bl/6 mice were transduced with BCR-ABL retroviruses expressing GFP and transferred to sub-lethally irradiated mouse hosts. Such mice develop a reproducible myeloproliferative disease similar to human CML. Treatment with BCR-ABL inhibitors Imatinib, Nilotinib and Dasatinib prolonged survival of these mice for 3-4 weeks and leukemic stem cells in these mice are resistant to therapy as in human subjects, suggesting kinase inhibitor therapy is not curative. Groups of mice (n=6) were treated with Imatinib at a dose of 100 mg/kg/day, BCI at a dose of 5 mg/kg/day targeting Dusp-1, and curcumin at a dose of 50 mg/kg/day targeting c-Fos by intraperitoneal injection. An identical dose of combination of drugs, Imatinib and BCI, Imatinib and curcumin, BCI and curcumin, and Imatinib and BCI and curcumin, were injected intraperitoneally. Drug treatments were started on day 8 following the bone marrow transplants. Leukemic burden in mice was assessed weekly by monitoring the GFP positive cells in peripheral blood using FACS.

As shown in FIG. 5. the combination of Imatinib, BCI and curcumin cured mice from CML. In FIG. 5, from left to right, the six bars in each of the four groups (1st week, 3rd week, 5th week, 7th week) are, in this order, Imatinib, BCI, curcumin, curcumin+BCI, curcumin+Imatinib, curcumin+Imatinib+BCI. The histograms show the percentage of GFP positive cells from peripheral blood as leukemic burden in mice. Each histogram represented the average value of GFP positive cells from six mice. Single drug treatment, or a two drug combination treatment suppressed most leukemic cells, but there were residual leukemic cells in circulation at three weeks. However, a combination of Imatinib, BCI, and curcumin did not show any significant number of leukemic cells in circulation. Mice treated with the Imatinib, BCI and curcumin (the rightmost bar in each group) did not relapse following drug withdrawal. This result suggested these mice were cured from the disease.

A way to ascertain that there are no leukemic stem cells in mice is stop drug treatment and test for disease relapse. Any leukemic stem cells surviving in bone marrow will repopulate the disease, while curing the disease will fail to do so. Also as shown in FIG. 5, drug treatment was thus stopped after the fourth week for the analysis of disease relapse. Leukemic cell analysis from peripheral blood in the fifth and seventh week clearly demonstrated that the mice treated with single and two drugs relapsed, while triple drug treatment had no sign of leukemic cells in peripheral blood. These results suggested that mice in this treatment group were cured of the disease.

Given the problems associated with curcumin absorption and bioavailability, other c-FOS inhibitors were evaluated. The c-fos inhibitors nordihydroguaiaretic acid (NDGA) and difluorinated curcumin (DFC) were tested in two different mouse models of leukemia, namely, retroviral-bone marrow transplant model, and a BCR/ABL transgenic mouse model that allows expression of BCR/ABL only in primitive and multiprogenitors (MPPs) hematopoietic stem cells. Assessing efficacy of these drug combinations in transgenic mouse models permitted analysis of LSC dynamics and survival, and provided definitive proof for eradication of LSCs.

The data demonstrated that a combination of DFC, BCI, and Imatinib was more potent than combinations with curcumin, BCI, and Imatinib, and with NDGA, BCI, and Imatinib, as shown in FIGS. 6 and 7A-D.

Figure 6:
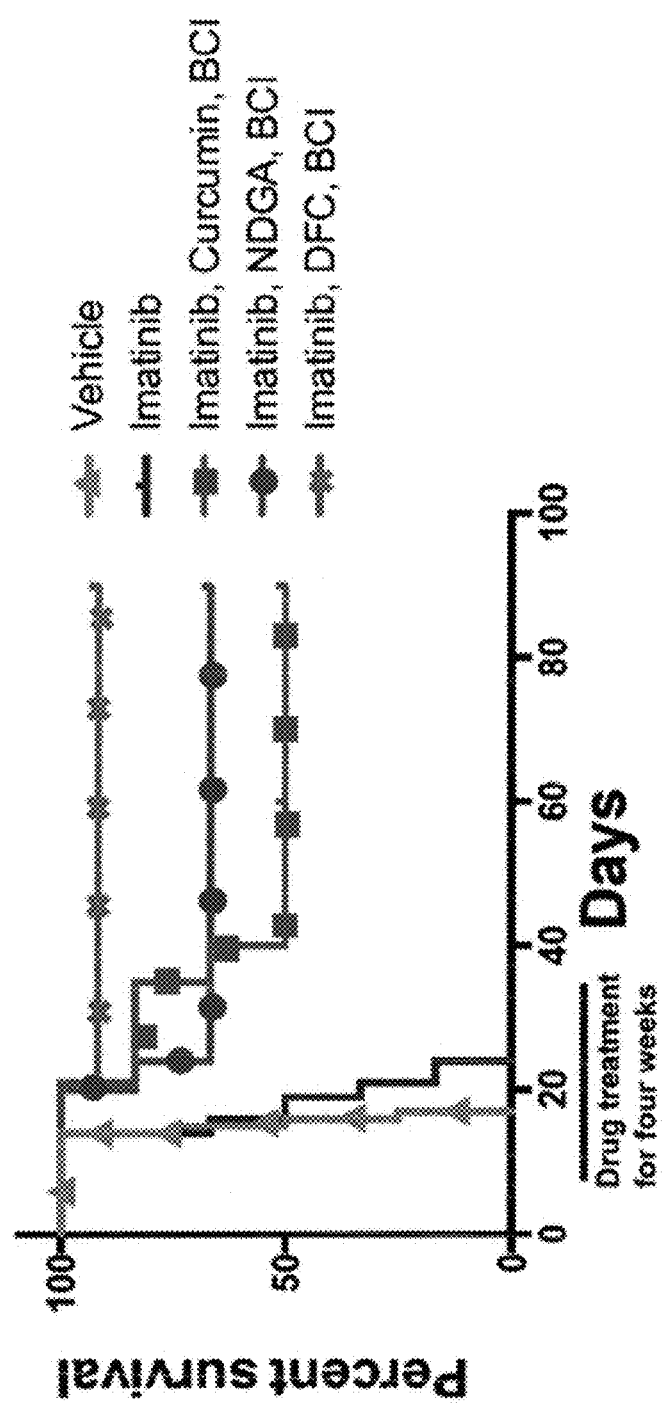
FIG. 6 demonstrates efficacy of compositions in curing mice with leukemia in retroviral-transduction bone marrow transplantation mouse model of chronic myelogenous leukemia (CML).
Figure 7A:
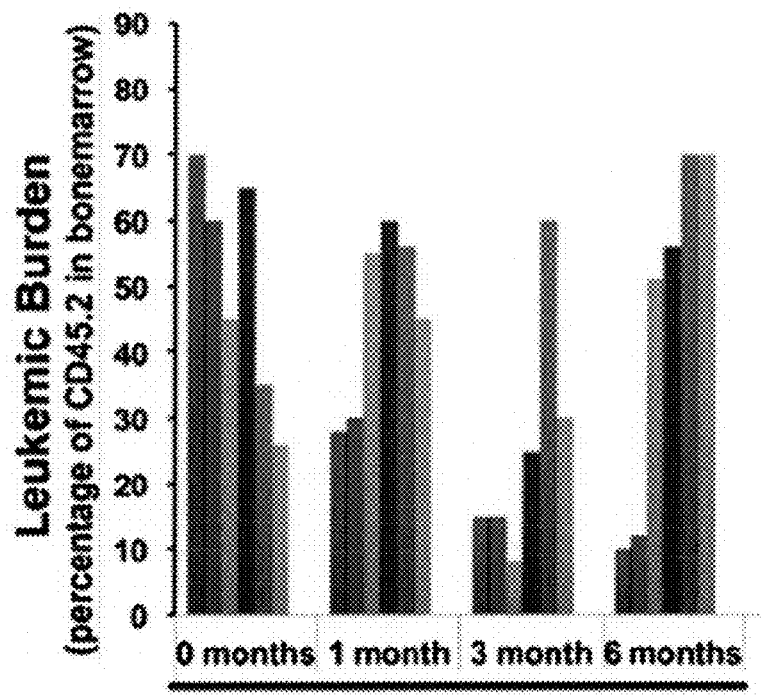
FIGS. 7A-D demonstrate ability of inventive compositions to eradicate leukemic stem cells from SCL-BCR/ABL mice.
Figure 7B:
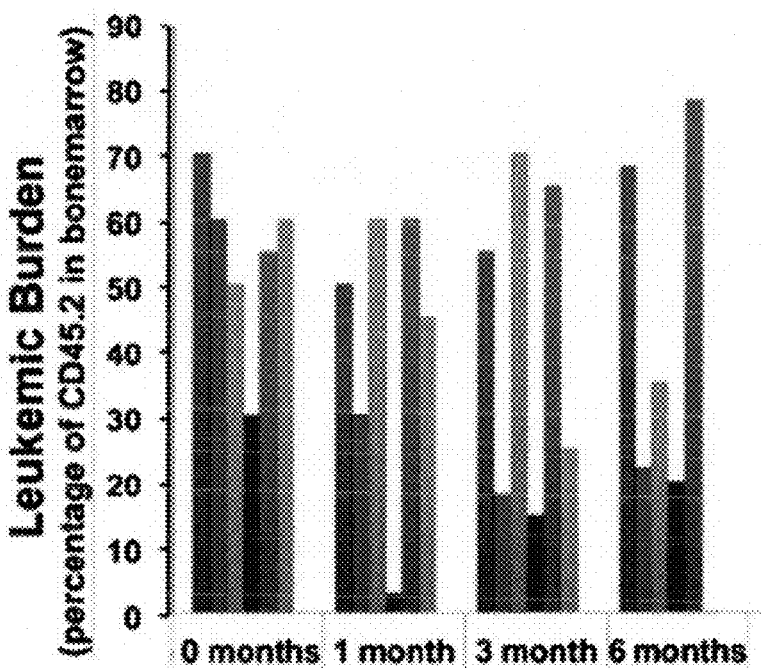
Figure 7C:
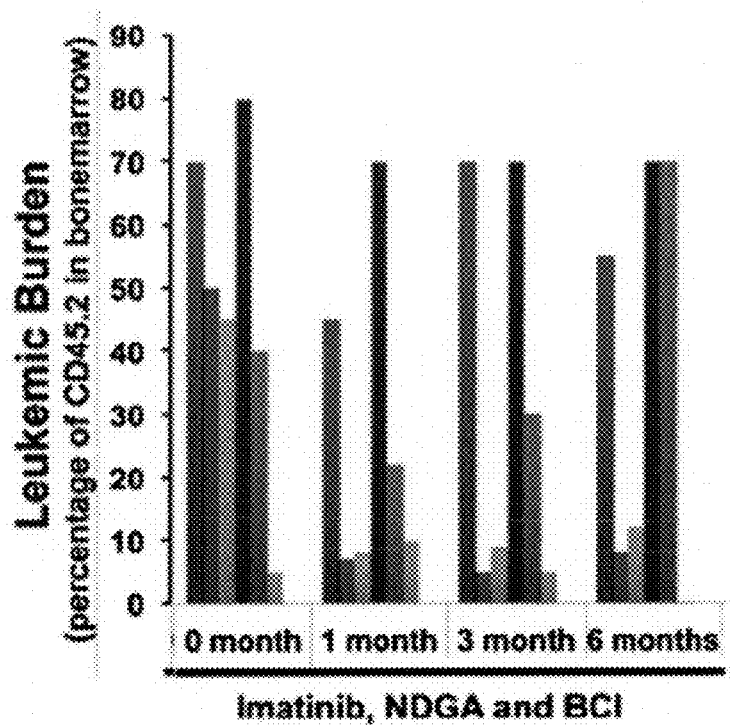
Figure 7D:
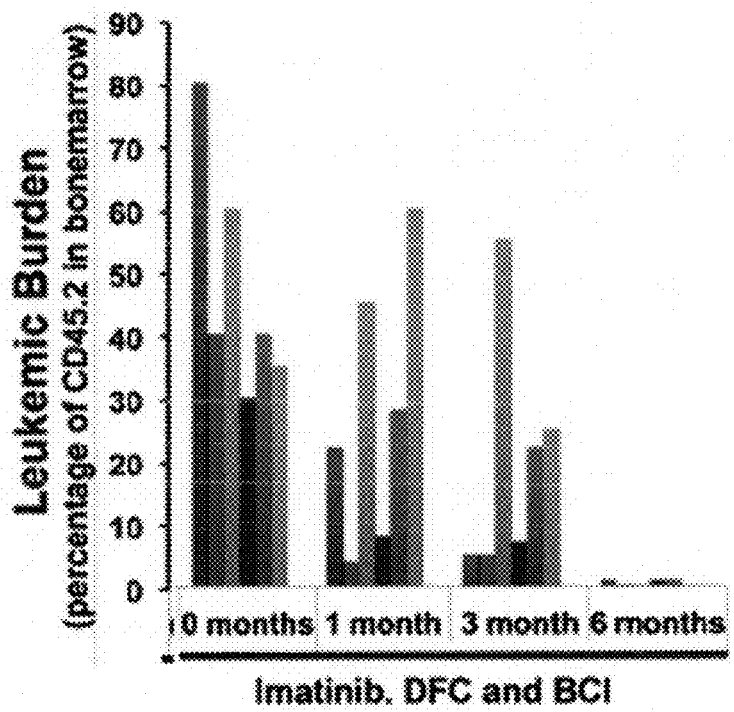

FIG. 6 shows that the combination of Imatinib, DFC and BCI was more effective in curing the mice from leukemia in retroviral-transduction bone marrow-transplantation mouse model of CML. Briefly, c-Kit positive bone marrow cells were harvested from wild type mice and transduced with retroviruses expressing BCR/ABL followed with transplantation of 100,000 transduced cell in each mice with 1 million normal bone marrow cells. In this model, mice develop leukemia within two weeks and all mice die within three to four weeks.

All three combinations, namely DFC, BCI, and Imatinib; curcumin, BCI, and Imatinib; and NDGA, BCI, and Imatinib, cured mice from the disease. DFC, BCI, and Imatinib was most effective in curing mice from the disease. While not being bound by a single theory, the greater efficacy of DFC, BCI, and Imatinib was likely due to DFC's greater bioavailability and binding with c-Fos.

FIGS. 7A-D show that the combination of Imatinib, DFC and BCI completely eradicated the leukemic stem cells from the SCL-BCR/ABL mice. Briefly, bone marrow cells were harvested from the SCL-BCRABL mice and transplanted in Boy/J mice with equal amount of BM cells from the Boy/J mice. After one month, transplantation chimerism was recorded by measuring the percentage of CD45.2 (BCR/ABL) from the bone marrow aspirates which is labeled as 0 month. After one-month drug treatments were started, and leukemic burdens were monitored by measuring the levels of CD45.2. As shown in FIGS. 7A-D, the combination of Imatinib, DFC and BCI completely cured the mice.

In vivo data unequivocally demonstrated that Dusp-1 and c-Fos mediated BCR-ABL addiction and leukemic stem cell biology. Dusp-1 and c-Fos inhibitors are thus targets for curative therapy in CML.

Tyrosine-kinase inhibitor (TKI) therapy for human cancers is not curative, and relapse occurs owing to the continued presence of tumor cells, referred to as minimal residual disease (MRD). The survival of MRD stem or progenitor cells in the absence of oncogenic kinase signaling, a phenomenon referred to as intrinsic resistance, depends on diverse growth factors. Here we report that oncogenic kinase and growth-factor signaling converge to induce the expression of the signaling proteins FBJ osteosarcoma oncogene (c-FOS, encoded by Fos) and dual-specificity phosphatase 1 (DUSP1). Genetic deletion of Fos and Dusp1 suppressed tumor growth in a BCR-ABL fusion protein kinase-induced mouse model of chronic myeloid leukemia (CML). Pharmacological inhibition of c-FOS, DUSP1 and BCR-ABL eradicated MRD in multiple in vivo models, as well as in mice xenotransplanted with patient-derived primary CML cells. Growth-factor signaling also conferred TKI resistance and induced FOS and DUSP1 expression in tumor cells modeling other types of kinase-driven leukemias. Our data demonstrate that c-FOS and DUSP1 expression levels determine the threshold of TKI efficacy, such that growth-factor-induced expression of c-FOS and DUSP1 confers intrinsic resistance to TKI therapy in a wide-ranging set of leukemias, and might represent a unifying Achilles' heel of kinase-driven cancers.

Protein kinases are frequently activated in a variety of human cancers and represent attractive drug targets. In this regard, chronic myeloid leukemia (CML) represents an important paradigm, given that the success of imatinib in treating patients with CML provided proof of concept for targeted anti-kinase therapy and paved the way for the development of TKI therapy for several solid tumor types (Daley, G. Q., Van Etten, R. A. & Baltimore, D. Induction of chronic myelogenous leukemia in mice by the P210bcr/abl gene of the Philadelphia chromosome. Science 247, 824-830 (1990); Druker, B. J. et al. Effects of a selective inhibitor of the Abl tyrosine kinase on the growth of Bcr-Abl positive cells. Nat. Med. 2, 561-566 (1996)). Despite the impressive response to TKI therapy in the clinic, it is not curative because a small population of cancer cells are insensitive to treatment, manifesting as minimal residual disease (MRD) (O'Hare, T., Zabriskie, M. S., Eiring, A. M. & Deininger, M. W. Pushing the limits of targeted therapy in chronic myeloid leukaemia. Nat. Rev. Cancer 12, 513-526 (2012)). The cells responsible for MRD in CML are referred to as leukemia-initiating cells (LICs), whereas those responsible for MRD in solid tumors are referred to as cancer stem cells (CSCs). In ~50-60% of patients with CML, continuous drug treatment is needed to prevent MRD cells from reinstating the disease (Rousselot, P. et al. Imatinib mesylate discontinuation in patients with chronic myelogenous leukemia in complete molecular remission for more than 2 years. Blood 109, 58-60 (2007); Mahon, F. X. et al. Discontinuation of imatinib in patients with chronic myeloid leukaemia who have maintained complete molecular remission for at least 2 years: the prospective, multicentre Stop Imatinib (STIM) trial. Lancet Oncol. 11, 1029-1035 (2010); Ross, D. M. et al. Safety and efficacy of imatinib cessation for CML patients with stable undetectable minimal residual disease: results from the TWISTER study. Blood 122, 515-522 (2013)). MRD cells serve as a reservoir that can develop TKI resistance by acquiring mutations or by activating alternative survival mechanisms (Chu, S. et al. Detection of BCR-ABL kinase mutations in CD34+ cells from chronic myelogenous leukemia patients in complete cytogenetic remission on imatinib mesylate treatment. Blood 105, 2093-2098 (2005); Savona, M. & Talpaz, M. Getting to the stem of chronic myeloid leukaemia. Nat. Rev. Cancer 8, 341-350 (2008); Azam, M., Latek, R. R. & Daley, G. Q. Mechanisms of autoinhibition and STI-571/imatinib resistance revealed by mutagenesis of BCR-ABL. Cell 112, 831-843 (2003)). Even the most potent kinase inhibitors are ineffective against LICs that are present in MRD (O'Hare, T., Zabriskie, M. S., Eiring, A. M. & Deininger, M. W. Pushing the limits of targeted therapy in chronic myeloid leukaemia. Nat. Rev. Cancer 12, 513-526 (2012); Krause, D. S. & Van Etten, R. A. Tyrosine kinases as targets for cancer therapy. N. Engl. J. Med. 353, 172-187 (2005)).

Oncogene addiction refers to the exquisite dependence of transformed cells on a single mutant protein or signaling pathway for survival and proliferation (Weinstein, I. B. Cancer. Addiction to oncogenes—the Achilles heal of cancer. Science 297, 63-64 (2002)). The therapeutic response to TKIs is mediated by oncogene addiction to mutant tyrosine-kinase oncoproteins (Weinstein, I. B. Cancer. Addiction to oncogenes—the Achilles heal of cancer. Science 297, 63-64 (2002); Sawyers, C. L. Shifting paradigms: the seeds of oncogene addiction. Nat. Med. 15, 1158-1161 (2009); Pagliarini, R., Shao, W. & Sellers, W. R. Oncogene addiction: pathways of therapeutic response, resistance, and road maps toward a cure. EMBO Rep. 16, 280-296 (2015)). Multiple theories, including signaling-network dysregulation, synthetic lethality (Reddy, A. & Kaelin, W. G., Jr. Using cancer genetics to guide the selection of anticancer drug targets. Curr. Opin. PharmacoL 2, 366-373 (2002); Kaelin, W. G., Jr. The concept of synthetic lethality in the context of anticancer therapy. Nat. Rev. Cancer 5, 689-698 (2005)), genetic streamlining (Kamb, A. Consequences of nonadaptive alterations in cancer. Mol. Biol. Cell 14, 2201-2205 (2003); Mills, G. B., Lu, Y. & Kohn, E. C. Linking molecular therapeutics to molecular diagnostics: inhibition of the FRAP/RAFT/TOR component of the PI3K pathway preferentially blocks PTEN mutant cells in vitro and in vivo. Proc. Natl. Acad. Sci. USA 98, 10031-10033 (2001)), and oncogenic shock (Sharma, S. V. & Settleman, J. Exploiting the balance between life and death: targeted cancer therapy and "oncogenic shock". Biochem. Pharmacol. 80, 666-673 (2010); Sharma, S. V. & Settleman, J. Oncogene addiction: setting the stage for molecularly targeted cancer therapy. Genes Dev. 21, 3214-3231 (2007)), have attempted to explain how cells become oncogene addicted and how acute inhibition of an oncoprotein induces cell death. However, it is still not understood how MRD cells that do not respond to TKI therapy escape addiction to the driver oncogene. Recent studies have revealed that growth-factor signaling mediates resistance to TKI therapy in both leukemia and solid organ tumors (Corbin, A. S. et al. Human chronic myeloid leukemia stem cells are insensitive to imatinib despite inhibition of BCR-ABL activity. J. Clin. Invest. 121, 396-409 (2011); Straussman, R. et al. Tumour micro-environment elicits innate resistance to RAF inhibitors through HGF secretion. Nature 487, 500-504 (2012); Wilson, T. R. et al. Widespread potential for growth-factor-driven resistance to anticancer kinase inhibitors. Nature 487, 505-509 (2012)), but it remains to be determined whether intrinsic resistance conferred by a diverse set of growth factors utilizes distinct or shared molecular pathways. For instance, interleukin (IL)-3, IL-6, stem cell factor (SCF), fms-like tyrosine kinase 3 ligand (FLT3L) and granulocyte colony-stimulating factor (G-CSF) signaling in CML progenitor cells confer intrinsic resistance to imatinib. Similarly, hepatocyte growth factor (HGF) and neuregulin 1 (NRG1) signaling confer intrinsic resistance to protooncogene protein B-raf (BRAF) and epidermal growth factor receptor (EGFR) inhibitors in solid tumors (Corbin, A. S. et al. Human chronic myeloid leukemia stem cells are insensitive to imatinib despite inhibition of BCR-ABL activity. J. Clin. Invest. 121, 396-409 (2011); Straussman, R. et al. Tumour micro-environment elicits innate resistance to RAF inhibitors through HGF secretion. Nature 487, 500-504 (2012); Wilson, T. R. et al. Widespread potential for growth-factor-driven resistance to anticancer kinase inhibitors. Nature 487, 505-509 (2012)).

Growth-factor-induced Expression of c-FOS and DUSP1 Confers TKI Resistance

Figure 8A:
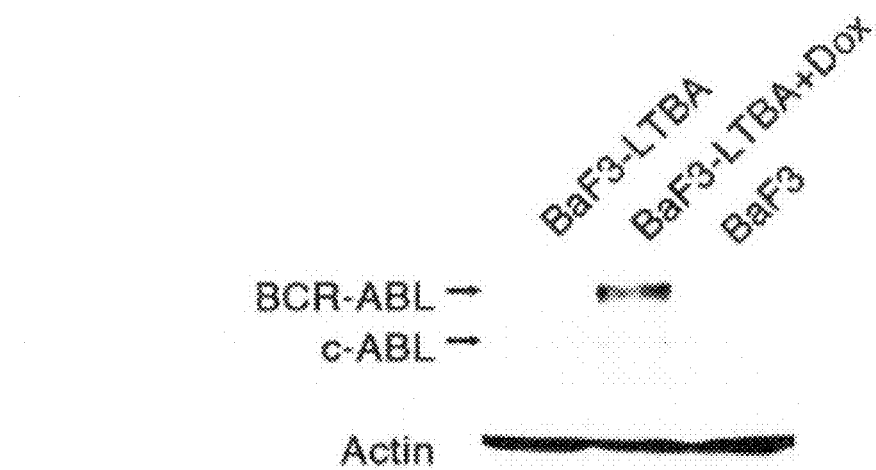
Figure 8B:
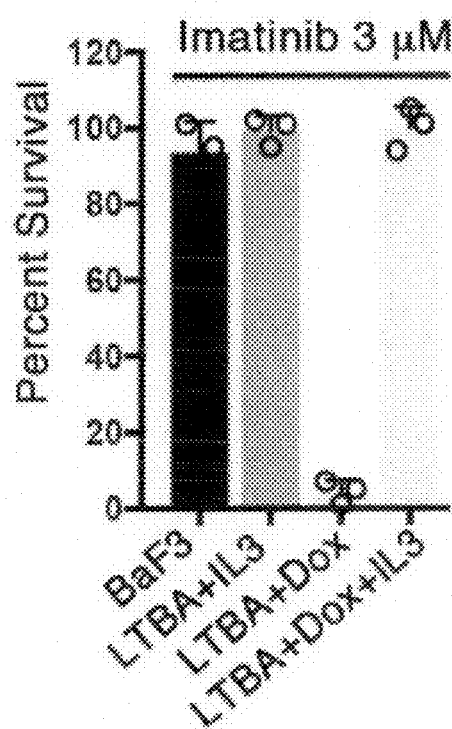
Figure 8C:
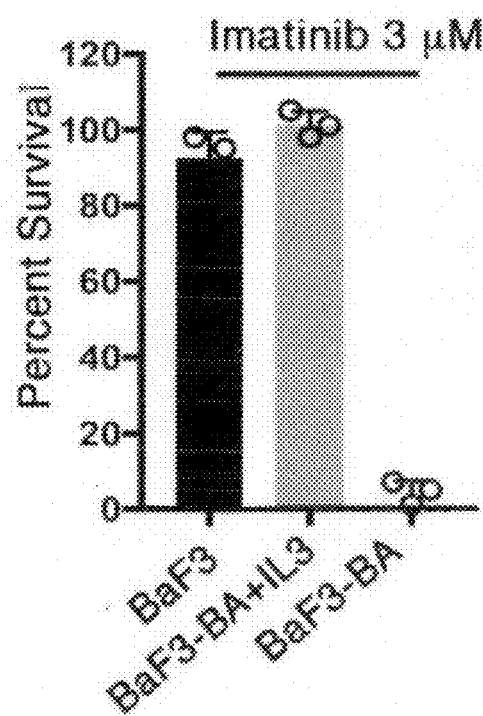
Figure 8D:
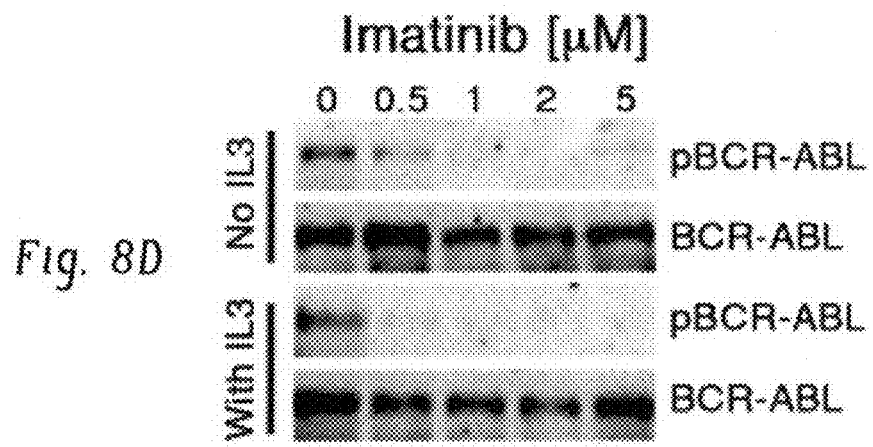
Figure 8E:
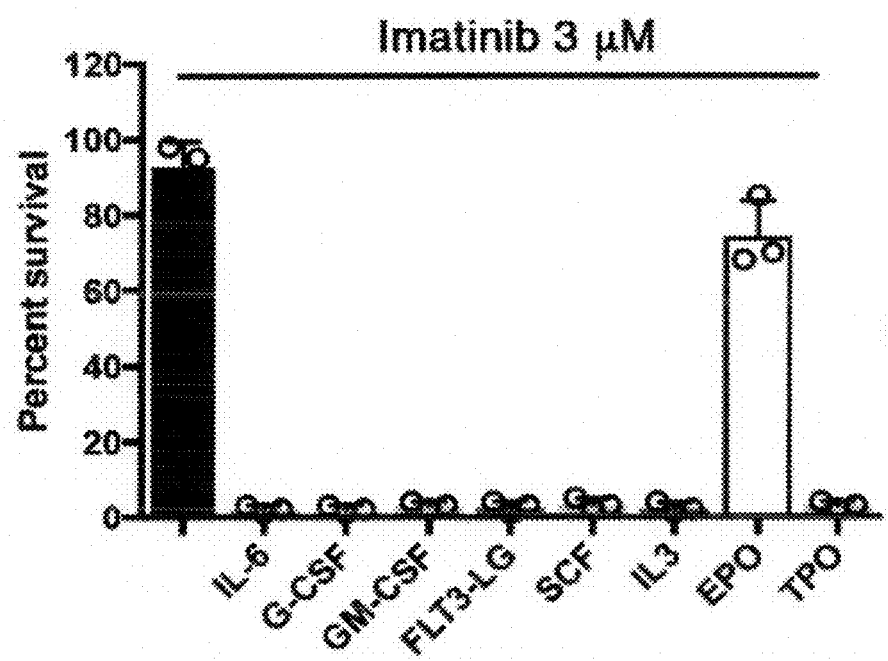
Figure 9A:
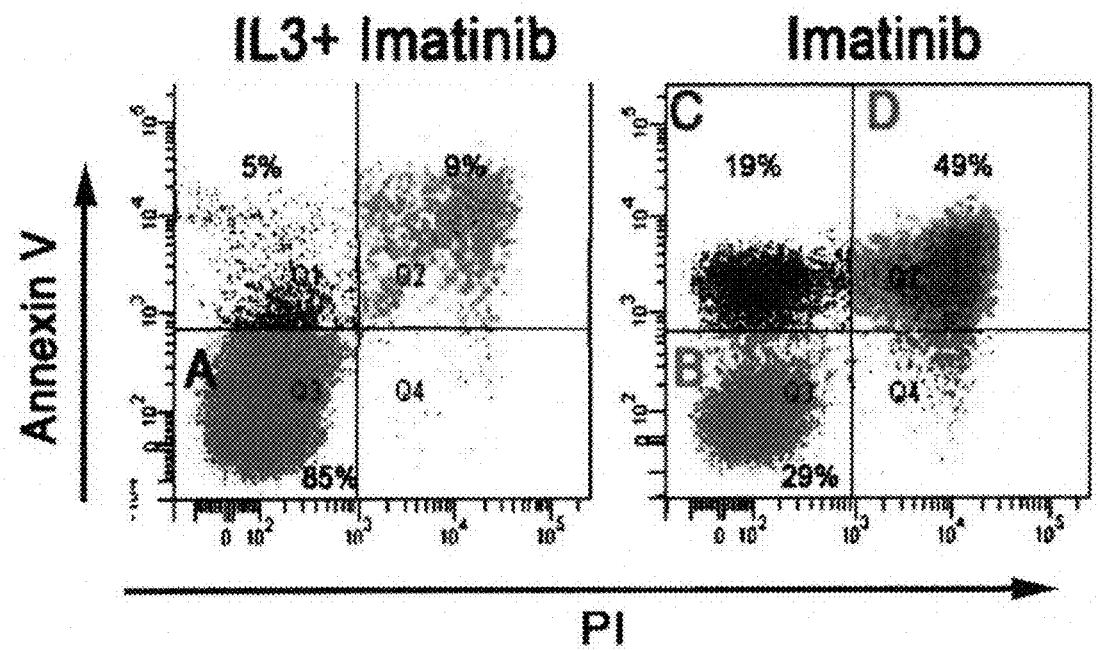
Figure 9B:
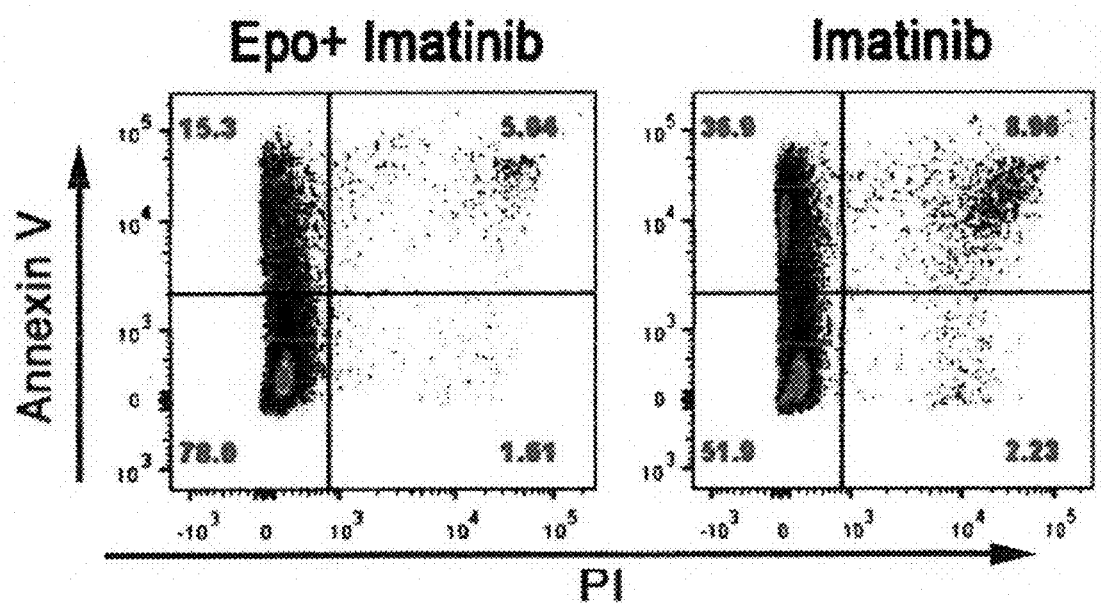

To understand how growth-factor signaling induces intrinsic resistance to TKI treatment, we modeled growth-factor-induced-mitigation of TKI response using the IL-3-dependent BaF3 mouse cell line. We generated BaF3 cells with tetracycline-inducible expression of BCRABL (BaF3-LTBA; FIG. 8A), as well as cells with constitutive BCR-ABL expression (BaF3-BA9). Imatinib treatment of both BaF3-LTBA cells and BaF3-BA cells caused cell death, whereas the addition of IL-3 conferred resistance to imatinib, even in the case of sustained inhibition of BCR-ABL enzymatic activity (FIG. 8B-D and FIG. 9A). Similarly, erythropoietin treatment conferred imatinib resistance in the human BCR-ABL+ cell line K562 (an erythromyeloblastoid leukemia cell line derived from a patient with blast-crisis CML; FIG. 8E and FIG. 9B). Thus, we were able to recapitulate cytokine and/or growth-factor-induced resistance to imatinib in vitro.

Figure 8F:
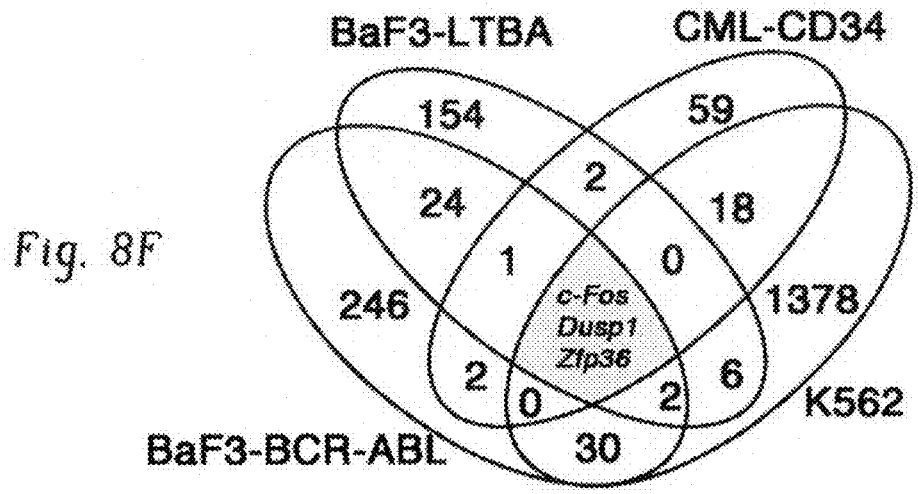
Figure 8C:
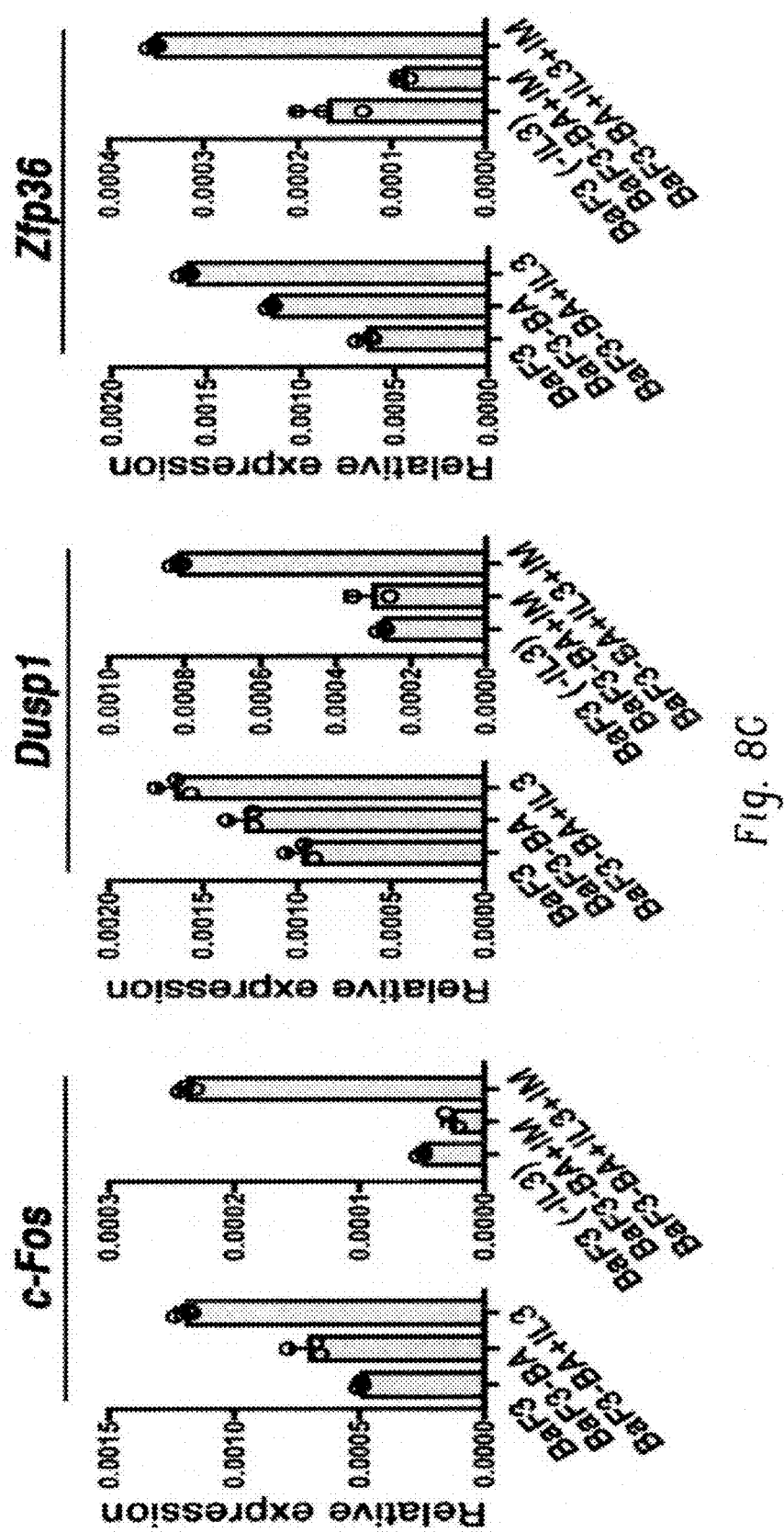

We hypothesized that expression of the critical genes mediating TKI resistance would be modulated by BCR-ABL, growth-factor signaling, and TKI treatment. We therefore compared the expression profiles of BCR-ABL-induced BaF3-LTBA cells with and without IL-3 treatment (192 genes were differentially expressed; FIG. 9C), as well as imatinib-treated BaF3-BA cells with and without IL-3 (308 genes were differentially expressed; FIG. 9D). Next, we evaluated erythropoietin-modulated gene expression in imatinib-treated K562 cells (1,338 genes were differentially expressed; FIG. 9E). Finally, we analyzed existing gene-expression profiles from primary bone marrow (BM)-derived BCR-ABL+CD34+ cells collected from patients with CML before and after 1 week of imatinib treatment (Bruennert, D. et al. Early in vivo changes of the transcriptome in Philadelphia chromosome-positive CD34+ cells from patients with chronic myelogenous leukaemia following imatinib therapy. Leukemia 23, 983-985 (2009)), and we identified genes that were differentially expressed in the surviving marrow cells (85 genes were differentially expressed; FIG. 9F). When these four data sets were compared, only three differentially expressed genes were common to all comparisons: FOS (also known as c-FOS), dual-specificity phosphatase-1 (DUSP1) and ZFP36 (FIG. 8F and FIG. 9G). c-Fos belongs to the family of activator protein 1 (AP1) transcription factors implicated in the regulation of cell proliferation, survival, apoptosis, transformation, and oncogenesis (Eferl, R. & Wagner, E. F. AP-1: a double-edged sword in tumorigenesis. Nat. Rev. Cancer 3, 859-868 (2003)). DUSP1 is a nuclear protein that provides feedback regulation to MAPK signaling by inactivating MAPKs25 and has been implicated in the regulation of inflammation, immune regulation, and chemoresistance in cancer (Lawan, A., Shi, H., Gatzke, F. & Bennett, A. M. Diversity and specificity of the mitogen-activated protein kinase phosphatase-1 functions. Cell. MoL Life Sci. 70, 223-237 (2013); Jeffrey, K. L., Camps, M., Rommel, C. & Mackay, C. R. Targeting dual-specificity phosphatases: manipulating MAP kinase signalling and immune responses. Nat. Rev. Drug Discov. 6, 391-403 (2007)). ZFP36 is an RNA-binding protein that has been implicated in cancer development, inflammation, and immune functions (Brooks, S. A. & Blackshear, P. J. Tristetraprolin (TTP): interactions with mRNA and proteins, and current thoughts on mechanisms of action. Biochim. Biophys. Acta 1829, 666-679 (2013)).

Figure 8H:
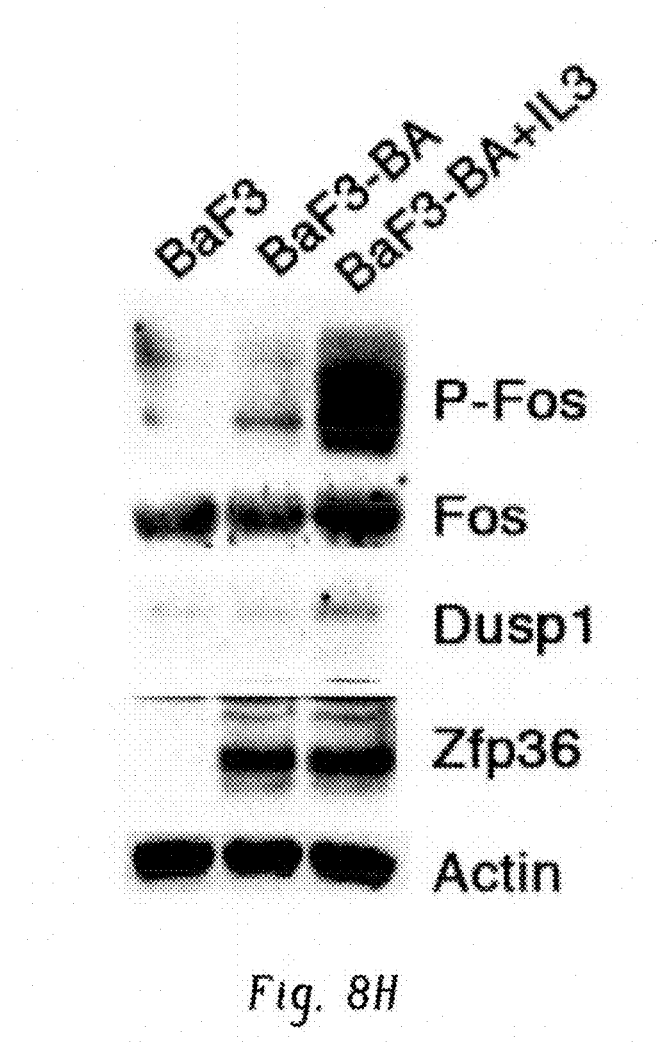
Figure 8I:
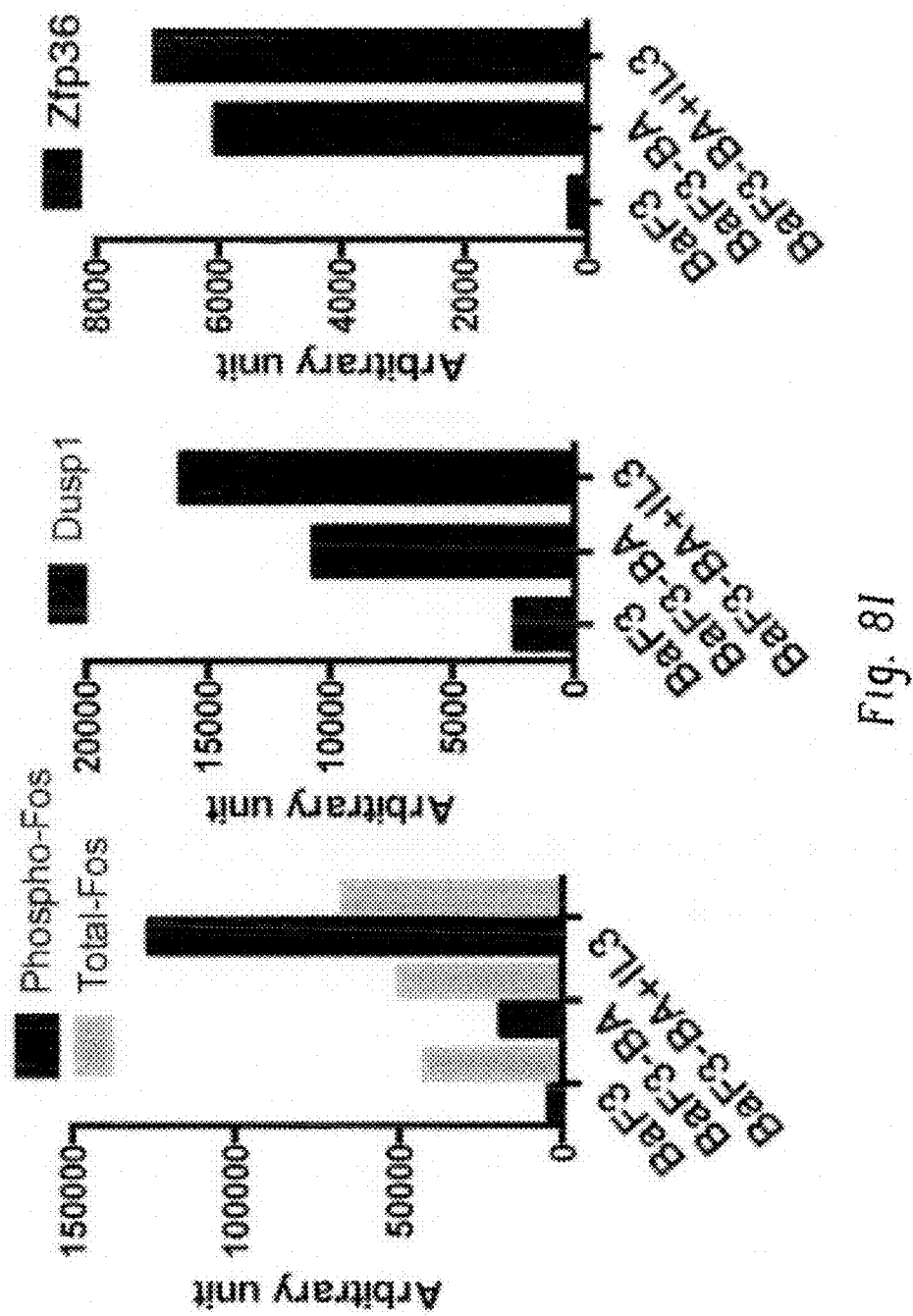
Figure 8J:
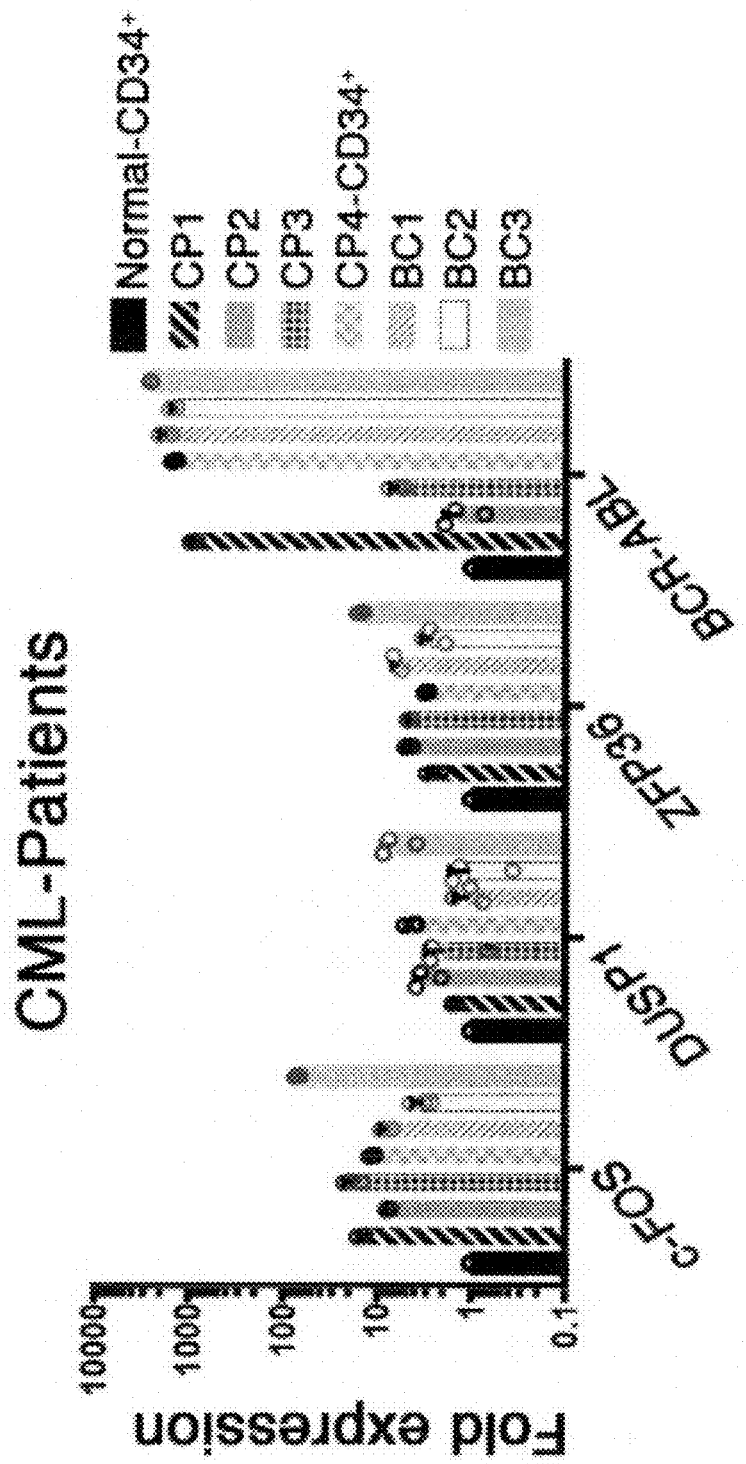
Figure 10A:
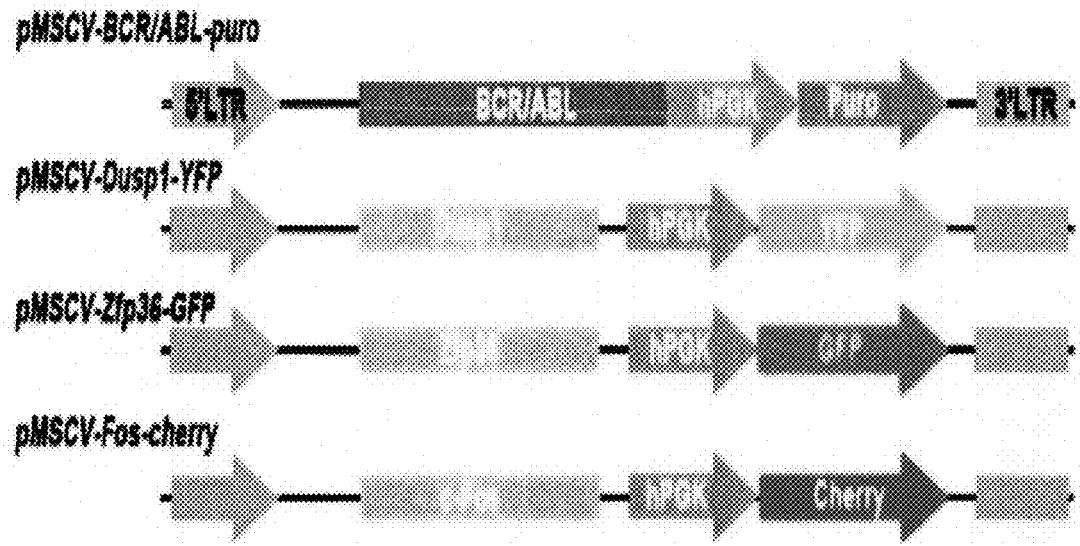
Figure 10B:
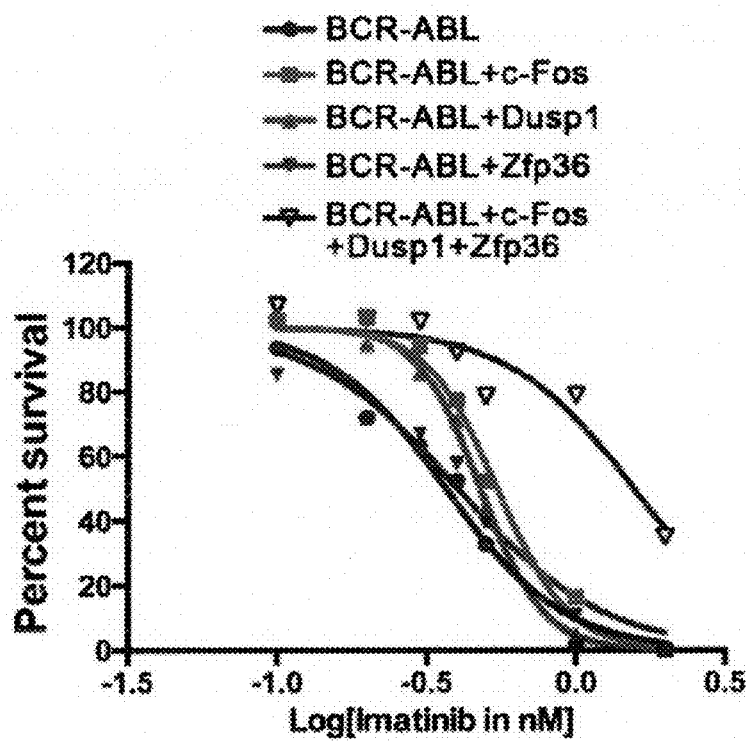
Figure 10G:
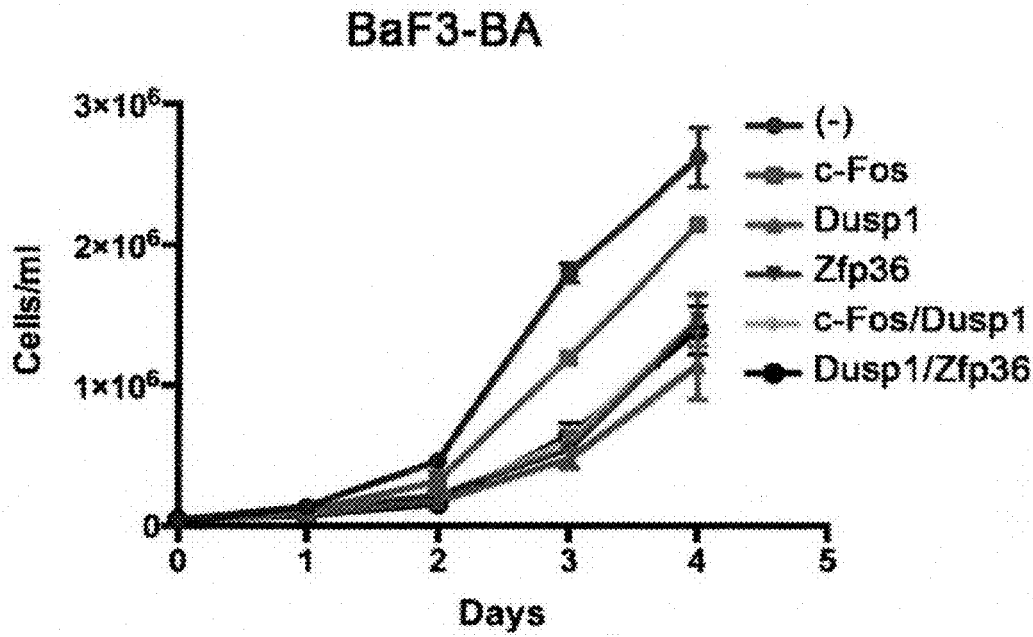
Figure 10F:
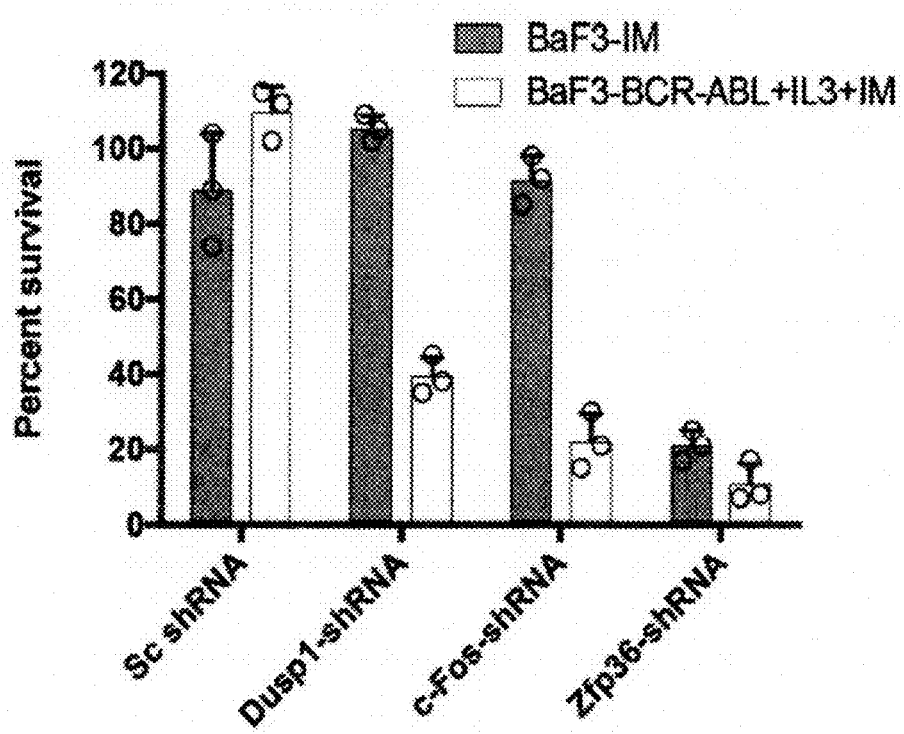

In support of the hypothesis that oncogenic and growth-factor signaling modulate Fos, Dusp1, and Zfp36 expression, we found that both BCR-ABL and imatinib induced expression of these genes in BaF3-BA cells (FIG. 8G-I). Similarly, expression analysis of patient samples from chronic and blast-phase CML revealed higher (2-10-fold) expression of FOS, DUSP1, and ZFP36 as compared to that in normal CD34+ cells (FIG. 8J; the CML patient samples used in this study are described in Table 2). Whereas treatment with imatinib alone downregulated the expression of these genes, treatment with imatinib plus growth factor (IL-3) resulted in 4-5-fold higher expression of these genes, as compared to BaF3-BA plus imatinib (FIG. 8G). In the absence of IL-3, ectopic expression of either c-Fos or DUSP1 led to modest resistance to imatinib, whereas ectopic expression of ZFP36 did not have an effect (FIG. 10A,B). However, similarly to IL-3, ectopic expression of Fos, Dusp1, and Zfp36 together in BaF3-BA cells impaired the inhibitory effect of imatinib on cell survival (FIG. 10B). Conversely, the depletion of Fos, Dusp1, and Zfp36 (either each alone or in combination) by shRNA-mediated knockdown reduced BCR-ABL-dependent proliferation and survival in BaF3-BA cells, whereas parental BaF3 cells were not affected (FIG. 10C-F). These results suggest that Fos, Dusp1, and Zfp36 are functional mediators of growthfactor-induced imatinib resistance. Furthermore, knockdown of Fos and Dusp1 alone or together sensitized BaF3-BA cells to imatinib, even in the presence of IL-3 (FIG. 10G). However, the depletion of Zfp36 sensitized parental BaF3 and BaF3-BA cells equally to imatinib, which suggests that, unlike Fos and Dusp1, Zfp36 is not differentially required by BCR-ABL-expressing cells. Therefore, we focused subsequent analyses on Fos and Dusp1.

TABLE 2

Table 2. Description of CML patient samples

| Sample ID | Diagnosis | Treatment | Age | Sex | FISH (% Ph+) | Karyotype comments | Origin | BCR-ABL1 sequencing |
|---|---|---|---|---|---|---|---|---|
| CP1 | CML - Chronic Phase | Treated with Hydrea (1000 mg) | 40 | Male | 98 | 46, XY, t(9; 22) | Peripheral Blood | WT |
| CP2 | CML - Chronic Phase | Untreated | 30 | Female | 13 | 46, XX, t(9; 22) | Bone Marrow | WT |
| CP3 | CML - Chronic Phase | Untreated | 30 | Female | 64 | 46, XX, t(9; 22) | Bone Marrow | WT |
| CP4 | CML - Chronic Phase | Untreated | 35 | Male | 99.2 | 46, XY, t(9; 22) | Peripheral Blood | WT |
| BC1 | CML - Blast Crisis | Untreated | 38 | Male | 72.5 | 46, XY, t(9; 22) | Peripheral Blood | WT |
| BC2 | CML - Blast Crisis | Untreated | 59 | Female | 13.5 | 46, XX, t(9; 22) | Peripheral Blood | WT |
| BC3 | CML - Blast Crisis | Untreated | 34 | Male | 64 | 46, XY, t(9; 22). Mutation in ASXL1. | Peripheral Blood | WT |

Deletion of Fos and Dusp1 Abrogates Intrinsic TKI Resistance

Figure 11A:
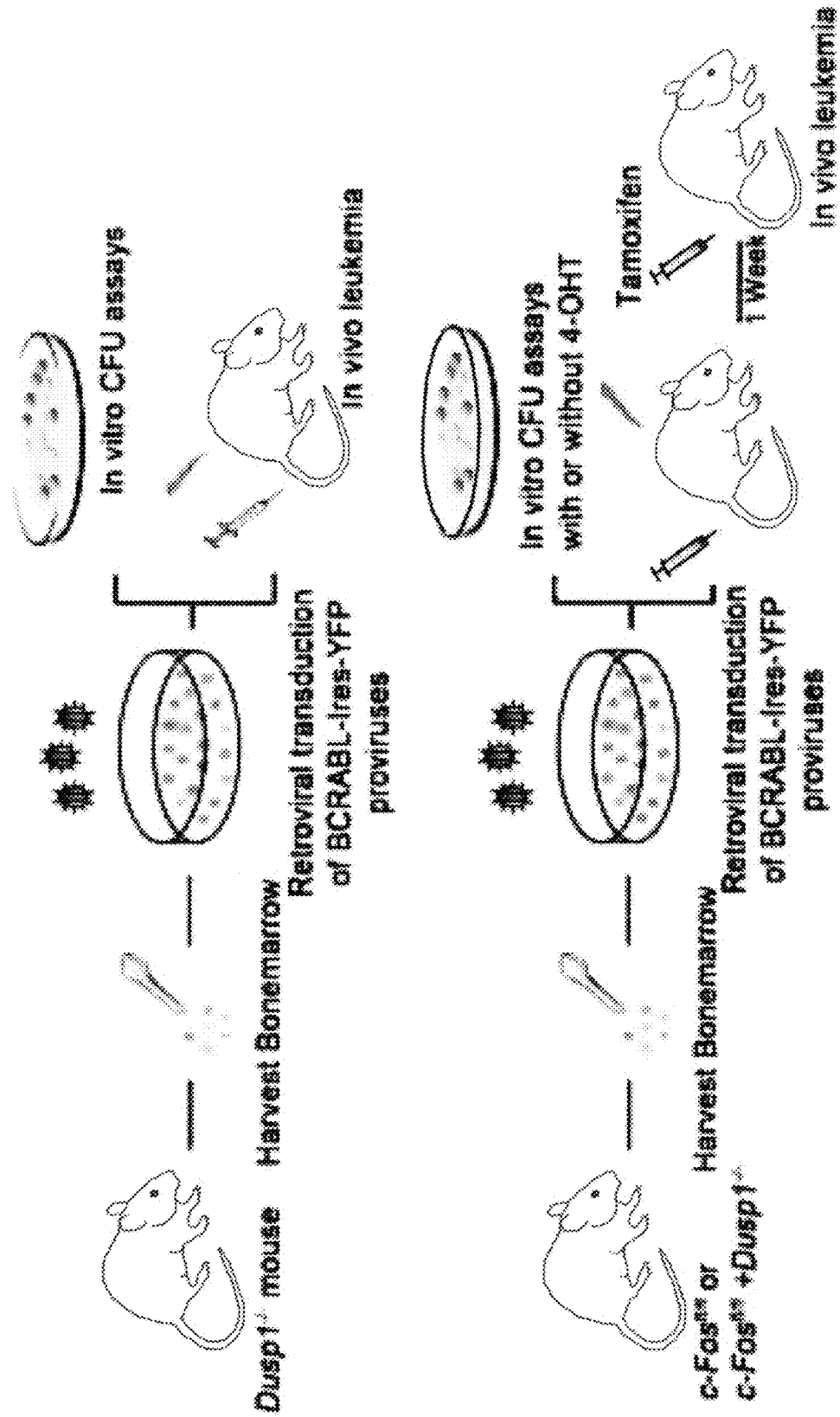
FIGS. 11A-O show genetic deletion of Fos and Dusp1 increases the response of BCR-ABL-induced leukemia to imatinib.
Figures 11B, 11C, 11D:
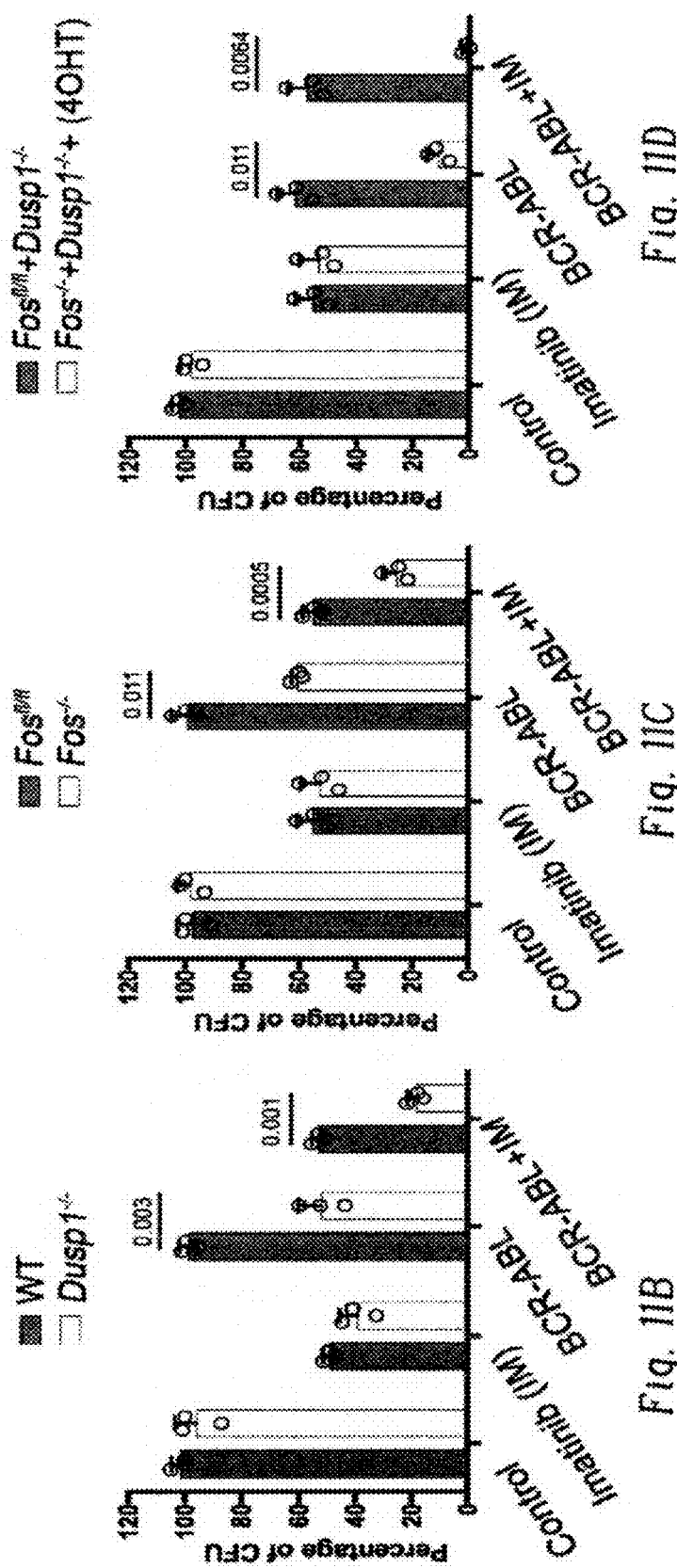
FIGS. 11B-D show percentage of CFUs from Kit$^+$ cells expressing BCR-ABL in the absence of Dusp1 (FIG. 11B), Fos (FIG. 11C), and both Fos and Dusp1 (FIG. 11D). The data show the mean colony number±s.d. (n=3; P values are shown above the compared bars by Student's t-test).
Figure 11E:
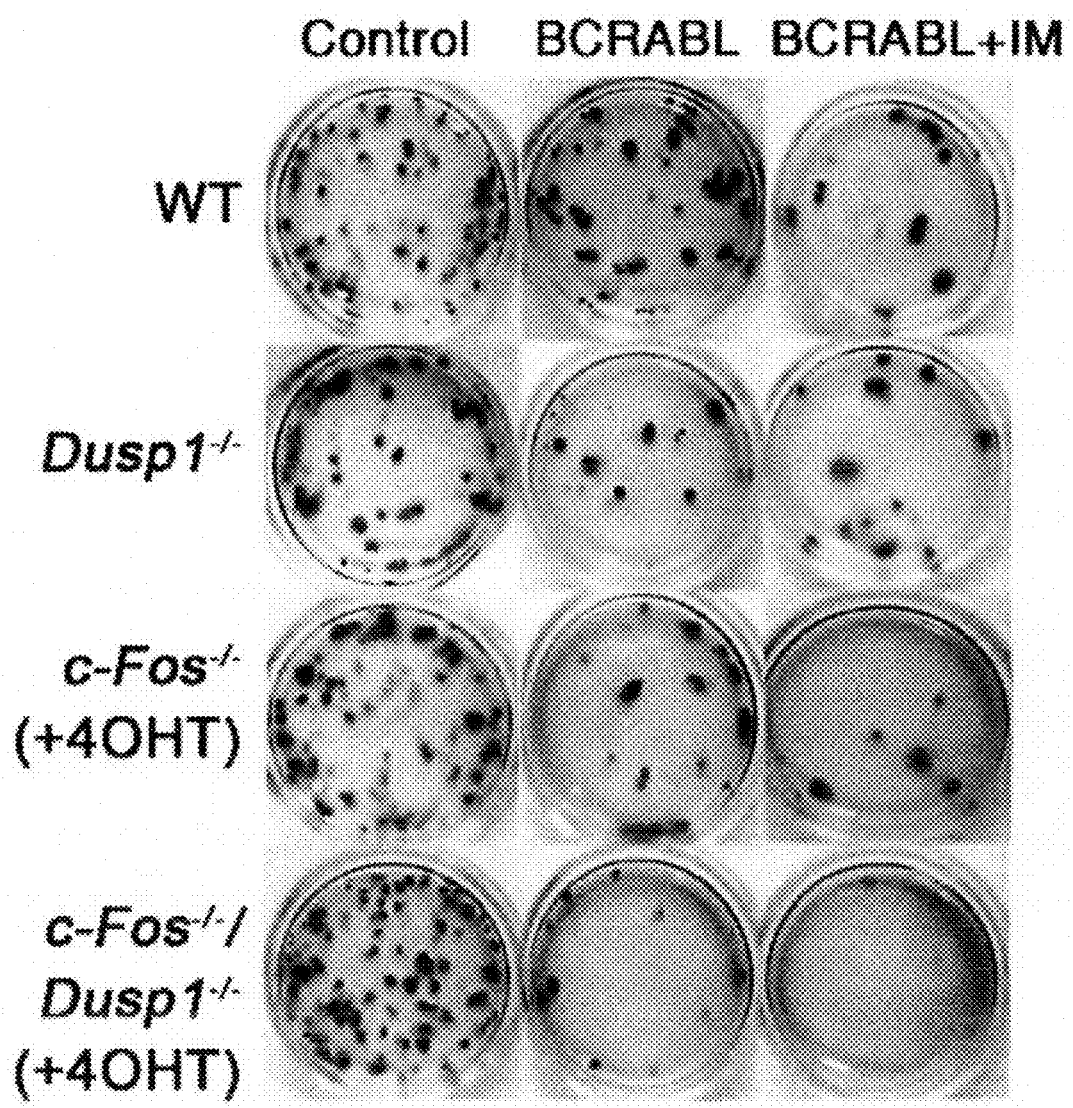
FIG. 11E shows representative photographs of BCR-ABL-positive colonies described in FIGS. 11B-D.
Figures 11F, 11G, 11H:
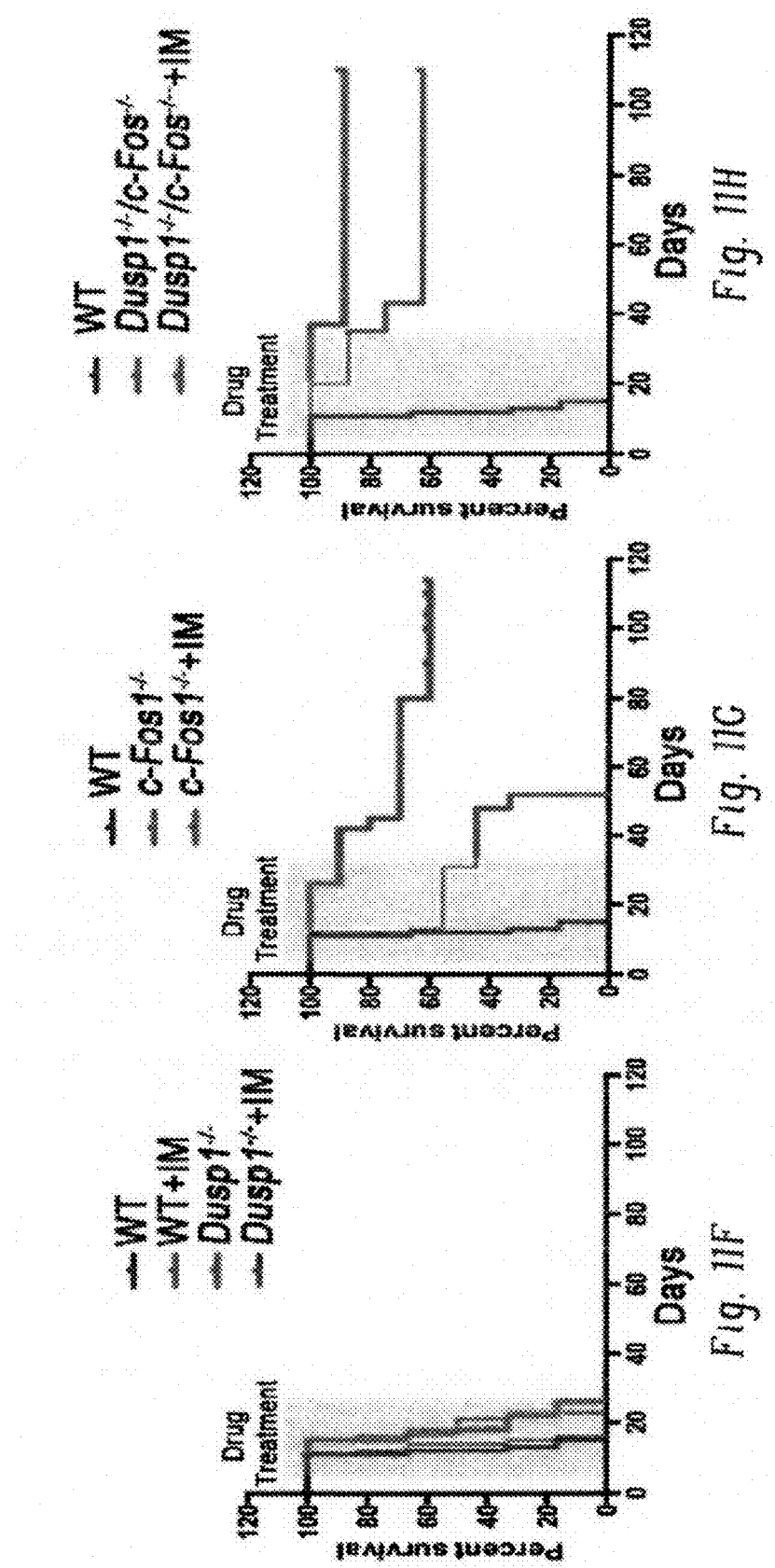
FIGS. 11F, H, J show survival curves of mice transplanted with BCR-ABL-YFP transduced Kit$^+$ cells from WT, Dusp1$^{-/-}$ mice (FIG. 11F) ROSACre$^{ERT2}$Fos$^{fl/fl}$ mice (FIG. 11H), and ROSACre$^{ERT2}$Fos$^{fl/fl}$Dusp1$^{-/-}$ mice (FIG. 11J). Mice were untreated or treated with imatinib. Data are from two independent transplantation experiments (n=6 mice per group)
In FIGS. 11H, J, transplant recipients were treated with three doses of 2 mg/kg tamoxifen injection to delete Fos.
FIGS. 11G, I, K show leukemic burden in mice transplanted with Dusp1$^{-/-}$ (FIG. 11G), Fos$^{-/-}$ (FIG. 11I), and Fos$^{-/-}$Dusp1$^{-/-}$ (FIG. 11K) Kit+ cells, as measured by the percentage of YFP+ cells in peripheral blood. Dead mice are represented with an X.
Figure 12A:
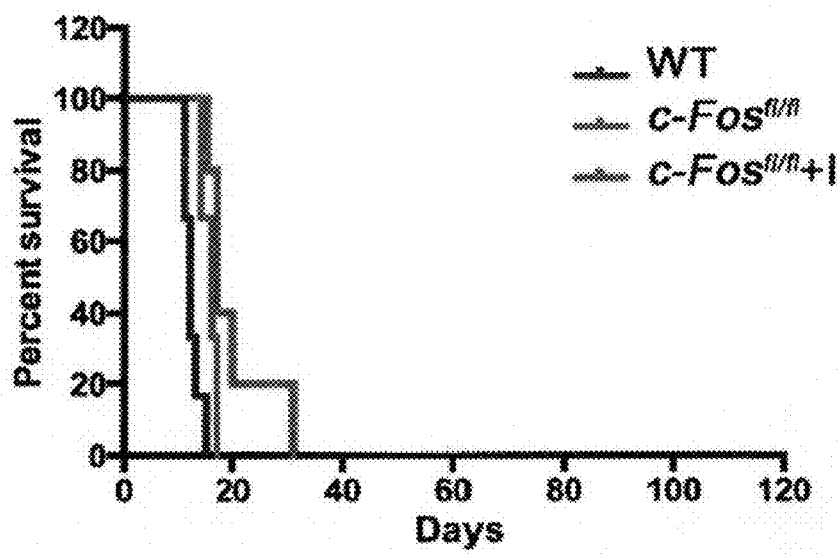
Figure 12B:
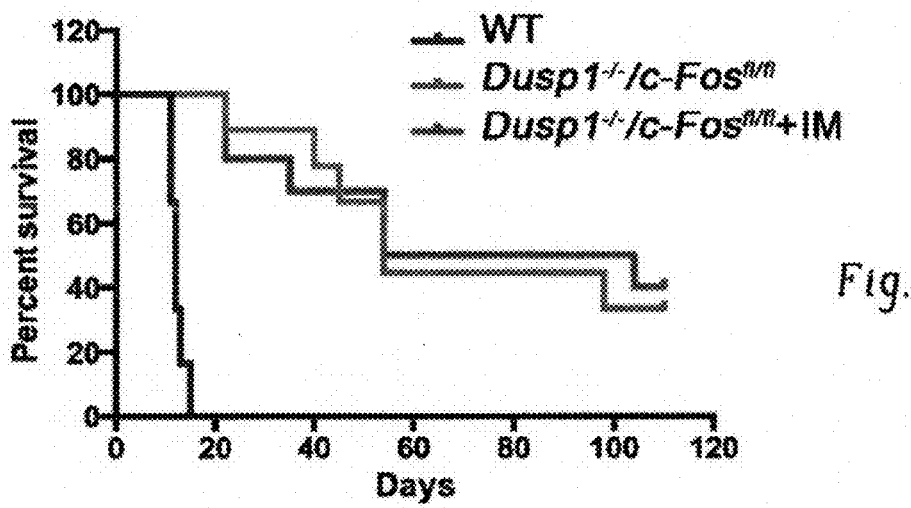
Figure 12C:
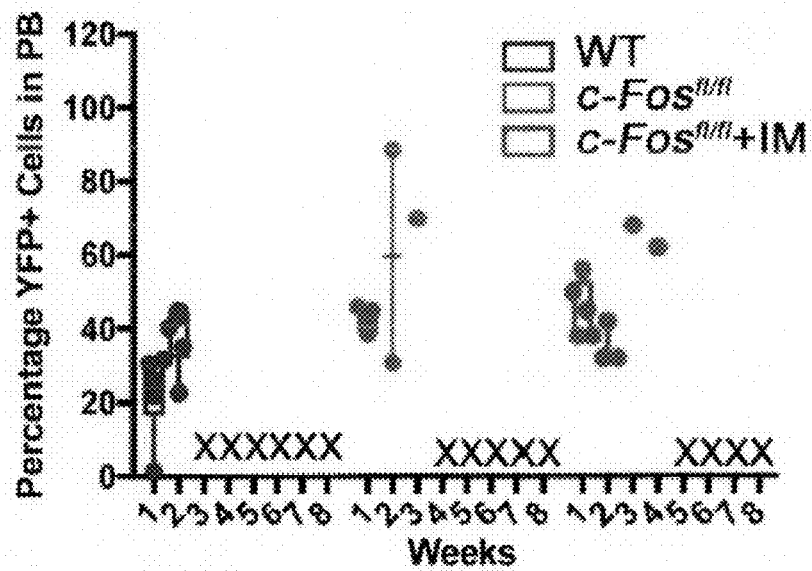
Figure 12D:
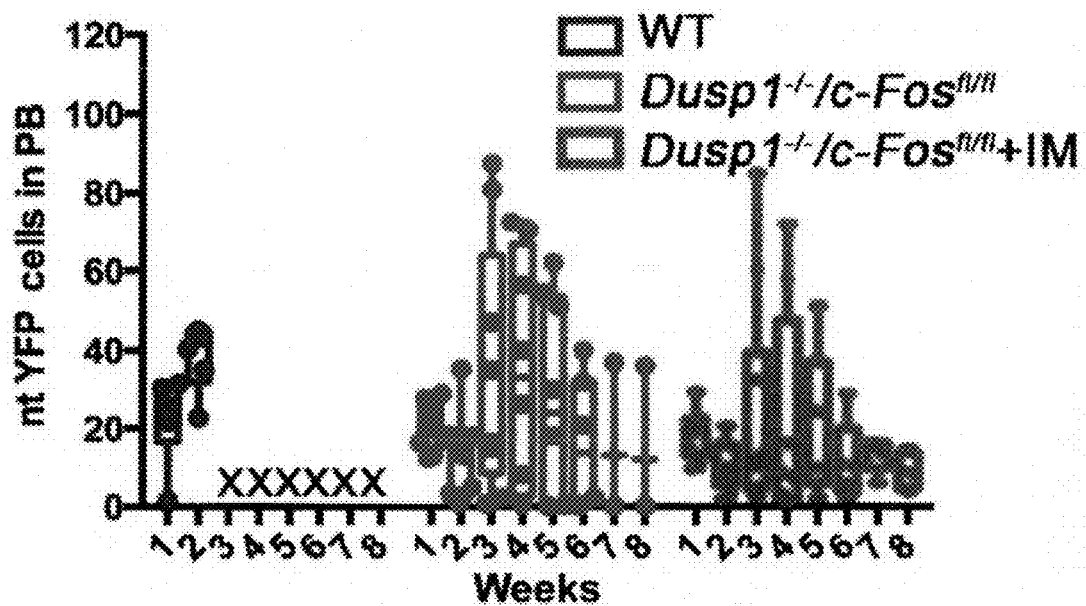

To determine the roles of c-Fos and DUSP1 in BCR-ABL-induced leukemogenesis, we determined the effects of the deletion of either Dusp1$^{-/-}$ (Dorfman, K. et al. Disruption of the erp/mkp-1 gene does not affect mouse development: normal MAP kinase activity in ERP/MKP-1-deficient fibroblasts. Oncogene 13, 925-931 (1996)) or Fos$^{fl/fl}$ (ROSACre$^{ERT2}$Fos$^{fl/fl}$) (Zhang, J. et al. c-fos regulates neuronal excitability and survival. Nat. Genet. 30, 416-420 (2002)), or both genes (ROSACre$^{ERT2}$Fos$^{fl/fl}$;Dusp1$^{-/-}$). We used hematopoietic Kit+ cells transduced with BCR-ABL-Ires-YFP retroviruses for in vitro colony-forming unit (CFU) assays and for generating an in vivo model of CML (FIG. 11A). Genetic deletion of Fos or Dusp1 significantly reduced (by 50%) the number of CFUs generated by BCR-ABL-expressing Kit+ cells, whereas CFU generation by control cells (Kit+ cells transduced with a MSCV-Ires-YFP virus) was not affected (FIG. 11B,C). The deletion of Fos and Dusp1 alone sensitized BCR-ABL-expressing Kit+ cells to imatinib treatment (~80% reduction, as compared to 50% reduction in wild-type (WT) controls). Strikingly, the deletion of both Fos and Dusp1 suppressed the number of CFUs generated by BCR-ABL expressing cells (~90%), and treatment with imatinib completely eradicated BCR-ABL-positive colonies (FIG. 11D,E). For analysis in vivo, mice were transplanted with 40,000 Kit+BM cells expressing BCR-ABL and YFP. Recipient mice developed fatal leukemia with a disease latency of 2-3 weeks (Zhao, C. et al. Hedgehog signalling is essential for maintenance of cancer stem cells in myeloid leukaemia. Nature 458, 776-779 (2009)). Imatinib treatment did not result in a significant reduction in leukemic burden as compared to vehicle treatment, and all mice died in 3-4 weeks (FIG. 11F,G). By contrast, the deletion of Dusp1 delayed BCR-ABL-induced leukemia by 1 week, and deletion of Fos led to a disease latency of 7-8 weeks (FIG. 11F-G). Notably, imatinib treatment of mice transplanted with c-Fos-deficient cells for 1 month led to a significant reduction in leukemic burden (to 0.5-4%); ~50% of mice survived, and treatment discontinuation did not result in disease relapse (FIG. 11H,I), which suggests that TKI resistant MRD was eliminated. In control experiments in which Fos was not deleted (using non-tamoxifen-treated ROSACreERT2Fosfl/fl donor cells), recipients showed disease-latency periods similar to those observed in WT mice in both imatinib-treated and untreated groups (FIG. 12A,C).

Figure 12E:
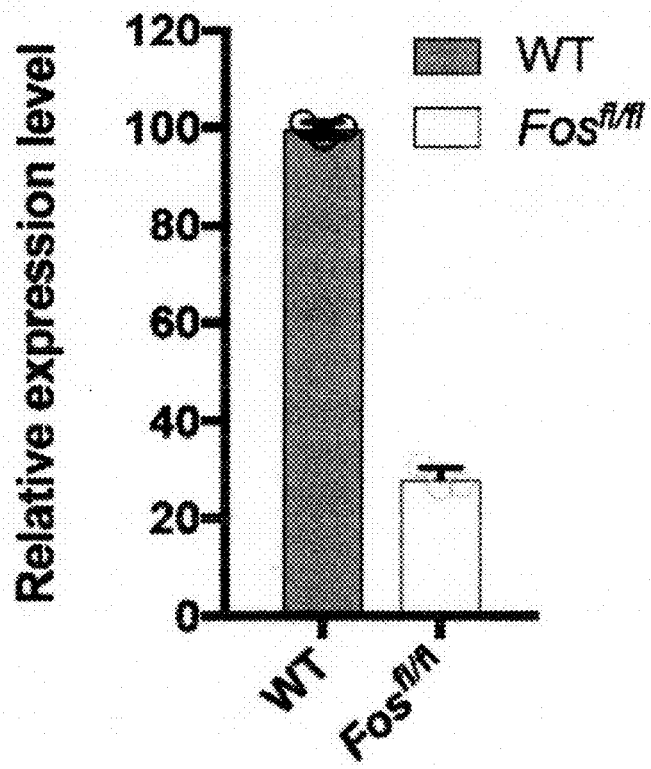

The deletion of both Fos and Dusp1 had a greater effect than deletion of either gene alone, rescuing ~60% of the mice from leukemic death and significantly reducing leukemic burden (FIG. 11H,K). Control ROSACreERT2Fosfl/fl; Dusp1−/− mice, not treated with tamoxifen, showed modestly prolonged survival as compared to WT controls (FIG. 12B,D), which was correlated with lower Fos mRNA expression (FIG. 12E). Deletion of both Fos and Dusp1, when combined with a 5-week course of imatinib treatment, eradicated all leukemic cells from peripheral blood and bone marrow, and discontinuation of treatment did not result in disease relapse, as assessed by YFP+ cell burden in blood and bone marrow at the end of the experiment, 4 months after tumor cell transplantation (FIG. 11J,K). Thus, genetic deletion of Fos and Dusp1 sensitizes BCR-ABL-expressing cells (but not WT cells) to imatinib treatment and eliminates TKI-resistant MRD. Moreover, the deletion of Fos and Dusp1 in ROSACreERT2Fosfl/fl;Dusp1−/− mice by tamoxifen injection did not show any apparent hematopoietic defects, and c-Fos- and Dusp1-deficient cells were maintained in the peripheral blood and bone marrow (FIG. 12F), which supports the concept that these genes are required for BCR-ABL-induced transformation and leukemia development but are dispensable for normal hematopoiesis.

Figure 12G:
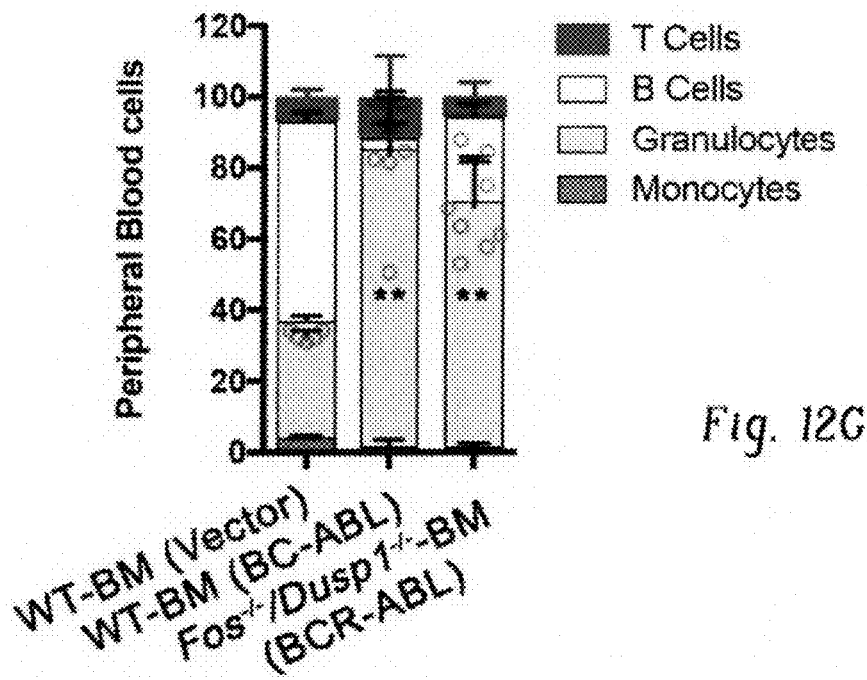
Figure 12H:
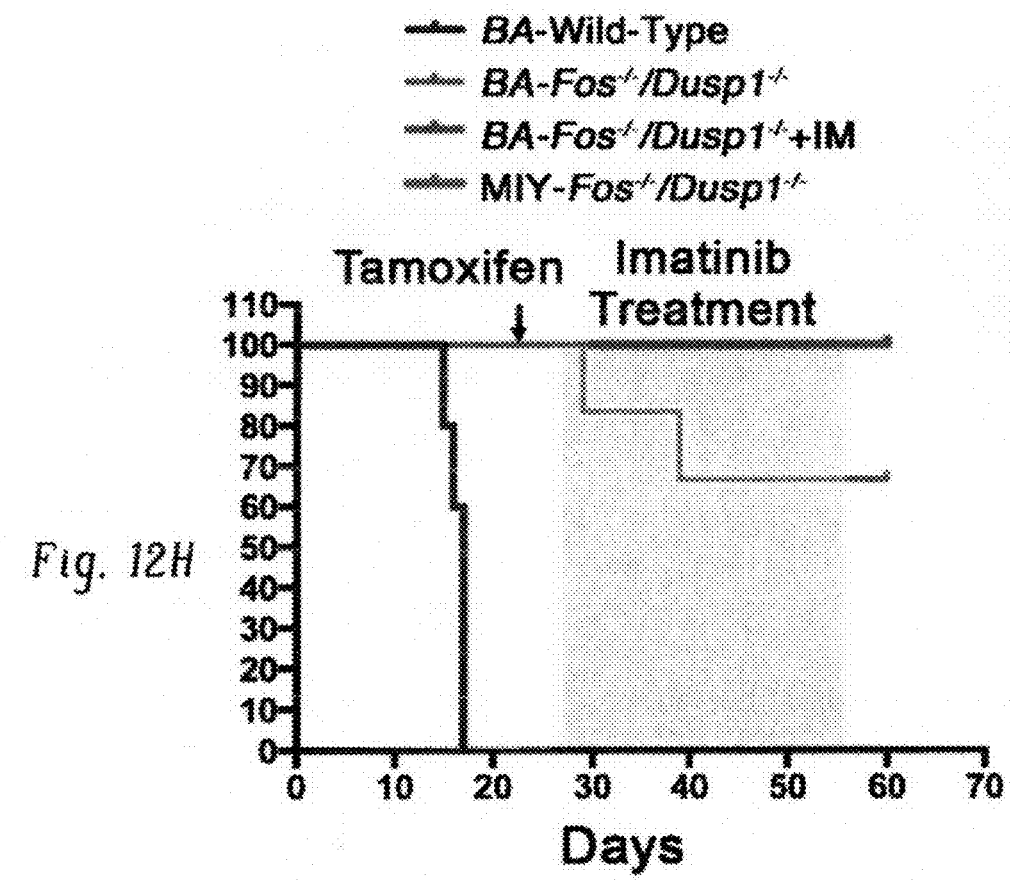
Figure 12I:
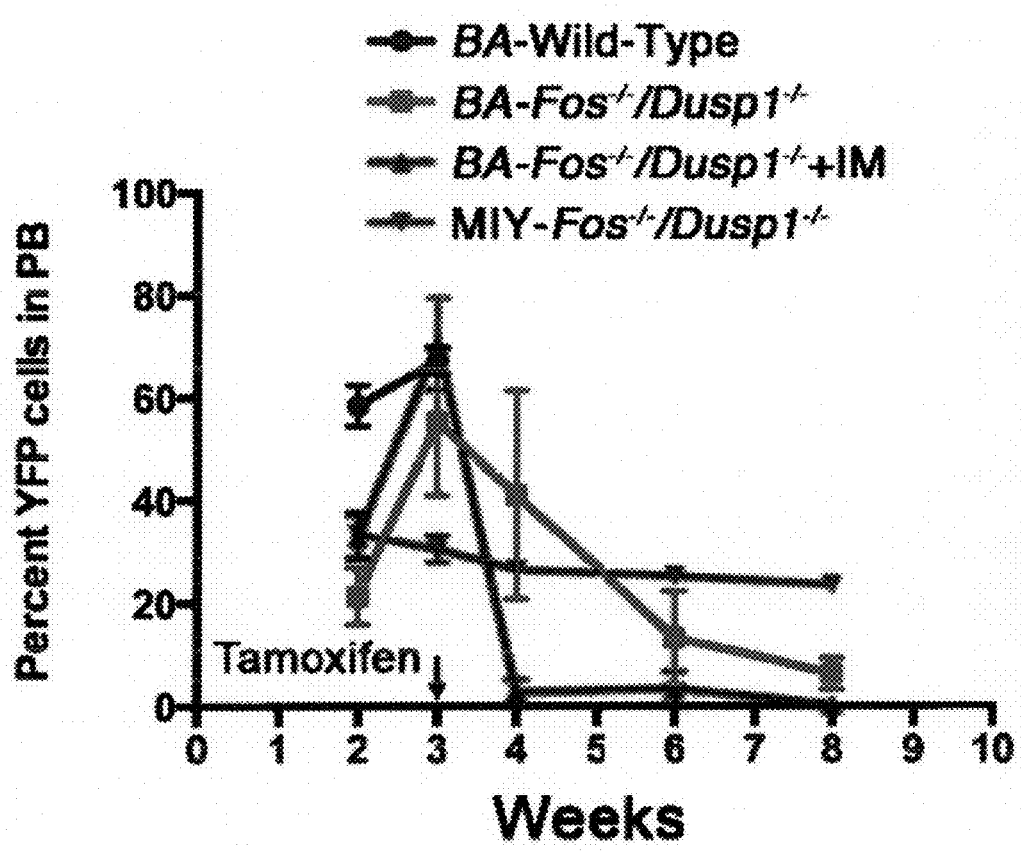

To test whether c-Fos is required for the maintenance of disease, we deleted Fos after the onset of disease (3 weeks after tumor cell transplantation). At 2 weeks after transplantation, both WT and ROSACreERT2Fosfl/fl;Dusp1−/− mice showed an increase in granulocytes (~70-80% of peripheral blood cells, as compared to 32% in WT controls) at the expense of B cells (FIG. 12G). As shown above, the deletion of both Fos and Dusp1 at week 3 rescued ~60% of the mice from leukemia (FIG. 12H). Imatinib treatment rescued mice transplanted with Fos- and Dusp1-deleted cells expressing BCR-ABL from leukemia and led to rapid clearance of the leukemic cells. Whereas non-imatinib-treated mice transplanted with cells expressing BCR-ABL in which Fos and Dusp1 had been deleted showed gradual depletion of leukemic cells, vector-only control cells not expressing BCR-ABL with the same deletion showed stable engraftment (FIG. 12H,I). Taken together, these data suggest that genetic loss of Fos and Dusp1 together sensitizes leukemic cells to TKI in CML and confers synthetic lethality to BCR-ABL-transformed cells, given that leukemic cells are gradually depleted even without TKI treatment.

Figure 11L:
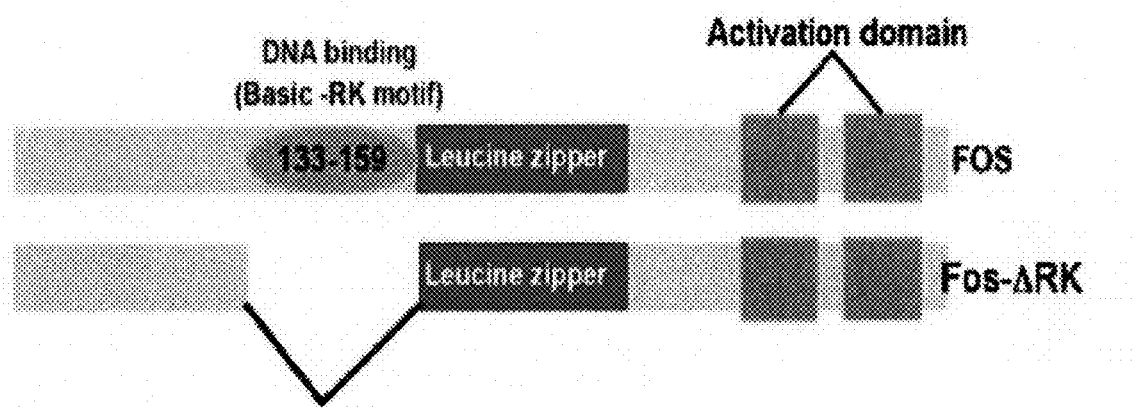
FIG. 11I shows primary structure of c-Fos and its dominant-negative version, c-Fos-ΔRK, which lacks the DNA-binding domain consisting of a basic-RK motif (amino acid residues 133-159).
FIG. 11M shows tertiary structure of Fos and Jun bound to AP1 site on DNA, illustrating the homo/heterodimer assembly of Fos with Jun.
FIG. 11N shows percentage of CFUs from wild-type (WT) BCR-ABL-YFP+ Kit+ cells expressing dominant-negative c-Fos-ΔRK with or without imatinib, as compared to Fos$^{-/-}$ BCR-ABL-YFP+ Kit+ cells with or without imatinib.
Figure 11M:
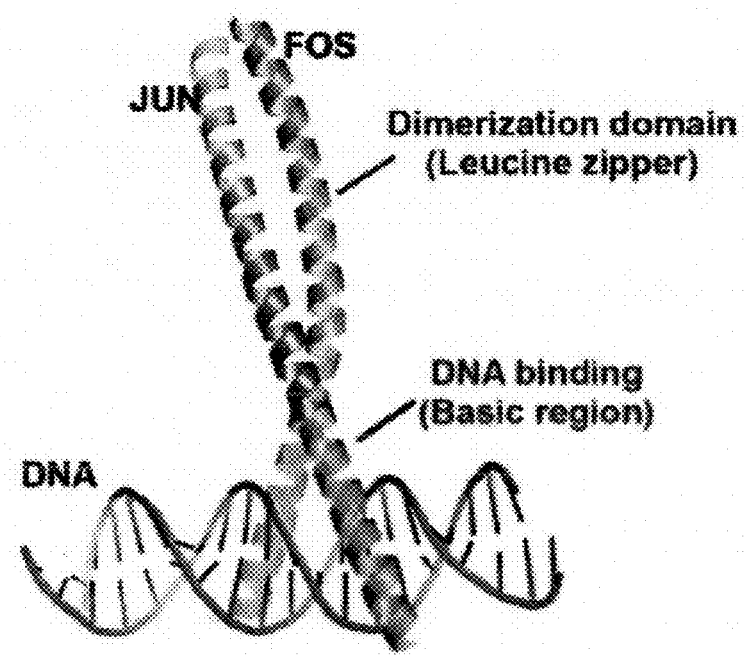
Figure 11N:
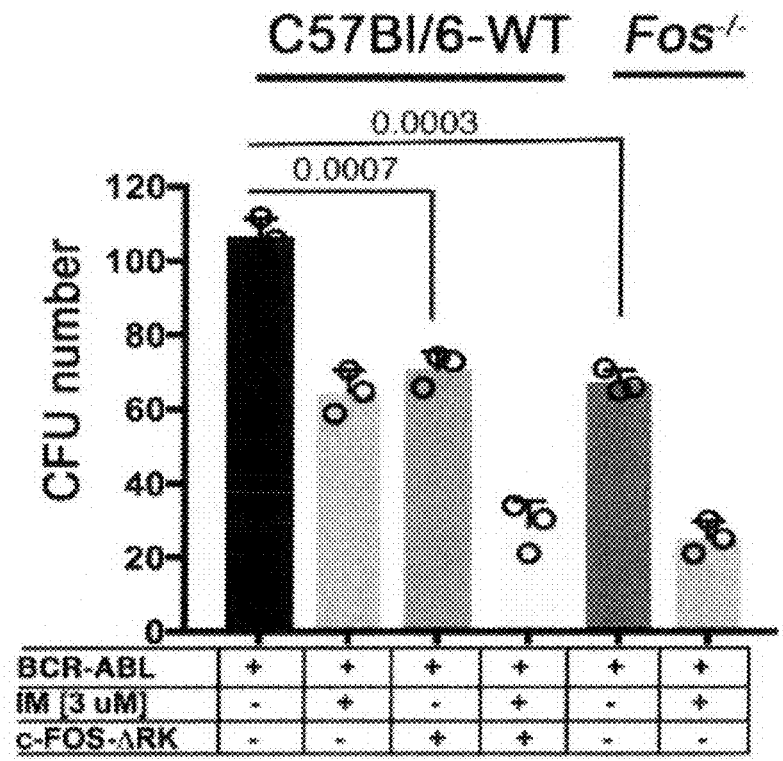
Figure 11O:
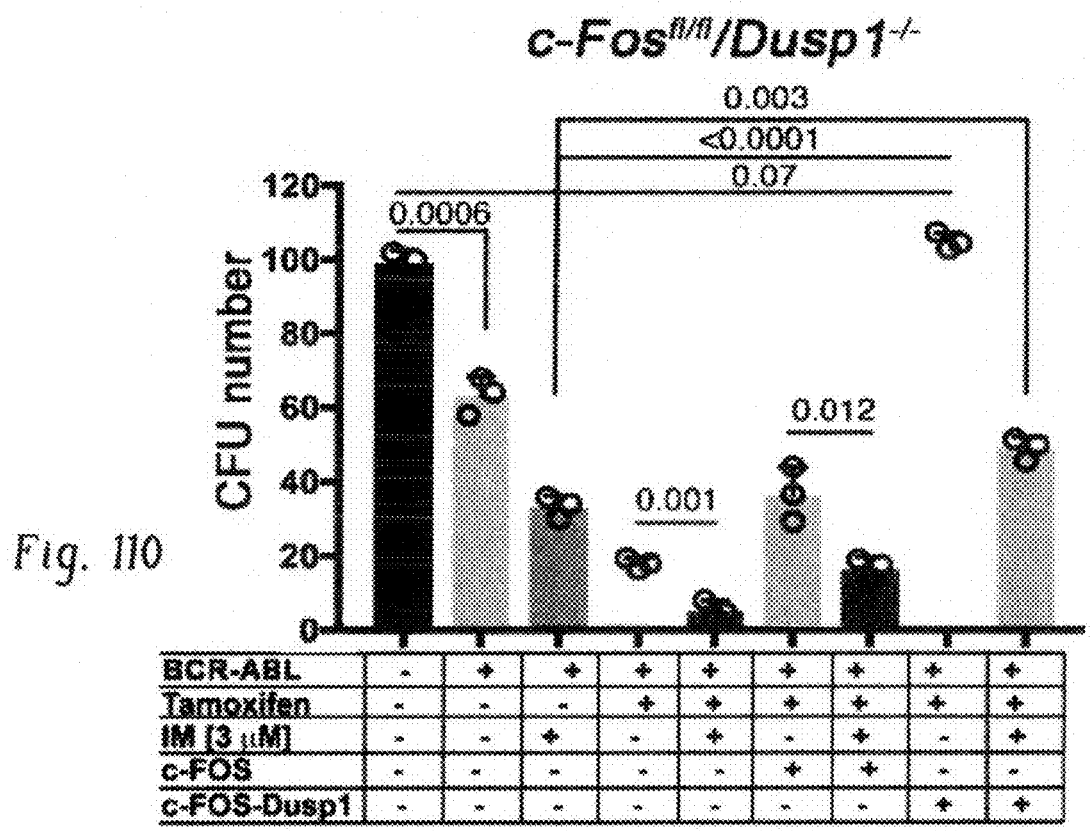

To rule out potential nonspecific effects of Fos or Dusp1 deletion on BCR-ABL-induced leukemia, we performed two additional experiments. First, we expressed a dominant-negative c-FOS (lacking the DNA-binding domain (Ransone, L. J., Visvader, J., Wamsley, P. & Verma, I. M. Trans-dominant negative mutants of Fos and Jun. Proc. Natl. Acad. Sci. USA 87, 3806-3810 (1990)); FIG. 11L,M) together with BCR-ABL in WT C57BL/6 bone marrow cells. Expression of dominant-negative c-FOS had effects that were similar to those observed for Fos deletion; i.e., >50% reduction in the number of BCR-ABL-dependent CFUs (FIG. 11N). Second, expression of VT c-FOS partially rescued the phenotype, whereas expression of both c-FOS and Dusp1 using a monocistronic vector (P2A peptide cleavage) restored CFU numbers to normal levels (FIG. 11O).

Figure 13A:
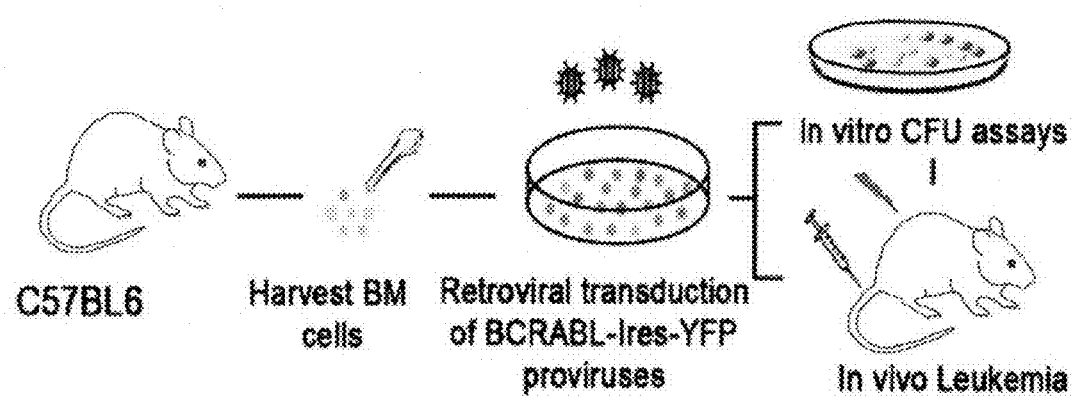
FIGS. 13A-G show chemical inhibition of c-Fos, Dusp1, and BCR-ABL eradicates minimal MRD in mice.
Figure 13B:
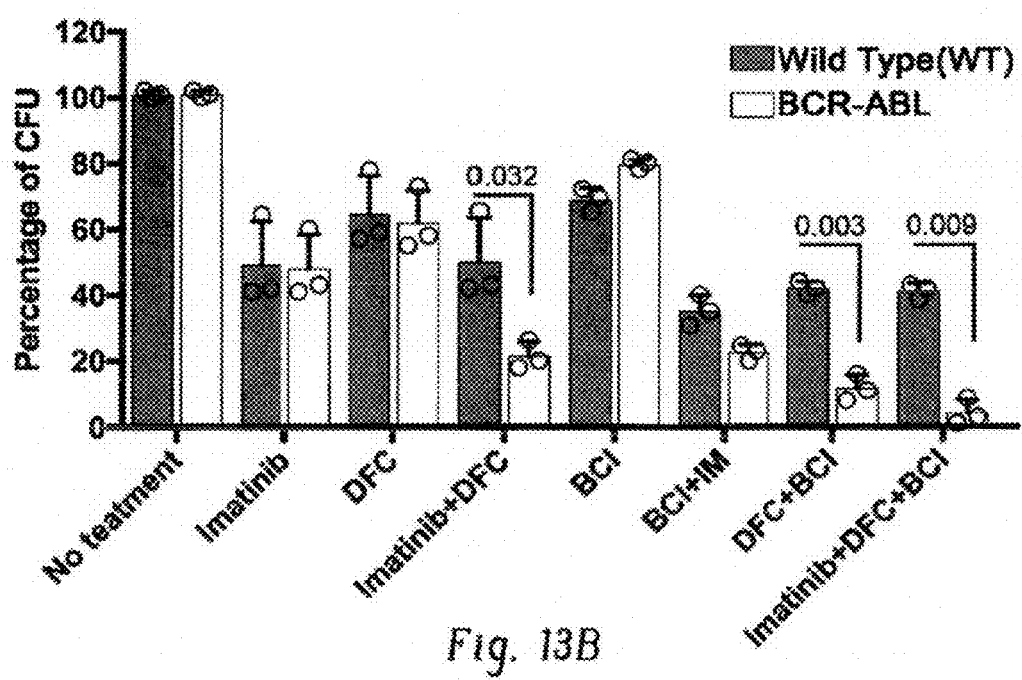
Figure 13C:
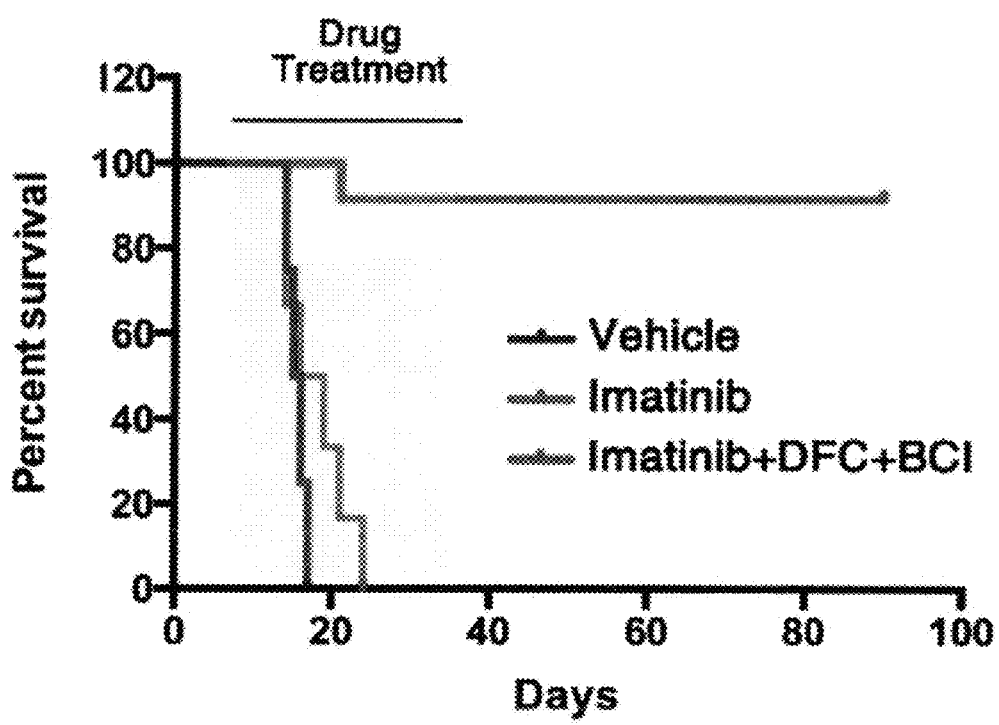
Figure 13D:
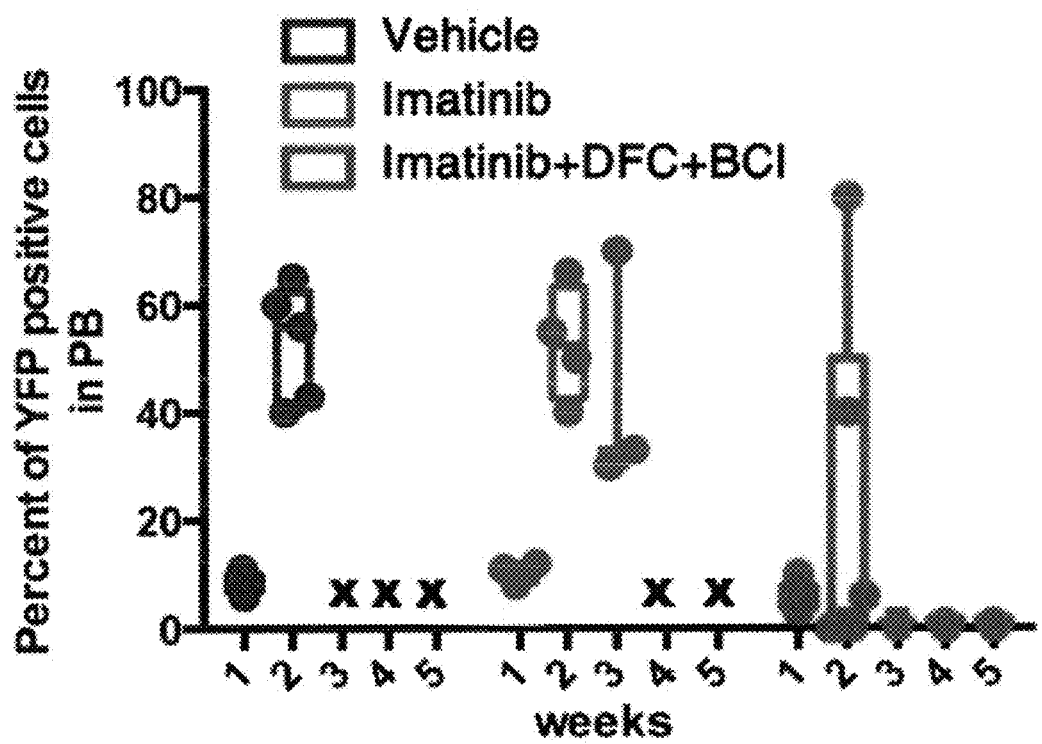
Figure 14B:
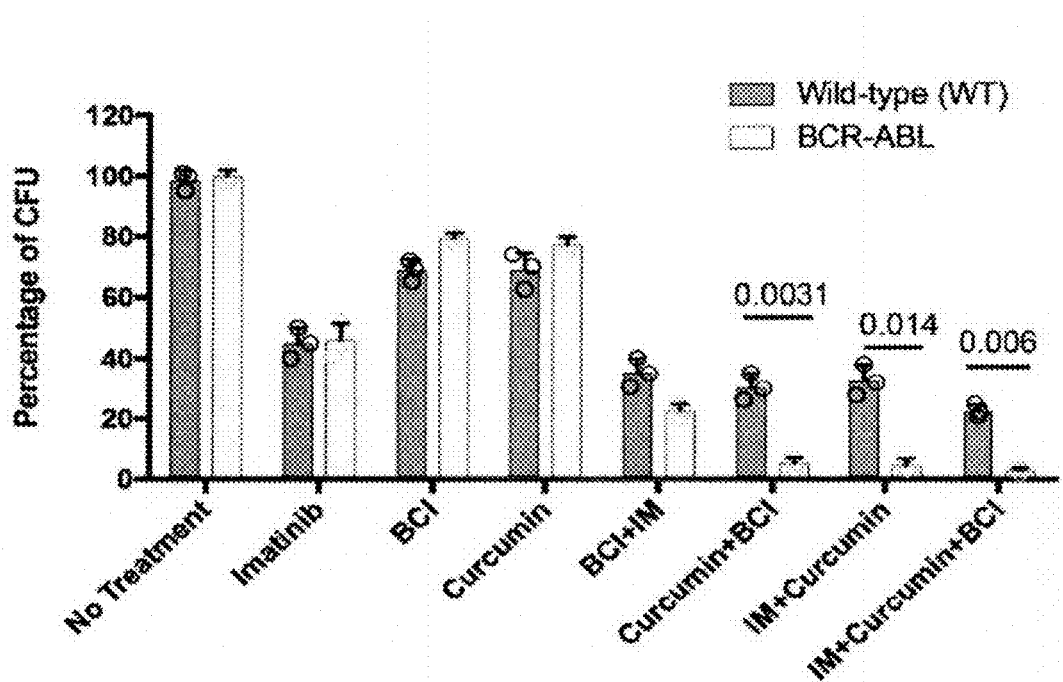
Figure 14C:
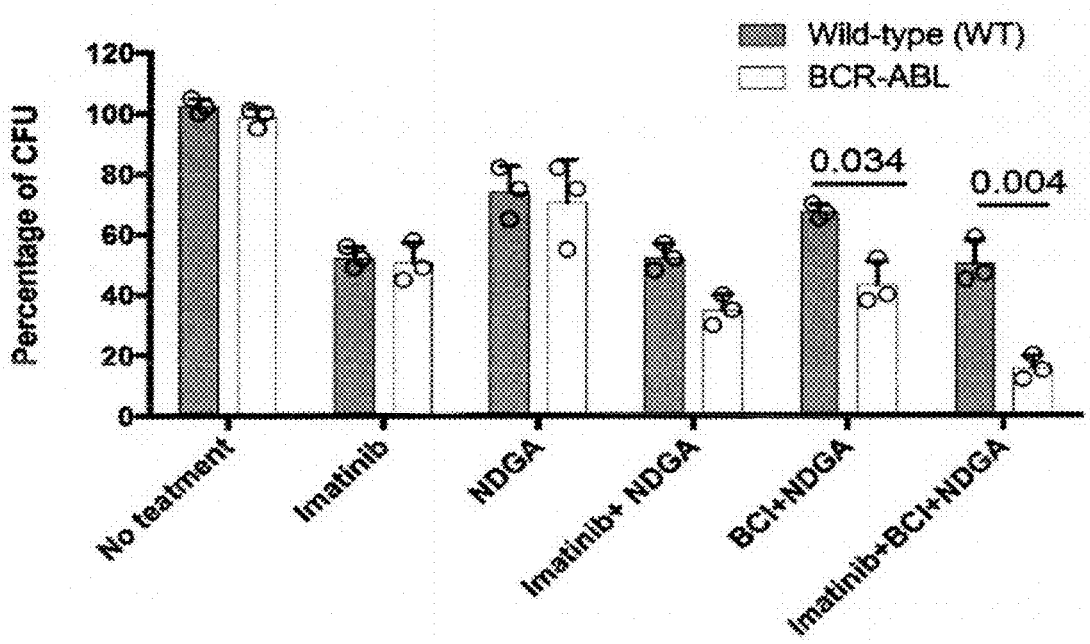
Figure 14D:
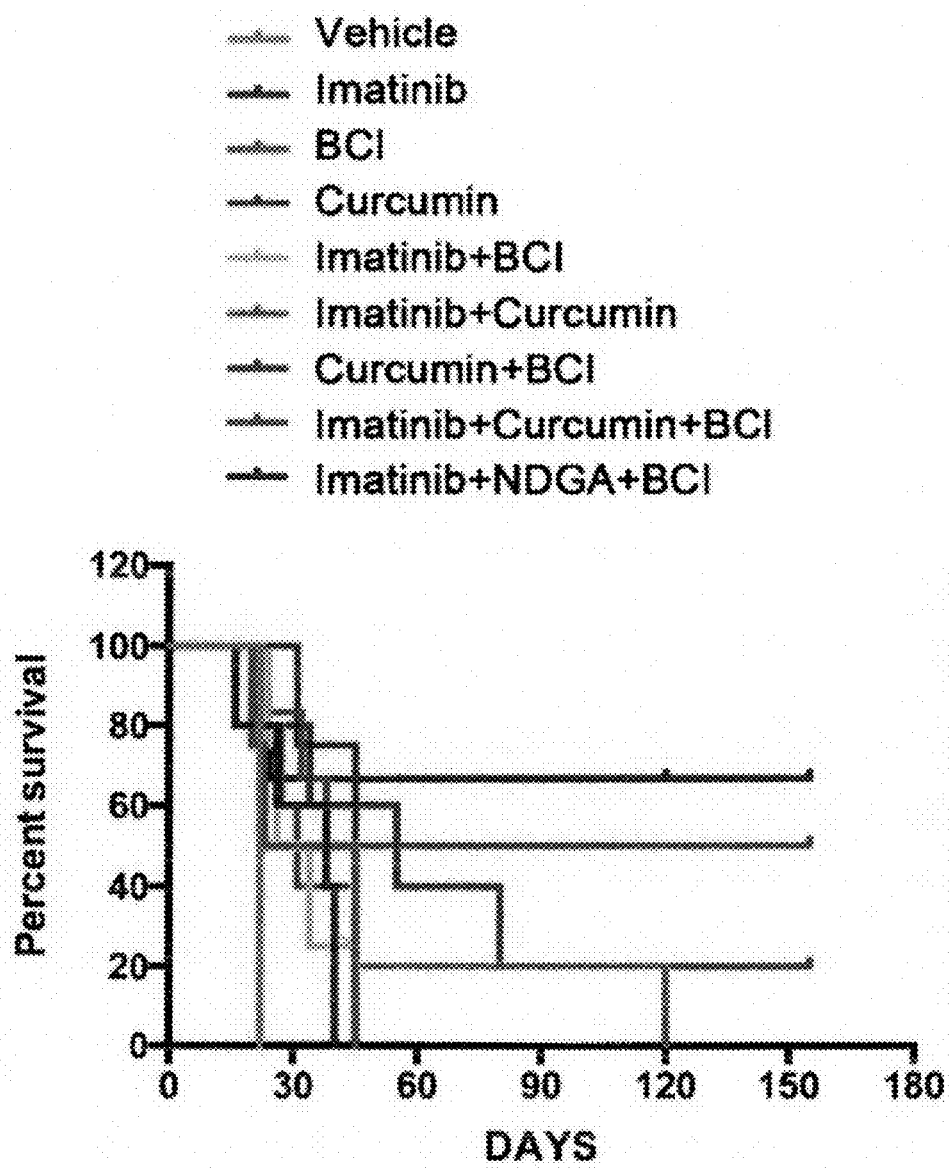

Inhibition of c-Fos, Dusp1, and BCR-ABL by Small-molecule Inhibitors Cures Mice of CML To test the potential of targeting c-Fos and Dusp1 for therapy, we performed in vitro and in vivo experiments using small-molecule inhibitors of c-Fos and Dusp1 (FIG. 13A). CFU analysis of BCR-ABLLSK cells (bone-marrow-derived Lin-Sca1+Kit+ (LSK) cells represent hematopoietic stem and progenitor cells) treated with c-Fos and Dusp1 inhibitors recapitulated the genetic data. Specifically, combined treatment with a Dusp1 and Dusp6 inhibitor ((E)-2-benzylidene-3-(cyclohexylamino)-2,3-dihydro-1H-inden-1-one; BCI) (Molina, G. et al. Zebrafish chemical screening reveals an inhibitor of Dusp6 that expands cardiac cell lineages. Nat. Chem. Biol. 5, 680-687 (2009)), a c-Fos inhibitor (curcumin) (Huang, T. S., Lee, S. C. & Lin, J. K. Suppression of c-Jun/AP-1 activation by an inhibitor of tumor promotion in mouse fibroblast cells. Proc. Natl. Acad. Sci. USA 88, 5292-5296 (1991)) and a BCR-ABL inhibitor (imatinib) completely suppressed CFU formation (imatinib+curcumin+BCI; FIG. 14A,B). To address the possibility of off-target effects of curcumin, we tested two other chemically distinct compounds targeting c-Fos: nordihydroguaiaretic acid (Park, S., Lee, D. K. & Yang, C. H. Inhibition of fos-jun-DNA complex formation by dihydroguaiaretic acid and in vitro cytotoxic effects on cancer cells. Cancer Lett. 127, 23-28 (1998)) (NDGA) and difluorinated curcumin (Padhye, S. et al. Fluorocurcumins as cyclooxygenase-2 inhibitor: molecular docking, pharmacokinetics and tissue distribution in mice. Pharm. Res. 26, 2438-2445 (2009)) (DFC). Both NDGA and DFC (imatinib+NDGA+BCI and imatinib+DFC+BCI) were effective at suppressing BCR-ABL-dependent CFU formation (FIG. 13B and FIG. 14C), which suggests that c-Fos is the relevant target of these compounds. Next, we examined the efficacy of these compounds in vivo by using a retroviral bone marrow transduction transplantation leukemogenesis model. A 1-month course of treatment with individual compounds with imatinib (BCI, curcumin, and NDGA) or without imatinib (BCI and curcumin) did not effectively treat leukemogenesis; however, treatment with imatinib+curcumin+BCI and imatinib+NDGA+BCI rescued 50% and 60% of the recipient mice, respectively (FIG. 14D). By contrast, a 1-month course of treatment with imatinib+DFC+BCI rescued ~90% of mice, and we were unable to detect MRD by flow cytometry (FIG. 13C, D).

Figure 13E:
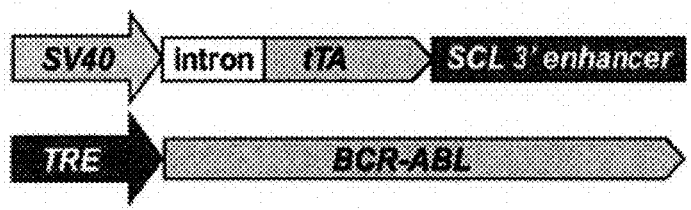
Figure 13F:
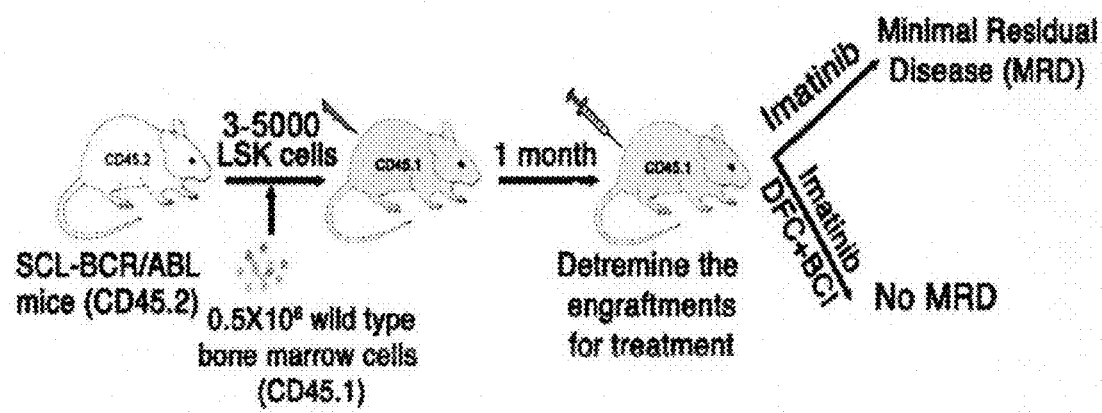
Figure 13G:
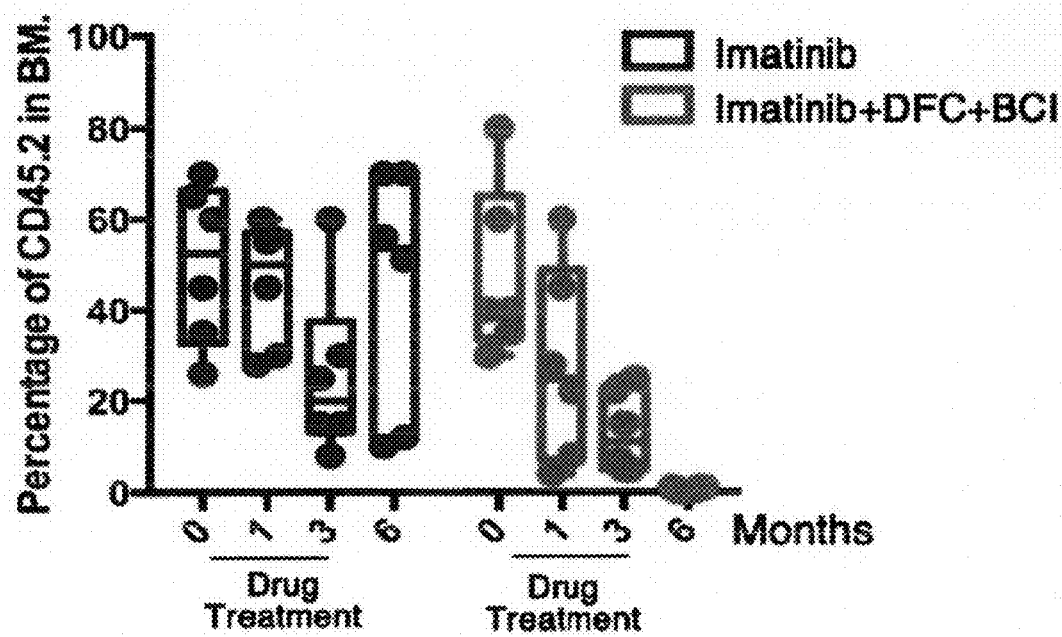
Figure 15A:
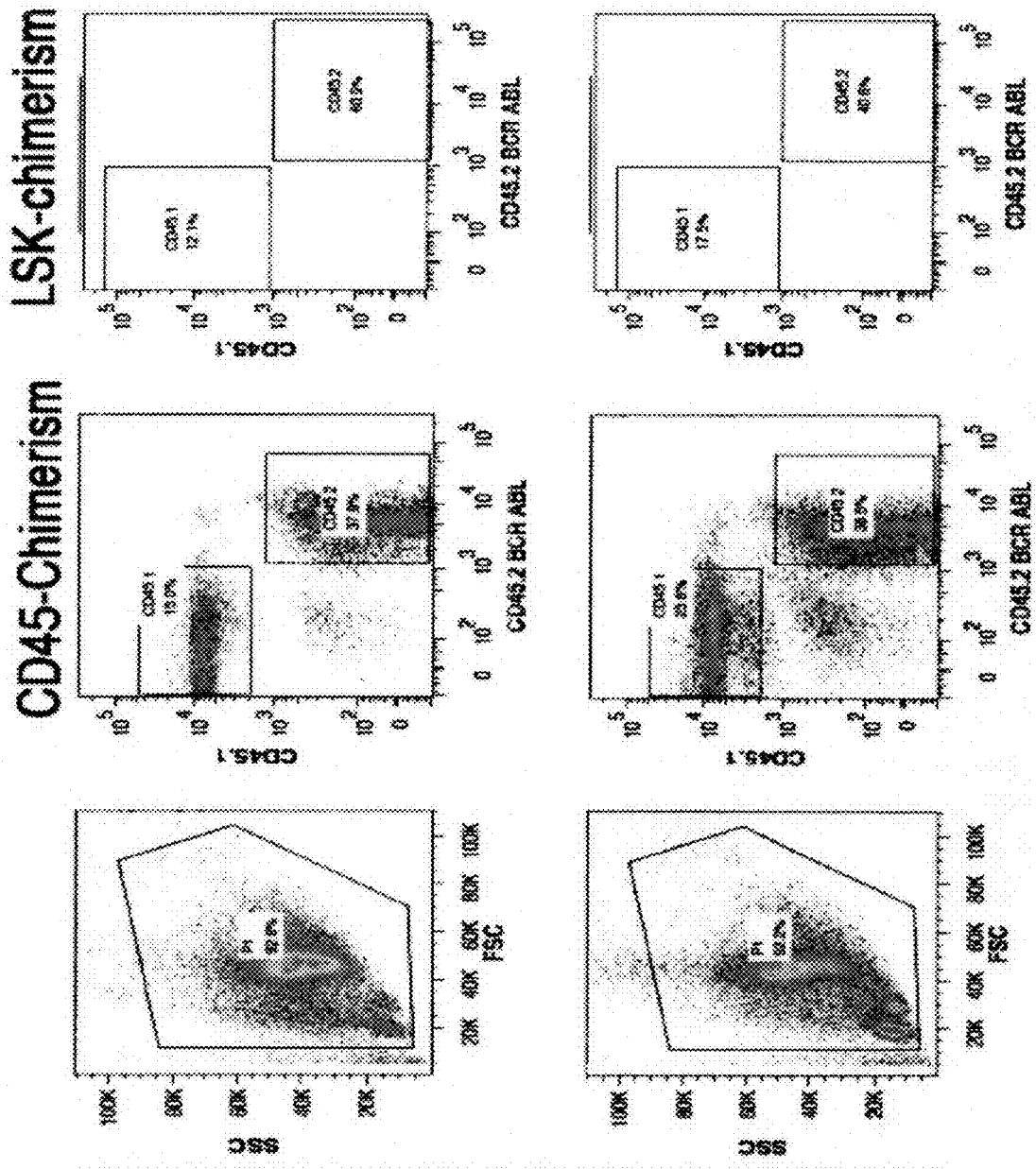
FIGS. 15A-D show inhibition of c-Fos, Dusp1 and BCR-ABL eradicated the leukemic stem cells.
Figure 15B:
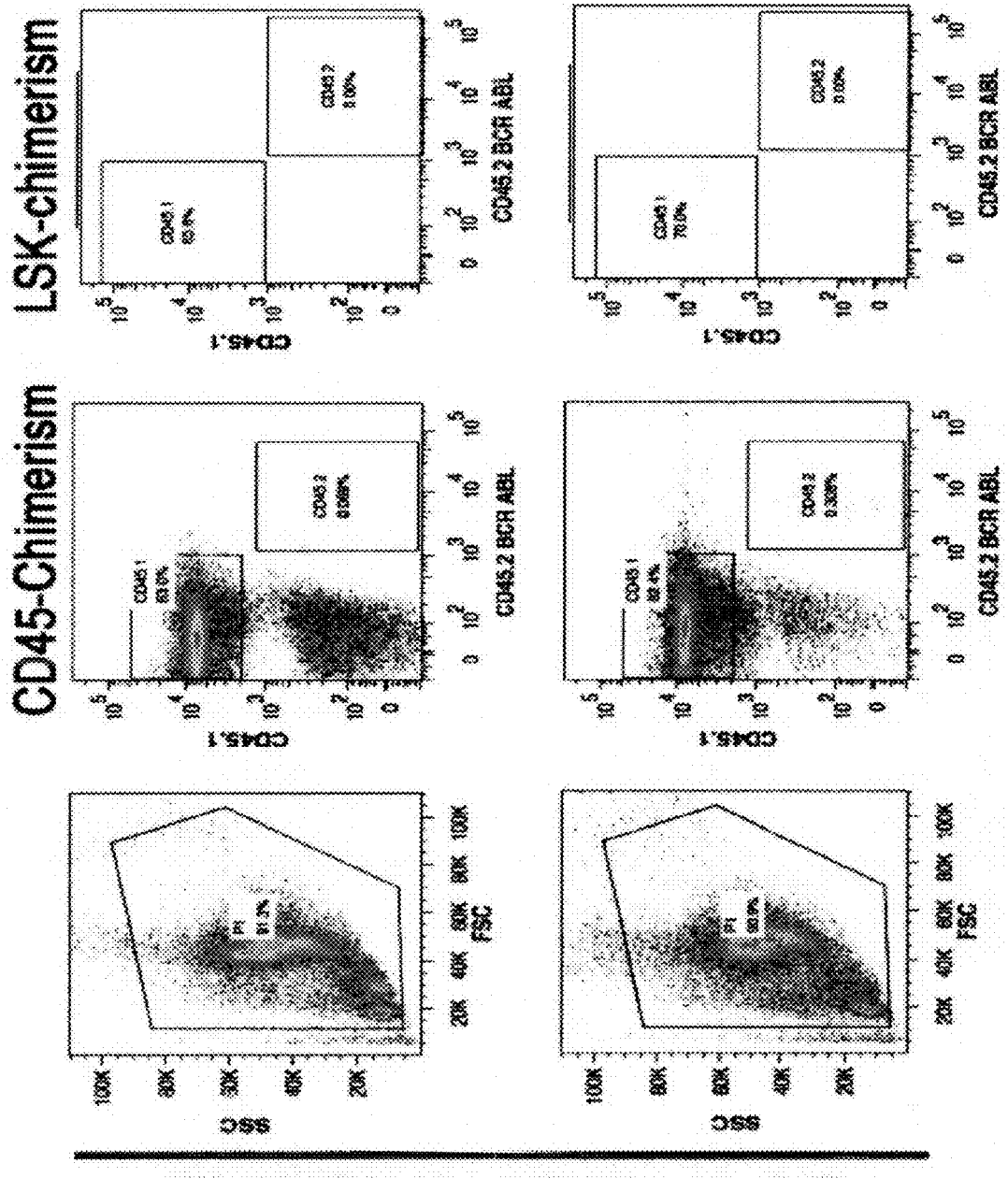
Figure 15C:
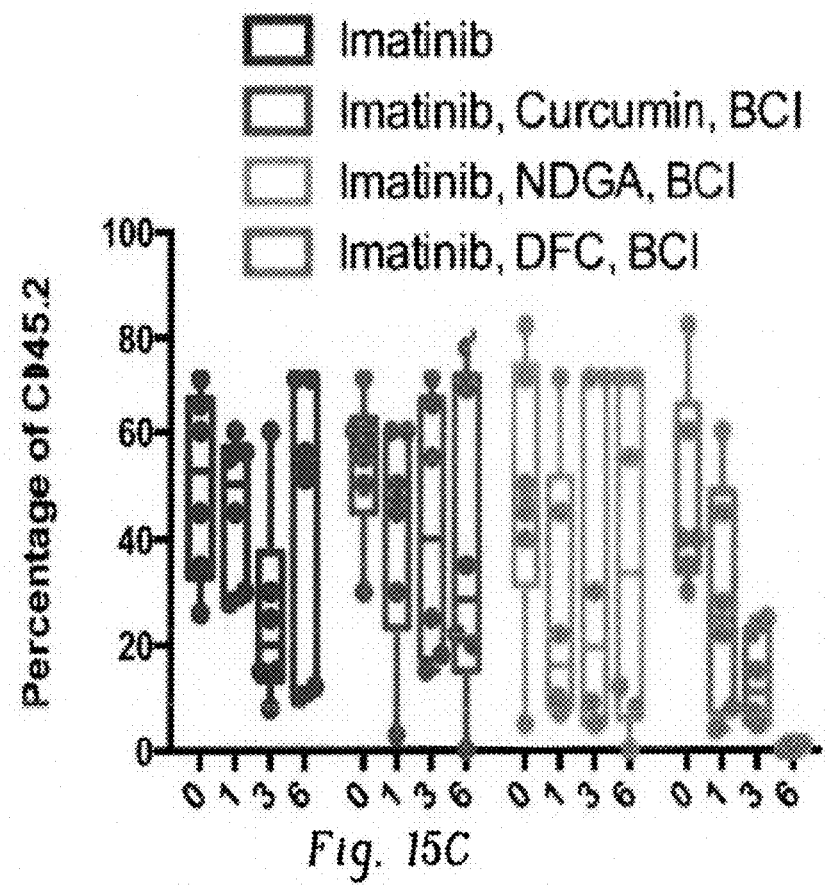

Given the lack of MRD in the treated mice, we next wished to test the effectiveness of c-FOS and Dusp1 inhibition in a tumor model in which leukemic stem cells drive leukemogenesis. To this end, we used transgenic mice in which the 3' enhancer of the Scl gene drives expression of the tetracycline transactivator (tTA) to regulate tet-0-BCR-ABL transgene expression in hematopoietic stem and progenitor cells (Koschmieder, S. et al. Inducible chronic phase of myeloid leukemia with expansion of hematopoietic stem cells in a transgenic model of BCR-ABL leukemogenesis. Blood 105, 324-334 (2005)) (FIG. 13E). We transplanted 3,000-5,000 bone marrow LSK cells into irradiated BoyJ mice, which developed leukemia within 4-6 weeks. 4 weeks after transplantation, drug treatment was started (FIG. 13F). Treatment with imatinib alone for 3 months resulted in a reduction (~60%) of CML cells in the bone marrow; however, a substantial percentage of BCR-ABL-positive cells were present in the bone marrow (FIG. 13G). Moreover, when treatment was discontinued, disease relapse occurred in all mice, replicating the clinical course of TKI therapy in CML (FIG. 13G). By contrast, not only did treatment with imatinib+DFC+BCI for 3 months eradicate the donor-derived BCR-ABL-positive leukemic cells (CD45.2) in the bone marrow, but no relapse occurred when treatment was discontinued (FIG. 13G and FIG. 15A-C). Similarly to the retroviral CML model (FIG. 13C), treatment with imatinib+curcumin+BCI or imatinib+NDGA+BCI resulted in effective eradication of CML stem progenitor cells, but a few recipient mice in these treatment groups relapsed once treatment was discontinued (FIG. 15C). Taken together, these results suggest that treatment with imatinib+DFC+BCI is more efficient than the combinations (imatinib+BCI+curcumin or imatinib+BCI+NDGA) at targeting leukemic stem cells that persist in MRD, perhaps owing to superior pharmacokinetics of DFC over curcumin (Padhye, S. et al. Fluorocurcumins as cyclooxygenase-2 inhibitor: molecular docking, pharmacokinetics and tissue distribution in mice. Pharm. Res. 26, 2438-2445 (2009)).

Inhibition of c-FOS and DUSP1 Sensitizes Patient-derived LICs to Imatinib

Figure 15D:
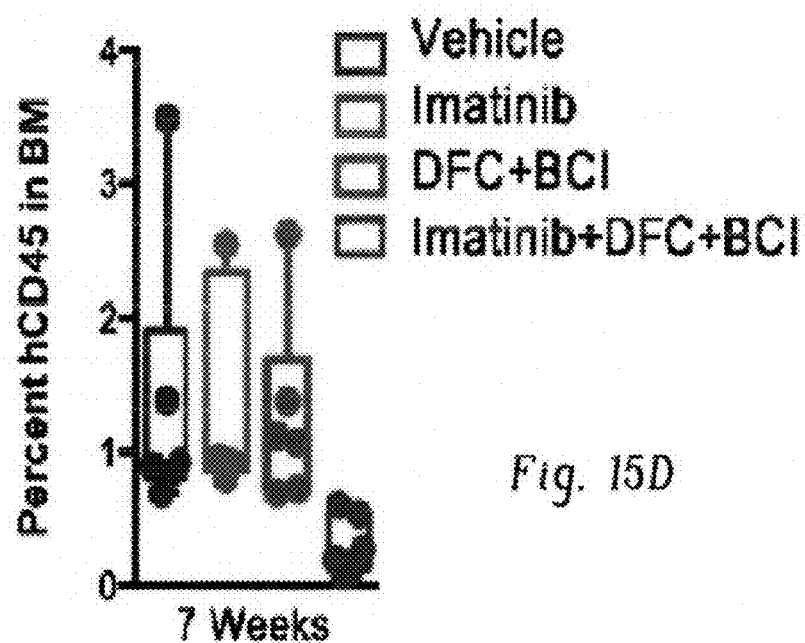
Figure 16A:
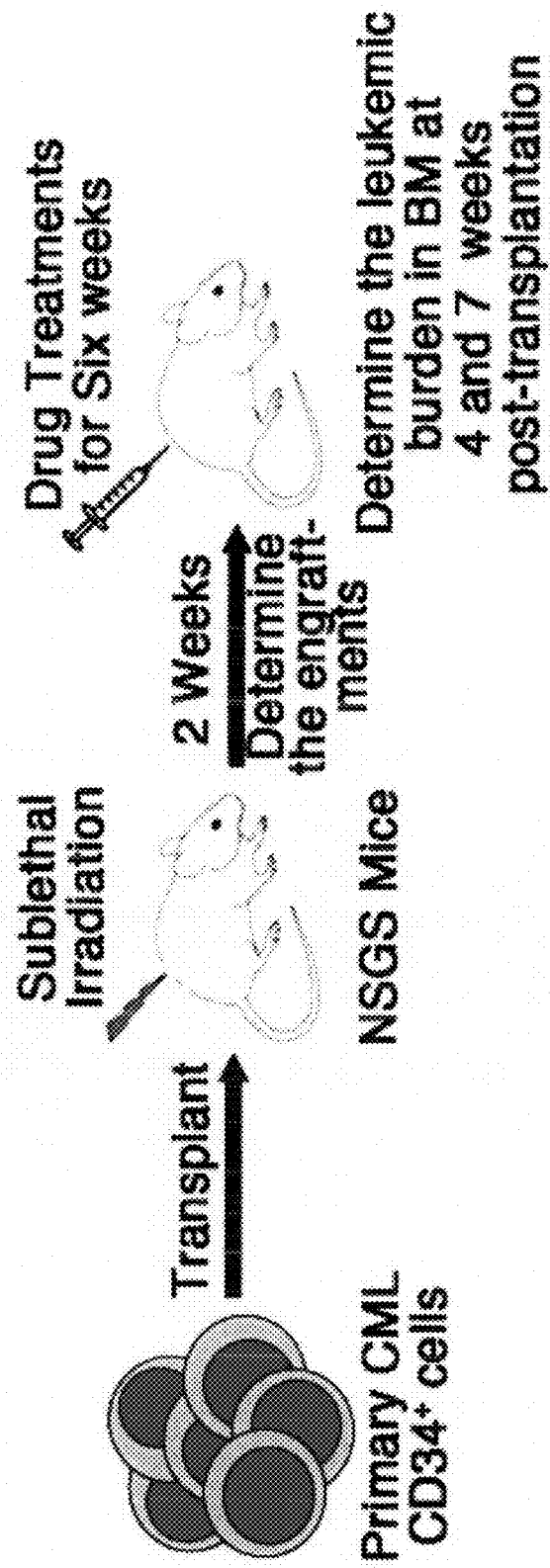
FIGS. 16A-C show inhibition of c-Fos, Dusp1, and BCR-ABL selectively eradicates CML cells.
Figure 16B:
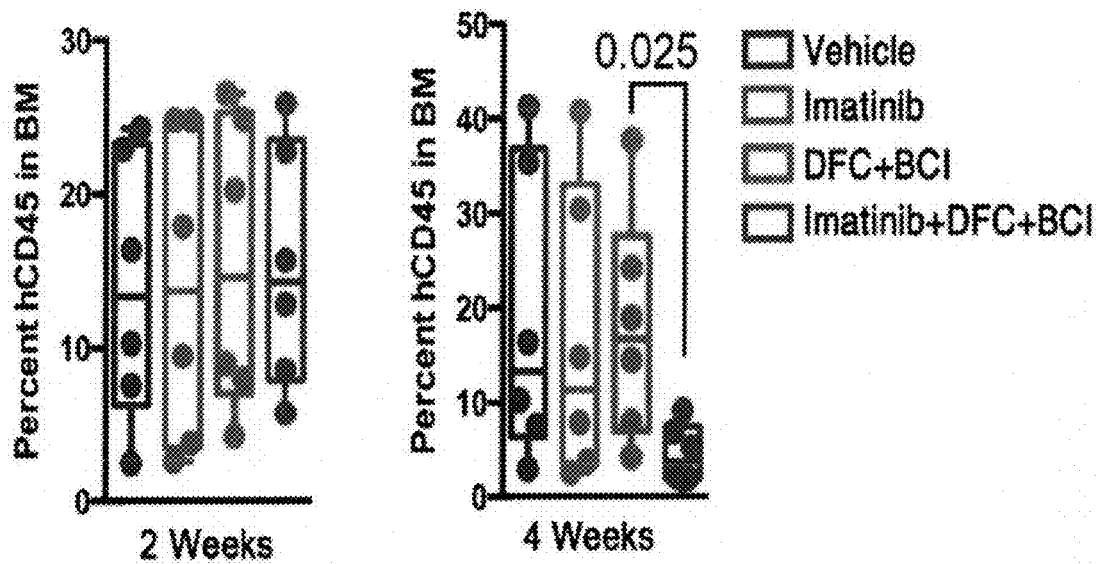

To extend these findings to human cells, we tested the effect of c-FOS and DUSP1 inhibition on the survival of primary CML patient samples (Table 2). Mice transplanted with 3,000 CD34+ cells from the primary patient sample CP4 showed robust cell engraftment within 2 weeks (FIG. 16A,B). Drug treatment was started 2 weeks after transplantation and continued for a period of 4-6 weeks, using imatinib alone, DFC and BCI, or imatinib+DFC+BCI. As expected, treatment with imatinib+DFC+BCI for 3 weeks resulted in effective inhibition of leukemic cells, whereas treatment with imatinib alone or DFC+BCI was ineffective (FIG. 16B). As previously reported (Li, L. et al. Activation of p53 by SIRT1 inhibition enhances elimination of CML leukemia stem cells in combination with imatinib. Cancer Cell 21, 266-281 (2012)), leukemic engraftment in this model is not stable, and most mice lost grafts within 7-8 weeks after transplantation (FIG. 15D), which precluded further investigation of the effect of drug treatment on MRD.

Next, to test the efficacy of these drugs on primitive LSCs, we performed long-term-culture-initiating cell (LTC-IC) assays, a stringent in vitro assay for the detection of primitive hematopoietic or leukemic stem cells, using mononuclear cells from the CP1 sample, CD34+ cells from the CP4 sample, and CD34+ cells from a healthy donor as a control.

Figure 16C:
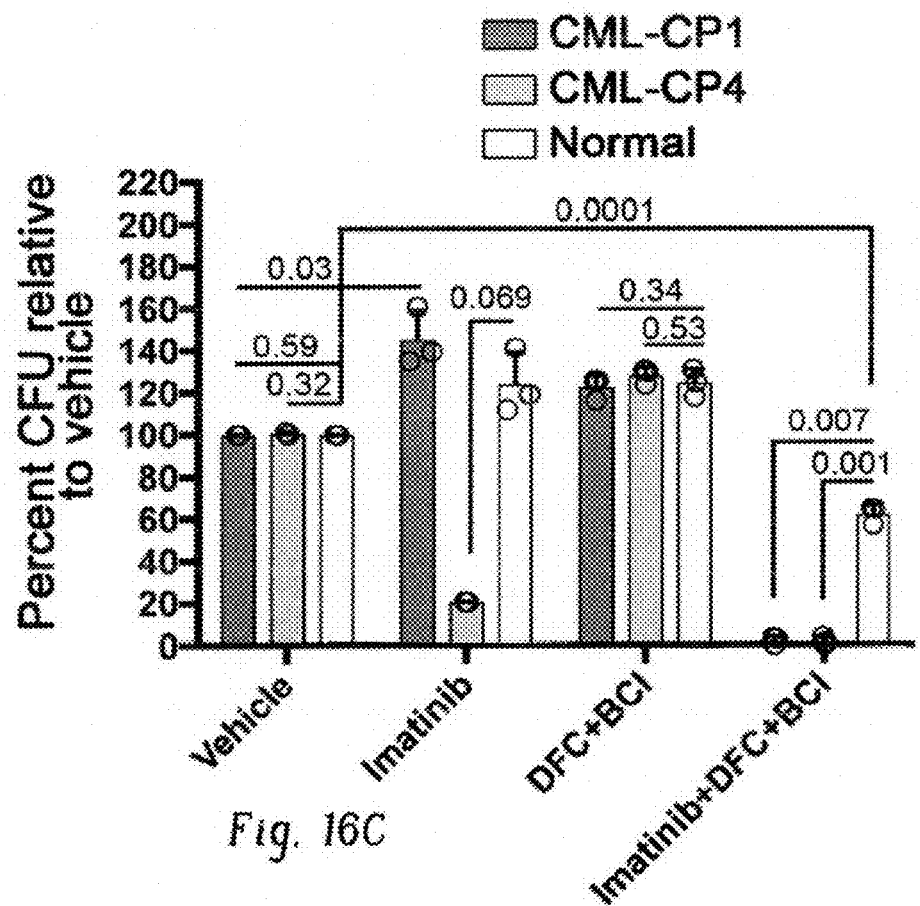

As expected, LTC-IC activity was increased in imatinib-treated CP1 cells as compared to the vehicle-treated controls (FIG. 16C), in agreement with previous studies (Copland, M. et al. BMS-214662 potently induces apoptosis of chronic myeloid leukemia stem and progenitor cells and synergizes with tyrosine kinase inhibitors. Blood 111, 2843-2853 (2008)). However, imatinib treatment of sample CP4 showed a significant decrease in LTC-IC activity as compared to the vehicle treated controls (FIG. 16C). Although the basis for the sensitivity of the CP4 sample to imatinib is unknown-perhaps underlying patient specific genetic or epigenetic changes confer TKI sensitivity—the difference in the responses between these two samples underscores the heterogeneous nature of LSCs in the context of TKI therapy. Notably, treatment with DFC+BCI did not affect LTC-IC activity in leukemic or normal cells (FIG. 16C). As expected, treatment with DFC+BCI+imatinib selectively eradicated the LTC-IC activity of leukemic cells (FIG. 16C); however, as opposed to the results with genetic deletion, this drug treatment partially inhibited normal cell growth, perhaps owing to off-target toxicity. Taken together, these results provide evidence that a combination of DFC+BCI+imatinib selectively targets CML stem and progenitor cells but spares normal CD34+ cells.

c-Fos and Dusp1 Deficiency Alters the AP1-regulated Networks

Figure 17A:
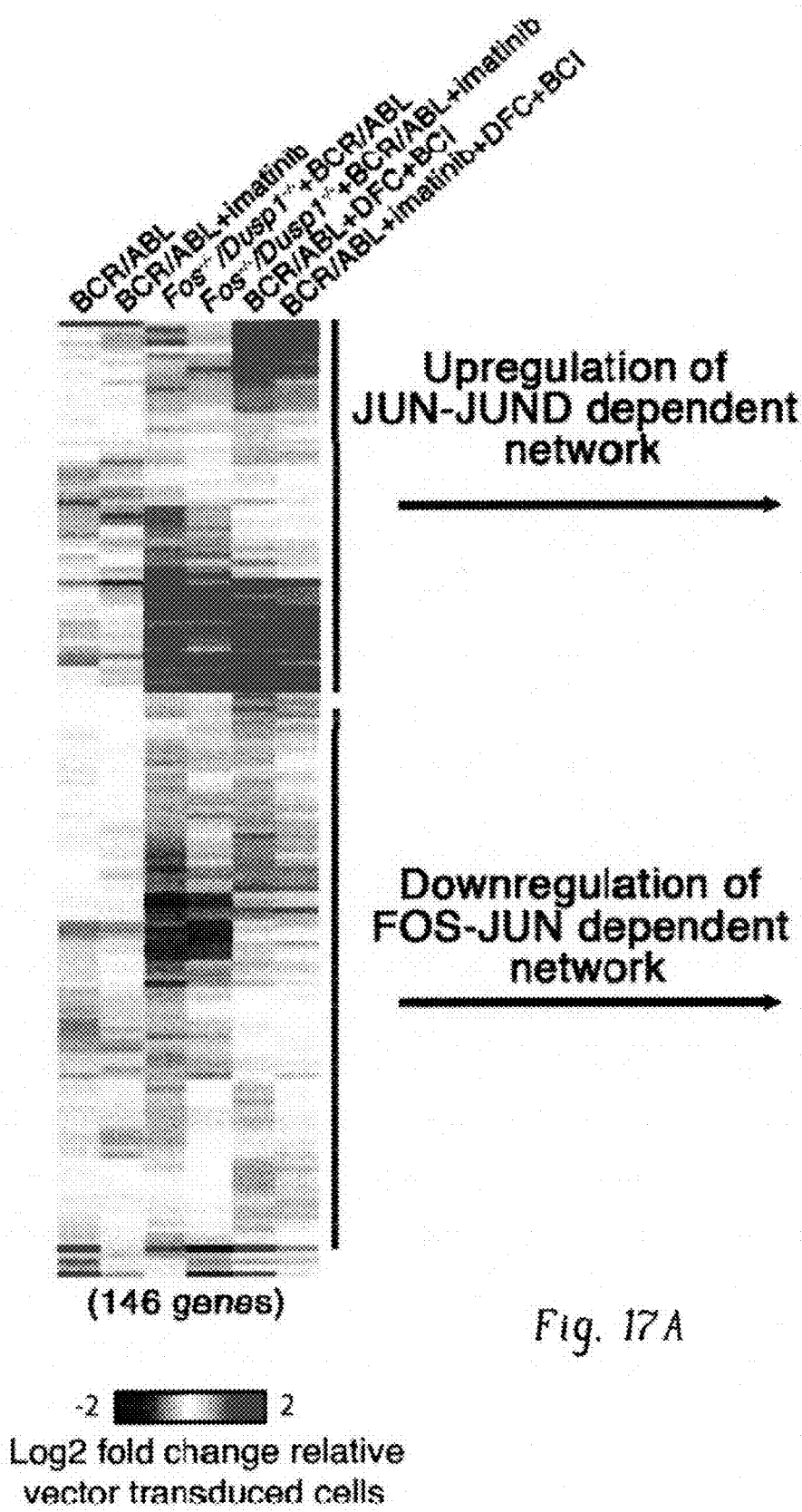
FIGS. 17A-C show genetic or chemical inhibition of c-Fos and Dusp1 downregulates the Fos-Jun network while activating Jun-JunD target genes.
Figure 17B:
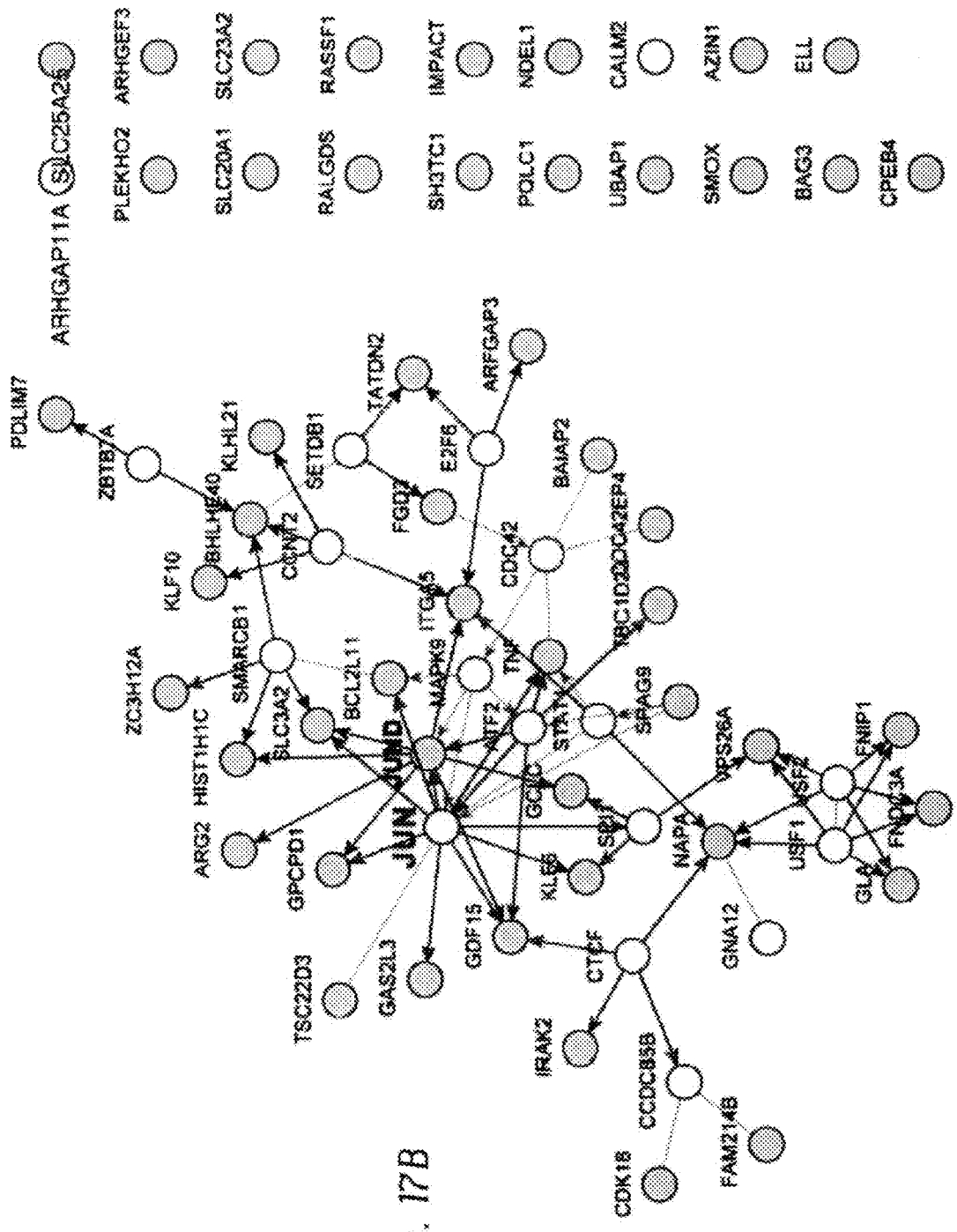
Figure 17C:
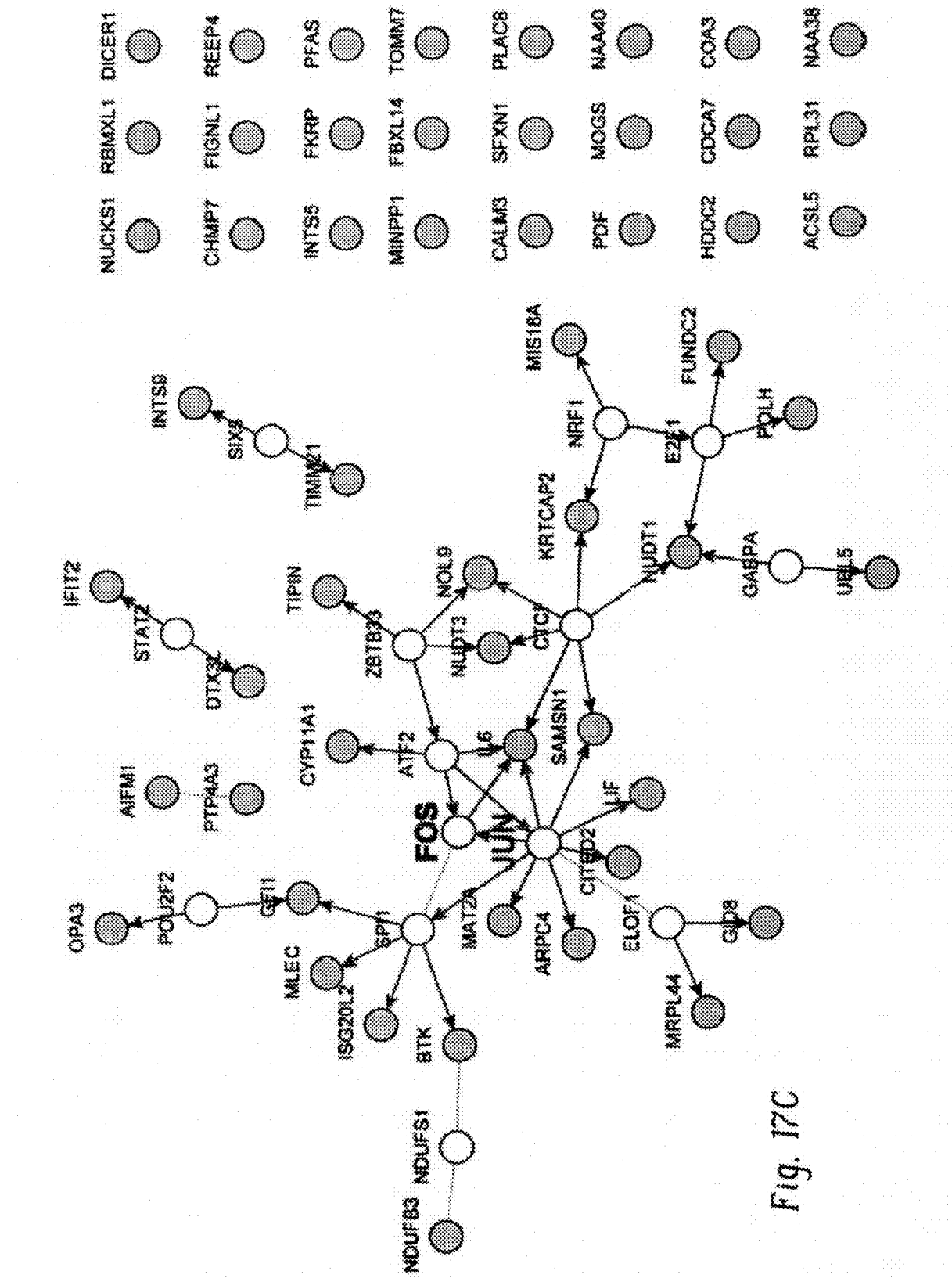

Given that curcumin and its analogs target many different proteins in addition to c-Fos, we compared the effects of chemical inhibition and genetic loss of c-Fos on gene expression. We performed whole-genome RNA-seq analysis on wild-type Kit+ cells expressing BCR-ABL treated with imatinib, DFC+BCI, DFC+BCI+imatinib and nontreated controls. Similarly, BCR-ABL-expressing Kit+ cells lacking c-Fos and DUSP1, treated with and without imatinib, were subjected to RNA-seq analysis. We compared gene expression in these samples to that of Kit+ cells transduced with the control vector (pMSCV-Ires-GFP) from WT mice. Consistent with the notion that DFC+BCI treatment inhibits c-Fos and Dusp1, we found a striking similarity between DFC+BCI-treated WT cells and Fos- and Dusp1-double-knockout BCR-ABL-expressing cells: 146 genes were regulated in common (58 upregulated and 88 downregulated) relative to those in untreated BCR-ABL-expressing cells (FIG. 17A). Further analysis of these differentially expressed genes, using Netwalker, suggests that the inhibition of c-Fos and Dusp1 in the context of BCR-ABL expression leads to both downregulation of a Fos-Jun-associated gene network and the induction of a Jun-JunD associated gene network (FIG. 17B,C).

The AP1 transcription factor is a dimeric complex that contains members of the JUN (JUN, JUNB, and JUND) and FOS (FOS, FOSB, FRA1, and FRA2) protein families (Angel, P. & Karin, M. The role of Jun, Fos and the AP-1 complex in cell-proliferation and transformation. Biochim. Biophys. Acta 1072, 129-157 (1991)). The final outcome of AP1 activity is dependent on AP1 dimer composition, as well as on the cellular and genetic context (Eferl, R. & Wagner, E. F. AP-1: a double-edged sword in tumorigenesis. Nat. Rev. Cancer 3, 859-868 (2003)). Our data show that, in the context of BCRABL expression, the absence of c-Fos and Dusp1 results in a net AP1 transcriptional output that is antiproliferative (reduced expression of Gfi1, ll6, Lif, and Cited2, and overexpression of JunD) and pro-apoptotic (overexpression of BCL2L11) (FIG. 17B,C). This analysis suggests that acute inhibition of BCR-ABL in c-Fos- and Dusp1-inhibited or c-Fos- and Dusp1-deficient cells undergo apoptotic shock (Pagliarini, R., Shao, W. & Sellers, W. R. Oncogene addiction: pathways of therapeutic response, resistance, and road maps toward a cure. EMBO Rep. 16, 280-296 (2015); Sharma, S. V. & Settleman, J. Oncogene addiction: setting the stage for molecularly targeted cancer therapy. Genes Dev. 21, 3214-3231 (2007)) owing to elevated expression of pro-apoptotic genes.

Dusp6 Deficiency Confers Imatinib Resistance

Because BCI inhibits both Dusp6 and Dusp1 (Molina, G. et al. Zebrafish chemical screening reveals an inhibitor of Dusp6 that expands cardiac cell lineages. Nat. Chem. Biol. 5, 680-687 (2009)), to determine whether the therapeutic efficacy of BCI is due to the inhibition of Dusp1 or Dusp6, we tested the effects of BCI on MAPK signaling in BaF3 and BaF3-BA cells overexpressing Dusp1 or Dusp6. Although all Dusp family members have the ability to dephosphorylate MAPKs, each Dusp shows a high degree of specificity toward its specific substrates (Lawan, A., Shi, H., Gatzke, F. & Bennett, A. M. Diversity and specificity of the mitogen-activated protein kinase phosphatase-1 functions. Cell. MoL Life Sci. 70, 223-237 (2013); Jeffrey, K. L., Camps, M., Rommel, C. & Mackay, C. R. Targeting dual-specificity phosphatases: manipulating MAP kinase signalling and immune responses. Nat. Rev. Drug Discov. 6, 391-403 (2007); Owens, D. M. & Keyse, S. M. Differential regulation of MAP kinase signalling by dual-specificity protein phosphatases. Oncogene 26, 3203-3213 (2007); Boutros, T., Chevet, E. & Metrakos, P. Mitogen-activated protein (MAP) kinase/MAP kinase phosphatase regulation: roles in cell growth, death, and cancer. Pharmacol. Rev. 60, 261-310 (2008)). For instance, Dusp6 and Dusp9 show a preference for dephosphorylating ERK2 over p38 or JNK (Groom, L. A., Sneddon, A. A., Alessi, D. R., Dowd, S. & Keyse, S. M. Differential regulation of the MAP, SAP and RK/p38 kinases by Pystl, a novel cytosolic dual-specificity phosphatase. EMBO J. 15, 3621-3632 (1996); Fjeld, C. C., Rice, A. E., Kim, Y., Gee, K. R. & Denu, J. M. Mechanistic basis for catalytic activation of mitogen-activated protein kinase phosphatase 3 by extracellular signal-regulated kinase. J. Biol. Chem. 275, 6749-6757 (2000)), whereas Dusp8, Dusp10 and Dusp16 specifically dephosphorylate JNK and p38 kinases (Jeffrey, K. L., Camps, M., Rommel, C. & Mackay, C. R. Targeting dual-specificity phosphatases: manipulating MAP kinase signalling and immune responses. Nat. Rev. Drug Discov. 6, 391-403 (2007)). Similarly, studies from mice lacking Dusp1 have revealed that it preferentially targets p38 and JNK (Dorfman, K. et al. Disruption of the erp/mkp-1 gene does not affect mouse development: normal MAP kinase activity in ERP/MKP-1-deficient fibroblasts. Oncogene 13, 925-931 (1996); Zhao, Q. et al. MAP kinase phosphatase 1 controls innate immune responses and suppresses endotoxic shock J. Exp. Med. 203, 131-140 (2006)). Overall, Dusp-mediated MAPK regulation is dependent on the cellular, genetic, and signaling contexts (Lawan, A., Shi, H., Gatzke, F. & Bennett, A. M. Diversity and specificity of the mitogen-activated protein kinase phosphatase-1 functions. Cell. MoL Life Sci. 70, 223-237 (2013); Jeffrey, K. L., Camps, M., Rommel, C. & Mackay, C. R. Targeting dual-specificity phosphatases: manipulating MAP kinase signalling and immune responses. Nat. Rev. Drug Discov. 6, 391-403 (2007); Hirsch, D. D. & Stork, P. J. Mitogen-activated protein kinase phosphatases inactivate stress-activated protein kinase pathways in vivo. J. Biol. Chem. 272, 4568-4575 (1997)).

Figure 18B:
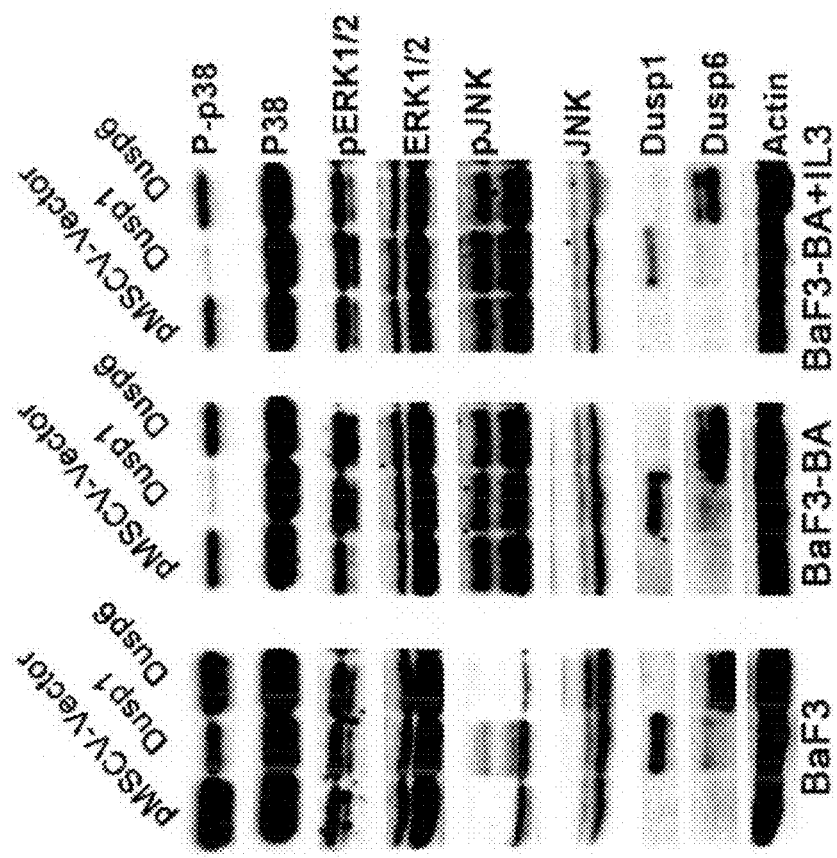
Figure 18A:
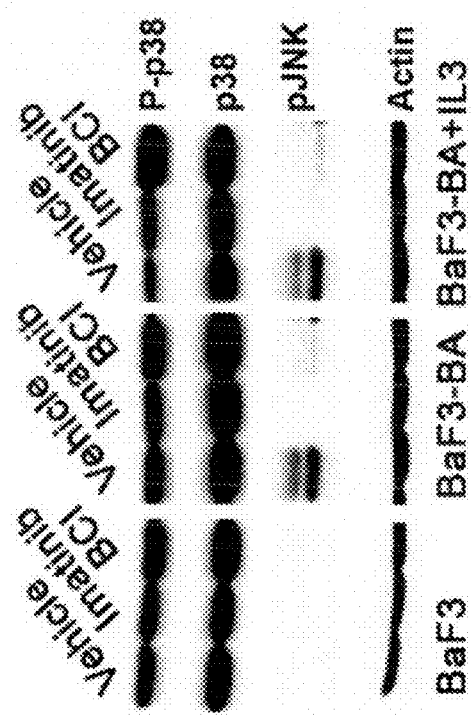

In accord with this complexity, BCI treatment resulted in enhanced phospho-p38 levels in both BaF3 and BaF3-BA cells and decreased phospho-JNK in BaF3-BA cells; the effects in BaF3-BA cells were observed with or without IL-3 co-treatment (FIG. 18A). Ectopic expression of Dusp1 in BaF3 and BaF3-BA cells reduced phospho-p38 levels, whereas the expression of Dusp6 did not modify the levels of phospho-ERK1/2, phospho-p38 or phospho-JNK in either cell type (FIG. 18B). Furthermore, overexpression of Dusp1, but not Dusp6, conferred resistance to BCI in BaF3-BA cells (FIG. 19A). These data support the hypothesis that BCI-mediated inhibition of Dusp1 activates p38 to induce TKI sensitivity and suggests that p38 inhibition would confer resistance to imatinib. Accordingly, we found that inhibition of p38 (using SB202190, a derivative of SB20358046), but not inhibition of JNK (using SP600125, which is 100-fold more selective for inhibition of JNK as compared to p38 (Bennett, B. L. et al. SP600125, an anthrapyrazolone inhibitor of Jun N-terminal kinase. Proc. Natl. Acad. Sci. USA 98, 13681-13686 (2001)), conferred imatinib resistance in BaF3-BA cells (FIG. 18C). Notably, coexpression of WT Dusp6 with BCR-ABL in WT bone marrow-derived Kit+ cells resulted in a significant reduction in CFU formation (~55%, P=0.001), but did not affect the cells expressing either vector or Dusp1 (FIG. 19B). Importantly, overexpression of Dusp1 but not of Dusp6 conferred resistance to drug (imatinib+BCI) treatment (FIG. 19B). Notably, unlike Dusp1-/- cells, Dusp6-/- cells were resistant to drug (imatinib+BCI) treatment and displayed normal CFU activity in comparison to untreated WT cells (FIG. 19C). Moreover, ectopic expression of Dusp6 in Dusp6-/- cells abolished drug resistance and restored TKI sensitivity to a normal level (FIG. 19C). Previous work has shown that Dusp6 expression might be a requirement for oncogenic transformation in B-ALL but not CML (Shojaee, S. et al. Erk negative feedback control enables pre-B cell transformation and represents a therapeutic target in acute lymphoblastic leukemia. Cancer Cell 28, 114-128 (2015)), and loss of Dusp6 expression in lung cancer confers TKI resistance (Hrustanovic, G. et al. RAS-MAPK dependence underlies a rational polytherapy strategy in EML4-ALK-positive lung cancer. Nat. Med. 21, 1038-1047 (2015)). Taken together with these previous results, our data suggest that the inhibition of Dusp6 favors cancer cell survival upon TKI treatment, and conversely, that the inhibition of Dusp1 modulates p38 activity to promote TKI-induced cell death in LICs.

Mutations Affecting the Allosteric Domain of Dusp1 Confer Resistance to BCI

Figure 18E:
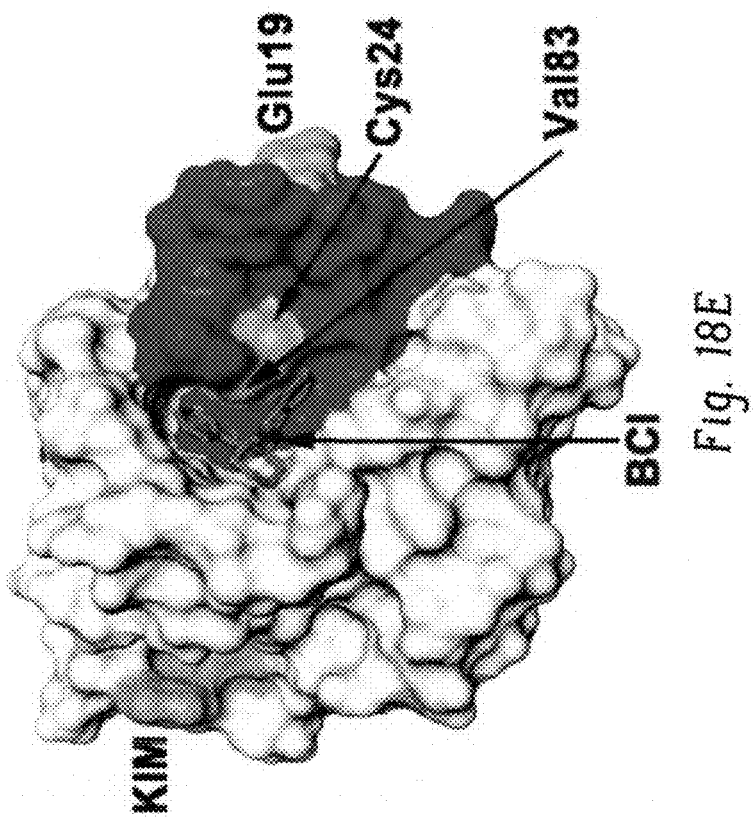
Figure 18D:
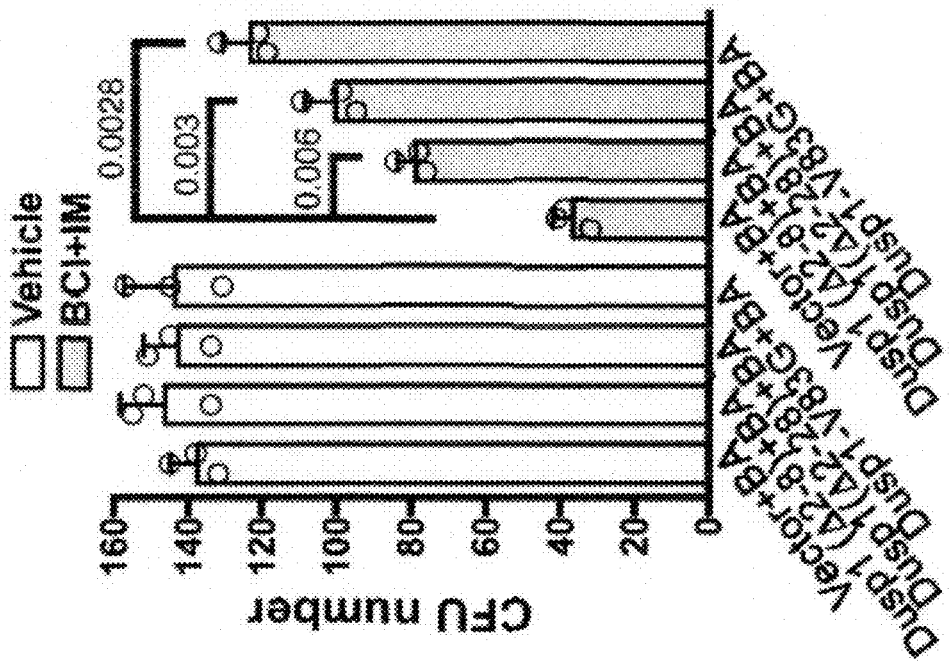
Figure 19D:
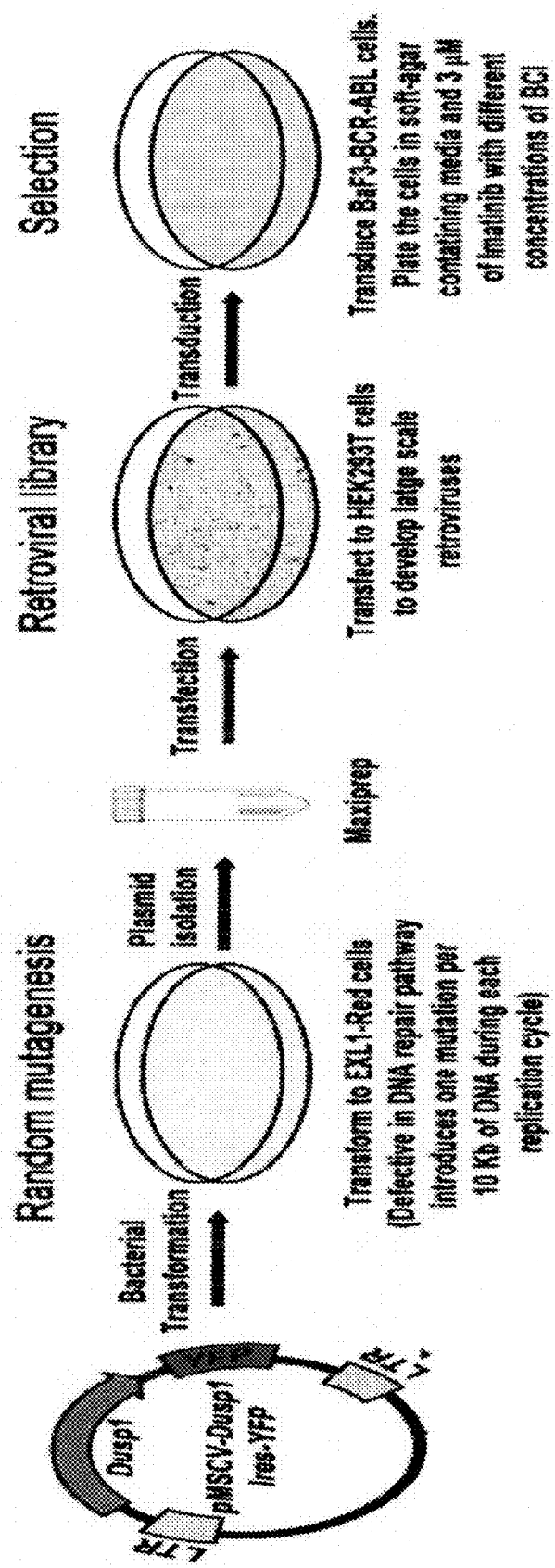
Figures 19E, 19F:
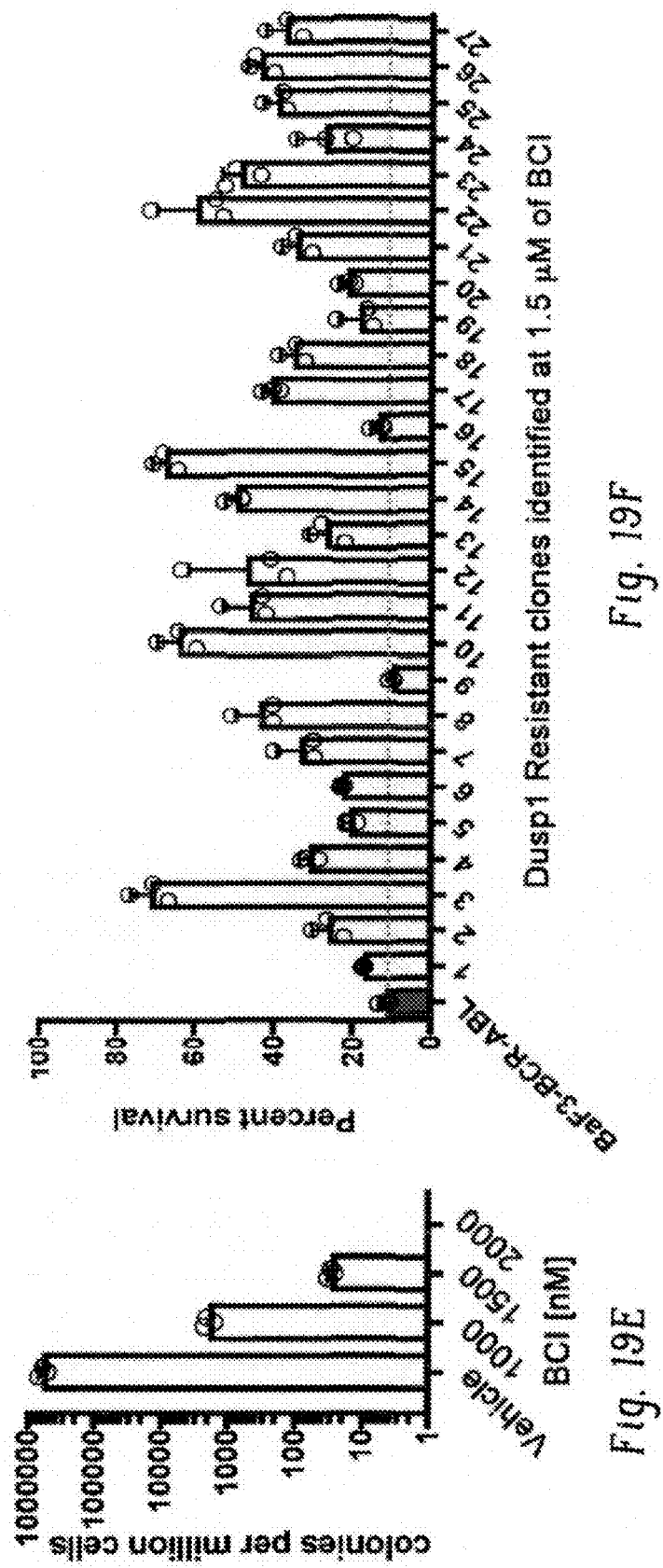
Figure 19G:
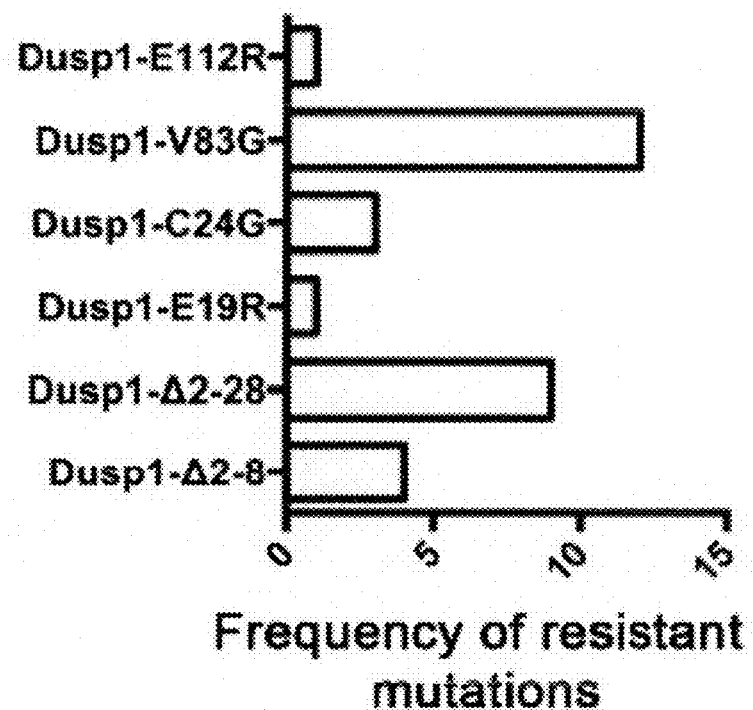
Figure 19H:
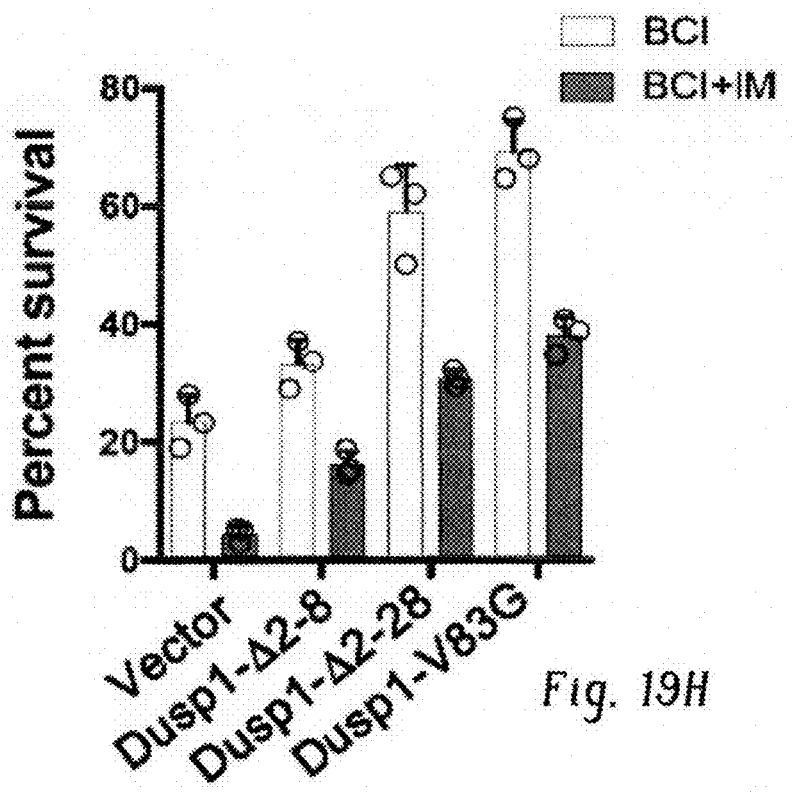
Figure 20E:
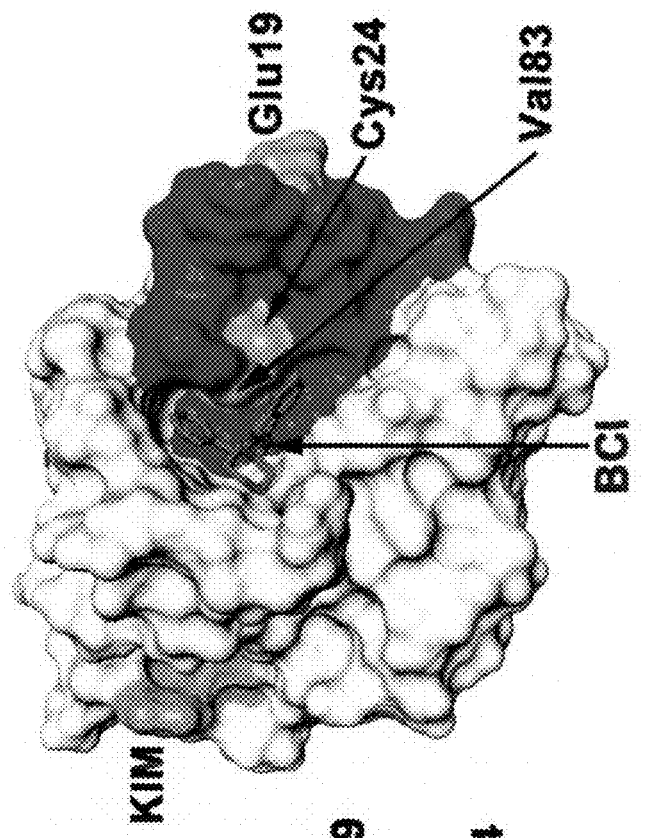
Figure 20D:
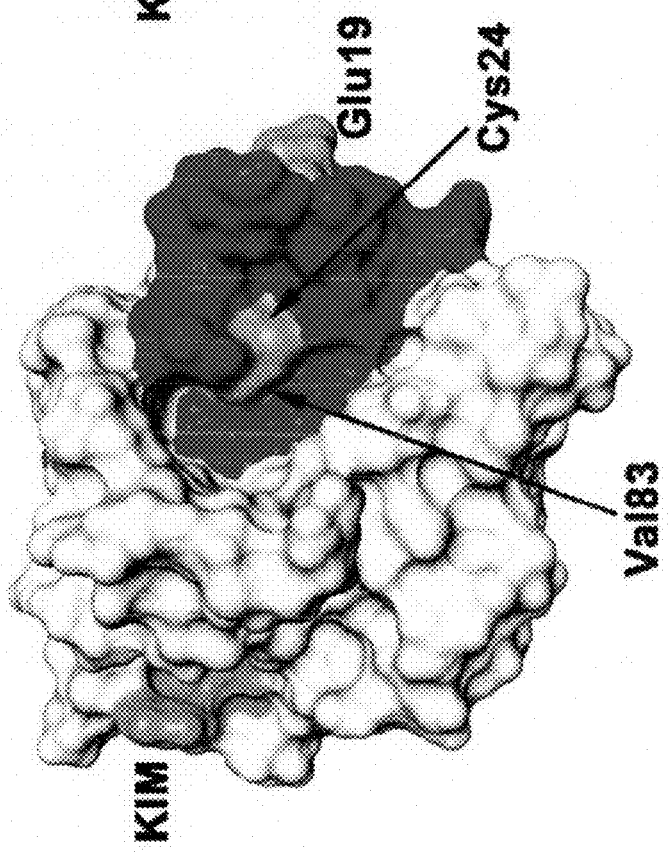

To determine the relevant target of BCI more conclusively, we performed in vitro drug-resistant screening to select for BCI-resistant mutations in Dusp1. BaF3-BA cells transfected with an expression library of randomly mutagenized Dusp1 construct were used for the selection of mutations conferring resistance to different concentrations of BCI (FIG. 19D). At 1 µM and 1.5 µM BCI, resistant clones emerged with a frequency of 1,200 clones and 27 clones per million cells, respectively, whereas selection at 2 µM of BCI did not yield any resistant clones (FIG. 19E). 27 clones that emerged in 1.5 µM of BCI were randomly selected and further analyzed. Dose-response analysis confirmed their resistance to BCI (FIG. 19F). Sequencing of the Dusp1 gene in these clones identified four different substitution mutations (E19R, C24G, V83G, and E112R) and two deletion mutations at the N terminus (Δ2-8 and Δ2-28; FIG. 19G). Because most resistant clones carried two or more mutations, we generated clones with individual mutations for further analysis. Expression of these resistant variants in BaF3-BA cells conferred resistance to BCI (FIG. 19H). Notably, the Dusp1-V83G variant demonstrated higher resistance than other tested variants, which potentially explains why it was more frequently observed in the screen (FIG. 19H). Similarly, expression of these resistant variants in BCR-ABL expressing BM-derived Kit+ cells conferred resistance to BCI treatment, and the Dusp1-V83G variant conferred greater resistance than the other variants tested (FIG. 18D). We mapped these resistant mutations on a homology-based structural model of Dusp1 and found that they clustered at the N terminus of the allosteric domain (rhodanese domain) rather than at the catalytic domain (FIG. 20). Furthermore, an unbiased docking of BCI using a structural model of the Dusp1 rhodanese domain identified the putative site to which BCI binds, with a predicted free energy of ΔG=−7.63 (FIG. 18E). Taken together, these data provide clear evidence that BCI-induced cell death is mediated by the inhibition of Dusp1 (rather than of Dusp6).

In Vivo Inhibition of c-Fos and Dusp1 Targets by DFC and BCI

To model the therapeutic potential of c-Fos and Dusp1 inhibition in vivo, we performed a pharmacodynamic analysis for BCI and DFC. We obtained peripheral blood mononuclear cells 6 h before and after BCI injection, and measured the levels of phospho-p38 and of the c-Fos-target genes Bcl2l11, ll6, and Lif (FIG. 18F,G). As expected, cells from mice injected with BCI showed an increase (by 4-8 fold) in phospho-p38 levels (FIG. 18F). Moreover, treatment with DFC+BCI induced Bcl2l11 expression while dampening the expression of Lif and ll6 (FIG. 18G). Notably, elevated serum IL-6 levels have been reported to be required for leukemic disease development (Zhang, B. et al. Altered microenvironmental regulation of leukemic and normal stem cells in chronic myelogenous leukemia. Cancer Cell 21, 577-592 (2012); Reynaud, D. et al. IL-6 controls leukemic multipotent progenitor cell fate and contributes to chronic myelogenous leukemia development. Cancer Cell 20, 661-673 (2011)), and IL-6-neutralizing antibodies can suppress disease development (Weiner, R. S. et al. Treatment of chronic myelogenous leukemia by blocking cytokine alterations found in normal stem and progenitor cells. Cancer Cell 27, 671-681 (2015)). Our data suggest that these markers (phospho-p38, IL6, and Lif) could potentially help to test the efficacy of c-Fos and Dusp1 inhibition and evaluate disease progression.

Deletion of Fos and Dusp1 Blocks BCR-ABL-induced B-ALL Development

Given that growth-factor signaling mediates intrinsic resistance to TKI therapy in both leukemia and solid organ tumors (Corbin, A. S. et al. Human chronic myeloid leukemia stem cells are insensitive to imatinib despite inhibition of BCR-ABL activity. J. Clin. Invest. 121, 396-409 (2011); Straussman, R. et al. Tumour micro-environment elicits innate resistance to RAF inhibitors through HGF secretion. Nature 487, 500-504 (2012); Wilson, T. R. et al. Widespread potential for growth-factor-driven resistance to anticancer kinase inhibitors. Nature 487, 505-509 (2012)), we reasoned that c-FOS and DUSP1 might have crucial roles in other types of kinase-driven leukemia. First, we tested the roles of Fos and Dusp1 in BCR-ABL-induced B-ALL, which, similarly to BCR-ABL-induced CML, is driven by a diverse spectrum of oncogenic tyrosine kinases and cytokine receptors (Roberts, K. G. et al. Genetic alterations activating kinase and cytokine receptor signaling in high-risk acute lymphoblastic leukemia. Cancer Cell 22, 153-166 (2012)); moreover, similarly to BCR-ABL-induced CML, most patients with BCR-ABL-induced B-ALL relapse under TKI treatment (Druker, B. J. et al. Activity of a specific inhibitor of the BCR-ABL tyrosine kinase in the blast crisis of chronic myeloid leukemia and acute lymphoblastic leukemia with the Philadelphia chromosome. N. Engl. J. Med. 344, 1038-

Figure 21A:
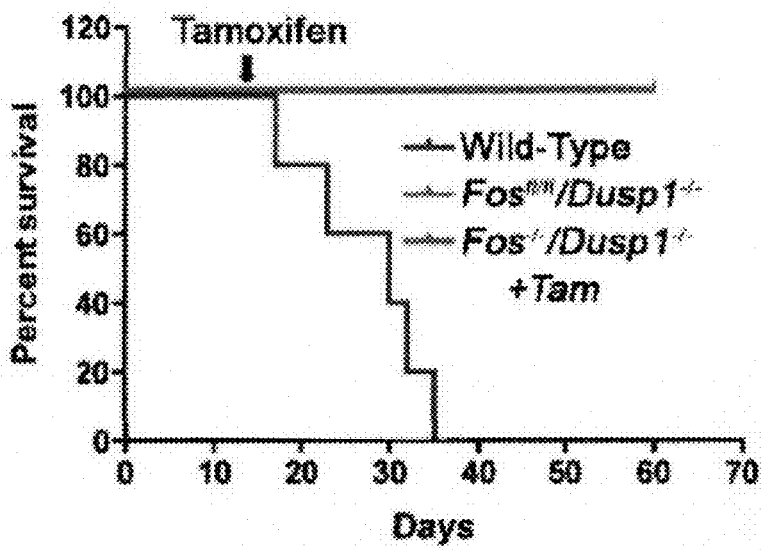
FIGS. 21A-G show deletion of Fos and Dusp1 is synthetic lethal to B-ALL development.
Figure 21B:
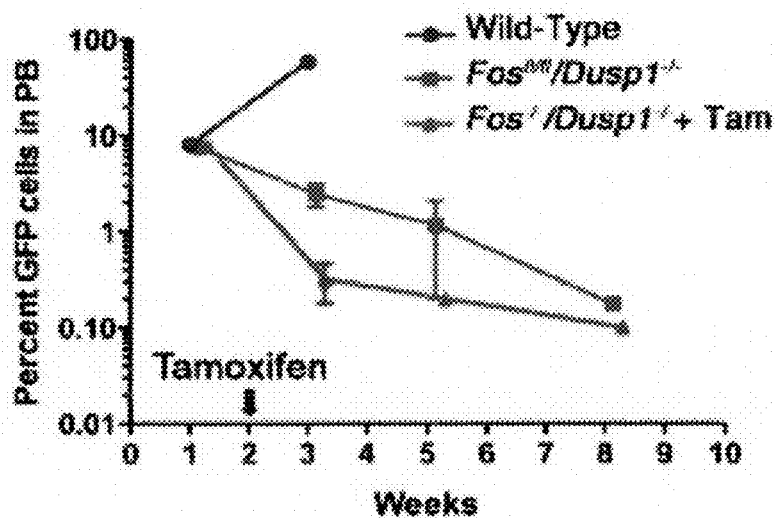
Figure 21C:
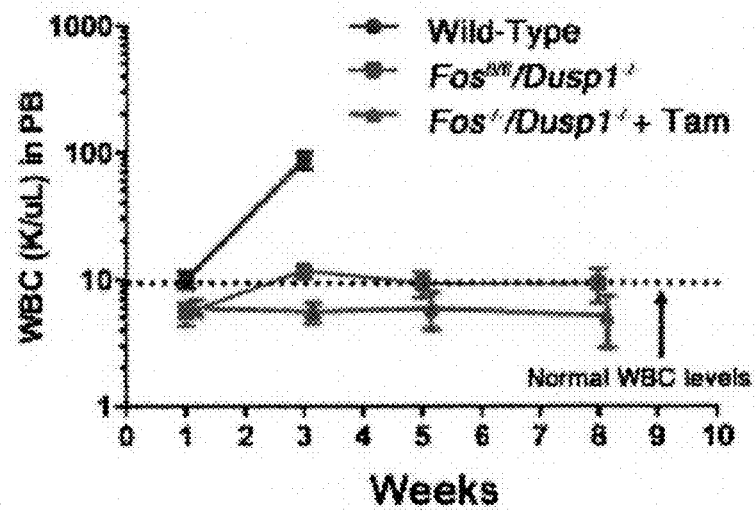

1042 (2001)). To model B-ALL in vivo in mice, we used bone marrow-derived mononuclear cells (MNCs) from WVT and ROSACreERT2Fosfl/fl;Dusp1−/− mice transduced with BCR-ABL-Ires-YFP (P190) retroviruses (Chang, K. H. et al. Vav3 collaborates with p190-BCR-ABL in lymphoid progenitor leukemogenesis, proliferation, and survival. Blood 120, 800-811 (2012)). Fos was deleted after 2 weeks of transplantation by tamoxifen injection. Recipients of WT BM-derived cells developed lethal leukemia with a disease latency of 4-5 weeks; by contrast, the deletion of both Fos and Dusp1 led to complete suppression of disease development and the eradication of leukemic cells within 3 weeks after tamoxifen injection (FIG. 21A-C). These data provide evidence that loss of c-Fos and Dusp1 together results in synthetic lethality in BCR-ABL expressing B-ALL cells. Surprisingly, mice that received BCR-ABL transduced ROSACreERT2Fosfl/flDusp1−/− cells, but that were not treated with tamoxifen, did not develop leukemia; leukemic cells disappeared from these mice, although with a delayed latency when compared to tamoxifen-treated mice (FIG. 21A-C), most likely owing to lower Fos mRNA expression in these mice as compared to WVT mice (FIG. 12E). Taken together, these data suggest that, unlike in CML, deletion of Fos and Dusp1 are sufficient to completely eradicate BCR-ABL-induced B-ALL.

Induction of c-Fos and Dusp1 by the Oncogenic Kinases FLT3-ITD and JAK2-V617F

Figure 21D:
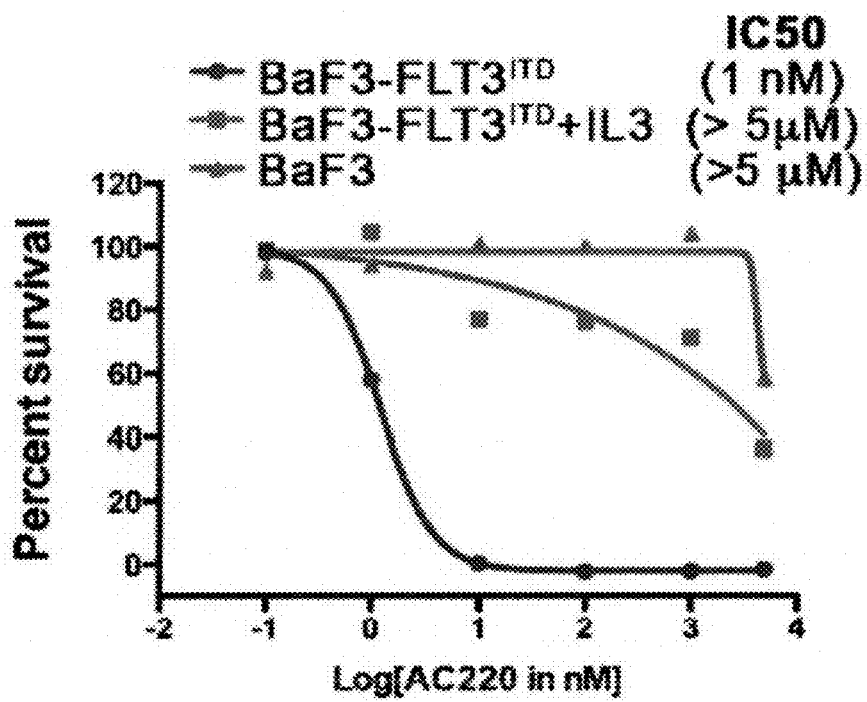
Figure 21E:
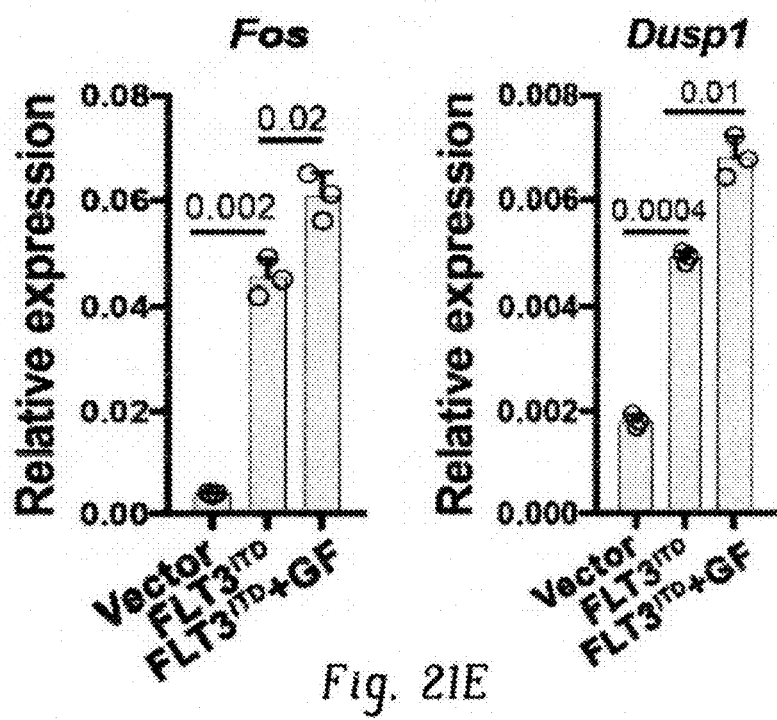
Figure 21F:
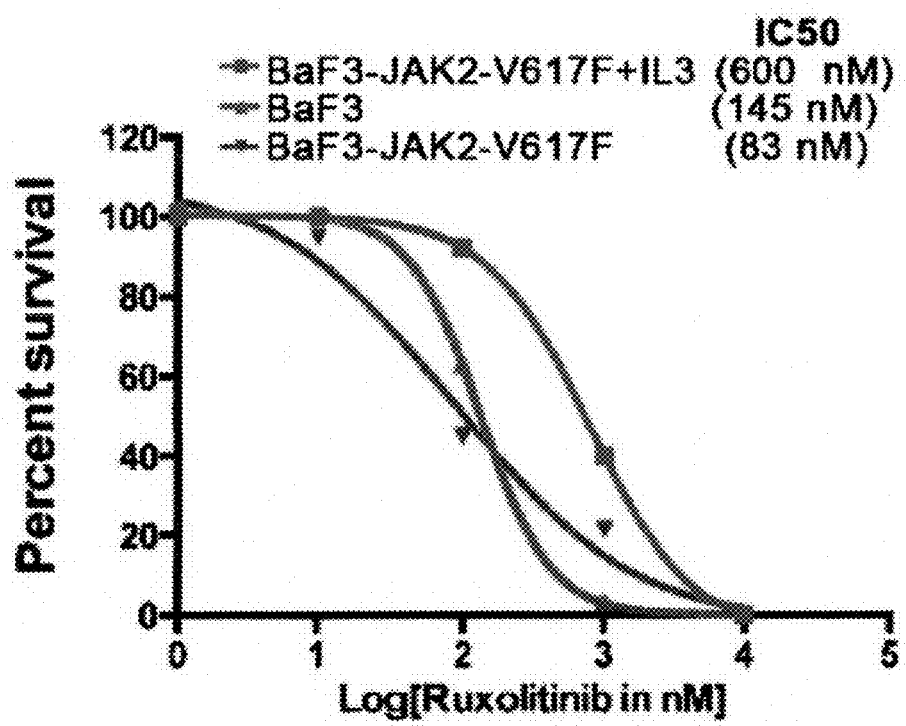
Figure 21G:
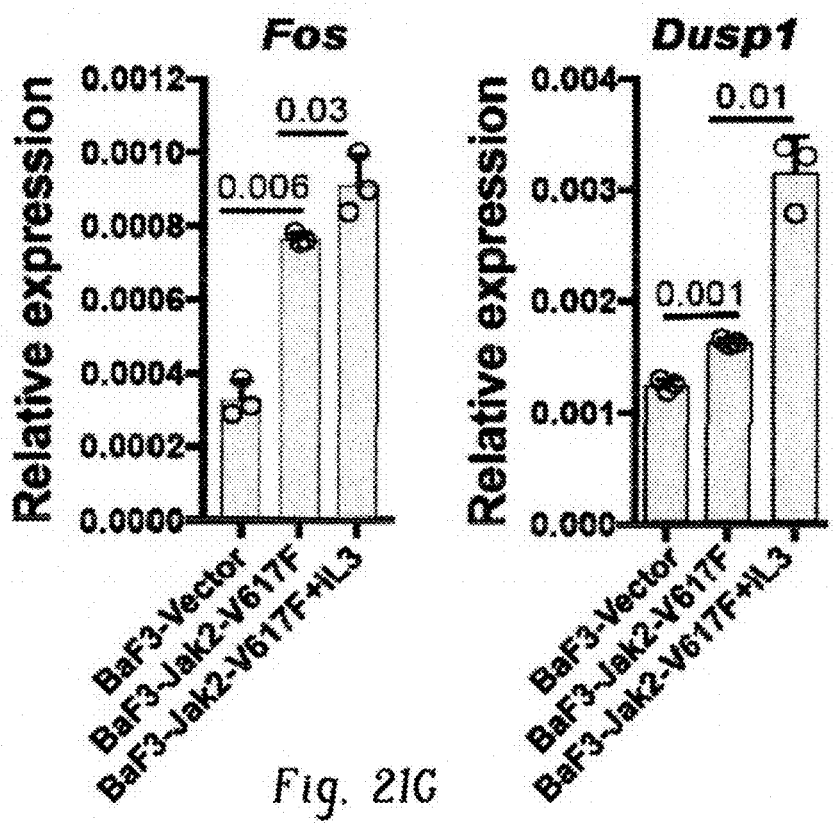

Next, we analyzed whether growth-factor signaling can confer resistance to the inhibitors of the oncogenic kinases Flt3 and Jak2. As expected, growth-factor signaling conferred resistance to the Flt3 inhibitor AC220 and the Jak2 inhibitor ruxolitinib in BaF3-FLT3-ITD and BaF3-Jak2-V617F cells, respectively (FIG. 21D,F). Similarly to BCR-ABL, the expression of FLT3-ITD and JAK2-V617F induced the expression of c-Fos and Dusp1 (FIG. 21E,G). This induction suggests a more general role for c-Fos and Dusp1 in TKI resistance.

c-Fos and Dusp1 in Normal Hematopoietic Cells

Figure 22A:
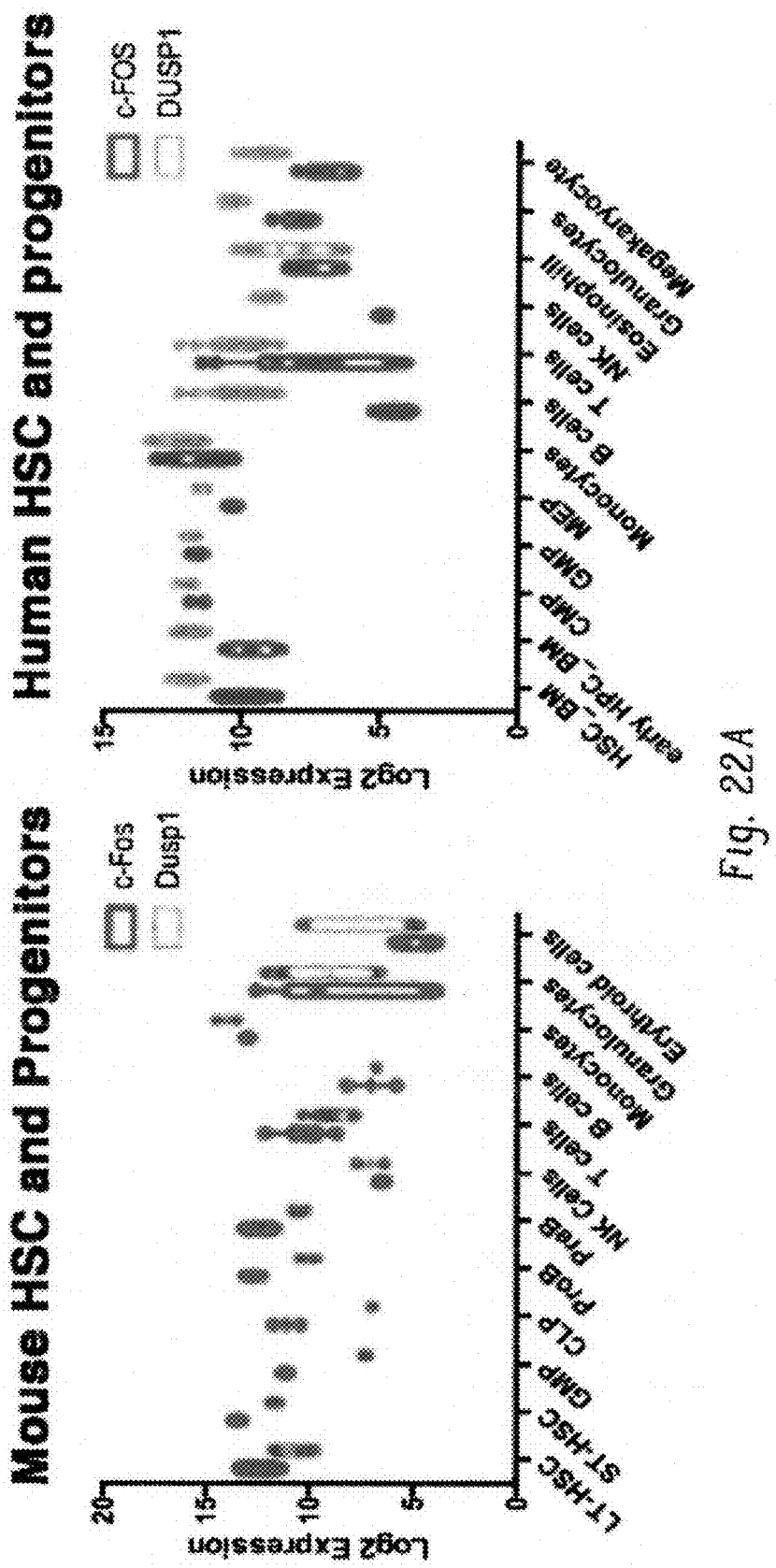
Figure 22B:
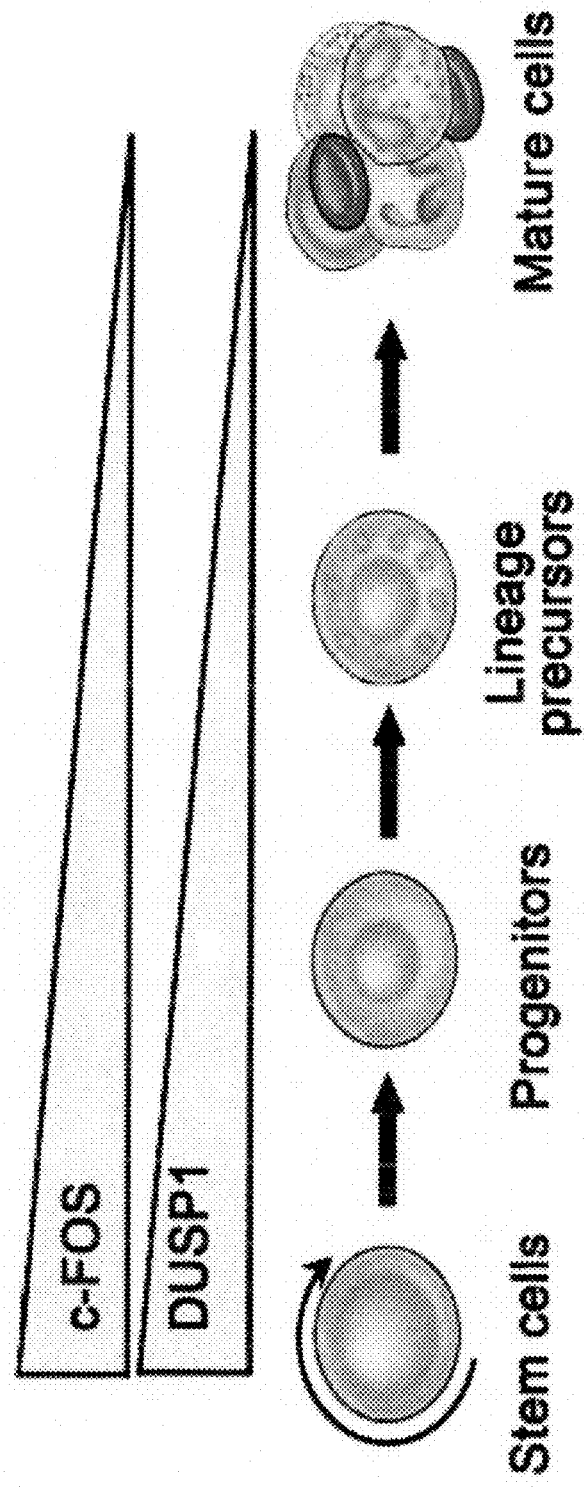

Both HSCs and LSCs (BCR-ABL-expressing HSCs) are dependent on growth factor-signaling, which suggests that elevated Fos and Dusp1 expression in these cells confer intrinsic resistance to TKI. As expected, we found that HSCs have higher levels of FOS and DUSP1 in both humans and mice (Bagger, F. O. et al. BloodSpot: a database of gene expression profiles and transcriptional programs for healthy and malignant haematopoiesis. Nucleic Acids Res. 44D1, D917-D924 (2016)) (FIG. 22A, B). Expression of BCR-ABL in mouse hematopoietic stem and progenitor cells (LSK cells) induced expression of c-Fos and Dusp1, as compared to vector transduced LSK cells (FIG. 22C), perhaps owing to the convergence of oncogenic and growth-factor signaling at these signaling nodes. Similarly, LSCs (CD34+ and CD38− cells) from patients with CML showed higher expression of FOS and DUSP1 as compared to normal HSCs (CD34+ and CD38− cells) (FIG. 22D).

Growth Factor Signaling Induces Pro-survival and Anti-apoptotic Genes

Figure 22E:
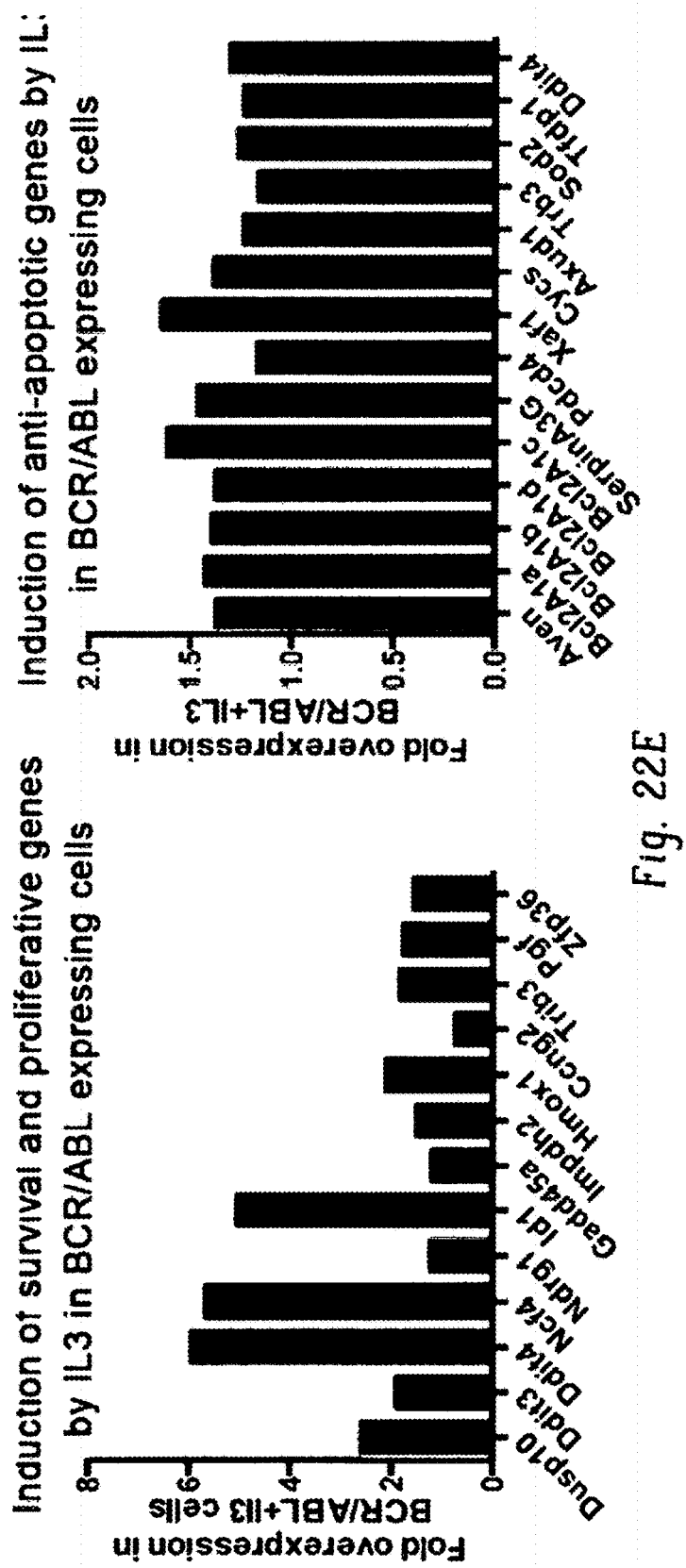

Expression analysis of BaF3-LTBA cells treated with IL-3 showed that higher Fos and Dusp1 expression, as compared to untreated BaF3-LTBA cells (FIG. 9C), is correlated with induced expression of pro-survival and anti-apoptotic genes (FIG. 22E), which might represent a protective mechanism. Notably, expression of these pro-survival and anti-apoptotic genes is dependent upon Fos and Dusp1 function, as shown using FOS and DUSP1 inhibitors (FIG. 22E,F). Taken together, these data provide evidence that higher levels of Fos and Dusp1 are required to maintain growth factor-induced expression of pro-survival and anti-apoptotic genes.

Figures 22G, 22H, 22I:
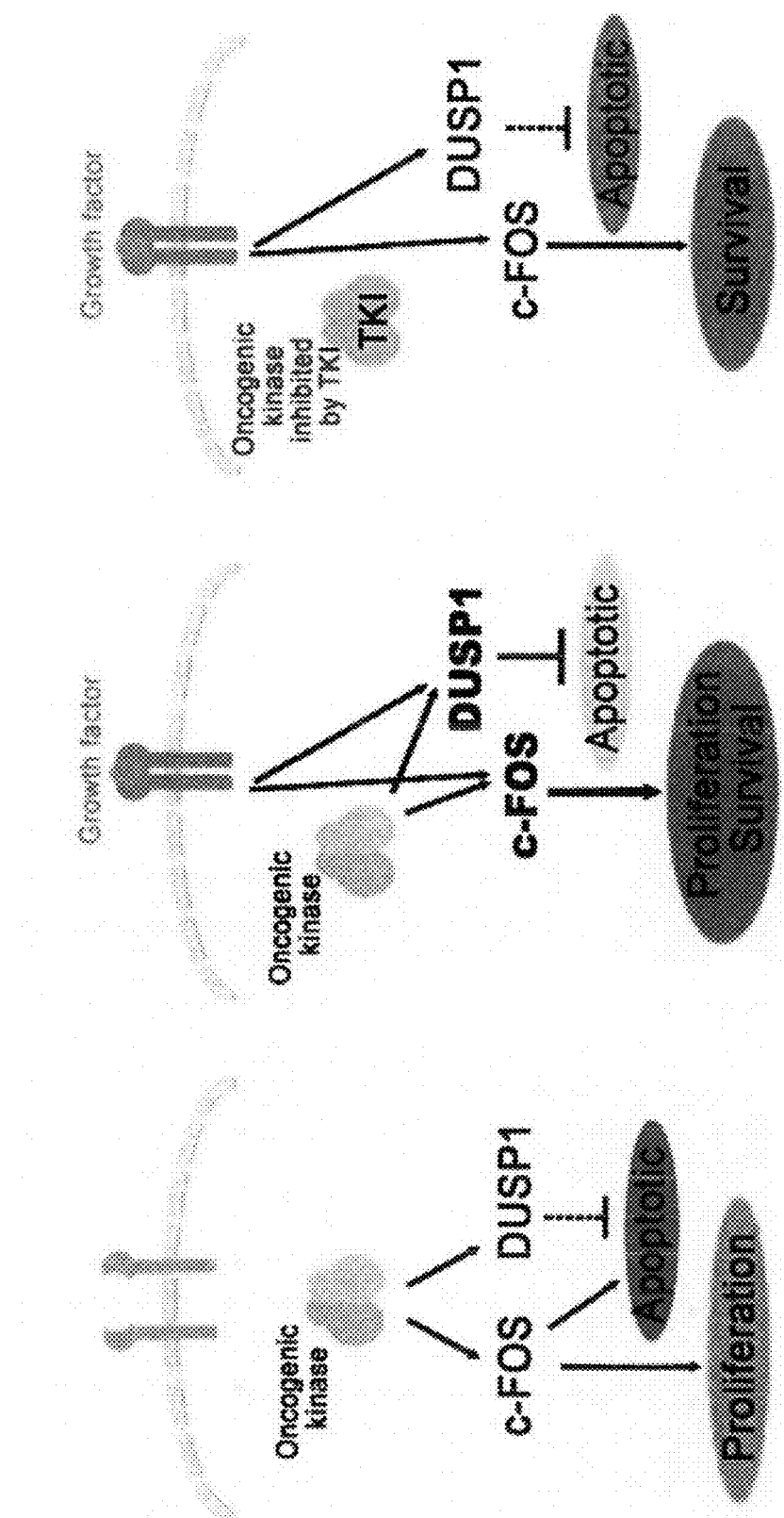

Initial excitement over the targeting of BCR-ABL with imatinib, a small-molecule TKI, has been tempered by the observation that LSCs from patients with CML can survive TKI treatment. Although this resistance was first thought to be due perhaps to incomplete inhibition of kinase activity, given that LSCs under imatinib treatment displayed residual kinase activity, later studies showed that LSCs survive even when treated with a next-generation BCR-ABL inhibitor, such as nilotinib, which fully quenches kinase activity in vivo (Jorgensen, H. G., Allan, E. K., Jordanides, N. E., Mountford, J. C. & Holyoake, T. L. Nilotinib exerts equipotent antiproliferative effects to imatinib and does not induce apoptosis in CD34+ CML cells. Blood 109, 4016-4019 (2007)). One could conclude from these data that LSCs are not oncogene dependent. According to our model (FIG. 22G-I), the expression of an activated kinase such as BCR-ABL usurps c-Fos- and Dusp1-mediated regulation of cell proliferation and survival. TKI treatment downregulates c-Fos and Dusp1 expression, leading to apoptosis in the bulk tumor; however, within TKI resistant cells (LSCs or BaF3-BA cells treated with IL3), growth-factor signaling can rescue c-Fos and Dusp1 expression, leading to sustained expression of pro-survival and anti-apoptotic genes and TKI resistance. Previous work showing a lack of addiction to BCR-ABL in LSCs from patients with CML prompted many researchers to identify pathways and potential therapeutic targets in these LSCs, such as phosphoinositide 3-kinase (PI3K)-AKT serine/threonine kinase 1 (AKT1); transforming growth factor (TGF)-β-Forkhead box O (FoxO), Hedgehog, and Wnt-β-catenin pathways (Holyoake, T. L. & Vetrie, D. The chronic myeloid leukemia stem cell: stemming the tide of persistence. Blood https://doi.org/10.1182/blood-2016-09-696013 (2017)). Although inhibition of these targets either alone or in combination with kinase inhibitors inhibits the survival of LSCs, such therapy has been shown to be detrimental to normal HSCs, because of the requirement of the targeted pathways for cell survival and self-renewal pathways in normal HSCs.

Our study shows that c-FOS and DUSP1 are activated by both kinase oncoproteins and growth factors, and that their expression levels are uniquely critical for the maintenance of growth-factor mediated rescue of MRD in mouse models of TKI-treated leukemia. Moreover, our data show that normal HSCs do not have a critical requirement for c-Fos and Dusp1, given that BM-derived cells lacking Fos and Dusp1 do not show any functional impairment, as assessed by transplantation experiments. We speculate that kinase-driven LSCs differ from normal HSCs because they have adapted to chronic kinase signaling and have become addicted to elevated c-Fos and Dusp1 activity, a growth-factor-induced signaling node. The levels of c-Fos and Dusp1 might dictate the threshold of TKI efficacy, such that lower levels confer sensitivity, whereas higher levels drive intrinsic resistance that leads to MRD in leukemia, and as described below, in solid organ cancers. Thus, these proteins may represent a unifying Achilles' heel of kinase-driven cancers. Our findings provide proof of principle that MRD can be treated through the inhibition of a convergent signaling node that mediates growth-factor-dependence in kinase-induced leukemia.

Methods

Mice. All mice were housed in the barrier facility at Cincinnati Children's Hospital (CCHMC). All experiments were performed under an IACUC approved protocol of the Cincinnati Children's Hospital in accordance with accepted national standards and guidelines. To generate conditional Fos mice, Fosfl/fl mice (Zhang, J. et al. c-fos regulates neuronal excitability and survival. Nat. Genet. 30, 416-420 (2002)) were crossed with ROSACreERT2 mice (Jackson laboratory, Bar Harbor, Me.) to generate ROSACreERT-Fosfl/fl mice. To create the doubleknockout mice, ROSACreERT2Fosfl/fl mice were bred with Dusp1−/−mice (Dorfman, K. et al. Disruption of the erp/mkp-1 gene does not affect mouse development: normal MAP kinase activity in ERP/MKP-1-deficient fibroblasts. Oncogene 13, 925-931 (1996)) to generate ROSACreERT2Fosfl/fl;Dusp1−/− mice. BoyJ mice were purchased from the mouse core facility at CCHMC. C57BL6 mice were purchased from Jackson Laboratory. Scl-tTA transgenic mice were obtained from the lab of C. Huettner. Mouse genotypes were confirmed by PCR analysis using gene-specific primers (Dorfman, K. et al. Disruption of the erp/mkp-1 gene does not affect mouse development: normal MAP kinase activity in ERP/MKP-1-deficient fibroblasts. Oncogene 13, 925-931 (1996); Zhang, J. et al. c-fos regulates neuronal excitability and survival. Nat. Genet. 30, 416-420 (2002)). Athymic Ncr nu/nu, NOD.Cg-Prkdcscid IL2rgtm1Wjl/SzJ (NSG) and hSCF, hIL-3, and h-GM-CSF transgenic NSG-derived (NSGS) mice were purchased from the CCHMC mouse core. 6-8-week-old mice were used in all experiments. Mice with the indicated genotypes were included in the study without any further preselection or formal randomization, and both male and female mice were used; we used age- and gender-matched mice. The investigators were not blinded to genotype group allocations.

Human specimens. Umbilical cord blood (UCB) cells, normal BM, CML (p210-BCR-ABL+) and blastic-phase leukemia specimens were obtained through Institutional Review Board-approved protocols (Institutional Review Board: Federalwide Assurance #00002988 Cincinnati Children's Hospital Medical Center) and donor-informed consent from CCHMC and University of Cincinnati. The patient samples are described in Table 1.

Plasmids and constructs. BCR-ABL was cloned into the pLVX-puro and pLVX-Tet-On-Puro (Clontech, USA) plasmids to yield pLVBA and pLTBA for constitutive and inducible expression, respectively. The plasmid pEYKBA9 was digested with EcoRI to release the BCR-ABL fragment that was purified and ligated to EcoRI-digested pLVX-puro and pLVX-Tet-On-Puro to generate the plasmids pLVBA and pLTBA, respectively. To create the dominant-negative c-Fos (c-Fos-ART), the basic region of FOS DNA-binding domain (amino acid residues 133-159) was deleted by PCR using primers (c-FOS-DRK-FP and c-FOS-DRK-RP) by QuikChange lightning multi-site directed mutagenesis kit (Agilent Technologies). The PCR reaction was carried out using template DNA (pDonor201-FOS obtained from PlasmID at Harvard cat. #HsCD00001156). Subsequently, these entry vectors were used to develop retroviral expression clones using destination vector (pMSCV-Ires-GFP. GW) by recombination cloning using LR clonase from Invitrogen. Similarly, retroviral expression vectors for Dusp1 and Dusp6 (pMSCV-Dusp1-Myc-Ires-cherry and pMSCV-Dusp6-Ires-GFP) were created by recombination cloning using entry clones (pENTR-Dusp1, pENTR-Dusp6 obtained from PlasmID at Harvard). BCI-resistant mutations of Dusp1 were created by site-directed mutagenesis kit, as described above, using pMSCV-Dusp1-Myc-Ires-cherry as template. All pENTR clones were confirmed by sequencing. Retroviral expression vectors (pMSCV-Fos-P2A-Dusp1) expressing Fos, and Dusp1 as a polycistronic construct, were cloned by recombination cloning using plasmids (pENTR-FOS/HA, pENTR-Dusp1/Myc). The retroviral vector pMSCV-BCR-ABL-IRES-YFP, a gift from T. Reya (Zhao, C. et al. Hedgehog signalling is essential for maintenance of cancer stem cells in myeloid leukaemia. Nature 458, 776-779 (2009)), was used to express BCR-ABL in primary mouse bone marrow cells for colony-formation cell assays and for in vivo transplantation and leukemia development.

Chemical reagents and cytokines. Kinase inhibitor imatinib was purchased from LC laboratories (Woburn, Mass.). Inhibitors for c-Fos, diflouro-curcumin (DFC) and curcumin, were purchased from LKT laboratories. The Dusp1 inhibitor BCI was synthesized by Chemzon Scientific (Montreal, Canada). Mouse cytokines (IL-3, SCF, IL-6 and Flt3L) were purchased from Peprotech, NJ, USA. Human cytokine erythropoietin was purchased from Amgen, CA. NDGA, tamoxifen, and 4-hydroxy tamoxifen were purchased from Sigma-Aldrich. Hydrocortisone was purchased from STEMCELL technologies.

Cell culture. BaF3, K562, and HEK293T cells were obtained from G. Daley's lab. MS5 was a gift. BaF3 and K562 were cultured and maintained in RPMI supplemented with 10% FBS and 100 IU/ml penicillin, 100 µg/ml streptomycin, and 2 mM l-glutamine. HEK293T cells were maintained in DMEM supplemented with 10% FBS and 100 IU/ml penicillin, 100 µg/ml streptomycin, and 2 mM l-glutamine. BaF3 parental cells were grown in RPMI with 10% WEHI conditioned media, used as a source of IL-3. BAF3 cells with BCR-ABL were maintained in RPMI without IL-3 supplementation.

Generation of stable cell lines. Cells stably expressing the BCR-ABL, Fos, Dusp1, and Dusp6 were generated by transducing with high-titer retroviruses, as described earlier (Kesarwani, M. et al. Targeting substrate-site in Jak2 kinase prevents emergence of genetic resistance. Sci. Rep. 5, 14538 (2015)). Inducible expression of BCR-ABL in BaF3 cells was achieved by transducing these cells with pLVX-Tet-On-Hygro viruses (Clontech), followed by selection for hygromycin resistance (selected at 600 µg/ml). Finally, BaF3 cells were transduced with pLTBA-puro viruses. Cells were selected for puromycin resistance at 3 µg/ml, generating the inducible-expression cell line BaF3-LTBA.

Cell-proliferation assay. $1 \times 10^4$ cells were seeded in 96-well plates in 100 µl of media with or without growth factors (50 ng/ml) and appropriate drug concentrations. The cells were incubated for 60 h. Cell viability was assessed with the WST-1 reagent (Roche) according to the manufacturer's recommendations, and read with a 96-well plate reader at 450 nm. All assays were performed in triplicate, and readings were averaged. A dose-response analysis to determine half-maximal inhibitory concentration (IC50) values was performed by sigmoidal curve fitting in GraphPad6, as described previously (Kesarwani, M. et al. Targeting substrate-site in Jak2 kinase prevents emergence of genetic resistance. Sci. Rep. 5, 14538 (2015)).

Apoptosis assay. BaF3-BA and K562 cells constitutively expressing BCR-ABL were grown with or without growth factors to the logarithmic phase. The cells from each group were treated with imatinib (5 µM) for 6 hours. The cells were then stained with APC-conjugated Annexin V (BD Biosciences), according to the supplier's instructions. 5 µl of propidium iodide (PI) was added to each sample after annexin-V staining, and the cells were subjected to FACS analysis (BD Canto II). Single annexin-V-positive cells were considered to be early apoptotic cells, whereas PI and Annexin-V-double-positive cells were considered to be late apoptotic or dead cells.

RNA isolation and gene-expression profiling. 5-6 million BaF3 and BaF3-LTBA cells grown with or without doxycycline (500 ng/ml) and IL-3 from the logarithmic phase were collected and resuspended in Qiazol for RNA isolation. Similarly, BaF3-BA cells (with constitutive expression of BCR-ABL) were grown with or without IL-3 and treated with imatinib (3 μM) for 6 h. Similarly, K562 cell lines were grown with or without erythropoietin (100 U/ml). After 6 h of imatinib (3 μM) treatment, cells were stained with annexin V and PI to quantify the levels of apoptotic cell death. The three separate populations of cells (double-negative cells (live cells), APC, or annexin-V-positive cells (early apoptotic cells) and double-positive cells (late apoptotic cells)) were sorted in PBS from each of the cell lines. 2 million sorted cells from each condition were immediately pelleted and frozen in 700 μl of Qiazol for RNA extraction. Total RNA was quantified, and 1 μg of RNA was used for expression profiling on the Mouse ST_1.0 Gene Chip Array (Affymetrix) for BaF3 cells and ExonExprChip. HuGene-1_0-st-v1 (Affymetrix) for K562 cells, at the Cincinnati Children's Gene Expression Core. The data were collected and .cel files were generated in the MASS suite (Affymetrix). The .cel files were imported into GeneSpring-GX 12.6.1 (Agilent Technologies) and analyzed using the latest annotation available. All biological replicates were averaged. For the first experiment (experiment 1; conditional expression of BCR-ABL in the presence or absence of IL-3, with the aim of determining changes in gene expression that are modulated by IL-3 in an oncogenic condition), the data were normalized to the median of parental BaF3 cells. After normalization, the genes were filtered on the basis of expression, and genes with probe-intensity values less than the 20th percentile in at least one condition were eliminated. For the second experiment (experiment 2; imatinib-induced changes in gene expression in BaF3-BA cells treated with or without IL-3) and the third experiment (experiment 3; imatinib-induced changes in gene expression in K562 cells treated with or without EPO), the data were normalized to the median of all samples followed by filtering on the basis of expression, and genes with probe-intensity values less than the 40th percentile in at least one condition were eliminated. Lists of genes that are differentially expressed were created using filtered genes with fold-change analysis between the cells grown with or without the growth factors for all three of the experiments. The fold-change cut-off was set to 1.5 for experiment 1 and was set to 2.0 for experiments 2 and 3. A published data set (GSE12211) that describes gene expression of CML-CD34+ cells during imatinib therapy (Bruennert, D. et al. Early in vivo changes of the transcriptome in Philadelphia chromosome-positive CD34+ cells from patients with chronic myelogenous leukaemia following imatinib therapy. Leukemia 23, 983-985 (2009)) was similarly analyzed using GeneSpring GX software. The samples were normalized to the median of control sample and filtered on the basis of expression, and genes with probe intensity values below the 50th percentile in at least one condition were eliminated. Gene lists were created containing genes that were differentially expressed by more than 2.0-fold between imatinib-treated and untreated samples. Finally, to identify commonly regulated genes in all four data sets, data sets were analyzed in GeneSpring GX, and the results are presented as a Venn diagram.

Real-time qPCR analysis. Candidate genes picked by microarray analysis were validated by real time qPCR. Total RNA was isolated as described above. The RNA was first subjected to DNase treatment using DNA-free DNase kit (Ambion, Life technologies). 2 μg of total RNA was converted to cDNA with Superscript III first-strand synthesis kit (Life technologies). qPCR reactions were performed with the human gene-specific primers using the SYBR green method and using a Mastercycler RealPlex2 instrument (Eppendorf). All PCR reactions were performed in triplicate and the real-time data was normalized to β-actin expression.

Western blotting. 4-6 million cells were collected, and whole-cell extracts were prepared using lysis buffer supplemented with a protease-inhibitor cocktail (Roche) and phosphatase-inhibitor cocktail 2 (Sigma-Aldrich), as described previously (Azam, M., Seeliger, M. A., Gray, N. S., Kuriyan, J. & Daley, G. Q. Activation of tyrosine kinases by mutation of the gatekeeper threonine. Nat. Struct. Mol. Biol. 15, 1109-1118 (2008)). The proteins were resolved on 10% SDS-PAGE gels and transferred to nitrocellulose membranes (Bio-Rad). Membranes were blocked in TBST with 5% nonfat milk and probed with appropriate antibodies as indicated. Densitometry was carried out using ImageJ software.

Colony-forming cell assays. Kit+ cells from the BM of WT, Dusp1−/−, ROSACreERT2Fosfl/fl, or ROSACreERT2Fosfl/fl;Dusp1−/− mice were isolated using the CD117 MicroBead Kit (Miltenyi biotec), according to the manufacturer's instructions. The cells were incubated overnight in IMDM media supplemented with 10% FBS and a cytokine cocktail with FLT3 (20 ng/ml), IL-6 (10 ng/ml), IL-3 (10 ng/ml), and mSCF (50 ng/ml). After 12 h of stimulation, the cells were transduced with BCR-ABL-IRES-YFP virus using retronectin (Takara). 5,000 YFP-positive cells (isolated by FACS) were plated on MethoCult GF M3434 (STEMCELL technologies containing imatinib (3 μM), DFC (0.2 μM), and BCI (0.5 μM)) alone or in combinations on three replicate plates. Similarly, curcumin (5 μM) or NDGA (5 μM) was used alone or in combination with imatinib (3 μM) and BCI (0.5 μM). Colony numbers were recorded after 1 week of plating. To delete Fos, the cells were plated on MethoCult GF M3434 containing 4-hydroxy tamoxifen (1 μg/ml).

BM cell transduction transplantation model of CML. Kit+ cells from the BM of 6-8-week-old WT C57BL/6, Dusp1−/−, ROSACreERT2Fosfl/fl, or ROSACreERT2 c-Fosfl/fl;Dusp1−/− mice were isolated and transduced with MSCV-BCR-ABLIRES-YFP, as described above. The transduced cells were cultured overnight. The percentage of BCR-ABL-positive cells was determined by measuring the level of YFP-positive cells after 20 h of viral transduction using flow cytometry (Fortessa I). 40,000 YFP-positive cells with 0.3 million normal BM-derived cells as carriers were transplanted into each mouse through tail-vein injection. After 1 week of transplantation, engraftment was determined by analyzing the YFP-positive cells from the peripheral blood using FACS. Transplanted mice that showed 10-40% YFP-positive cells in the peripheral blood were used for the experiment. Mice that had less than 2% YFP-positive cells were discarded from the study. To delete the Fosfl/fl allele, tamoxifen (100 mg/kg in corn oil) was i.p. injected into mice 1 week of transplantation, every day for three consecutive days. After tamoxifen treatment, where appropriate, the mice were grouped for drug treatments (n=5 per group). Mice were monitored for leukemia progression and survival, and the leukemic burden (YFP-positive cells) was determined weekly for up to 8 weeks in surviving mice. Animal numbers were chosen on the basis of previous experience and published data (Zhao, C. et al. Hedgehog signalling is essential for maintenance of cancer stem cells in myeloid leukaemia. Nature 458, 776-779 (2009)) for the transplantation of BCR-ABL-positive cells.

BM cell transduction transplantation model of B-ALL. BM cells were harvested from WT and ROSACreERT2Fosfl/fl;Dusp1−/− mice. Total mononuclear cells (TMNCs) were isolated by gradient centrifugation using Ficoll. Cells were washed and resuspended in 1 ml IMDM media+10% FBS supplemented with SCF (50 ng/ml; Prospec) and IL-7 (20 ng/ml; Peprotech). The cells were transduced with pMSCV-BCRABL (p190)-Ires-GFP virus. After 8 h of transduction, the cells were washed and injected (2×106 cells) into tail veins by i.v. into lethally irradiated C57BL/6 mice. After 2 weeks of transplantation, mice were injected with tamoxifen (100 mg/kg once per day for 3 d) to delete Fos. Peripheral blood from the transplanted mice was used to determine the leukemic burden (% GFP-positive cells), and the levels of white blood cells by complete blood counter (Hemavet, Drew Scientific, Oxford, Conn.).

BCR-ABL transgenic mouse model. Total BM cells from Scl-tTA transgenic mice (Koschmieder, S. et al. Inducible chronic phase of myeloid leukemia with expansion of hematopoietic stem cells in a transgenic model of BCR-ABL leukemogenesis. Blood 105, 324-334 (2005)) were isolated and followed with lineage depletion using lineage antibody cocktail from Milteny biotec, according to the manufacturer's instructions. Isolated Lin_cells were labeled with anti-Kit and anti-Sca1 antibodies to isolate LSK (Lin-Sca1+Kit+) cells by FACS. 3,000-5,000 BCR-ABL-LSK cells with 0.3 million helper bone marrow cells from WT BoyJ mice were injected via the tail vein into lethally irradiated BoyJ mice. 4 weeks post-transplantation, recipient mice were analyzed for CD45.1- and CD45.2-positive cells by FACS analysis to determine leukemic engraftment and chimerism. Mice were grouped into four groups (n=6 per group). Mice were treated with imatinib (75 mg/kg twice daily) alone and in combination with DC+BCI (both drugs were given at a dose of 10 mg/kg twice daily). Similarly, other groups were treated with combinations of imatinib (75 mg/kg)+curcumin (150 mg/kg)+BCI (10 mg/kg), and imatinib (75 mg/kg)+NDGA (100 mg/kg)+BCI (10 mg/kg), for 3 months twice a day by i.p. injection. The mice were analyzed for leukemic chimerism by determining the percentage of CD45.2-positive cells once a month for 6 months.

RNAseq analyses of Kit+ cells from WT and Fos- and Dusp1-knockout mice. Kit+ cells from the BM of VT and ROSACreERT2Fosfl/fl;Dusp1−/− mice were isolated using the CD117 MicroBead Kit (Miltenyi biotec), according to the manufacturer's instructions. These cells were incubated overnight in IMDM media supplemented with 10% FBS and a cytokine cocktail of FLT3 (50 ng/ml), IL-6 (10 ng/ml), IL-3 (10 ng/ml), and mSCF (50 ng/ml). After 12 h of stimulation, the cells were transduced with BCR-ABL-IRES-YFP virus using retronectin (Takara). 1-2 million positive cells (isolated by FACS) from each group was treated for 4 h with imatinib alone, DFC+BCI, or imatinib+DFC+BCI (3 µM imatinib, 0.2 µM DFC and 0.5 µM BCI alone or in combinations. The treatments were done in two replicates. To delete FOS, 4-hydroxy tamoxifen (1 µg/ml) was added to the media where applicable. Total RNA was isolated, and RNA-seq (20 million reads with paired ends) was performed at the DNA-sequencing core of Cincinnati Children's Hospital. Genes with an absolute log 2 change of 1 in BCR-ABL-expressing Fos−/−;Dusp1−/− cells (Fos was deleted by adding 4-hydroxy tamoxifen (1 µg/ml) treated with DFC+BCI, as compared to BCR-ABL WT cells (680 genes), were selected. From this list of genes, genes with similar profiles (146) in both Fos−/−;Dusp1−/− expressing BCR-ABL and WT cells expressing BCR-ABL that were treated with DFC+BCI were selected. To build a gene network, downregulated or upregulated genes were used as seeds to build a coherent network using the GeneConnector functionality in NetWalker suite (Komurov, K., Dursun, S., Erdin, S. & Ram, P. T. NetWalker: a contextual network analysis tool for functional genomics. BMC Genomics 13, 282 (2012)).

Mouse models of CML with patient-derived cells. 3 million CD34+ cells from CML patient CP4 (described in Table 1) were transplanted into sublethally irradiated 8-week-old NSG mice. 2 weeks after transplantation, leukemic engraftment in bone marrow was determined by FACS using mouse and human specific antibodies against CD45. Mice were grouped into four different cohorts (n=6/group) for treatment with vehicle, imatinib (75 mg/kg), DFC+BCI (both at 10 mg/kg), and imatinib (75 mg/kg)+DFC+BCI (both at 10 mg/kg). Drugs were diluted in PBS (vehicle) and administered by intraperitoneal injection twice daily. Mice were treated for 6 weeks, and the leukemic burden was determined every 2 weeks, until week 8 after transplantation.

LTC-IC assay. The LTC-IC assay was performed according to the instruction manual of StemCell Technologies. 5,000 CD34+ cells from patient CP4 or 1 million total MNCs from patient CP1 were cultured in StemSpan SFEM medium containing 50 ng/ml SCF, 5 ng/ml IL-3, 20 ng/ml IL-6, 50 ng/ml Flt3L, and 100 ng/ml GM-CSF for 24 h in the following conditions: untreated; imatinib (3 µM), DFC (200 nM)+BCI (500 nM), and imatinib (3 µM)+DFC (200 nM)+BCI (500 nM). After 24 h, the cells were washed in human long-term culture medium (HLTM; MyeloCult H5100 media containing 1 µM hydrocortisone) and were plated on irradiated MS-5 stromal cells. Cultures were maintained for 5 weeks with weekly half-medium changes. Cells were then harvested, counted, and transferred to methylcellulose-containing media (MethoCult Express, StemCell Technologies) for colony-forming assays. At the end of week 5, adherent and nonadherent cells were isolated and plated in methylcellulose (METHOCULT H4434 classic, stem cell technology) for CFU analysis in triplicate. Plates were incubated at 37° C., and colonies were scored 2 weeks after plating.

Pharmacodynamic analysis of Dusp1 and c-Fos targets. Phospho-p38 analysis. Three leukemic mice (8-12 weeks old), which had received transplants of BCR-ABL-expressing Kit+ cells, were injected with BCI (10 mg/kg) by intraperitoneal injection 4 weeks after transplantation. Phospho-p38 levels were quantified in peripheral blood MNCs using the Phosflow kit (BD Biosciences), according to the supplier's instructions. In brief, blood was collected from each mouse before and 6 hours after drug injection. Mononuclear cells were isolated by RBC depletion: RBCs were lysed twice using 4 ml Pharmlyse solution (BD Biosciences) per 100 µl of peripheral blood by mixing and incubated on ice for 5 min. After the second lysis step, cell pellets were washed with 1 ml 2% BSA in PBS followed by fixation using 100 µl of fixation and permeabilization solutions (BD Biosciences) for 20 min at 4° C. in the dark. The pellets were washed with 1 ml of 1×BD Perm/wash buffer. After fixation, the cells were blocked using 300 µl 2% BSA in Perm/wash buffer (BD Biosciences) at room temperature for 20 min. The cells were divided into three equal aliquots, 100 µl each (~1 million), and incubated with 1 µl total p-38 antibody, 1 µl phospho-p38 antibody, or 1 µl isotype IgG control, overnight at 4° C. The cells were then washed and incubated with secondary antibody (1 µl of AlexaFluor-488-conjugated secondary antibody) for 1 h at room temperature. Cells were washed once again and suspended in 200 µl PBS. Data were acquired by FACS on Fortessa instrument, and the data were analyzed by FlowJo software. The mean fluorescence intensity (MFI) of the IgG control was deducted from the MFI of the experimental samples. The MFI values of phospho-p38 were normalized to those of total p38 to determine the phospho-p38 levels after BCI injection. Quantitative gene-expression analysis of target genes. Three mice (8-12 weeks old) with leukemia, which had received transplants of BCR-ABL expressing Kit+ cells, were injected with DFC+BCI (10 mg/kg each). Peripheral blood was collected from each mouse before and 6 h after drug injection. Mononuclear cells were isolated by RBC depletion, as above. MNCs were pelleted and resuspended in Qiazol lysis buffer (Qiagen). Total RNA was extracted, followed by cDNA synthesis and qPCR analysis of Bcl2l11, Lif, and ll6 using gene-specific primers.

Drug preparation. All drugs were prepared as 10 mM stocks in DMSO and stored at −20° C. until use. For in vivo injection, the stocks of imatinib and BCI were diluted in PBS, whereas the DFC stock was diluted in alkaline PBS containing 15 mM of sodium hydroxide. All drugs were injected into mice via i.p injection.

FACS analysis. Peripheral blood (PB) cells were collected from transplant-recipient mice once per week via tail bleeding. 20 μl of blood were lysed using Pharmlyse solution (BD Biosciences), and the remaining mononucleated cells were pelleted by centrifugation. The cell pellets were washed once with cold PBS. The percentage of leukemic chimerism was determined by quantifying the levels of YFP-positive cells (BCR-ABL-Ires-YFP), analyzed by FACS. BM cells from mice transplanted with Scl-ttA-BCR-ABL cells or patient-derived cells were aspirated from the mouse femurs to determine the levels of CD45.2 and human CD45. These BM cells were blocked with FcR block (BD bioscience) followed by staining with anti-mouse FITC labeled CD45.1 and anti-mouse PE CD45.2. The FACS analysis was performed on an LSRII instrument, and the data were analyzed using FACSDIVA software. For the analysis of human grafts, bone marrow cells were aspirated every 2 weeks from femurs of the transplanted mice. RBCs were lysed using RBC lysis buffer as above, and the total MNCs were pelleted by centrifugation. The pellet was washed once with cold 1×PBS. The cells were blocked with human FcR block and mouse FcR Block (Miltenyi Biotec), followed by staining with anti-human CD45 FITC and anti-mouse CD45 APC Cy7 overnight at 4° C. The FACS analysis was performed on an LSRII instrument, and the data were analyzed using FACSDIVA software. For differential analysis of peripheral blood (PB) cells, 20 μl of blood was lysed using RBC lysis buffer and the TMNCs were pelleted by centrifugation and washing as described above. The cells were then blocked for 10 min at room temperature using mouse FcR blocking reagent (Miltenyi Biotec) followed by staining with the following antibodies for 30 min at 4° C.: anti-CD11 b (recognizes monocytes), anti-CD3 (recognizes T cells), anti-B220 (recognizes B cells), and anti-Gr1 (recognizes granulocytes). The FACS analysis was performed on an LSRII instrument, and the data were analyzed using FloJo software.

Random mutagenesis and screening of Dusp1 mutants. A Gateway entry clone containing mouse Dusp1 complementary DNA was purchased from the Harvard PalsmiD repository (cat. #MmCD00312825). The Dusp1 coding region was transferred into the retroviral gateway vector pMSCV-Ires-GFP.GW59 by recombination cloning. Mutagenesis and resistance screening were performed as described previously (Azam, M., Latek, R. R. & Daley, G. Q. Mechanisms of autoinhibition and STI-571/imatinib resistance revealed by mutagenesis of BCR-ABL. Cell 112, 831-843 (2003)). Mutants isolated in the screen were engineered into the pMSCV-Dusp1-Ires-GFP vector, using the QuikChange II XL Site-Directed Mutagenesis Kit (Agilent). The sequence of each point mutation was confirmed by sequence analysis.

Dusp1 structural modeling and inhibitor docking. Structural models of Dusp1 domains were built by homology-based modeling using SWISS-MODEL software, and crystal structures, as described previously (Kesarwani, M. et al. Targeting substrate-site in Jak2 kinase prevents emergence of genetic resistance. Sci. Rep. 5, 14538 (2015)). A model of the Dusp1 phosphatase domain was built using the crystal structures of Dusp4 (PDB: 3EZZ; Dusp4 has 85% sequence identity with Dusp1 and Dusp6 (PDB: 1MKP; Dusp6 has 48% sequence identity with Dusp1. The structure of the N-terminal rhodanese domain of Dusp1 was built using the crystal structure of Dusp16 (PDB: 2VSW; the N-terminal domain of Dusp16 has 26% sequence identity to Dusp1). Only three structures of a Dusp allosteric domain are available in the database (for Dusp6, Dusp10, and Dusp16), and a sequence analysis did not show sufficient sequence identity of the Dusp1 rhodanese domain with the N-terminal domains of Dusp6 and Dusp10 (less than 17%); we therefore used only the Dusp16 structure (PDB: 2VSW) to build the model. Blind docking of BCI to the rhodanese domain model of Dusp1 was performed using SwissDock software (Kesarwani, M. et al. Targeting substrate-site in Jak2 kinase prevents emergence of genetic resistance. Sci. Rep. 5, 14538 (2015)). Modules with the most favorable energies were clustered. For each cluster, binding modules with the lowest energy (i.e., the most likely to represent true binding) were selected to validate the model by site-directed mutagenesis, given that mutation V83G conferred resistance to BCI. Figures were generated using PyMol software.

Statistical analysis. Unless otherwise specified, results are depicted as the mean±s.d. Statistical analyses were performed using one-tailed Student's t test using GraphPad Prism (v6 GraphPad). Mantel-Cox test was used to perform Kaplan-Meier survival analysis in GraphPad Prism (v6, GraphPad).

Myeloproliferative Neoplasms (MPNs) are blood cancers that occur when the body makes too many white or red blood cells, or platelets. This overproduction of blood cells in the bone marrow can create problems for blood flow and lead to various symptoms. MPNs were called Myeloproliferative Diseases until 2008 when the World Health Organization reclassified them as cancers and renamed them Myeloproliferative Neoplasms. There are three main types of MPNs: Polycythemia vera (PV), Essential thrombocythemia (ET), and Myelofibrosis (MF). With the discovery of specific gene mutations in MPN, medications were designed to inhibit the abnormal proteins related to these mutations. The drug imatinib (Gleevec) was developed because it can inhibit the abnormal BCR-ABL protein in chronic myeloid leukemia cells. Ruxolitinib (Jakafi) is a JAK1/JAK2 inhibitor, and it is used to treat intermediate-to-high risk myelofibrosis (including primary myelofibrosis and myelofibrosis related to polycthemia vera or essential thrombocythemia).

Figure 23A:
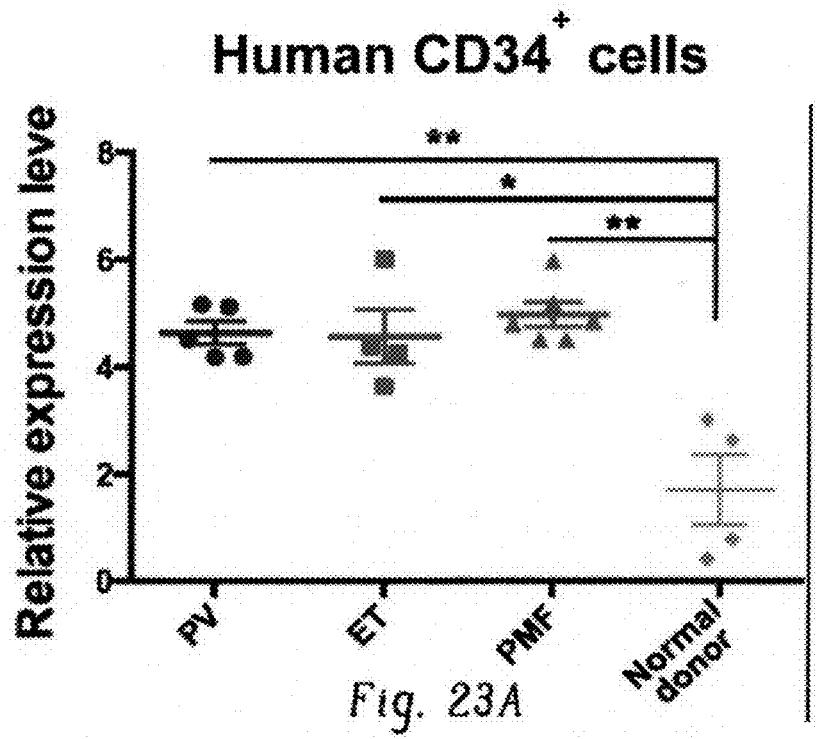
FIGS. 23A-B show overexpression of DUSP1 not c-FOS in MPN.
Figure 23B:
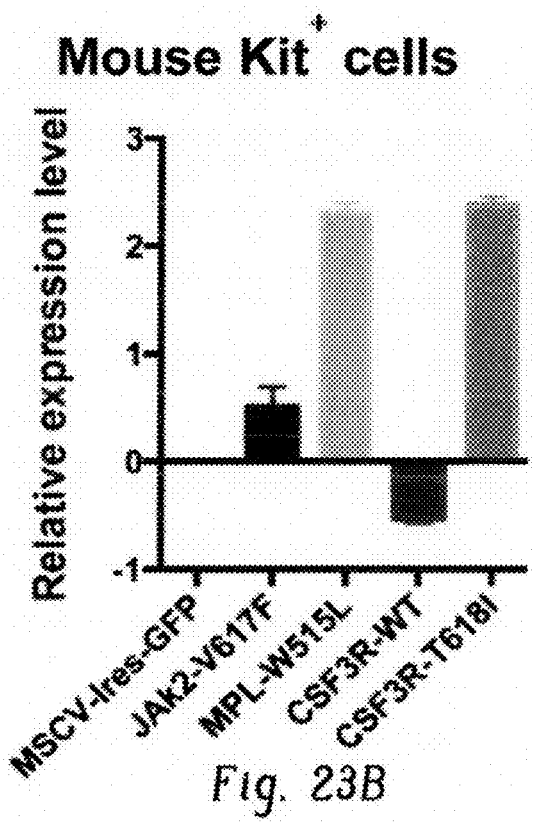
Figure 24A:
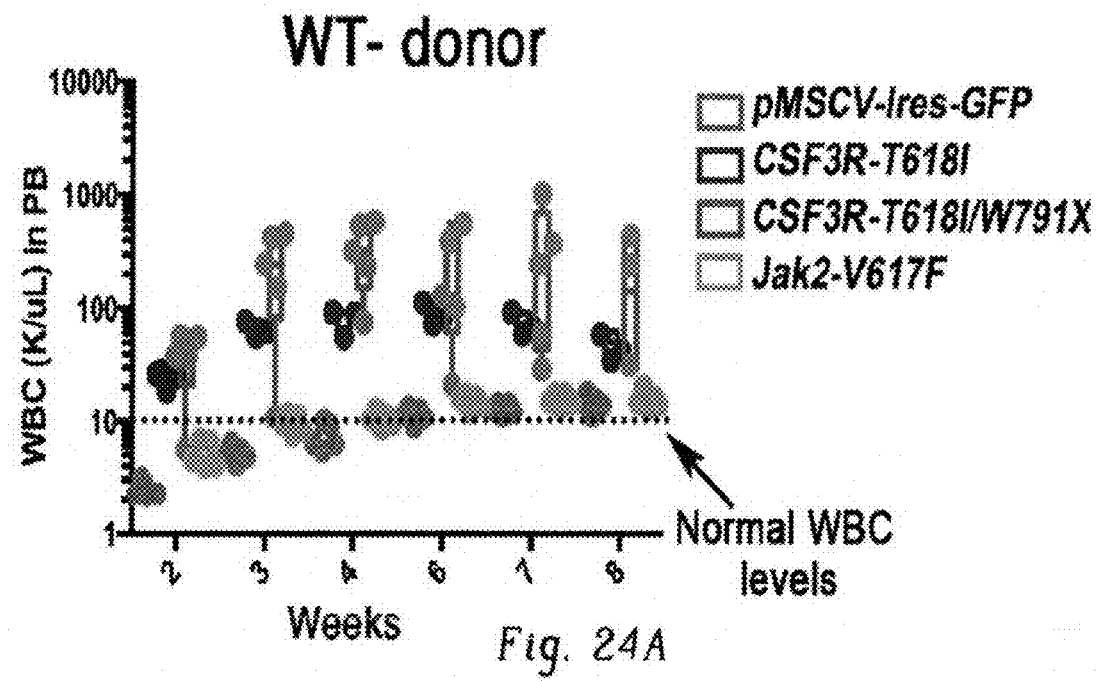
FIGS. 24A-D show lack of Dusp1 is synthetic lethal to MPN development in mice. BM derived Kit+ cells from wild type and Dusp1−/− mice were transduced with retroviruses expressing CSF3R-T618I, CSF3R-T618I-W791X, MPL-W515L, and Jak2 V617F.
Figure 24B:
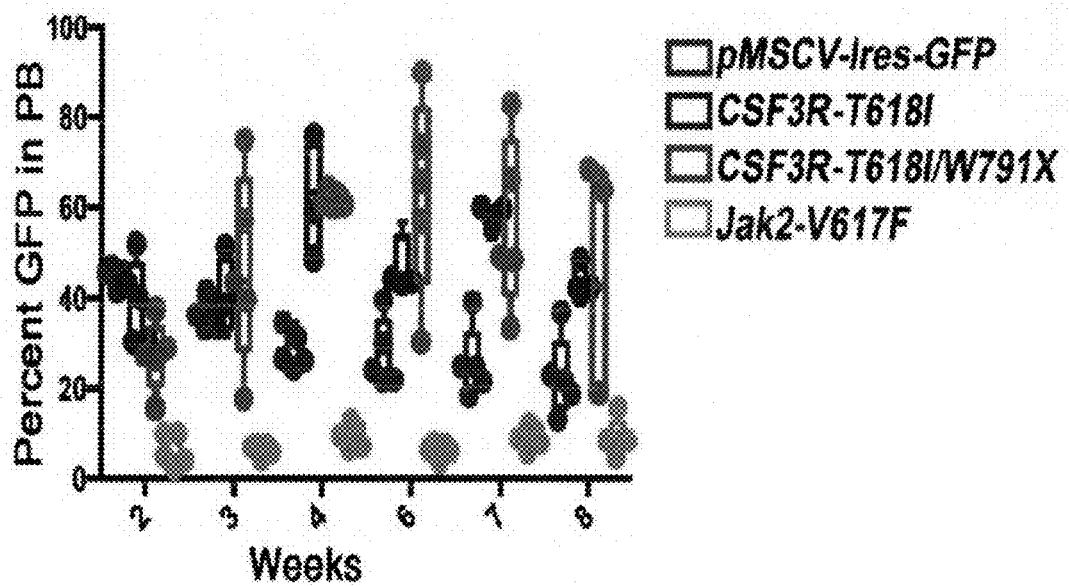
Figure 24C:
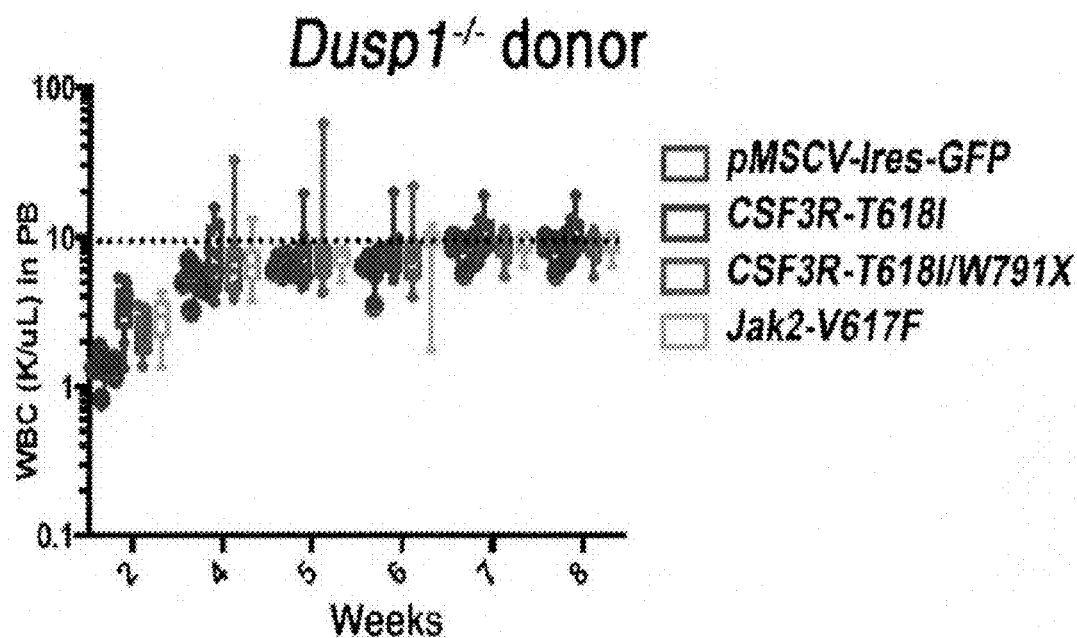
Figure 24D:
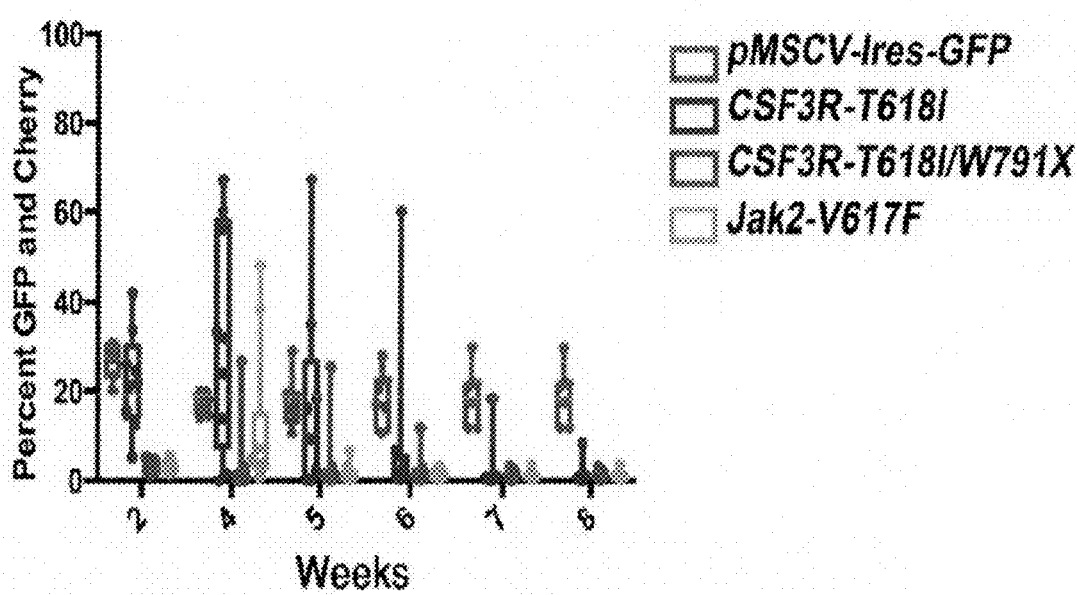

As shown in FIG. 23, DUSP1 but not c-FOS is overexpressed in MPN. As shown in FIG. 23A, CD34+ cells from six patients representing each subtype were analyzed and showed overexpression of DUSP1 in the 3 forms of MPN as compared to healthy donor. As shown in FIG. 23B, induction of Dusp1 in MPN cells is shown by qPCR analysis of Dusp1 in Kit+ cells expressing Jak2-V617F, CSF3R-WT, CSF3R-T618 and Mpl-W515L normalized to vector control. As shown in FIG. 24, lack of Dusp1 is synthetic lethal to MPN development in mice. BM derived Kit+ cells from wild type and Dusp1−/− mice were transduced with retroviruses expressing CSF3R-T618I, CSF3R-T618I-W791X, MPL-W515L, and Jak2 V617F. As shown in FIG. 24A, mice transplanted with wild type cells showing robust leukemia development by CSF3R and Mpl mutants, while mice received Jak2-V617F cells showed mild elevation in WBC, but showed significant increase in red cells and reticulocytes. As shown in FIG. 24B, leukemic burden as GFP+ cells over a period of eight weeks is shown. FIG. 24C shows that mice that received cells lacking Dusp1 did not show any signs of leukemia. FIG. 24D shows that all the GFP positive cells were abolished over the period of seven weeks in oncogenic conditions, while vector transduced cells have maintained normal engraftments. These data clearly show that the lack of Dusp1 is synthetic lethal to MPN development.

Figure 25A:
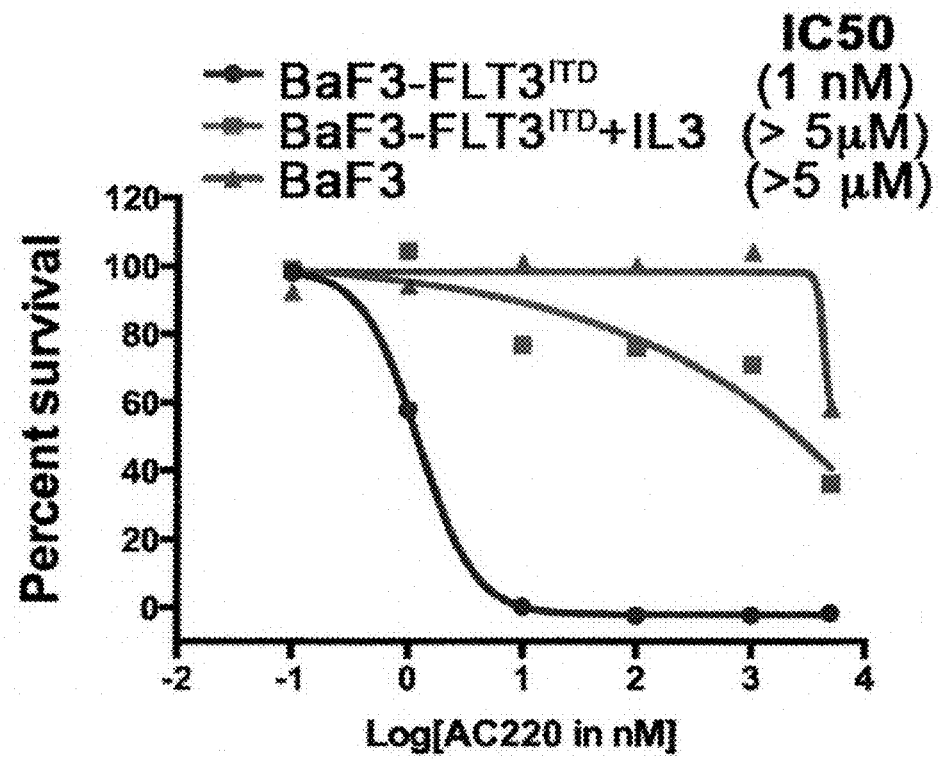
FIGS. 25A-B show induction of FOS and DUSP1 in AML and MPN confers TKI resistance. Growth factor (GF) signaling abrogates oncogene dependence and confers TKI resistance.
Figure 25B:
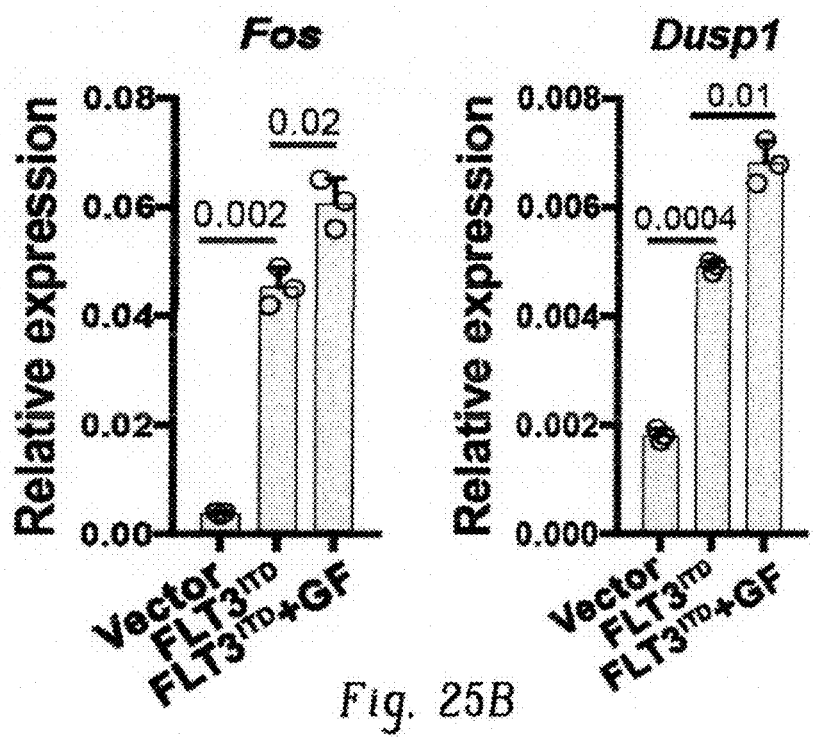
Figure 27A:
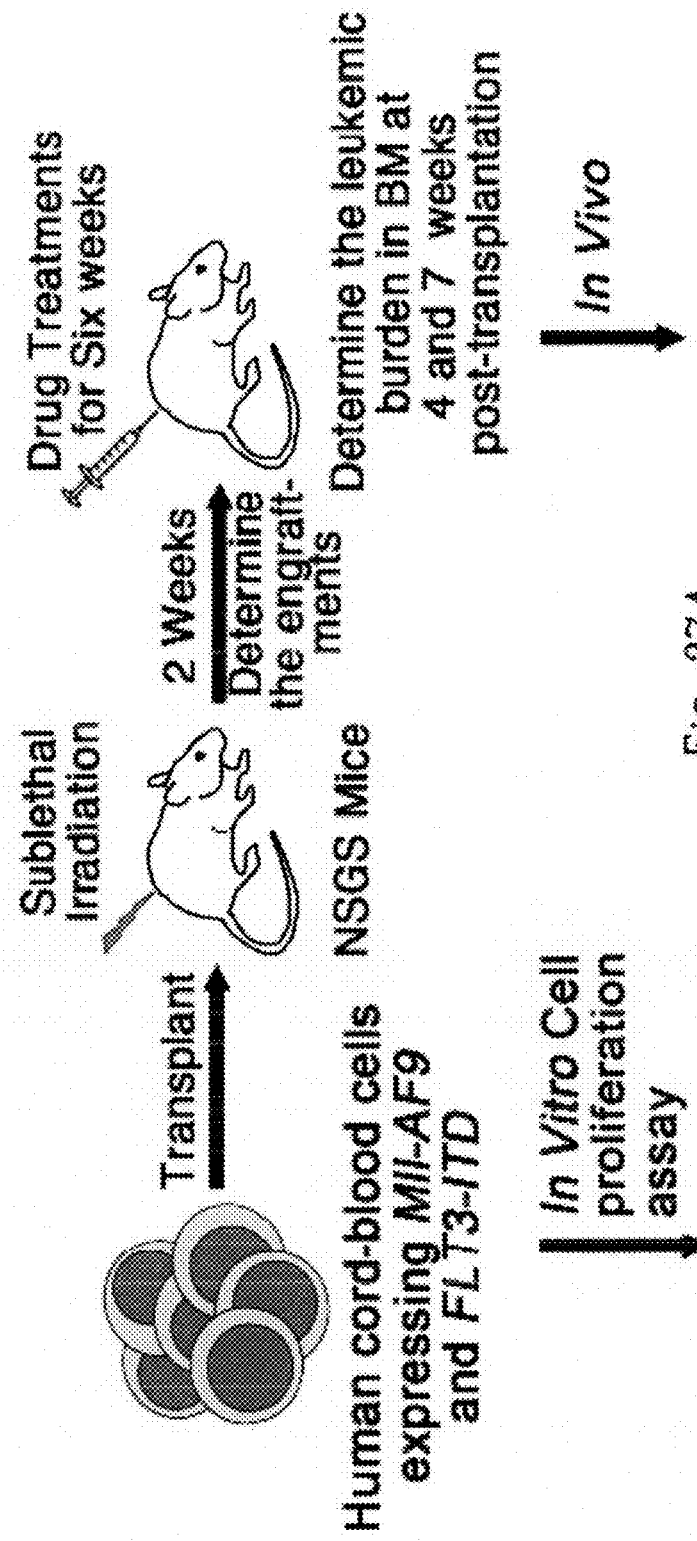
FIGS. 27A-C show deletion of FOS and DUSP1 is synthetic lethal to AML development. c-Fos and Dusp1 confer oncogene-dependence in high-risk FLT3ITD:MLLAF9 driven AML.
Figure 27C:
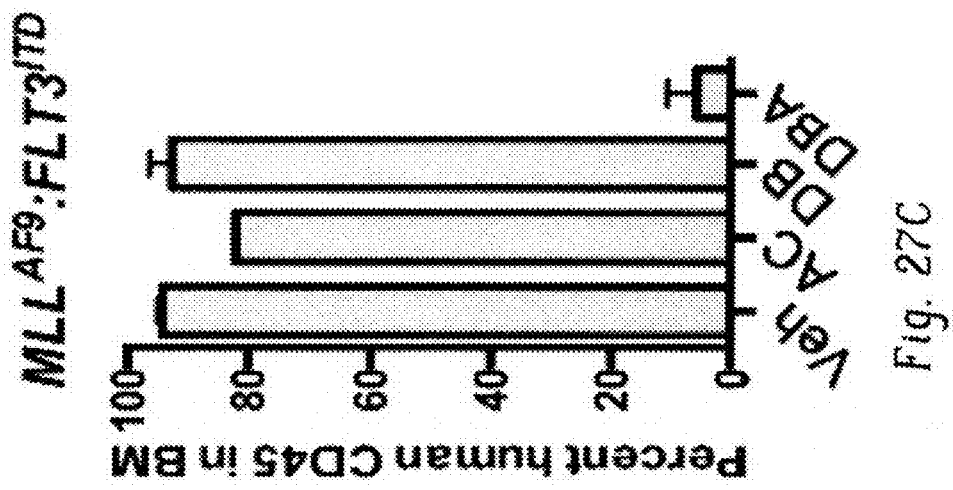
Figure 27B:
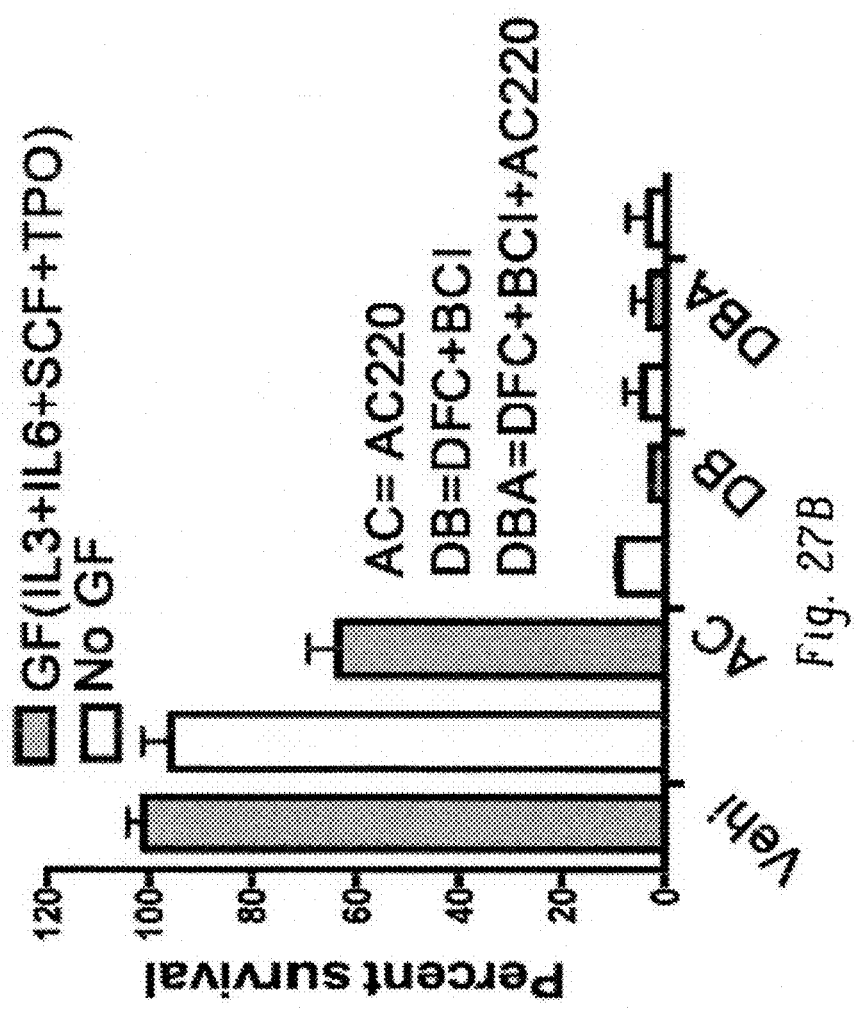

Acute myeloid leukemia (AML) is a cancer of the myeloid line of blood cells, characterized by the rapid growth of abnormal cells that build up in the bone marrow and blood and interfere with normal blood cells. Although progress has been made in treating many types of cancers during recent years, AML remains a deadly disease with survival rate lagging behind other blood cancers. A combination of toxic chemotherapies has been the standard AML treatment for more than 40 years. With efforts to define the pathogenesis of AML, therapeutic drugs targeting key molecular defects in AML are being used. Mutated in nearly 30% of AML, FMS-like tyrosine kinase 3 (FLT3) represents one of the most used targets. FLT3 mutants resulted from either internal tandem duplication (ITD) or point mutations possess enhanced kinase activity and cause constitutive activation of signaling. To date, several small molecule inhibitors of FLT3 have been developed but their clinical efficacy is limited due to a lack of potency and the generation of drug resistance. KIT is mutated in 8.0% of acute myeloid leukemia (AML). Oncogenic KIT mutations occur primarily in core binding factor (CBF). KIT mutations occur primarily in exon 17 and affect the activation loop of the kinase domain. These changes result in improved survival and growth of tumor cells. Induction of FOS and DUSP1 in AML and MPN confers tyrosine kinase inhibitor (TKI) resistance. FIG. 25 shows that growth factor (GF) signaling abrogates oncogene dependence and confers TKI resistance. FIG. 25A shows a dose response curve of BaF3 and BaF3-FLT3ITD cells showing resistance to Flt3 inhibitor (AC220 or quizartinib) in the presence of growth factor, IL3. IC50 for AC220 is shown in the parenthesis. FIGS. 25B-C show bar graphs showing the induction of c-Fos and Dusp1 by both FLT3ITD and GF signaling. FIG. 26 shows that deletion of FOS and DUSP1 is synthetic lethal to AML development. c-Fos and Dusp1 constitute non-oncogene addiction in FLT3ITD:MLLAF9 driven AML. FIG. 26A shows a scheme to test the role of Fos and Dusp1 in AML. FIG. 26B shows a bar graph showing CFU assays using Kit+ cells from the wild type and Fos−/−/Dusp1−/− mice. CFU assays were performed with and without Flt3 TKI (5 nM of AC220). Note, cells expressing FLT3ITD and MLLAF9 are resistant to TKI while cells lacking Fos and Dusp1 show synthetic lethality to oncogene expression, suggesting these genes are essential for AML development, however, they are indispensable for normal hematopoiesis because vector transduced cells do not show any defect in CFU formation (data not presented). FIG. 27 shows that c-Fos and Dusp1 confer oncogene-dependence in high-risk FLT3ITD:MLLAF9 driven AML. FIG. 27A shows a humanized AML model. CD34 cells from human cord blood were transduced by retroviruses expressing FLT3ITD-Ires-Cherry and MLLAF9-Ires-GFP. Double positive (GFP+Cherry) cells were sorted by FACS followed with in vitro and in vivo analysis. FIG. 27B shows histograms showing resistance to AC220 in the presence of GF (IL3, IL6, SCF and TPO) in in-vitro assay and FIG. 27C shows transplanted NSGS mice die of leukemia within six weeks and show complete eradication of leukemic cells when treated with combination of DFC+BCI+AC220 while AC220 or DFC+BCI alone are ineffective.

Figures 28A, 28B:
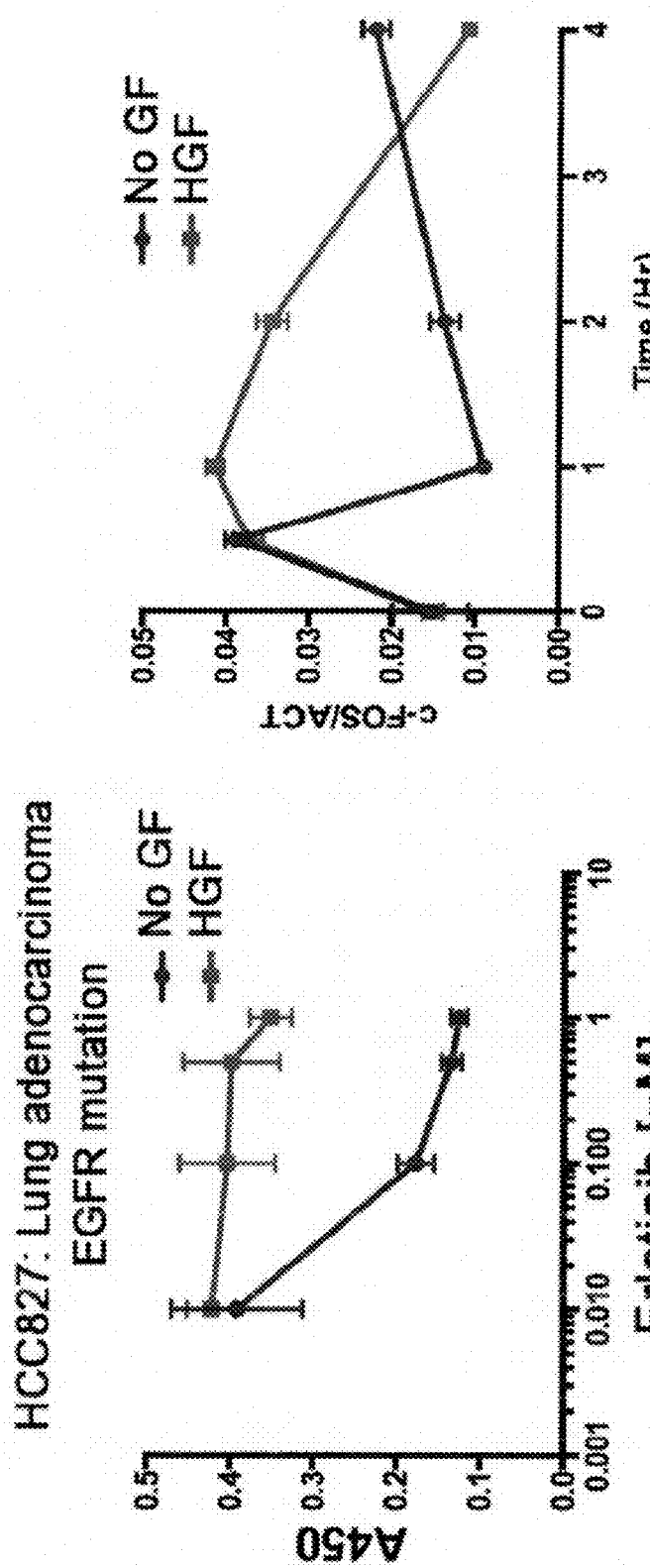
Figure 28E:
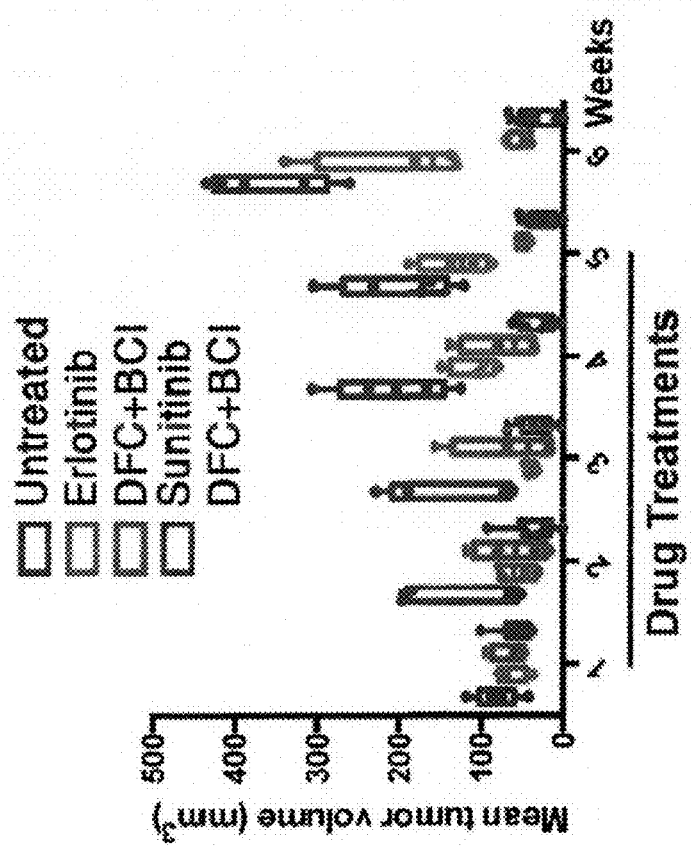
Figure 28F:
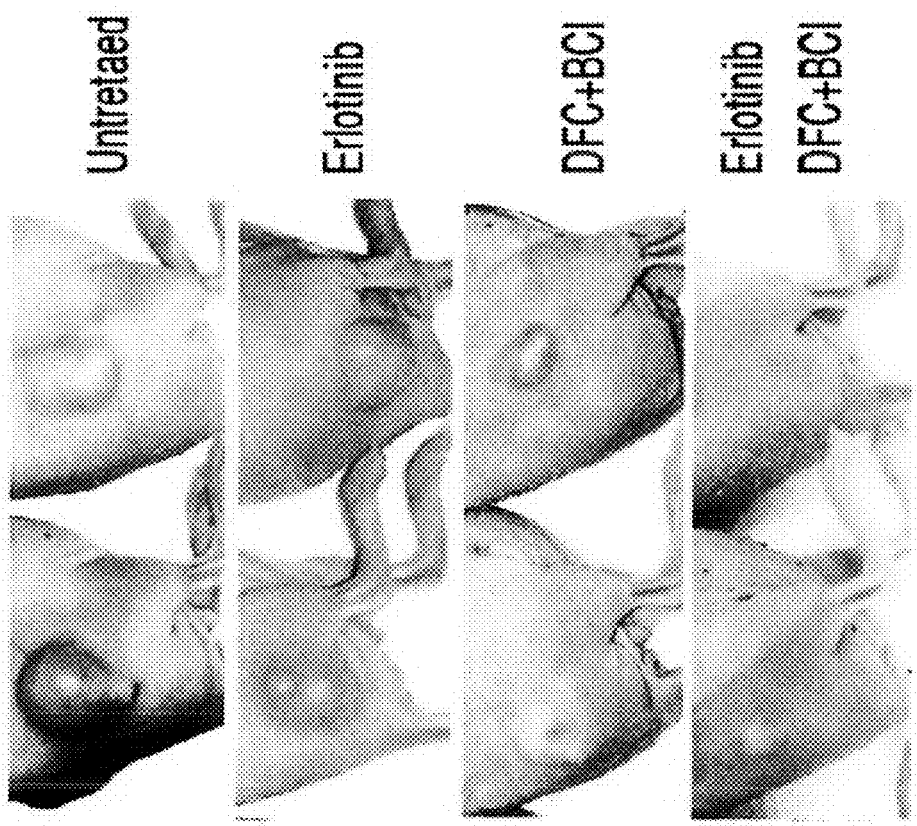

Lung cancer is the leading cause of cancer-related mortality in both men and women. Although chemotherapy recently has shown promising results in the adjuvant clinical setting and there has been some progress in the treatment of locally advanced and advanced disease, treatment outcomes for non-small cell lung cancer (NSCLC) patients are in general disappointing. Somatic, activating mutations in EGFR identify a significant minority of patients with non-small cell lung cancer (NSCLC). Although these mutations are associated with an approximately 70% response rate to some EGFR tyrosine kinase inhibitors (gefitinib, erlotinib, and afatinib), patients develop resistance (i.e., "acquired resistance") after a median of 9 to 12 months. As shown in FIG. 28, inhibition of FOS and DUSP1 with TKI treatment cured EGFR driven lung cancers. Growth-factor-induced TKI resistance in solid tumors is mediated by c-FOS and DUSP1. FIG. 28A shows a dose response curve of the HCC827 cell line (lung adenocarcinoma; EGFR-DelE746A750) to erlotinib+/−hepatocyte growth factor (HGF). FIGS. 28B-C show real-time qPCR analysis illustrating induction of c-FOS (FIG. 28B) and DUSP1 (FIG. 28C) expression by HGF (indicated times after addition of erlotinib). FIG. 28D shows cell survival of HCC827 cells (WST assay) when treated with DFC, BCI and erlotinib alone and in combination. Note inhibition of DUSP1 alone sensitized the cells for erlotinib, while concomitant inhibition of both DUSP1 and c-FOS is sufficient to inhibit proliferation and survival. FIG. 28E shows HCC827 xenograft growth in recipients treated with erlotinib (red), DFC+BCI (green) and DFC+BCI+erlotinib (purple). Treatment started after one week of transplant (n=8 per group, each mouse represented by single dot). FIG. 28F shows representative images of mouse tumors from cohorts in FIG. 28E.

Platelet-derived growth factor receptors (PDGFRs), including PDGFRα and PDGFRβ, belong to the family of cell surface type III receptor tyrosine kinases (RTKs). Upon binding of the ligands, platelet-derived growth factors (PDGFs), the receptor complex is activated and the cytosolic domains serve as docking sites for coactivators and subsequently initiate downstream signaling cascades such as MAPK, PI3K, and STAT3 pathways. PDGFR signaling regulates a variety of biological processes, including cellular growth, cellular differentiation, cell migration, and angiogenesis. Deregulated PDGFR signaling has been implicated in the pathogenesis of several human diseases and malignancies. For example, in patients with gastrointestinal stromal tumors, chronic myelomonocytic leukemia, glioblastoma multiforme, and lung cancer, mutations have been identified in the genes encoding PDGFR, which results in constitutive activation of the kinase activity, overstimulation of signal transduction, interaction with adjacent stroma and vasculature, and eventually tumor cell growth. Current NSCLC therapies include several agents involved directly or indirectly platelet-derived growth factors (PDGFs) and its receptors (PDGFRs), e.g., sorafenib, sunitunib, imatinib, and bevacizumab. As shown in FIG. 29, inhibition of FOS and DUSP1 is sufficient to cure PDGFR driven lung cancer.

Figures 29A, 29B:
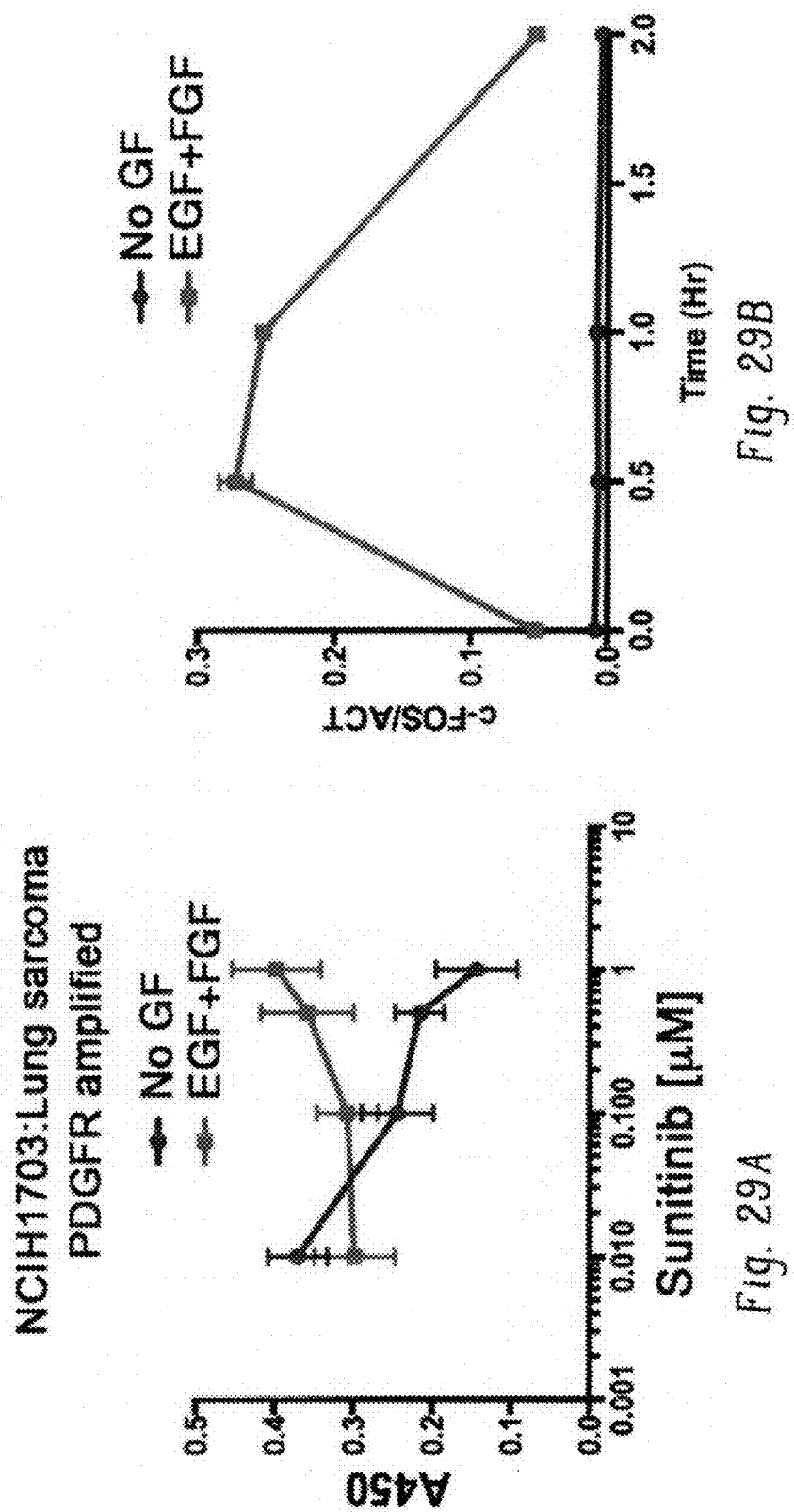
Figures 29E, 29F:
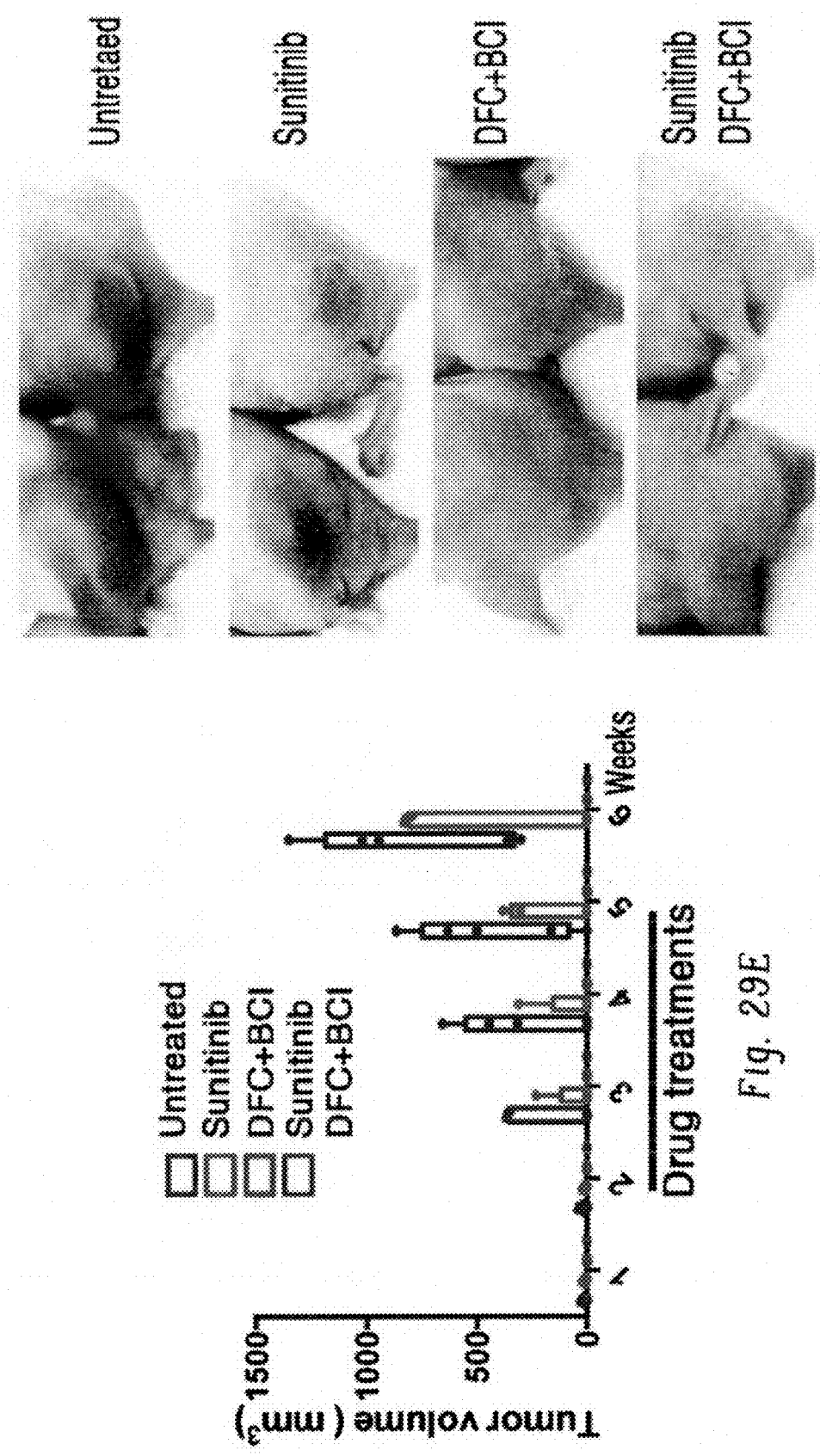

As shown in FIG. 29A, dose response curve of NCI-H1703 (lung squamous carcinoma; PDGFR amplification) showing resistance to sunitinib in the presence of epidermal growth factor and fibroblast growth factor (EGF+FGF). FIGS. 29B-C show real-time qPCR analysis illustrating induction of FOS (FIG. 29B) and DUSP1 (FIG. 29C) expression by EGF and FGF (indicated times after addition of sunitinib). FIG. 29D shows cell survival of NCI-H1703 cells (WST assay) when treated with DFC, BCI and sunitinib alone and in combination. Concomitant inhibition of both DUSP1 and c-FOS is sufficient to inhibit proliferation and survival. FIG. 29E shows mouse xenografts of NCI-H1703 treated with sunitinib, DFC+BCI and sunitinib+DFC+BCI (n=5). Treatments were started two weeks after xenotransplantation. Mice treated with either DFC+BCI or sunitinib+DFC+BCI showed complete response. Treatment with sunitinib alone showed initial response but three mice showed tumor regrowth after three weeks of treatment. FIG. 29F shows representative images of mouse tumors from cohorts in FIG. 29E.

Growth factor induced TKI resistance in solid tumors is mediated by c-FOS and DUSP1. ERBB2 is a transmembrane tyrosine kinase receptor and a member of the ErbB protein family (ie, the epidermal growth factor receptor [EGFR] family). ERBB2 is most commonly known as HER2 and sometimes also as NEU. HER2 gene product is overexpressed in 18-20% of invasive breast cancers. Lapatinib is an orally active drug for breast cancer and other solid tumours. It is a dual tyrosine kinase inhibitor which interrupts the HER2/neu and epidermal growth factor receptor (EGFR) pathways. It is used in combination therapy for HER2-positive breast cancer. It is used for the treatment of patients with advanced or metastatic breast cancer whose tumors overexpress HER2 (ErbB2). Lapatinib is used as a treatment in patients who have HER2-positive advanced breast cancer that has progressed after previous treatment with other chemotherapeutic agents, such as anthracycline, taxane-derived drugs, or trastuzumab (Herceptin).

Muscle invasive bladder cancer (MIBC) is a highly aggressive disease, with a 5 year survival rate post-diagnosis of approximately 50%. Although the implementation of neoadjuvant chemotherapy extended overall patient survival prior to the recent advent of immune checkpoint inhibitors, no relevant new therapies have been introduced in the last 3 decades. This is in stark contrast to several other major cancers. MIBC has the third highest rate of ERBB2 amplification (after breast and gastric cancer) and demonstrates frequent Her2 overexpression. Even so, anti-Her2 treatments in MIBC have not been as encouraging.

Melanoma is an increasingly common cancer and a major cause of cancer-related death. Metastatic melanoma has a low survival rate and few effective treatments, thus new targets are needed for effective therapy. A molecule implicated in metastasis of cancer in general is c-Met, a receptor tyrosine kinase (RTK) involved in cell proliferation, migration, and invasion. c-Met and its ligand, hepatocyte growth factor (HGF), are upregulated in metastatic melanoma and are implicated in invasion and clinical disease progression. The discovery that ~50-60% of melanomas carry $BRAF^{V600E}$ point mutations prompted the generation of compounds specifically targeting this hyperactive mutated kinase. One such compound, PLX4032, has shown therapeutic efficacy in clinical trials and was therefore FDA-approved for clinical therapy under the name vemurafenib. Despite its remarkable efficacy, almost all patients receiving BRAF inhibitor treatment relapsed after weeks to months of therapy.

Figure 30C:
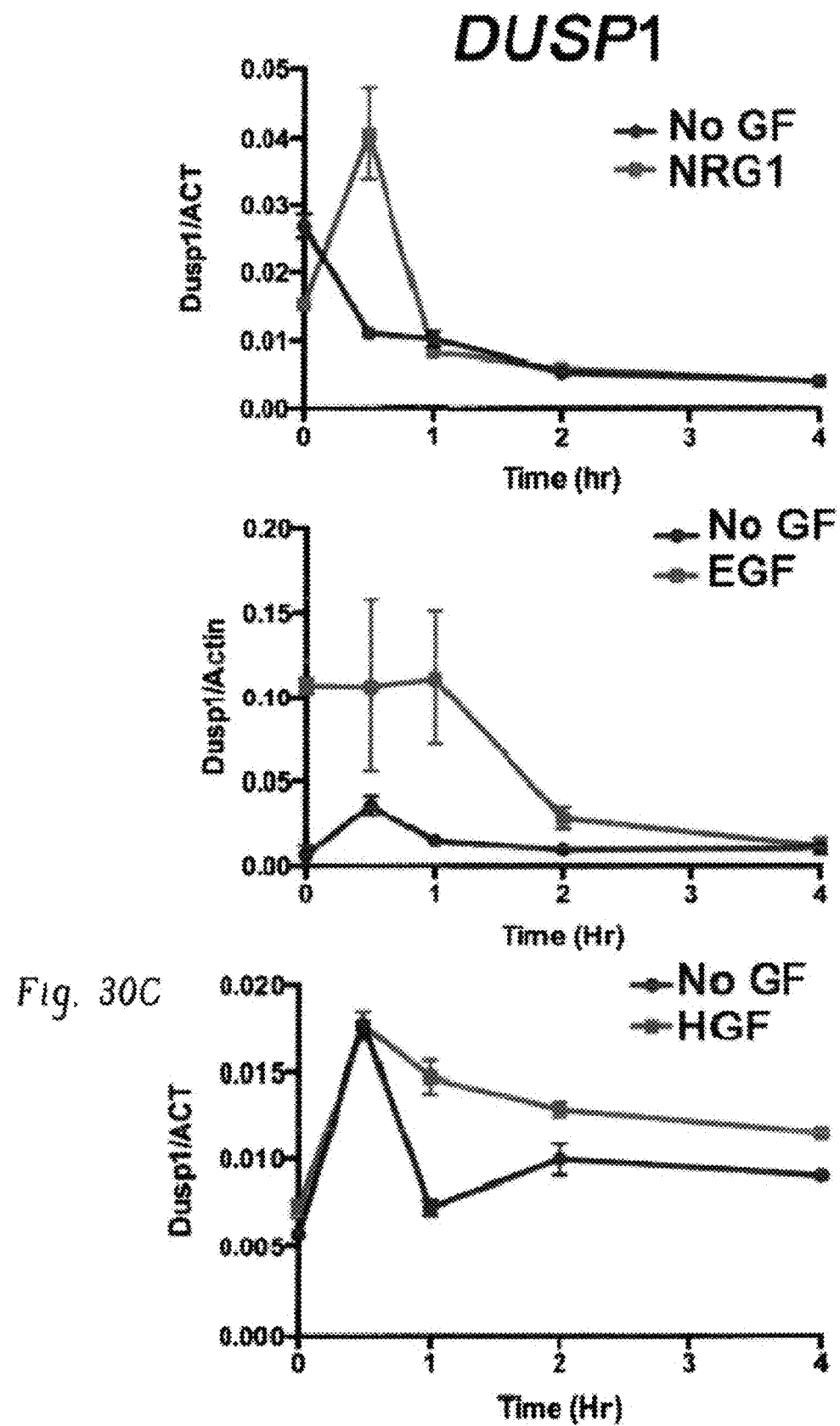

As shown in FIG. 30, growth factor induced TKI resistance in solid tumors is mediated by c-FOS and DUSP1. FIG. 30A shows dose response curves showing TKI resistance in solid tumor cell lines in the presence of growth factors. AU565 (breast cancer HER2 amplified AU565) conferred resistance to lapatinib by growth factor, neuregulin 1-NRG1. RT4 (bladder carcinoma, EGFR amplified) conferred resistance to lapatinib in the presence of EGF. SKMEL28 (melanoma, BRAF-V600E) conferred resistance to PLX4720 in the presence of HGF. FIGS. 30B-C show real-time qPCR analysis illustrating induction of c-FOS (FIG. 30B) and DUSP1 (FIG. 30C) expression by growth factors (indicated times after addition of erlotinib). Time at 0 hours represents the level of expression without TKI+/−GF. Note that the growth factors induce higher expression of c-FOS in all cell lines and DUSP1 in RT4 at 0 hours, while the addition of both TKI and growth factors induced both c-FOS and DUSP1. FIG. 30D shows bar graphs showing cell survival by WST assay when treated with DFC, BCI and TKI alone and in combination. Note inhibition of c-FOS and DUSP1 is sufficient to kill AU565 cells, while their inhibition in RT4 and SKMEL28 cells restored the TKI sensitivity in the presence of growth factors.

Chronic lymphocytic leukemia (CLL) is characterized by constitutive activation of the B-cell receptor (BCR) signaling pathway, but variable responsiveness of the BCR to antigen ligation. Bruton's tyrosine kinase (BTK) shows constitutive activity in CLL and is the target of irreversible inhibition by ibrutinib, an orally bioavailable kinase inhibitor that has shown outstanding activity in CLL. However, early clinical results in CLL with other reversible and irreversible BTK inhibitors have been less promising.

Each of the following references is expressly incorporated by reference herein in its entirety:

Aikawa et al. "Treatment of arthritis with a selective inhibitor of c-Fos/activator protein-1," Nature Biotechnology, vol. 26, no. 7 (2008), pp. 817-823.

Day et al., "Small Molecule Inhibitors of DUSP6 and Uses Therefor," WO2010/108058, Sep. 23, 2010.

Park et al., "Inhibition of fos-jun-DNA complex formation by dihydroguaiaretic acid and in vitro cytotoxic effects on cancer cells," Cancer Letters, vol. 127 (1998), pp. 23-28.

Padhye S, et al. New difluoro Knoevenagel condensates of curcumin, their Schiff bases and copper complexes as proteasome inhibitors and apoptosis inducers in cancer cells. Pharm Res 2009; 26:1874-80.

Padhye S et al. Fluorocurcumins as cyclooxygenase-2 inhibitor: molecular docking, pharmacokinetics and tissue distribution in mice. Pharm Res. 2009 November; 26(11): 2438-45.

Daley, G. Q., Van Etten, R. A. & Baltimore, D. Induction of chronic myelogenous leukemia in mice by the P210bcr/abl gene of the Philadelphia chromosome. Science 247, 824-830 (1990).

Druker, B. J. et al. Effects of a selective inhibitor of the Abl tyrosine kinase on the growth of Bcr-Abl positive cells. Nat. Med. 2, 561-566 (1996).

O'Hare, T., Zabriskie, M. S., Eiring, A. M. & Deininger, M. W. Pushing the limits of targeted therapy in chronic myeloid leukaemia. Nat. Rev. Cancer 12, 513-526 (2012).

Rousselot, P. et al. Imatinib mesylate discontinuation in patients with chronic myelogenous leukemia in complete molecular remission for more than 2 years. Blood 109, 58-60 (2007).

Mahon, F. X. et al. Discontinuation of imatinib in patients with chronic myeloid leukaemia who have maintained complete molecular remission for at least 2 years: the prospective, multicentre Stop Imatinib (STIM) trial. Lancet Oncol. 11, 1029-1035 (2010).

Ross, D. M. et al. Safety and efficacy of imatinib cessation for CML patients with stable undetectable minimal residual disease: results from the TWISTER study. Blood 122, 515-522 (2013).

Chu, S. et al. Detection of BCR-ABL kinase mutations in CD34+ cells from chronic myelogenous leukemia patients in complete cytogenetic remission on imatinib mesylate treatment. Blood 105, 2093-2098 (2005).

Savona, M. & Talpaz, M. Getting to the stem of chronic myeloid leukaemia. Nat. Rev. Cancer 8, 341-350 (2008).

Azam, M., Latek, R. R. & Daley, G. Q. Mechanisms of autoinhibition and STI-571/imatinib resistance revealed by mutagenesis of BCR-ABL. Cell 112, 831-843 (2003).

Krause, D. S. & Van Etten, R. A. Tyrosine kinases as targets for cancer therapy. N. Engl. J. Med. 353, 172-187 (2005).

Weinstein, I. B. Cancer. Addiction to oncogenes—the Achilles heal of cancer. Science 297, 63-64 (2002).

Sawyers, C. L. Shifting paradigms: the seeds of oncogene addiction. Nat. Med. 15, 1158-1161 (2009).

Pagliarini, R., Shao, W. & Sellers, W. R. Oncogene addiction: pathways of therapeutic response, resistance, and road maps toward a cure. EMBO Rep. 16, 280-296 (2015).

Reddy, A. & Kaelin, W. G., Jr. Using cancer genetics to guide the selection of anticancer drug targets. Curr. Opin. Pharmacol. 2, 366-373 (2002).

Kaelin, W. G., Jr. The concept of synthetic lethality in the context of anticancer therapy. Nat. Rev. Cancer 5, 689-698 (2005).

Kamb, A. Consequences of nonadaptive alterations in cancer. Mol. Biol. Cell 14, 2201-2205 (2003).

Mills, G. B., Lu, Y. & Kohn, E. C. Linking molecular therapeutics to molecular diagnostics: inhibition of the FRAP/RAFT/TOR component of the PI3K pathway preferentially blocks PTEN mutant cells in vitro and in vivo. Proc. Natl. Acad. Sci. USA 98, 10031-10033 (2001).

Sharma, S. V. & Settleman, J. Exploiting the balance between life and death: targeted cancer therapy and "oncogenic shock". Biochem. Pharmacol. 80, 666-673 (2010).

Sharma, S. V. & Settleman, J. Oncogene addiction: setting the stage for molecularly targeted cancer therapy. Genes Dev. 21, 3214-3231 (2007).

Corbin, A. S. et al. Human chronic myeloid leukemia stem cells are insensitive to imatinib despite inhibition of BCR-ABL activity. J. Clin. Invest. 121, 396-409 (2011).

Straussman, R. et al. Tumour micro-environment elicits innate resistance to RAF inhibitors through HGF secretion. Nature 487, 500-504 (2012).

Wilson, T. R. et al. Widespread potential for growth-factor-driven resistance to anticancer kinase inhibitors. Nature 487, 505-509 (2012).

Bruennert, D. et al. Early in vivo changes of the transcriptome in Philadelphia chromosome-positive CD34+ cells from patients with chronic myelogenous leukaemia following imatinib therapy. Leukemia 23, 983-985 (2009).

Eferl, R. & Wagner, E. F. AP-1: a double-edged sword in tumorigenesis. Nat. Rev. Cancer 3, 859-868 (2003).

Lawan, A., Shi, H., Gatzke, F. & Bennett, A. M. Diversity and specificity of the mitogen-activated protein kinase phosphatase-1 functions. Cell. Mol. Life Sci. 70, 223-237 (2013).

Jeffrey, K. L., Camps, M., Rommel, C. & Mackay, C. R. Targeting dual-specificity phosphatases: manipulating MAP kinase signalling and immune responses. Nat. Rev. Drug Discov. 6, 391-403 (2007).

Brooks, S. A. & Blackshear, P. J. Tristetraprolin (TTP): interactions with mRNA and proteins, and current thoughts on mechanisms of action. Biochim. Biophys. Acta 1829, 666-679 (2013).

Dorfman, K. et al. Disruption of the erp/mkp-1 gene does not affect mouse development: normal MAP kinase activity in ERP/MKP-1-deficient fibroblasts. Oncogene 13, 925-931 (1996).

Zhang, J. et al. c-fos regulates neuronal excitability and survival. Nat. Genet. 30, 416-420 (2002).

Zhao, C. et al. Hedgehog signalling is essential for maintenance of cancer stem cells in myeloid leukaemia. Nature 458, 776-779 (2009).

Ransone, L. J., Visvader, J., Wamsley, P. & Verma, I. M. Trans-dominant negative mutants of Fos and Jun. Proc. Natl. Acad. Sci. USA 87, 3806-3810 (1990).

Molina, G. et al. Zebrafish chemical screening reveals an inhibitor of Dusp6 that expands cardiac cell lineages. Nat. Chem. Biol. 5, 680-687 (2009).

Huang, T. S., Lee, S. C. & Lin, J. K. Suppression of c-Jun/AP-1 activation by an inhibitor of tumor promotion in mouse fibroblast cells. Proc. Natl. Acad. Sci. USA 88, 5292-5296 (1991).

Park, S., Lee, D. K. & Yang, C. H. Inhibition of fos-jun-DNA complex formation by dihydroguaiaretic acid and in vitro cytotoxic effects on cancer cells. Cancer Lett. 127, 23-28 (1998).

Padhye, S. et al. Fluorocurcumins as cyclooxygenase-2 inhibitor: molecular docking, pharmacokinetics and tissue distribution in mice. Pharm. Res. 26, 2438-2445 (2009).

Koschmieder, S. et al. Inducible chronic phase of myeloid leukemia with expansion of hematopoietic stem cells in a transgenic model of BCR-ABL leukemogenesis. Blood 105, 324-334 (2005).

Li, L. et al. Activation of p53 by SIRT1 inhibition enhances elimination of CML leukemia stem cells in combination with imatinib. Cancer Cell 21, 266-281 (2012).

Copland, M. et al. BMS-214662 potently induces apoptosis of chronic myeloid leukemia stem and progenitor cells and synergizes with tyrosine kinase inhibitors. Blood 111, 2843-2853 (2008).

Angel, P. & Karin, M. The role of Jun, Fos and the AP-1 complex in cell-proliferation and transformation. Biochim. Biophys. Acta 1072, 129-157 (1991).

Owens, D. M. & Keyse, S. M. Differential regulation of MAP kinase signalling by dual-specificity protein phosphatases. Oncogene 26, 3203-3213 (2007).

Boutros, T., Chevet, E. & Metrakos, P. Mitogen-activated protein (MAP) kinase/MAP kinase phosphatase regulation: roles in cell growth, death, and cancer. Pharmacol. Rev. 60, 261-310 (2008).

Groom, L. A., Sneddon, A. A., Alessi, D. R., Dowd, S. & Keyse, S. M. Differential regulation of the MAP, SAP and RK/p38 kinases by Pyst1, a novel cytosolic dual specificity phosphatase. EMBO J. 15, 3621-3632 (1996).

Fjeld, C. C., Rice, A. E., Kim, Y., Gee, K. R. & Denu, J. M. Mechanistic basis for catalytic activation of mitogen-activated protein kinase phosphatase 3 by extracellular signal-regulated kinase. J. Biol. Chem. 275, 6749-6757 (2000).

Zhao, Q. et al. MAP kinase phosphatase 1 controls innate immune responses and suppresses endotoxic shock. J. Exp. Med. 203, 131-140 (2006).

Hirsch, D. D. & Stork, P. J. Mitogen-activated protein kinase phosphatases inactivate stress-activated protein kinase pathways in vivo. J. Biol. Chem. 272, 4568-4575 (1997).

Young, P. R. et al. Pyridinyl imidazole inhibitors of p38 mitogen-activated protein kinase bind in the ATP site. J. Biol. Chem. 272, 12116-12121 (1997).

Bennett, B. L. et al. SP600125, an anthrapyrazolone inhibitor of Jun N-terminal kinase. Proc. Natl. Acad. Sci. USA 98, 13681-13686 (2001).

Shojaee, S. et al. Erk negative feedback control enables pre-B cell transformation and represents a therapeutic target in acute lymphoblastic leukemia. Cancer Cell 28, 114-128 (2015).

Hrustanovic, G. et al. RAS-MAPK dependence underlies a rational polytherapy strategy in EML4-ALK-positive lung cancer. Nat. Med. 21, 1038-1047 (2015).

Zhang, B. et al. Altered microenvironmental regulation of leukemic and normal stem cells in chronic myelogenous leukemia. Cancer Cell 21, 577-592 (2012).

Reynaud, D. et al. IL-6 controls leukemic multipotent progenitor cell fate and contributes to chronic myelogenous leukemia development. Cancer Cell 20, 661-673 (2011).

Welner, R. S. et al. Treatment of chronic myelogenous leukemia by blocking cytokine alterations found in normal stem and progenitor cells. Cancer Cell 27, 671-681 (2015).

Roberts, K. G. et al. Genetic alterations activating kinase and cytokine receptor signaling in high-risk acute lymphoblastic leukemia. Cancer Cell 22, 153-166 (2012).

Druker, B. J. et al. Activity of a specific inhibitor of the BCR-ABL tyrosine kinase in the blast crisis of chronic myeloid leukemia and acute lymphoblastic leukemia with the Philadelphia chromosome. N. Engl. J. Med. 344, 1038-1042 (2001).

Chang, K. H. et al. Vav3 collaborates with p190-BCR-ABL in lymphoid progenitor leukemogenesis, proliferation, and survival. Blood 120, 800-811 (2012).

Bagger, F. O. et al. BloodSpot: a database of gene expression profiles and transcriptional programs for healthy and malignant haematopoiesis. Nucleic Acids Res. 44D1, D917-D924 (2016).

Jørgensen, H. G., Allan, E. K., Jordanides, N. E., Mountford, J. C. & Holyoake, T. L. Nilotinib exerts equipotent antiproliferative effects to imatinib and does not induce apoptosis in CD34+ CML cells. Blood 109, 4016-4019 (2007).

Holyoake, T. L. & Vetrie, D. The chronic myeloid leukemia stem cell: stemming the tide of persistence. Blood https://doi.org/10.1182/blood-2016-09-696013 (2017).

Kesarwani, M. et al. Targeting substrate-site in Jak2 kinase prevents emergence of genetic resistance. Sci. Rep. 5, 14538 (2015).

Azam, M., Seeliger, M. A., Gray, N. S., Kuriyan, J. & Daley, G. Q. Activation of tyrosine kinases by mutation of the gatekeeper threonine. Nat. Struct. Mol. Biol. 15, 1109-1118 (2008).

Komurov, K., Dursun, S., Erdin, S. & Ram, P. T. NetWalker: a contextual network analysis tool for functional genomics. BMC Genomics 13, 282 (2012).

Other variations or embodiments will be apparent to a person of ordinary skill in the art from the above description. Thus, the foregoing embodiments are not to be construed as limiting the scope of the claimed invention.

What is claimed is:

1. A pharmaceutically acceptable composition comprising at least one biocompatible excipient and, as the only active agents, (a) a c-Fos inhibitor, (b) a Dusp-1 inhibitor, and (c) at least one oncogenic kinase inhibitor, where the oncogenic kinase is selected from the group consisting of BCR-ABL, BTK, FLT3, MET, KIT, JAK2, MEK, EGFR, PDGFR, ALK, HER2, B-Raf, FGFR2, RAF, P13K, and combinations thereof.

2. The pharmaceutically acceptable composition of claim 1 wherein,
   a) the c-Fos inhibitor is selected from the group consisting of curcumin, difluorinated curcumin (DFC), [3-{5-[4-(cyclopentyloxy)-2-hydroxpenzoyl]-2-[(3-hydroxy-1,2-benzisoxazol-6-yl) methoxy]phenyl}propionic acid] (T5224), nordihydroguaiaretic acid (NOGA), dihydroguaiaretic acid (DHGA), and [(E,E,Z,E)-3-methyl-7-(4-methylphenyl)-9-(2,6,6-trimethyl-1-cyclohexen-1-yl)-2,4,6,8-nonatetraenoic acid (SR11302);
   (b) the Dusp-1 inhibitor is selected from the group consisting of (E)-2-benzylidene-3-(cyclohexylamino)-2,3-dihydro-1 H-inden-1-one (BCI—also known as NSC 150117), TPI-2, TPI-3, and triptolide; and
   (c) the tyrosine kinase inhibitor is selected from the group consisting of Imatinib, Dasatinib, Ponatinib or Nilotinib when the oncogenic kinase is BCR-ABL; Ibrutinib when the oncogenic kinase is BTK; Ruxolitinib, Crizotinib, or Quizartinib when the oncogenic kinase is one of FL T3, MET, KIT, or JAK2; Ruxolitinib or Trametinib when the oncogenic kinase is JAK2 or MEK; Gefitinib or Axitinib when the oncogenic kinase is one of EGFR, PDGFR, or ALK; Gefitinib, Axitinib, or dasatinib when the oncogenic kinase is one of EGFR or PDGFR; Gefitinib or Axitinib when the oncogenic kinase is one of HER2 or EGFR; Vemurafenib or Sorafenib when the oncogenic kinase is one of B-Raf or MEK; Crizotinib or Dasatinib when the oncogenic kinase is one of MET, FGFR2, or HER2; Ceritinib, Alectinib or Crizotinib when the oncogenic kinase is one of MET, FGFR2, or HER2; Ceritinib, Alectinib or Crizotinib when the oncogenic kinase is one of ALK, KIT, or FGFR; and Vemurafenib, Sorafenib or Idelalisib when the oncogenic kinase is one of RAF or P13K.

3. A pharmaceutically acceptable composition comprising at least one biocompatible excipient and, as the only active agents, (E)-2-benzylidene-3-(cyclohexylamino)-2,3-dihydro-1 H-inden-1-one (BCI), difluorinated curcumin (DFC), and at least one oncogenic kinase inhibitor selected from the group consisting of Imatinib, Dasatinib, Ponatinib, Nilotinib, Ibrutinib, Ruxolitinib, Crizotinib, Quizartinib, Trametinib, Gefitinib, Axitinib, Dasatinib, Vemurafenib, Sorafenib, Ceritinib, Alectinib, Vemurafenib, and Idelalisib.

4. A method of treating a kinase-dependent malignancy in a patient, the method comprising administering to the patient in need thereof a composition containing at least one biocompatible excipient and, as the only active agents, a combination of
   (a) an inhibitor of c-Fos resulting in inhibition of c-Fos,
   (b) an inhibitor of Dusp-1 resulting in inhibition of Dusp-1, and
   (c) at least one inhibitor of an oncogenic kinase resulting in inhibition of the oncogenic kinase, wherein the composition is administered to the patient in a dosing regimen for a period sufficient to provide treatment for the kinase-dependent malignancy in the patient in need thereof, and wherein the kinase-dependent malignancy is:
   Chronic myeloid leukemia (CML) and the at least one inhibitor is Imatinib, Dasatinib, Ponatinib and/or Nilotinib;
   Chronic lymphocytic leukemia (CLL) and the at least one inhibitor is Ibrutinib;

Acute myeloid leukemia (AML) and the at least one inhibitor is Ruxolitinib, Crizotinib, and/or Quizartinib;

Myeloproliferative Neoplasm (MPN) and the at least one inhibitor is Ruxolitinib and/or Trametinib;

lung cancer and the at least one inhibitor is Gefitinib and/or Axitinib;

brain tumor and the at least one inhibitor is Gefitinib, Axitinib, and/or Dasatinib;

breast cancer and the at least one inhibitor is Gefitinib and/or Axitinib;

bladder carcinoma and the at least one inhibitor is Gefitinib and/or Axitinib;

melanoma and the at least one inhibitor is Vemurafenib and/or Sorafenib;

pancreatic cancer and the at least one inhibitor is Crizotinib and/or Dasatinib;

colon cancer and the at least one inhibitor is Ceritinib, Alectinib and/or Crizotinib; and prostate cancer and the at least one inhibitor is Vemurafenib, Sorafenib and/or Idelalisib.

5. The method of claim 4, wherein (a) the c-Fos inhibitor is selected from the group consisting of curcumin, difluorinated curcumin (DFC), [3-{5-[4-(cyclopentyloxy)-2-hydroxpenzoyl]-2-[(3-hydroxy-1,2-benzisoxazol-6-yl) methoxy]phenyl}propionic acid] (T5224), nordihydroguaiaretic acid (NOGA), dihydroguaiaretic acid (DHGA), and [(E,E,Z,E)-3-methyl-7-(4-methylphenyl)-9-(2,6,6-trimethyl-1-cyclohexen-1-yl)-2,4,6,8-nonatetraenoic acid (SR11302); and (b) the Dusp-1 inhibitor is selected from the group consisting of (E)-2-benzylidene-3-(cyclohexylamino)-2,3-dihydro-1 H-inden-1-one (BCI—also known as NSC 150117), TPI-2, TPI-3, and triptolide.

6. The method of claim 4, wherein the treatment is curative.

7. A method to eradicate leukemia initiating cells (LIC) or cancer stem cells (CSC) in a patient being treated with a tyrosine kinase inhibitor (TKI), the method comprising administering to the patient in need thereof a composition containing at least one biocompatible excipient and a combination of (a) an inhibitor of c-Fos resulting in inhibition of c-Fos, and (b) an inhibitor of Dusp-1 resulting in inhibition of Dusp-1, the composition administered to the patient in a dosing regimen for a period sufficient to eradicate the LIC or CSC cells.

* * * * *